(12) United States Patent
Sabbagh et al.

(10) Patent No.: US 11,505,611 B2
(45) Date of Patent: Nov. 22, 2022

(54) FGFR3 ANTIBODIES AND METHODS OF USE

(71) Applicant: GENZYME CORPORATION, Cambridge, MA (US)

(72) Inventors: Yves Sabbagh, Framingham, MA (US); Yangde Chen, Wellesley, MA (US); William Brondyk, Mansfield, MA (US); Huawei Qiu, Westborough, MA (US); Sunghae Park, Waban, MA (US); Ronnie Wei, Needham, MA (US); Yu Qiu, Framingham, MA (US); Yanfeng Zhou, Framingham, MA (US); Cendrine Lemoine, Vitry-sur-Seine (FR); HyunSuk Cho, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 17/407,774

(22) Filed: Aug. 20, 2021

(65) Prior Publication Data

US 2022/0056142 A1 Feb. 24, 2022

Related U.S. Application Data

(60) Provisional application No. 63/068,575, filed on Aug. 21, 2020.

(51) Int. Cl.
*C07K 16/28* (2006.01)
*A61P 19/08* (2006.01)
*A61K 39/00* (2006.01)

(52) U.S. Cl.
CPC .......... *C07K 16/2863* (2013.01); *A61P 19/08* (2018.01); *A61K 2039/505* (2013.01); *C07K 2317/52* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,670,323 A | 9/1997 | Nova et al. | |
| 5,707,632 A | 1/1998 | Williams et al. | |
| 6,193,980 B1 | 2/2001 | Efstathiou et al. | |
| 6,350,593 B1 | 2/2002 | Williams et al. | |
| 6,355,440 B1 | 3/2002 | Williams et al. | |
| 6,384,191 B1 | 5/2002 | Williams et al. | |
| 6,517,872 B1 | 2/2003 | Yayon et al. | |
| 7,135,311 B1 | 11/2006 | Cappellen et al. | |
| 7,479,367 B1 | 1/2009 | Luyten et al. | |
| 7,498,416 B2 | 3/2009 | Yayon et al. | |
| 7,598,027 B2 | 10/2009 | Fernandez-Salas et al. | |
| 7,612,181 B2 | 11/2009 | Wu et al. | |
| 8,043,618 B2 | 10/2011 | Sun et al. | |
| 8,101,721 B2 | 1/2012 | Yayon et al. | |
| 8,101,725 B2 | 1/2012 | Kim et al. | |
| 8,124,331 B2 | 2/2012 | Martínez et al. | |
| 8,128,940 B2 | 3/2012 | Steward et al. | |
| 8,158,360 B2 | 4/2012 | Heise et al. | |
| 8,173,134 B2 | 5/2012 | Bosch et al. | |
| 8,182,815 B2 | 5/2012 | Sun et al. | |
| 8,187,601 B2 | 5/2012 | Weng et al. | |
| 8,404,240 B2 | 3/2013 | Sun | |
| 8,410,250 B2 | 4/2013 | Ashkenazi et al. | |
| 8,529,898 B2 | 9/2013 | Daugherty et al. | |
| 8,710,189 B2 | 4/2014 | Ashkenazi et al. | |
| 8,828,385 B2 | 9/2014 | Yayon et al. | |
| 9,161,977 B2 | 10/2015 | Ashkenazi et al. | |
| 9,334,331 B2 * | 5/2016 | Igawa | C07K 16/40 |
| 9,375,488 B2 | 6/2016 | Balderes et al. | |
| 9,481,911 B2 | 11/2016 | Suzuki et al. | |
| 9,499,623 B2 | 11/2016 | Ashkenazi et al. | |
| 9,822,173 B2 | 11/2017 | Kannan et al. | |
| 10,000,571 B2 | 6/2018 | Ashkenazi et al. | |
| 10,287,356 B2 | 5/2019 | Ashkenazi et al. | |
| 10,421,807 B2 * | 9/2019 | Gonzales | A61P 17/08 |
| 10,436,786 B2 | 10/2019 | Singh et al. | |
| 2003/0143676 A1 | 7/2003 | Strachan et al. | |
| 2004/0057950 A1 | 3/2004 | Waksal et al. | |
| 2007/0248605 A1 | 10/2007 | Hestir et al. | |
| 2008/0044419 A1 | 2/2008 | Yayon | |
| 2009/0175866 A1 | 7/2009 | Yayon et al. | |
| 2009/0202547 A1 | 8/2009 | Yayon et al. | |
| 2010/0003258 A1 | 1/2010 | Weng et al. | |
| 2012/0237512 A1 | 9/2012 | Daugherty et al. | |

(Continued)

FOREIGN PATENT DOCUMENTS

| | | |
|---|---|---|
| EP | 1659175 A1 | 5/2006 |
| EP | 1208231 B2 | 12/2009 |
| EP | 2028193 B1 | 3/2012 |
| EP | 1423428 B2 | 11/2012 |
| EP | 2679600 A1 | 1/2014 |
| EP | 2137535 B1 | 6/2015 |
| EP | 2411414 B1 | 7/2015 |
| EP | 2288717 B1 | 7/2017 |
| EP | 3258966 A1 | 12/2017 |
| EP | 2790718 B1 | 2/2018 |
| EP | 2824181 B1 | 11/2018 |
| WO | WO 1991/000916 A2 | 1/1991 |
| WO | WO 1994/000599 A2 | 1/1994 |
| WO | WO 1994/021813 A1 | 9/1994 |

(Continued)

OTHER PUBLICATIONS

Iwahashi et al., Molecular Immunology, 36:1079-1091, 1999.*

(Continued)

*Primary Examiner* — Marianne P Allen
(74) *Attorney, Agent, or Firm* — LATHROP GPM LLP; James H. Velema; Judith L. Stone-Hulslander

(57) ABSTRACT

Anti-FGFR3 antigen-binding proteins and antigen-binding binding fragments thereof are provided. Methods of inhibiting FGFR3 activity and methods of treating FGFR3-mediated diseases and disorders are also provided.

16 Claims, 23 Drawing Sheets

Specification includes a Sequence Listing.

(56) References Cited

U.S. PATENT DOCUMENTS

| | | |
|---|---|---|
| 2014/0187754 A1 | 7/2014 | Ashkenazi et al. |
| 2015/0165067 A1 | 6/2015 | Baldares et al. |
| 2016/0046705 A1 | 2/2016 | Kannan et al. |
| 2016/0123984 A1 | 5/2016 | Singh et al. |
| 2016/0243228 A1 | 8/2016 | Holash et al. |
| 2019/0111086 A1 | 4/2019 | Keller et al. |
| 2019/0330355 A1 | 10/2019 | Ashkenazi et al. |

FOREIGN PATENT DOCUMENTS

| | | |
|---|---|---|
| WO | WO 2000/068424 A2 | 11/2000 |
| WO | WO 2001/024833 A2 | 4/2001 |
| WO | WO 2002/102854 A2 | 12/2002 |
| WO | WO 2002/102973 A2 | 12/2002 |
| WO | WO 2003/063893 A2 | 8/2003 |
| WO | WO 2004/003179 A1 | 1/2004 |
| WO | WO 2004/022095 A1 | 3/2004 |
| WO | WO 2004/056865 A2 | 7/2004 |
| WO | WO 2004/074506 A2 | 9/2004 |
| WO | WO 2004/085676 A1 | 10/2004 |
| WO | WO 2005/058966 A2 | 6/2005 |
| WO | WO 2005/082096 A2 | 9/2005 |
| WO | WO 2005/115363 A2 | 12/2005 |
| WO | WO 2006/053788 A2 | 5/2006 |
| WO | WO 2006/072620 A1 | 7/2006 |
| WO | WO 2006/099590 A2 | 9/2006 |
| WO | WO 2007/014123 A2 | 2/2007 |
| WO | WO 2007/045243 A2 | 4/2007 |
| WO | WO 2007/067968 A2 | 6/2007 |
| WO | WO 2007/144893 A2 | 12/2007 |
| WO | WO 2008/127707 A1 | 10/2008 |
| WO | WO 2009/025846 A2 | 2/2009 |
| WO | WO 2009/108637 A1 | 9/2009 |
| WO | WO 2009/146033 A2 | 12/2009 |
| WO | WO 2009/148928 A1 | 12/2009 |
| WO | WO 2010/002862 A2 | 1/2010 |
| WO | WO 2010/048026 A1 | 4/2010 |
| WO | WO 2010/111367 A1 | 9/2010 |
| WO | WO 2011/088196 A2 | 7/2011 |
| WO | WO 2013/087725 A1 | 6/2013 |
| WO | WO 2013/133351 A1 | 9/2013 |
| WO | WO 2014/081955 A1 | 5/2014 |
| WO | WO 2014/085666 A1 | 6/2014 |
| WO | WO 2014/161075 A1 | 10/2014 |
| WO | WO 2015/094900 A1 | 6/2015 |
| WO | WO 2016/134234 A1 | 8/2016 |
| WO | WO 2018/145120 A1 | 8/2018 |

OTHER PUBLICATIONS

Al-Lazikani, et al., Standard Conformations for the Canonical Structures of Immunoglobulins, Journal of Molecular Biology, vol. 273, No. 4, pp. 927-948, Nov. 7, 1997.
Angal, et al., A Single Amino Acid Substitution Abolishes the Heterogeneity of Chimeric Mouse/Human (IgG4) Antibody, Molecular Immunology, vol. 30, No. 1, pp. 105-108, 1993.
Creative Biolabs, "Recombinant Human Anti-FGFR3 Antibody (R3Mab)" Published Data and Datasheet, accessed online Dec. 8, 2021: <<https://www.creativebiolabs.net/Anti-FGFR3-Recombinant-Antibody-clone-R3Mab-24653.htm>>.
Gefter, et al., A Simple Method for Polyethylene Glycol-promoted Hybridization of Mouse Myeloma Cells, Somatic Cell Genetics, vol. 3, pp. 231-236, 1977.
Honegger, et al., Yet Another Numbering Scheme for Immunoglobulin Variable Domains: an Automatic Modeling and Analysis Tool, Journal of Molecular Biology, vol. 309, No. 3, pp. 657-670, 2001.
Jones, Proteinase Mutants of *Saccharomyces cerevisiae*, Genetics, vol. 85, No. 1, pp. 23-33, 1977.
Kingsman, et al., Replication in *Saccharomyces cerevisiae* of Plasmid pBR313 Carrying DNA From the Yeast trpl Region, Gene, vol. 7, No. 2, pp. 141-152, 1979.
Laederich et al., "FGFR3 targeting strategies for achondroplasia", Expert Reviews in Molecular Medicine, Apr. 2012, 14: e11.
Lefranc, et al., IMGT Unique Numbering for Immunoglobulin and T Cell Receptor Variable Domains and Ig Superfamily V-like Domains, Developmental & Comparative Immunology, vol. 27, No. 1, pp. 55-77, Jan. 2003.
Lerner, How to Make a Hybridoma, The Yale Journal of Biology and Medicine, vol. 54, No. 5, pp. 387-402, 1981.
MacCallum, et al., Antibody-Antigen Interactions: Contact Analysis and Binding Site Topography, Journal of molecular biology, vol. 262, No. 5, pp. 732-745, Oct. 11, 1996.
Merchant, et al., Monovalent Antibody Design and Mechanism of Action of Onartuzumab, a MET Antagonist With Anti-tumor Activity as a Therapeutic Agent, Proceedings of the National Academy of Sciences, vol. 110, No. 32, pp. E2987-E2996, Jun. 3, 2013.
NCBI, Fibroblast Growth Factor Receptor 3 Isoform 1 Precursor [*Homo sapiens*], NCBI Reference Sequence: NP_000133.1, Retrieved from: <<https://www.ncbi.nlm.nih.gov/protein/NP_000133.1>>, Nov. 14, 2021.
Olsen, et al., Insights Into the Molecular Basis for Fibroblast Growth Factor Receptor Autoinhibition and Ligand-binding Promiscuity, Proceedings of the National Academy of Sciences, vol. 101, No. 4, pp. 935-940, Jan. 27, 2004.
Prądzińska, et al., Application of Amide Hydrogen/deuterium Exchange Mass Spectrometry for Epitope Mapping in Human Cystatin C, Amino Acids, vol. 48, pp. 2809-2820, Aug. 29, 2016.
Ridgway, Introduction of Vector into Host Cells, Mammalian Expression Vectors, Chapter 24.2, pp. 470-472, 1988.
Sarabipour, et al., Effect of the Achondroplasia Mutation on FGFR3 Dimerization and FGFR3 Structural Response to fgf1 and fgf2: A Quantitative Fret Study in Osmotically Derived Plasma Membrane Vesicles, Biochimica et Biophysica Acta (BBA)—Biomembranes, vol. 1858, Issue 7, Part A, pp. 1436-1442, Jul. 2016.
Shazeeb, et al., Skeletal Characterization of the Fgfr3 Mouse Model of Achondroplasia Using Micro-CT and MRI Volumetric Imaging, Scientific Reports, vol. 8, No. 469, pp. 1-13, Jan. 11, 2018.
Stinchcomb, et al., Isolation and Characterisation of a Yeast Chromosomal Replicator, Nature, vol. 282, No. 5734, pp. 39-43, Nov. 1, 1979.
Tschumper, et al., Sequence of a Yeast DNA Fragment Containing a Chromosomal Replicator and the TRP1 Gene, Gene, vol. 10, No. 2, pp. 157-166, Jul. 1, 1980.
Xu, et al., In Vitro Characterization of Five Humanized OKT3 Effector Function Variant Antibodies, Cellular Immunology, vol. 200, Issue 1, pp. 16-26, Feb. 25, 2000.
Yin, et al., Redesigning a Monospecific Anti-FGFR3 Antibody to Add Selectivity for FGFR2 and Expand Antitumor Activity, Molecular Cancer Therapeutics, vol. 14, Issue 10, pp. 2270-2278, Oct. 2015.
International Search Report and Written Opinion for PCT International Patent Application No. PCT/US2021/046958, dated Dec. 8, 2021.

* cited by examiner

```
                        SEQUENCE LISTING

<160> NUMBER OF SEQ ID NOS: 344

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
tatgcaaggc ttacaaccac a                                         21

<210> SEQ ID NO 2
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
gttaggagct gggcatttgt gacactcc                                  28

<210> SEQ ID NO 3
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
gttaggtgct gggcatttgc atggaggaca ggg                            33

<210> SEQ ID NO 4
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<210> SEQ ID NO 4

<400> SEQUENCE: 4
gtttggtggg catgaagaac ccgggg                                         26

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 5
ctcattcctg ttgaagctct tgac                                           24

<210> SEQ ID NO 6
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser
        115                 120

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 7

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110
```

<210> SEQ ID NO 8
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 8

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Asn Pro Asn Asn Gly Thr Arg Tyr Asn Gln Lys Phe
50                  55                  60

Lys Gly Lys Ala Thr Leu Thr Val Asn Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser
        115
```

<210> SEQ ID NO 9
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 9

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys
            100                 105
```

<210> SEQ ID NO 10
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser
        115

<210> SEQ ID NO 11
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Phe Cys Leu Gln Tyr Asp Asn Leu Leu Trp
                85                  90                  95

Thr Phe Gly Gly Gly Thr Lys Leu Glu Ile Lys
            100                 105

<210> SEQ ID NO 12
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser
            115

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Gly
            20                  25                  30

Val Ala Trp Tyr Gln Gln Lys Pro Gly Gln Ser Pro Gln Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Ile Leu Thr Ile Arg Ser Val Gln Ala
65                  70                  75                  80

Glu Asp Leu Ala Leu Tyr Tyr Cys Gln Gln His Tyr Ser Thr Pro Leu
                85                  90                  95

Thr Phe Gly Ala Gly Thr Lys Leu Glu Leu Lys
            100                 105

<210> SEQ ID NO 14
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
            50                  55                  60

Lys Gly Lys Ala Ile Leu Thr Ala Asp Arg Ser Ser Thr Ala Tyr
 65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
                100                 105                 110

Gly Thr Ser Val Thr Val Ser Ser
            115                 120

<210> SEQ ID NO 15
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asn Ile Met Met Thr Gln Ser Pro Ser Ser Leu Ala Val Ser Ala Gly
 1               5                   10                  15

Glu Lys Val Thr Met Ser Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Met Lys
                100                 105                 110

<210> SEQ ID NO 16
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Gln Gln Ser Gly Ala Glu Leu Val Arg Pro Gly Ala
 1               5                   10                  15

Ser Val Thr Leu Ser Cys Lys Ala Ser Gly Ser Thr Phe Thr Asp Phe
                20                  25                  30

Glu Ile His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Lys Phe
 50                  55                  60

Lys Gly Lys Ala Ile Leu Thr Ala Val Lys Ser Ser Ser Thr Ala Tyr
 65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser
        115                 120

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Ser Leu Ser
65                  70                  75                  80

Ile Ser Ser Val Gln Thr Glu Asp Leu Ala Val Tyr Tyr Cys His Gln
                85                  90                  95

Tyr Leu Ser Ser Tyr Thr Phe Gly Gly Gly Thr Arg Leu Glu Met Lys
            100                 105                 110

<210> SEQ ID NO 18
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Ala Pro Gly Lys Gly Leu Glu Trp Ile
        35                  40                  45

Gly Asp Val Asp Pro Glu Thr Gly Gly Thr Ala Tyr Ala Glu Lys Phe
50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser
        115                 120

<210> SEQ ID NO 19
<211> LENGTH: 112
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Asn Asn Asn Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Val Glu Ile Lys
            100                 105                 110

<210> SEQ ID NO 20
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Ser Asp Phe
            20                  25                  30

Glu Ile His Trp Val Arg Gln Ala Pro Gly Gln Gly Leu Glu Trp Ile
        35                  40                  45

Gly Gly Ile Asp Pro Glu Thr Gly Gly Thr Ala Tyr Asn Gln Lys Phe
    50                  55                  60

Gln Gly Arg Val Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Gln Thr Phe Asp Tyr Trp Gly Gln
            100                 105                 110

Gly Thr Leu Val Thr Val Ser Ser
            115                 120

<210> SEQ ID NO 21
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Leu Val Gln Ser Gly Ala Glu Val Lys Lys Pro Gly Ala
1               5                   10                  15
```

Ser Val Lys Val Ser Cys Lys Ala Ser Gly Ser Thr Phe Ser Asp Phe
            20                  25                  30

Glu Ile His Trp Val Arg Gln Ala Pro Gly Gln Gly Leu Glu Trp Ile
        35                  40                  45

Gly Gly Ile Asp Pro Glu Thr Gly Gly Thr Ala Tyr Asn Gln Lys Phe
    50                  55                  60

Gln Gly Arg Val Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Gln Thr Phe Asp Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Ser Asp Phe
            20                  25                  30

Glu Ile His Trp Val Arg Gln Ala Pro Gly Gln Gly Leu Glu Trp Ile
        35                  40                  45

Gly Gly Ile Asp Pro Glu Thr Gly Gly Thr Ala Tyr Asn Gln Lys Phe
    50                  55                  60

Gln Gly Arg Val Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Gln Thr Phe Asp Tyr Trp Gly Gln
            100                 105                 110

Gly Thr Leu Val Thr Val Ser Ser
        115                 120

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Ser Asp Phe
            20                  25                  30

Glu Ile His Trp Val Arg Gln Ala Pro Gly Gln Gly Leu Glu Trp Ile
        35                  40                  45

```
Gly Gly Ile Asp Pro Glu Thr Gly Gly Thr Ala Tyr Asn Gln Lys Phe
        50                  55                  60

Gln Gly Arg Val Thr Ile Thr Ala Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Asn Tyr Asp Gly Tyr Ser Gln Thr Phe Asp Tyr Trp Gly Gln
                100                 105                 110

Gly Thr Leu Val Thr Val Ser Ser
            115                 120
```

<210> SEQ ID NO 24
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Asp Ile Val Met Thr Gln Ser Pro Asp Ser Leu Ala Val Ser Leu Gly
 1               5                  10                  15

Glu Arg Val Thr Ile Asn Cys Lys Ser Ser Gln Ser Val Leu Tyr Ser
                 20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Leu Ser Ser Tyr Thr Phe Gly Gln Gly Thr Lys Leu Glu Ile Lys
                100                 105                 110
```

<210> SEQ ID NO 25
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

```
Asp Ile Val Met Thr Gln Ser Pro Asp Ser Leu Ala Val Ser Leu Gly
 1               5                  10                  15

Glu Arg Val Thr Ile Asn Cys Lys Ser Ser Gln Ser Val Leu Tyr Ser
                 20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Leu Ser Pro Tyr Thr Phe Gly Gln Gly Thr Lys Leu Glu Ile Lys
```

<210> SEQ ID NO 26
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
                20                  25                  30

Asp Asn Gln Lys Asn Tyr Leu Ala Trp Tyr Gln Lys Pro Gly Gln
            35                  40                  45

Ser Pro Lys Leu Leu Ile Tyr Tyr Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Pro Tyr Thr Phe Gly Gln Gly Thr Lys Leu Glu Ile Lys
            100                 105                 110
```

<210> SEQ ID NO 27
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
                20                  25                  30

Asp Asn Gln Lys Asn Tyr Leu Ala Trp Tyr Gln Lys Pro Gly Gln
            35                  40                  45

Ser Pro Lys Leu Leu Ile Tyr Phe Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Pro Tyr Thr Phe Gly Gln Gly Thr Lys Leu Glu Ile Lys
            100                 105                 110
```

<210> SEQ ID NO 28
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Thr Asp Phe
            20                  25                  30

Glu Ile His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Arg Thr Phe Asp Tyr Trp Gly Gln
            100                 105                 110

Gly Thr Leu Val Thr Val Ser Ser
        115                 120

<210> SEQ ID NO 29
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Thr Asp Phe
            20                  25                  30

Glu Ile His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Arg Thr Phe Asp Tyr Trp Gly Gln
            100                 105                 110

Gly Thr Leu Val Thr Val Ser Ser
        115                 120

<210> SEQ ID NO 30
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Thr Asp Phe
            20                  25                  30

```
Glu Ile His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
 50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Arg Thr Phe Asp Tyr Trp Gly Gln
            100                 105                 110

Gly Thr Leu Val Thr Val Ser Ser
        115                 120
```

<210> SEQ ID NO 31
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Thr Asp Phe
            20                  25                  30

Glu Ile His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
 50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Tyr Asp Gly Tyr Ser Arg Thr Phe Asp Tyr Trp Gly Gln
            100                 105                 110

Gly Thr Leu Val Thr Val Ser Ser
        115                 120
```

<210> SEQ ID NO 32
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

```
Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
```

```
              65                  70                  75                  80
Ile Ser Ser Leu Gln Ala Glu Asp Val Ala Val Tyr Tyr Cys His Gln
                        85                  90                  95

Tyr Leu Ser Ser Tyr Thr Phe Gly Gln Gly Thr Lys Leu Glu Ile Lys
                100                 105                 110

<210> SEQ ID NO 33
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                        85                  90                  95

Tyr Leu Ser Pro Tyr Thr Phe Gly Gln Gly Thr Lys Leu Glu Ile Lys
                100                 105                 110

<210> SEQ ID NO 34
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
                20                  25                  30

Asp Asn Gln Lys Asn Tyr Leu Ala Trp Tyr Gln Gln Lys Pro Gly Gln
            35                  40                  45

Ser Pro Lys Leu Leu Ile Tyr Tyr Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                        85                  90                  95

Tyr Leu Ser Pro Tyr Thr Phe Gly Gln Gly Thr Lys Leu Glu Ile Lys
                100                 105                 110

<210> SEQ ID NO 35
<211> LENGTH: 112
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 35

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Pro Tyr Thr Phe Gly Gln Gly Thr Lys Leu Glu Ile Lys
            100                 105                 110

<210> SEQ ID NO 36
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
```

| | | | | | |
|---|---|---|---|---|---|
| gaggtacaac | ttgtccagtc | aggtgcggag | gttaaaaaac | cgggggccac | agttaaactg | 60 |
| agctgcaagg | ctagcggtga | tacttttacc | gattttgaga | tacactgggt | tcagcaggct | 120 |
| ccggggaaag | ggcttgaatg | gattggtgat | gttgaccccg | aaacgggcgg | aaccgcgtat | 180 |
| gcagagaagt | ttcaaggtag | ggcaacgctc | actgcggaca | aagcacaga | cacggcatac | 240 |
| atggagctta | gttctctccg | ctctgaggat | accgctgttt | attattgtac | tagaacctat | 300 |
| gatggatatc | catacgcatt | cgattattgg | gggcaaggga | ctcttgtcac | agtcagctcc | 360 |
| gcttcaacca | agggaccttc | tgtctttcct | ctggccccct | caagcaagag | cacttccgga | 420 |
| gggactgccg | cactcgggtg | ccttgtgaaa | gattacttcc | cagagcctgt | gaccgtcagc | 480 |
| tggaattcag | gcgctctgac | tagcggagtg | cacaccttcc | ccgctgtgct | tcagtcctcc | 540 |
| ggactctact | ctctgagcag | cgtggtgacc | gtgccgtcct | cttctctggg | gacccagact | 600 |
| tatatctgca | acgtcaatca | taagccttct | aataccaagg | tggacaagaa | ggtggaaccc | 660 |
| aaatcatgtg | acaagaccca | cacctgtccg | ccctgtccgg | cacccgaact | gctgggtggc | 720 |
| ccttccgtgt | tccttttccc | tccaaagccg | aaggacactc | ttatgatttc | tcgcactccc | 780 |
| gaagtgactt | gcgtcgtggt | ggatgtgtcc | catgaggatc | cagaggtcaa | gttcaactgg | 840 |
| tacgtggacg | gtgtggaagt | ccacaacgcc | aagactaagc | cgagagagga | acagtacaat | 900 |
| tcaacctatc | gggtggtgag | cgtcctgacc | gtgctgcacc | aggactggct | taacggaaag | 960 |
| gagtacaagt | gcaaagtgtc | aaacaaggca | ctgcccgctc | cgatcgaaaa | gaccattagc | 1020 |
| aaagctaagg | gccagcccag | agaacccaa | gtctataccc | ttccacccag | ccgggacgag | 1080 |
| ctgaccaaaa | accaggtgtc | actcacttgt | ctcgtgaagg | gtttctaccc | ctcagacatc | 1140 |
| gccgtcgaat | gggagtccaa | tggtcagcca | gagaacaact | acaaaaccac | ccctcccgtg | 1200 |

```
ctggacagcg acgggtcttt ctttctctac tcaaagctga ccgtggataa gtctcgctgg    1260
cagcaaggga atgtgttttc ctgttcagtg atgcatgagg cccttcataa tcattacacc    1320
caaaagtcac tgagcctgtc tcccgga                                        1347
```

<210> SEQ ID NO 37
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
gacatagtga tgactcaatc cccagattca ctcgccgtat cactcggaga aagagccaca      60
attaattgta agagtagtca gtcagtcctt tactctaata acaacaaaaa ttacctggcc     120
tggtaccaac agaaaccagg tcaatctcct aaactgctta tctactgggc tagtacccga     180
gaatcaggag ttcccgatag gttttctggg tctgggagcg gcaccgactt cacactcaca     240
atctctagcg tacaggctga agatgtagcg gtgtattact gccaacagta ttattcatac     300
aggaccttcg gtggtggcac caaagtagaa atcaaacgca ctgtggcagc cccttctgtg     360
tttatcttcc caccctccga cgagcagctc aagtccggta ccgcctctgt cgtctgcctg     420
ctgaacaatt tctacccaag agaggccaag gtgcagtgga aggtggacaa cgcactgcaa     480
agcggtaatt cacaagagtc agtcaccgaa caagactcaa aggacagcac ctactcactg     540
tcatccaccc tgactctctc aaaggctgac tacgaaaagc acaaagtgta tgcttgtgaa     600
gtcactcatc agggcctttc tagccctgtg accaagagct tcaacagagg cgaatgc        657
```

<210> SEQ ID NO 38
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
caggtacagt tggtacagtc aggagcggag gttaaaaaac caggggcgtc tgtgaaagtc      60
tcatgtaaag cgagcggaag cacgtttagc gatttcgaga ttcactgggt gagacaagca     120
cccggtcagg gcctggaatg gattggaggg atcgacccgg aaacaggggg tacagcatat     180
aaccaaaagt ttcagggacg ggtcactata acggctgaca ggagcacgtc aactgcgtat     240
atggaattgt ccagtttgag gtcagaagat acggcagtct actactgcac aagaaattat     300
gatggatact ctcaaacgtt tgattattgg ggtcagggga ccctggtaac agtcagctca     360
gcttcaacca agggaccttc tgtctttcct ctggcccctt caagcaagag cacttccgga     420
gggactgccg cactcgggtg ccttgtgaaa gattacttcc cagagcctgt caccgtcagc     480
tggaattcag gcgctctgac tagcggagtg cacaccttcc ccgctgtgct tcagtcctcc     540
ggactctact ctctgagcag cgtggtgacc gtgccgtcct cttctctggg gacccagact     600
tatatctgca acgtcaatca taagccttct aataccaagg tggacaagaa ggtggaaccc     660
aaatcatgtg acaagaccca cacctgtccg cctgtccgg cacccgaact gctgggtggc     720
ccttccgtgt tccttttccc tccaaagccg aaggacactc ttatgatttc tcgcactccc     780
```

```
gaagtgactt gcgtcgtggt ggatgtgtcc catgaggatc cagaggtcaa gttcaactgg      840
tacgtggacg gtgtggaagt ccacaacgcc aagactaagc cgagagagga acagtacaat      900
tcaacctatc gggtggtgag cgtcctgacc gtgctgcacc aggactggct taacggaaag     960
gagtacaagt gcaaagtgtc aaacaaggca ctgcccgctc cgatcgaaaa gaccattagc     1020
aaagctaagg gccagcccag agaacccaa gtctataccc ttccacccag ccgggacgag      1080
ctgaccaaaa accaggtgtc actcacttgt ctcgtgaagg gtttctaccc ctcagacatc     1140
gccgtcgaat gggagtccaa tggtcagcca gagaacaact acaaaaccac ccctcccgtg     1200
ctggacagcg acgggtcttt ctttctctac tcaaagctga ccgtggataa gtctcgctgg     1260
cagcaaggga atgtgttttc ctgttcagtg atgcatgagg cccttcataa tcattacacc     1320
caaaagtcac tgagcctgtc tcccgga                                         1347
```

<210> SEQ ID NO 39
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
caggtacagt tggtacagtc aggagcggag gttaaaaaac caggggcgtc tgtgaaagtc       60
tcatgtaaag cgagcggaag cacgtttagc gatttcgaga ttcactgggt gagacaagca      120
cccggtcagg gcctggaatg gattggaggg atcgacccgg aaacaggggg tacagcatat      180
aaccaaaagt ttcagggacg ggtcactata acggctgaca ggagcacgtc aactgcgtat      240
atggaattgt ccagtttgag gtcagaagat acggcagtct actactgcac aagaaattat      300
gatggatact ctcaaacgtt tgattattgg ggtcagggga ccctggtaac agtcagctca     360
gcttcaacca agggaccttc tgtctttcct ctggccccct caagcaagag cacttccgga     420
gggactgccg cactcgggtg ccttgtgaaa gattacttcc cagagcctgt caccgtcagc     480
tggaattcag gcgctctgac tagcggagtg cacaccttcc ccgctgtgct tcagtcctcc    540
ggactctact ctctgagcag cgtggtgacc gtgccgtcct cttctctggg gacccagact     600
tatatctgca acgtcaatca taagccttct aataccaagg tggacaagaa ggtgaaccc     660 aaatcatgtg acaagaccca cacctgtccg ccctgtccgg cacccgaact gctgggtggc     720
ccttccgtgt tccttttccc tccaaagccg aaggacactc ttatgatttc tcgcactccc     780
gaagtgactt gcgtcgtggt ggatgtgtcc catgaggatc cagaggtcaa gttcaactgg      840
tacgtggacg gtgtggaagt ccacaacgcc aagactaagc cgagagagga acagtacaat      900
tcaacctatc gggtggtgag cgtcctgacc gtgctgcacc aggactggct taacggaaag     960
gagtacaagt gcaaagtgtc aaacaaggca ctgcccgctc cgatcgaaaa gaccattagc     1020
aaagctaagg gccagcccag agaacccaa gtctataccc ttccacccag ccgggacgag      1080
ctgaccaaaa accaggtgtc actcacttgt ctcgtgaagg gtttctaccc ctcagacatc     1140
gccgtcgaat gggagtccaa tggtcagcca gagaacaact acaaaaccac ccctcccgtg     1200
ctggacagcg acgggtcttt ctttctctac tcaaagctga ccgtggataa gtctcgctgg     1260
cagcaaggga atgtgttttc ctgttcagtg atgcatgagg cccttcataa tcattacacc     1320
caaaagtcac tgagcctgtc tcccgga                                         1347
```

<210> SEQ ID NO 40
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 40

```
caggtacagt tggtacagtc aggagcggag gttaaaaaac caggggcgtc tgtgaaagtc      60
tcatgtaaag cgagcggaag cacgtttagc gatttcgaga ttcactgggt gagacaagca     120
cccggtcagg gcctggaatg gattggaggg atcgacccgg aaacagggg tacagcatat      180
aaccaaaagt ttcagggacg ggtcactata acggctgaca ggagcacgtc aactgcgtat     240
atggaattgt ccagtttgag gtcagaagat acggcagtct actactgcac aagaaattat    300
gatggatact ctcaaacgtt tgattattgg ggtcagggga ccctggtaac agtcagctca     360
gcttcaacca agggaccttc tgtctttcct ctggccccctt caagcaagag cacttccgga   420
gggactgccg cactcgggtg ccttgtgaaa gattacttcc cagagcctgt caccgtcagc     480
tggaattcag cgctctgac tagcggagtg cacaccttcc ccgctgtgct tcagtcctcc    540
ggactctact ctctgagcag cgtggtgacc gtgccgtcct cttctctggg gacccagact    600
tatatctgca acgtcaatca taagccttct aataccaagg tggacaagaa ggtgaaccc     660
aaatcatgtg acaagaccca cacctgtccg ccctgtccgg cacccgaact gctgggtggc    720
ccttccgtgt tccttttccc tccaaagccg aaggacactc ttatgatttc tcgcactccc    780
gaagtgactt gcgtcgtggt ggatgtgtcc catgaggatc cagaggtcaa gttcaactgg   840
tacgtggacg gtgtggaagt ccacaacgcc aagactaagc cgagagagga acagtacaat    900
tcaacctatc gggtggtgag cgtcctgacc gtgctgcacc aggactggct aacggaaag    960
gagtacaagt gcaaagtgtc aaacaaggca ctgcccgctc cgatcgaaaa gaccattagc   1020
aaagctaagg gccagcccag agaaccccaa gtctataccc ttccacccag ccgggacgag    1080
ctgaccaaaa accaggtgtc actcacttgt ctcgtgaagg gtttctaccc ctcagacatc   1140
gccgtcgaat gggagtccaa tggtcagcca gagaacaact acaaaaccac ccctcccgtg   1200
ctggacagcg acgggtcttt cttctctac tcaaagctga ccgtggataa gtctcgctgg    1260
cagcaaggga atgtgttttc ctgttcagtg atgcatgagg cccttcataa tcattacacc    1320
caaaagtcac tgagcctgtc tcccgga                                        1347
```

<210> SEQ ID NO 41
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41

```
caggtacagt tggtacagtc aggagcggag gttaaaaaac caggggcgtc tgtgaaagtc      60
tcatgtaaag cgagcggaag cacgtttagc gatttcgaga ttcactgggt gagacaagca     120
cccggtcagg gcctggaatg gattggaggg atcgacccgg aaacagggg tacagcatat      180
aaccaaaagt ttcagggacg ggtcactata acggctgaca ggagcacgtc aactgcgtat     240
atggaattgt ccagtttgag gtcagaagat acggcagtct actactgcac aagaaattat    300
```

```
gatggatact ctcaaacgtt tgattattgg ggtcagggga ccctggtaac agtcagctca    360
gcttcaacca agggaccttc tgtctttcct ctggcccctt caagcaagag cacttccgga    420
gggactgccg cactcgggtg ccttgtgaaa gattacttcc cagagcctgt caccgtcagc    480
tggaattcag gcgctctgac tagcggagtg cacaccttcc ccgctgtgct tcagtcctcc    540
ggactctact ctctgagcag cgtggtgacc gtgccgtcct cttctctggg acccagact     600 tatatctgca acgtcaatca taagccttct aataccaagg tggacaagaa ggtgaaccc     660 aaatcatgtg acaagaccca cacctgtccg ccctgtccgg cacccgaact gctgggtggc    720
ccttccgtgt tccttttccc tccaaagccg aaggacactc ttatgatttc tcgcactccc    780
gaagtgactt gcgtcgtggt ggatgtgtcc catgaggatc cagaggtcaa gttcaactgg    840
tacgtggacg gtgtggaagt ccacaacgcc aagactaagc cgagagagga acagtacaat    900
tcaacctatc gggtggtgag cgtcctgacc gtgctgcacc aggactggct taacggaaag    960
gagtacaagt gcaaagtgtc aaacaaggca ctgcccgctc cgatcgaaaa gaccattagc   1020
aaagctaagg gccagcccag agaacccaa  gtctatacc  ttccacccag ccgggacgag   1080
ctgaccaaaa accaggtgtc actcacttgt ctcgtgaagg gtttctaccc ctcagacatc   1140
gccgtcgaat gggagtccaa tggtcagcca gagaacaact acaaaaccac ccctcccgtg   1200
ctggacagcg acgggtcttt ctttctctac tcaaagctga ccgtggataa gtctcgctgg   1260
cagcaaggga atgtgttttc ctgttcagtg atgcatgagg cccttcataa tcattacacc   1320
caaaagtcac tgagcctgtc tcccgga                                       1347

<210> SEQ ID NO 42
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
gatatagtta tgacacagag ccctgactct ctggctgtga gtttgggcga gcgagtaacc     60
attaattgta agagttctca atccgtcctc tactcaagca accagaaaaa ttacctcgcg    120
tggtaccagc aaaaaccagg acagagcccc aaactcttga tctattgggc gtccacccga    180
gagagtggcg tgccagatcg gttttcaggt tctggatctg gtaccgactt cacccttaca    240
atctcaagcc tgcaagcaga ggatgtcgca gtttattatt gccatcagta cctgagcagc    300
tacacattcg acaaggaac  gaaactggaa atcaaacgca ctgtggcagc cccttctgtg    360
tttatcttcc caccctccga cgagcagctc aagtccggta ccgcctctgt cgtctgcctg    420
ctgaacaatt tctacccaag agaggccaag gtgcagtgga aggtggacaa cgcactgcaa    480
agcggtaatt cacaagagtc agtcaccgaa caagactcaa aggacagcac ctactcactg    540
tcatccaccc tgactctctc aaaggctgac tacgaaaagc acaaagtgta tgcttgtgaa    600
gtcactcatc agggcctttc tagccctgtg accaagagct caacagagg  cgaatgc      657

<210> SEQ ID NO 43
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 43

```
gacatagtaa tgacccaaag tccagattct ttggccgtat ctttgggtga gcgcgttacc    60
atcaactgta agtcttccca gtctgtgttg tactcatcta atcaaaaaaa ctacctcgct   120
tggtaccagc agaagccagg tcaaagcccg aaactgctta tttattgggc gtctacgcga   180
gagtctgggg tccccgatcg gttttcaggg tcaggctctg gcactgattt tactctgact   240
atttcatccc tccaagccga agacgtggca gtgtattact gccaccagta tttgagccct   300
tacacgtttg gcaggggac taaacttgaa atcaagcgca ctgtggcagc cccttctgtg   360
tttatcttcc caccctccga cgagcagctc aagtccggta ccgcctctgt cgtctgcctg   420
ctgaacaatt tctacccaag agaggccaag gtgcagtgga aggtggacaa cgcactgcaa   480
agcggtaatt cacaagagtc agtcaccgaa caagactcaa aggacagcac ctactcactg   540
tcatccaccc tgactctctc aaaggctgac tacgaaaagc acaaagtgta tgcttgtgaa   600
gtcactcatc agggcctttc tagccctgtg accaagagct caacagagg cgaatgc      657
```

<210> SEQ ID NO 44
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 44

```
gatattgtga tgactcagtc acctgacagt ctggcggttt ctttgggcga aagagtgact    60
ataaattgca aaagcagcca gtcagttctc tattccgaca atcaaaagaa ctatctcgca   120
tggtatcagc agaagccagg gcaatcccca aaattgctta tatactatgc atcaacgcgc   180
gaaagcggtg tacccgatcg gttttcagga agtggcagtg ggaccgactt tacgctgaca   240
atctcttccc ttcaagcgga ggatgtcgcg gtttattatt gtcatcagta tctgagtcct   300
tacacctttg gtcaagggac gaagttggag atcaaacgca ctgtggcagc cccttctgtg   360
tttatcttcc caccctccga cgagcagctc aagtccggta ccgcctctgt cgtctgcctg   420
ctgaacaatt tctacccaag agaggccaag gtgcagtgga aggtggacaa cgcactgcaa   480
agcggtaatt cacaagagtc agtcaccgaa caagactcaa aggacagcac ctactcactg   540
tcatccaccc tgactctctc aaaggctgac tacgaaaagc acaaagtgta tgcttgtgaa   600
gtcactcatc agggcctttc tagccctgtg accaagagct caacagagg cgaatgc      657
```

<210> SEQ ID NO 45
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
gacatcgtaa tgacccagtc ccccgatagt ctggctgtgt ctttgggcga gagggtaacg    60
ataaactgta aatcaagtca gtcagtgctt tactcagata accagaagaa ctatcttgcg   120
tggtatcagc aaaagcccgg acagtctcca aaacttctta tatatttcgc ttctaccaga   180
gaatcaggtg taccagaccg cttttctgga agcggctctg gtactgactt taccctgaca   240
```

```
attagtagct tgcaagctga agatgttgcg gtatattatt gtcaccaata cttgagtccc    300 tatactttg gccaagggac aaaactggaa ataaagcgca ctgtggcagc cccttctgtg    360
tttatcttcc caccctccga cgagcagctc aagtccggta ccgcctctgt cgtctgcctg    420
ctgaacaatt tctacccaag agaggccaag gtgcagtgga aggtggacaa cgcactgcaa    480
agcggtaatt cacaagagtc agtcaccgaa caagactcaa aggacagcac ctactcactg    540
tcatccaccc tgactctctc aaaggctgac tacgaaaagc acaaagtgta tgcttgtgaa    600
gtcactcatc agggcctttc tagccctgtg accaagagct caacagagg cgaatgc      657
```

<210> SEQ ID NO 46
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

```
caggttcagc tggtacaatc tggcgcggaa gtcaaaaagc caggcgcaag tgttaaagtg    60
tcttgcaagg cttcaggatc taccttaca gattttgaaa tccactgggt aagacaagca    120
cctggccagg ggctggaatg gattggtgcc atagaccctg agacgggagg aaccgcatat    180
aaccagaaat tccaaggtcg agtgactatt actgcggaca gtcaacatc aactgcctat    240 atggagctgt cttctttgag gtcagaggat acagcagttt actactgcac tagaaattac    300
gatggttatt cacggaccctt cgattattgg ggtcaaggca ctctggtgac cgtgagttcc    360
gcttcaacca agggaccttc tgtctttcct ctggccccctt caagcaagag cacttccgga    420
gggactgccg cactcgggtg ccttgtgaaa gattacttcc cagagcctgt caccgtcagc    480
tggaattcag gcgctctgac tagcggagtg cacaccttcc ccgctgtgct tcagtcctcc    540
ggactctact ctctgagcag cgtggtgacc gtgccgtcct cttctctggg gacccagact    600
tatatctgca acgtcaatca taagccttct aataccaagg tggacaagaa ggtggaaccc    660
aaatcatgtg acaagaccca cacctgtccg ccctgtccgg cacccgaact gctgggtggc    720
ccttccgtgt tcctttttccc tccaaagccg aaggacactc ttatgatttc tcgcactccc    780
gaagtgactt gcgtcgtggt ggatgtgtcc catgaggatc cagaggtcaa gttcaactgg    840
tacgtggacg gtgtggaagt ccacaacgcc aagactaagc cgagagagga acagtacaat    900
tcaacctatc gggtggtgag cgtcctgacc gtgctgcacc aggactggct aaacggaaag    960
gagtacaagt gcaaagtgtc aaacaaggca ctgcccgctc cgatcgaaaa gaccattagc    1020
aaagctaagg gccagcccag agaacccaa gtctataccc ttccacccag ccgggacgag    1080
ctgaccaaaa accaggtgtc actcacttgt ctcgtgaagg gtttctaccc ctcagacatc    1140
gccgtcgaat gggagtccaa tggtcagcca gagaacaact acaaaaccac ccctcccgtg    1200
ctggacagcg acgggtcttt cttctctac tcaaagctga ccgtggataa gtctcgctgg    1260
cagcaaggga atgtgttttc ctgttcagtg atgcatgagg cccttcataa tcattacacc    1320
caaaagtcac tgagcctgtc tcccgga                                         1347
```

<210> SEQ ID NO 47
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 47

```
caggttcagc tggtacaatc tggcgcggaa gtcaaaaagc caggcgcaag tgttaaagtg    60
tcttgcaagg cttcaggatc tacctttaca gattttgaaa tccactgggt aagacaagca   120
cctggccagg ggctggaatg gattggtgcc atagaccctg agacgggagg aaccgcatat   180
aaccagaaat tccaaggtcg agtgactatt actgcggaca agtcaacatc aactgcctat   240
atggagctgt cttctttgag gtcagaggat acagcagttt actactgcac tagaaattac   300
gatggttatt cacggacctt cgattattgg ggtcaaggca ctctggtgac cgtgagttcc   360
gcttcaacca agggaccttc tgtctttcct ctggccccct caagcaagag cacttccgga   420
gggactgccg cactcgggtg ccttgtgaaa gattacttcc cagagcctgt caccgtcagc   480
tggaattcag gcgctctgac tagcggagtg cacaccttcc ccgctgtgct tcagtcctcc   540
ggactctact ctctgagcag cgtggtgacc gtgccgtcct cttctctggg acccagact   600
tatatctgca acgtcaatca taagccttct aataccaagg tggacaagaa ggtggaaccc   660
aaatcatgtg acaagaccca cacctgtccg ccctgtccgg cacccgaact gctgggtggc   720
ccttccgtgt ccttttccc tccaaagccg aaggacactc ttatgatttc tcgcactccc   780
gaagtgactt gcgtcgtggt ggatgtgtcc catgaggatc cagaggtcaa gttcaactgg   840
tacgtggacg gtgtggaagt ccacaacgcc aagactaagc cgagagagga acagtacaat   900
tcaacctatc gggtggtgag cgtcctgacc gtgctgcacc aggactggct aacggaaag    960
gagtacaagt gcaaagtgtc aaacaaggca ctgcccgctc cgatcgaaaa gaccattagc  1020
aaagctaagg gccagcccag agaacccccaa gtctataccc ttccacccag ccgggacgag  1080
ctgaccaaaa accaggtgtc actcacttgt ctcgtgaagg gtttctaccc ctcagacatc  1140
gccgtcgaat gggagtccaa tggtcagcca gagaacaact acaaaaccac ccctcccgtg  1200
ctggacagcg acgggtcttt cttttctctac tcaaagctga ccgtggataa gtctcgctgg  1260
cagcaaggga atgtgttttc ctgttcagtg atgcatgagg cccttcataa tcattacacc  1320
caaaagtcac tgagcctgtc tcccgga                                      1347
```

<210> SEQ ID NO 48
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 48

```
caggttcagc tggtacaatc tggcgcggaa gtcaaaaagc caggcgcaag tgttaaagtg    60
tcttgcaagg cttcaggatc tacctttaca gatttgaaa tccactgggt aagacaagca   120
cctggccagg ggctggaatg gattggtgcc atagaccctg agacgggagg aaccgcatat   180
aaccagaaat tccaaggtcg agtgactatt actgcggaca agtcaacatc aactgcctat   240
atggagctgt cttctttgag gtcagaggat acagcagttt actactgcac tagaaattac   300
gatggttatt cacggacctt cgattattgg ggtcaaggca ctctggtgac cgtgagttcc   360
gcttcaacca agggaccttc tgtctttcct ctggccccct caagcaagag cacttccgga   420
gggactgccg cactcgggtg ccttgtgaaa gattacttcc cagagcctgt caccgtcagc   480
```

```
tggaattcag gcgctctgac tagcggagtg cacaccttcc ccgctgtgct tcagtcctcc      540
ggactctact ctctgagcag cgtggtgacc gtgccgtcct cttctctggg gacccagact      600
tatatctgca acgtcaatca taagccttct aataccaagg tggacaagaa ggtggaaccc      660
aaatcatgtg acaagaccca cacctgtccg ccctgtccgg cacccgaact gctgggtggc      720
ccttccgtgt tccttttccc tccaaagccg aaggacactc ttatgatttc tcgcactccc      780
gaagtgactt gcgtcgtggt ggatgtgtcc catgaggatc cagaggtcaa gttcaactgg      840
tacgtggacg gtgtggaagt ccacaacgcc aagactaagc cgagagagga acagtacaat      900
tcaacctatc gggtggtgag cgtcctgacc gtgctgcacc aggactggct taacggaaag      960
gagtacaagt gcaaagtgtc aaacaaggca ctgcccgctc cgatcgaaaa gaccattagc     1020
aaagctaagg gccagcccag agaacccaa  gtctataccc ttccacccag ccggacgag      1080 ctgaccaaaa accaggtgtc actcacttgt ctcgtgaagg gtttctaccc ctcagacatc     1140
gccgtcgaat gggagtccaa tggtcagcca gagaacaact acaaaaccac ccctcccgtg     1200
ctggacagcg acgggtcttt cttctctac  tcaaagctga ccgtggataa gtctcgctgg     1260
cagcaaggga atgtgttttc ctgttcagtg atgcatgagg cccttcataa tcattacacc     1320
caaaagtcac tgagcctgtc tcccgga                                         1347

<210> SEQ ID NO 49
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
caggttcagc tggtacaatc tggcgcggaa gtcaaaaagc caggcgcaag tgttaaagtg       60
tcttgcaagg cttcaggatc tacctttaca gattttgaaa tccactgggt aagcaagca      120 cctggccagg ggctggaatg gattggtgcc atagaccctg agacgggagg aaccgcatat     180
aaccagaaat tccaaggtcg agtgactatt actgcggaca gtcaacatc  aactgcctat     240 atggagctgt cttctttgag gtcagaggat acagcagttt actactgcac tagaaattac     300
gatggttatt cacggacctt cgattattgg ggtcaaggca ctctggtgac cgtgagttcc     360
gcttcaacca agggaccttc tgtctttcct ctggccccct caagcaagag cacttccgga     420
gggactgccg cactcgggtg ccttgtgaaa gattacttcc cagagcctgt caccgtcagc     480
tggaattcag gcgctctgac tagcggagtg cacaccttcc ccgctgtgct tcagtcctcc     540
ggactctact ctctgagcag cgtggtgacc gtgccgtcct cttctctggg gacccagact     600
tatatctgca acgtcaatca taagccttct aataccaagg tggacaagaa ggtggaaccc     660
aaatcatgtg acaagaccca cacctgtccg ccctgtccgg cacccgaact gctgggtggc     720
ccttccgtgt tccttttccc tccaaagccg aaggacactc ttatgatttc tcgcactccc     780
gaagtgactt gcgtcgtggt ggatgtgtcc catgaggatc cagaggtcaa gttcaactgg     840
tacgtggacg gtgtggaagt ccacaacgcc aagactaagc cgagagagga acagtacaat     900
tcaacctatc gggtggtgag cgtcctgacc gtgctgcacc aggactggct taacggaaag     960
gagtacaagt gcaaagtgtc aaacaaggca ctgcccgctc cgatcgaaaa gaccattagc    1020
aaagctaagg gccagcccag agaacccaa  gtctataccc ttccacccag ccggacgag     1080 ctgaccaaaa accaggtgtc actcacttgt ctcgtgaagg gtttctaccc ctcagacatc    1140
```

```
gccgtcgaat gggagtccaa tggtcagcca gagaacaact acaaaaccac ccctcccgtg   1200
ctggacagcg acgggtcttt ctttctctac tcaaagctga ccgtggataa gtctcgctgg   1260
cagcaaggga atgtgttttc ctgttcagtg atgcatgagg cccttcataa tcattacacc   1320
caaaagtcac tgagcctgtc tcccgga                                        1347
```

<210> SEQ ID NO 50
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
gatatagtta tgacacagag ccctgactct ctggctgtga gtttgggcga gcgagtaacc    60
attaattgta agagttctca atccgtcctc tactcaagca accagaaaaa ttacctcgcg   120
tggtaccagc aaaaaccagg acagagcccc aaactcttga tctattgggc gtccacccga   180
gagagtggcg tgccagatcg ttttcaggt tctggatctg gtaccgactt caccttaca   240 atctcaagcc tgcaagcaga ggatgtcgca gtttattatt gccatcagta cctgagcagc   300
tacacattcg acaaggaac gaaactggaa atcaaacgca ctgtggcagc cccttctgtg   360
tttatcttcc caccctccga cgagcagctc aagtccggta ccgcctctgt cgtctgcctg   420
ctgaacaatt tctacccaag agaggccaag gtgcagtgga aggtggacaa cgcactgcaa   480
agcggtaatt cacaagagtc agtcaccgaa caagactcaa aggacagcac ctactcactg   540
tcatccaccc tgactctctc aaaggctgac tacgaaaagc acaaagtgta tgcttgtgaa   600
gtcactcatc agggcctttc tagccctgtg accaagagct caacagagg cgaatgc      657
```

<210> SEQ ID NO 51
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
gacatagtaa tgacccaaag tccagattct ttggccgtat ctttgggtga gcgcgttacc    60
atcaactgta agtcttccca gtctgtgttg tactcatcta atcaaaaaaa ctacctcgct   120
tggtaccagc agaagccagg tcaaagcccg aaactgctta tttattgggc gtctacgcga   180
gagtctgggg tccccgatcg ttttcaggg tcaggctctg gcactgattt tactctgact   240
atttcatccc tccaagccga agacgtggca gtgtattact gccaccagta tttgagccct   300
tacacgtttg gcaggggac taaacttgaa atcaagcgca ctgtggcagc cccttctgtg   360
tttatcttcc caccctccga cgagcagctc aagtccggta ccgcctctgt cgtctgcctg   420
ctgaacaatt tctacccaag agaggccaag gtgcagtgga aggtggacaa cgcactgcaa   480
agcggtaatt cacaagagtc agtcaccgaa caagactcaa aggacagcac ctactcactg   540
tcatccaccc tgactctctc aaaggctgac tacgaaaagc acaaagtgta tgcttgtgaa   600
gtcactcatc agggcctttc tagccctgtg accaagagct caacagagg cgaatgc      657
```

<210> SEQ ID NO 52

<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

| | | | | | |
|---|---|---|---|---|---|
| gatattgtga | tgactcagtc | acctgacagt | ctggcggttt | ctttgggcga | aagagtgact | 60 |
| ataaattgca | aaagcagcca | gtcagttctc | tattccgaca | atcaaaagaa | ctatctcgca | 120 |
| tggtatcagc | agaagccagg | gcaatcccca | aaattgctta | tatactatgc | atcaacgcgc | 180 |
| gaaagcggtg | tacccgatcg | gttttcagga | agtggcagtg | ggaccgactt | tacgctgaca | 240 |
| atctcttccc | ttcaagcgga | ggatgtcgcg | gtttattatt | gtcatcagta | tctgagtcct | 300 |
| tacacctttg | gtcaagggac | gaagttggag | atcaaacgca | ctgtggcagc | cccttctgtg | 360 |
| tttatcttcc | caccctccga | cgagcagctc | aagtccggta | ccgcctctgt | cgtctgcctg | 420 |
| ctgaacaatt | tctacccaag | agaggccaag | gtgcagtgga | aggtggacaa | cgcactgcaa | 480 |
| agcggtaatt | cacaagagtc | agtcaccgaa | caagactcaa | aggacagcac | ctactcactg | 540 |
| tcatccaccc | tgactctctc | aaaggctgac | tacgaaaagc | acaaagtgta | tgcttgtgaa | 600 |
| gtcactcatc | agggcctttc | tagccctgtg | accaagagct | caacagagg | cgaatgc | 657 |

<210> SEQ ID NO 53
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

| | | | | | |
|---|---|---|---|---|---|
| gacatcgtaa | tgacccagtc | ccccgatagt | ctggctgtgt | ctttgggcga | gagggtaacg | 60 |
| ataaactgta | atcaagtca | gtcagtgctt | tactcagata | accagaagaa | ctatcttgcg | 120 |
| tggtatcagc | aaaagcccgg | acagtctcca | aaacttctta | tatatttcgc | ttctaccaga | 180 |
| gaatcaggtg | taccagaccg | cttttctgga | agcggctctg | gtactgactt | taccctgaca | 240 |
| attagtagct | tgcaagctga | agatgttgcg | gtatattatt | gtcaccaata | cttgagtccc | 300 |
| tatactttg | gccaagggac | aaaactggaa | ataaagcgca | ctgtggcagc | cccttctgtg | 360 |
| tttatcttcc | caccctccga | cgagcagctc | aagtccggta | ccgcctctgt | cgtctgcctg | 420 |
| ctgaacaatt | tctacccaag | agaggccaag | gtgcagtgga | aggtggacaa | cgcactgcaa | 480 |
| agcggtaatt | cacaagagtc | agtcaccgaa | caagactcaa | aggacagcac | ctactcactg | 540 |
| tcatccaccc | tgactctctc | aaaggctgac | tacgaaaagc | acaaagtgta | tgcttgtgaa | 600 |
| gtcactcatc | agggcctttc | tagccctgtg | accaagagct | caacagagg | cgaatgc | 657 |

<210> SEQ ID NO 54
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Ala Ser Thr Lys Gly Pro Ser Val Phe Pro Leu Ala Pro Ser Ser Lys

```
             1               5                  10                 15
        Ser Thr Ser Gly Gly Thr Ala Ala Leu Gly Cys Leu Val Lys Asp Tyr
                     20                  25                 30

Phe Pro Glu Pro Val Thr Val Ser Trp Asn Ser Gly Ala Leu Thr Ser
                     35                  40                 45

Gly Val His Thr Phe Pro Ala Val Leu Gln Ser Ser Gly Leu Tyr Ser
                     50                  55                 60

Leu Ser Ser Val Val Thr Val Pro Ser Ser Leu Gly Thr Gln Thr
         65                  70                  75                 80

Tyr Ile Cys Asn Val Asn His Lys Pro Ser Asn Thr Lys Val Asp Lys
                             85                  90                 95

Lys Val Glu Pro Lys Ser Cys Asp Lys Thr His Thr Cys Pro Pro Cys
                     100                 105                110

Pro Ala Pro Glu Leu Leu Gly Gly Pro Ser Val Phe Leu Phe Pro Pro
                     115                 120                125

Lys Pro Lys Asp Thr Leu Met Ile Ser Arg Thr Pro Glu Val Thr Cys
                     130                 135                140

Val Val Val Asp Val Ser His Glu Asp Pro Glu Val Lys Phe Asn Trp
        145                 150                 155                160

Tyr Val Asp Gly Val Glu Val His Asn Ala Lys Thr Lys Pro Arg Glu
                             165                 170                175

Glu Gln Tyr Asn Ser Thr Tyr Arg Val Val Ser Val Leu Thr Val Leu
                     180                 185                190

His Gln Asp Trp Leu Asn Gly Lys Glu Tyr Lys Cys Lys Val Ser Asn
                     195                 200                205

Lys Ala Leu Pro Ala Pro Ile Glu Lys Thr Ile Ser Lys Ala Lys Gly
                     210                 215                220

Gln Pro Arg Glu Pro Gln Val Tyr Thr Leu Pro Pro Ser Arg Asp Glu
        225                 230                 235                240

Leu Thr Lys Asn Gln Val Ser Leu Thr Cys Leu Val Lys Gly Phe Tyr
                             245                 250                255

Pro Ser Asp Ile Ala Val Glu Trp Glu Ser Asn Gly Gln Pro Glu Asn
                     260                 265                270

Asn Tyr Lys Thr Thr Pro Pro Val Leu Asp Ser Asp Gly Ser Phe Phe
                     275                 280                285

Leu Tyr Ser Lys Leu Thr Val Asp Lys Ser Arg Trp Gln Gln Gly Asn
                     290                 295                300

Val Phe Ser Cys Ser Val Met His Glu Ala Leu His Asn His Tyr Thr
        305                 310                 315                320

Gln Lys Ser Leu Ser Leu Ser Pro Gly
                             325

<210> SEQ ID NO 55
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
             20                  25                  30
```

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 56
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Val Gln Leu Val Gln Ser Gly Ala Glu Val Lys Lys Pro Gly Ala
 1               5                  10                  15

Thr Val Lys Leu Ser Cys Lys Ala Ser Gly Asp Thr Phe Thr Asp Phe
                 20                  25                  30

Glu Ile His Trp Val Gln Gln Ala Pro Gly Lys Gly Leu Glu Trp Ile
             35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Phe Asp Tyr Trp Gly Gln
                100                 105                 110

Gly Thr Leu Val Thr Val Ser Ser
            115                 120

<210> SEQ ID NO 57
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Glu Val Gln Leu Val Gln Ser Gly Ala Glu Val Lys Lys Pro Gly Ala
 1               5                  10                  15

Thr Val Lys Leu Ser Cys Lys Ala Ser Gly Asp Thr Phe Thr Asp Phe
                 20                  25                  30

Glu Ile His Trp Val Gln Gln Ala Pro Gly Lys Gly Leu Glu Trp Ile
             35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

```
Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser
        115                 120

<210> SEQ ID NO 58
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser
        115                 120

<210> SEQ ID NO 59
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Asn Asn Asn Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Val Glu Ile Lys
            100                 105                 110
```

```
<210> SEQ ID NO 60
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Tyr Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 61
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 62
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
gaggttcagt tggtgcaaag tggggccgag gttaaaaaac caggtgcaac cgtgaaactg      60
```

```
tcctgcaagg cgagtggtga tacatttaca gattttgaaa ttcattgggt acagcaggca   120
cccggaaagg gattggaatg gataggagat gtggacccgg agactggcgg aaccgcgtac   180
gcggagaaat ttcagggcag agccactttg acggcggata aagtacgga tactgcctac    240 cttgaactga gttccttgcg gtccgaagat acggcagttt actattgtac tcgcacgtat   300
gatggctacc catacgcttt cgattattgg ggacaaggca ctctcgtgac cgtatcttca   360
gcttcaacca agggaccttc tgtctttcct ctggcccctt caagcaagag cacttccgga   420
gggactgccg cactcgggtg ccttgtgaaa gattacttcc cagagcctgt caccgtcagc   480
tggaattcag gcgctctgac tagcggagtg cacaccttcc ccgctgtgct tcagtcctcc   540
ggactctact ctctgagcag cgtggtgacc gtgccgtcct cttctctggg gacccagact   600
tatatctgca acgtcaatca taagccttct aataccaagg tggacaagaa ggtggaaccc   660
aaatcatgtg acaagaccca cacctgtccg ccctgtccgg cacccgaact gctgggtggc   720
ccttccgtgt tcctttttccc tccaaagccg aaggacactc ttatgatttc tcgcactccc   780
gaagtgactt gcgtcgtggt ggatgtgtcc catgaggatc cagaggtcaa gttcaactgg   840
tacgtggacg gtgtggaagt ccacaacgcc aagactaagc cgagagagga acagtacaat   900
tcaacctatc gggtggtgag cgtcctgacc gtgctgcacc aggactggct aacggaaaag   960
gagtacaagt gcaaagtgtc aaacaaggca ctgcccgctc cgatcgaaaa gaccattagc  1020
aaagctaagg gccagcccag agaacccaa gtctataccc ttccacccag ccgggacgag  1080
ctgaccaaaa accaggtgtc actcacttgt ctcgtgaagg gtttctaccc ctcagacatc  1140
gccgtcgaat gggagtccaa tggtcagcca gagaacaact acaaaaccac ccctcccgtg  1200
ctggacagcg acgggtcttt ctttctctac tcaaagctga ccgtggataa gtctcgctgg  1260
cagcaaggga atgtgttttc ctgttcagtg atgcatgagg cccttcataa tcattacacc  1320
caaaagtcac tgagcctgtc tcccgga                                      1347
```

<210> SEQ ID NO 63
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125
```

-continued

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 64
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 64
gaggttcagt tggtgcaaag tggggccgag gttaaaaaac caggtgcaac cgtgaaactg     60
tcctgcaagg cgagtggtga tacatttaca gattttgaaa ttcattgggt acagcaggca    120

```
cccggaaagg gattggaatg gataggagat gtggacccgg agactggcgg aaccgcgtac    180
gcggagaaat ttcagggcag agccactttg acggcggata gaagtacgga tactgcctac    240
cttgaactga gttccttgcg gtccgaagat acggcagttt actattgtac tcgcacgtat    300
gatggctacc catacgcttt cgattattgg ggacaaggca ctctcgtgac cgtatcttca    360
gcttcaacca agggaccttc tgtctttcct ctggcccctt caagcaagag cacttccgga    420
gggactgccg cactcgggtg ccttgtgaaa gattacttcc cagagcctgt caccgtcagc    480
tggaattcag gcgctctgac tagcggagtg cacaccttcc ccgctgtgct tcagtcctcc    540
ggactctact ctctgagcag cgtggtgacc gtgccgtcct cttctctggg acccagact    600 tatatctgca acgtcaatca taagccttct aataccaagg tggacaagaa ggtggaaccc    660
aaatcatgtg acaagaccca cacctgtccg ccctgtccgg acccgaact gctgggtggc    720 ccttccgtgt tccttttccc tccaaagccg aaggacactc ttatgatttc tcgcactccc    780
gaagtgactt gcgtcgtggt ggatgtgtcc catgaggatc cagaggtcaa gttcaactgg    840
tacgtggacg gtgtggaagt ccacaacgcc aagactaagc cgagagagga acagtacaat    900
tcaacctatc gggtggtgag cgtcctgacc gtgctgcacc aggactggct taacggaaag    960
gagtacaagt gcaaagtgtc aaacaaggca ctgcccgctc cgatcgaaaa gaccattagc   1020
aaagctaagg gccagcccag agaacccaa gtctataccc ttccacccag ccgggacgag   1080
ctgaccaaaa accaggtgtc actcacttgt ctcgtgaagg gtttctaccc ctcagacatc   1140
gccgtcgaat gggagtccaa tggtcagcca gagaacaact acaaaaccac ccctcccgtg   1200
ctggacagcg acgggtcttt ctttctctac tcaaagctga ccgtggataa gtctcgctgg   1260
cagcaaggga atgtgttttc ctgttcagtg atgcatgagg cccttcataa tcattacacc   1320
caaaagtcac tgagcctgtc tcccgga                                       1347
```

<210> SEQ ID NO 65
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

```
Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
        130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 66
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
gacattgtaa tgacacaatc tcccgactct cttgcagtca gcttgggtga acgagcaact    60
ataaattgta aaagcagcca gtctgtactc tactctaata caacaagaa ctacctcgca   120 tggtatcagc agaaaccggg gcaaagtcct aaactttga tctattgggc aagtaccagg   180
```

```
gagagcggag tacccgacag attcagcggg tctggatcag gcaccgattt tactctcacc    240
atttcttcag ttcaagctga agacgtcgca gtctactact gccagcagta ttacagttac    300
cgaacttttg gcggtggaac aaaagtggaa ataaagcgca ctgtggcagc cccttctgtg    360
tttatcttcc caccctccga cgagcagctc aagtccggta ccgcctctgt cgtctgcctg    420
ctgaacaatt tctacccaag agaggccaag gtgcagtgga aggtggacaa cgcactgcaa    480
agcggtaatt cacaagagtc agtcaccgaa caagactcaa aggacagcac ctactcactg    540
tcatccaccc tgactctctc aaaggctgac tacgaaaagc acaaagtgta tgcttgtgaa    600
gtcactcatc agggcctttc tagccctgtg accaagagct caacagagg cgaatgc       657
```

<210> SEQ ID NO 67
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 67

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Asn Asn Asn Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 68
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

```
gacatagtta tgacccagtc tccagactcc ctcgcagttt ctctcggcga gagagtaaca      60
atcaactgta agtcatcaca gtccgtactc tactctgaca accaaaagaa ttatttggct     120
tggtatcagc aaaagccagg acaaagcccc aaacttctta tctatttgc cagcactagg      180
gagtccgggg tacccgaccg ctttagtggc tcaggttctg ggacagactt tacactgacc     240
atttctagcg tacaggctga agacgttgca gtctactact gccagcaata ctattcttac     300
agaacgtttg gcgggggcac aaagttggag atcaaacgca ctgtggcagc ccttctgtg      360
tttatcttcc caccctccga cgagcagctc aagtccggta ccgcctctgt cgtctgcctg     420
ctgaacaatt tctacccaag agaggccaag gtgcagtgga aggtggacaa cgcactgcaa     480
agcggtaatt cacaagagtc agtcaccgaa caagactcaa aggacagcac ctactcactg     540
tcatccaccc tgactctctc aaaggctgac tacgaaaagc acaaagtgta tgcttgtgaa     600
gtcactcatc agggcctttc tagccctgtg accaagagct caacagagg cgaatgc        657
```

<210> SEQ ID NO 69
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

```
Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Asp Thr Phe Thr Asp Phe Glu
1               5

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ile Asp Pro Glu Thr Gly Gly Thr
1               5

<210> SEQ ID NO 72
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Thr Arg Thr Tyr Asp Gly Tyr Pro Tyr Ala Met Asp Tyr
1               5                   10

<210> SEQ ID NO 73
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Ser Leu Leu Tyr Ser Asn Asn Gln Lys Asn Tyr
1               5                   10

<210> SEQ ID NO 74
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Trp Ala Ser
1

<210> SEQ ID NO 75
<211> LENGTH: 8
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gln Gln Tyr Tyr Ser Tyr Arg Thr
1               5

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Tyr Thr Phe Thr Asp Tyr Asn
1               5

<210> SEQ ID NO 77
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ile Asn Pro Asn Asn Gly Gly Thr
1               5

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Ala Arg Glu Arg Asp Tyr Asp Gly Ala Met Asp Tyr
1               5                   10

<210> SEQ ID NO 79
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gln Asp Ile Asn Lys Phe
1               5

<210> SEQ ID NO 80
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 80

Tyr Thr Ser
1

<210> SEQ ID NO 81
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Leu Gln Tyr Asp Asn Leu Leu Trp Thr
1               5

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Tyr Thr Phe Thr Asp Tyr Asn
1               5

<210> SEQ ID NO 83
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ile Asn Pro Asn Asn Gly Gly Thr
1               5

<210> SEQ ID NO 84
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ala Arg Glu Arg Asp Tyr Asp Gly Ser Met Asp Phe
1               5                   10

<210> SEQ ID NO 85
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gln Asp Ile Asn Lys Phe
1               5

<210> SEQ ID NO 86
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Tyr Thr Ser
1

<210> SEQ ID NO 87
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Leu Gln Tyr Asp Asn Leu Leu Trp Thr
1               5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Tyr Thr Val Thr Asp Tyr Tyr
1               5

<210> SEQ ID NO 89
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ile Asn Pro Asn Asn Gly Val Thr
1               5

<210> SEQ ID NO 90
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ala Arg Glu Glu Asp Phe Asp Gly Phe Asp Tyr
1               5                   10

```
<210> SEQ ID NO 91
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gln Asp Val Ser Thr Gly
1               5

<210> SEQ ID NO 92
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Trp Ala Ser
1

<210> SEQ ID NO 93
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gln Gln His Tyr Ser Thr Pro Leu Thr
1               5

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Ser Thr Phe Ser Asp Phe Glu
1               5

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ile Asp Pro Glu Thr Gly Gly Thr
1               5

<210> SEQ ID NO 96
<211> LENGTH: 13
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 96

Thr Arg Asn Tyr Asp Gly Tyr Ser Gln Thr Met Asp Tyr
1               5                   10

<210> SEQ ID NO 97
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gln Ser Val Leu Tyr Ser Ser Asn Gln Lys Asn Tyr
1               5                   10

<210> SEQ ID NO 98
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Trp Ala Ser
1

<210> SEQ ID NO 99
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

His Gln Tyr Leu Ser Ser Tyr Thr
1               5

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Ser Thr Phe Thr Asp Phe Glu
1               5

<210> SEQ ID NO 101
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 101

Ile Asp Pro Glu Thr Gly Gly Thr
1               5

<210> SEQ ID NO 102
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Thr Arg Asn Tyr Asp Gly Tyr Ser Arg Thr Met Asp Tyr
1               5                   10

<210> SEQ ID NO 103
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gln Ser Val Leu Tyr Ser Ser Asn Gln Lys Asn Tyr
1               5                   10

<210> SEQ ID NO 104
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Trp Ala Ser
1

<210> SEQ ID NO 105
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

His Gln Tyr Leu Ser Ser Tyr Thr
1               5

<210> SEQ ID NO 106
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Asp Thr Phe Thr Asp Phe
            20                  25                  30

Glu Ile His Trp Val Arg Gln Ala Pro Gly Gln Gly Leu Glu Trp Ile
            35                  40                  45

Gly Asp Ile Asp Pro Glu Thr Gly Ser Thr Ser Tyr Ala Gln Lys Phe
    50                  55                  60

Gln Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Met Asp Tyr Trp Gly Gln
                100                 105                 110

Gly Thr Leu Val Thr Val Ser Ser
            115                 120
```

<210> SEQ ID NO 107
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 107

```
Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asp Tyr
            20                  25                  30

Glu Ile His Trp Val Arg Gln Ala Pro Gly Gln Gly Leu Glu Trp Ile
            35                  40                  45

Gly Asp Ile Asp Pro Glu Thr Gly Ser Thr Ser Tyr Ala Gln Lys Phe
    50                  55                  60

Gln Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Met Asp Tyr Trp Gly Gln
                100                 105                 110

Gly Thr Leu Val Thr Val Ser Ser
            115                 120
```

<210> SEQ ID NO 108
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

```
Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asp Tyr
            20                  25                  30

Glu Ile His Trp Val Arg Gln Ala Pro Gly Gln Gly Leu Glu Trp Ile
            35                  40                  45
```

Gly Asp Ile Asp Pro Glu Thr Gly Ser Thr Ser Tyr Ala Gln Lys Phe
        50                  55                  60

Gln Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Met Asp Tyr Trp Gly Gln
                100                 105                 110

Gly Thr Ser Val Thr Val Ser Ser
        115                 120

<210> SEQ ID NO 109
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Met Asp Tyr Trp Gly Gln
                100                 105                 110

Gly Thr Leu Val Thr Val Ser Ser
        115                 120

<210> SEQ ID NO 110
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Thr Arg Thr Tyr Glu Gly Tyr Pro Tyr Ala Met Asp Tyr Trp Gly Gln
            100                 105                 110

Gly Thr Leu Val Thr Val Ser Ser
        115                 120

<210> SEQ ID NO 111
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser
        115                 120

<210> SEQ ID NO 112
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
            85                  90                  95

Tyr Tyr Ser Tyr Arg Thr Phe Gly Gly Gly Thr Lys Val Glu Ile Lys
            100                 105                 110

<210> SEQ ID NO 113
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Val Glu Ile Lys
            100                 105                 110

<210> SEQ ID NO 114
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Asn Asn Asn Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Val Glu Ile Lys
            100                 105                 110

<210> SEQ ID NO 115
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Gln Val Gln Leu Val Gln Ser Gly Ala Glu Val Val Lys Pro Gly Ala
1               5                   10                  15

```
Thr Val Lys Ile Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Ile Asp Pro Glu Thr Gly Gly Thr Ala Tyr Asn Glu Lys Phe
    50                  55                  60

Gln Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Asp Gly Tyr Pro Tyr Ala Met Asp Tyr Trp Gly Gln
                100                 105                 110

Gly Thr Thr Val Thr Val Ser Ser
            115                 120

<210> SEQ ID NO 116
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Val Gln Leu Val Gln Ser Gly Ala Glu Val Val Lys Pro Gly Ala
1               5                   10                  15

Thr Val Lys Ile Ser Cys Lys Ala Ser Gly Tyr Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Tyr Asp Gly Tyr Pro Tyr Ala Met Asp Tyr Trp Gly Gln
                100                 105                 110

Gly Thr Thr Val Thr Val Ser Ser
            115                 120

<210> SEQ ID NO 117
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Gln Val Gln Leu Val Gln Ser Gly Ala Glu Val Val Lys Pro Gly Ala
1               5                   10                  15

Thr Val Lys Ile Ser Cys Lys Ala Ser Gly Tyr Thr Phe Thr Asp Phe
            20                  25                  30

Glu Ile His Trp Val Gln Gln Ala Pro Gly Lys Gly Leu Glu Trp Ile
        35                  40                  45
```

Gly Asp Val Glu Pro Glu Thr Gly Thr Ala Tyr Ala Glu Lys Phe
            50                  55                  60

Gln Gly Arg Ala Thr Ile Thr Ala Asp Arg Ser Thr Ser Thr Ala Tyr
 65                  70                  75                  80

Met Glu Leu Ser Ser Leu Arg Ser Glu Asp Ala Ala Val Tyr Tyr Cys
                 85                  90                  95

Ala Arg Thr Tyr Asp Gly Tyr Pro Tyr Ala Met Asp Val Trp Gly Gln
            100                 105                 110

Gly Thr Thr Val Thr Val Ser Ser
            115                 120

<210> SEQ ID NO 118
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gln Val Gln Leu Val Gln Ser Gly Ala Glu Val Val Lys Pro Gly Ala
 1               5                  10                  15

Thr Val Lys Leu Ser Cys Lys Ala Ser Gly Asp Thr Phe Thr Asp Phe
                20                  25                  30

Glu Ile His Trp Val Lys Gln Ala Pro Gly Lys Gly Leu Glu Trp Ile
            35                  40                  45

Gly Asp Ile Asp Pro Glu Thr Gly Thr Ala Tyr Asn Glu Lys Phe
            50                  55                  60

Gln Gly Arg Ala Thr Leu Thr Ala Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Met Asp Tyr Trp Gly Gln
            100                 105                 110

Gly Thr Thr Val Thr Val Ser Ser
            115                 120

<210> SEQ ID NO 119
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gln Val Gln Leu Val Gln Ser Gly Ala Glu Val Val Lys Pro Gly Ala
 1               5                  10                  15

Ser Val Lys Val Ser Cys Lys Ala Ser Gly Asp Thr Phe Thr Asp Phe
                20                  25                  30

Glu Ile His Trp Val Lys Gln Ala Pro Gly Gln Gly Leu Glu Trp Ile
            35                  40                  45

Gly Asp Ile Asp Pro Glu Ser Gly Gly Thr Ala Tyr Asn Gln Lys Phe
            50                  55                  60

Gln Gly Arg Val Thr Met Thr Ala Asp Arg Ser Ile Ser Thr Ala Tyr
 65                  70                  75                  80

Met Glu Leu Ser Arg Leu Arg Ser Asp Asp Thr Ala Val Tyr Tyr Cys

```
                85                  90                  95
Ala Arg Thr Tyr Asp Gly Tyr Pro Tyr Ala Met Asp Tyr Trp Gly Gln
            100                 105                 110

Gly Thr Thr Val Thr Val Ser Ser
        115                 120

<210> SEQ ID NO 120
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asp Phe
            20                  25                  30

Glu Ile His Trp Val Lys Gln Ala Pro Gly Gln Gly Leu Glu Trp Ile
        35                  40                  45

Gly Asp Ile Asp Pro Glu Ser Gly Gly Thr Ala Tyr Asn Gln Lys Phe
    50                  55                  60

Gln Gly Arg Val Thr Met Thr Ala Asp Arg Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Asp Gly Tyr Pro Tyr Ala Met Asp Tyr Trp Gly Gln
            100                 105                 110

Gly Thr Thr Val Thr Val Ser Ser
        115                 120

<210> SEQ ID NO 121
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asp Phe
            20                  25                  30

Glu Ile His Trp Val Lys Gln Ala Pro Gly Gln Gly Leu Glu Trp Ile
        35                  40                  45

Gly Asp Ile Glu Pro Glu Ser Gly Gly Thr Ala Tyr Asn Gln Lys Phe
    50                  55                  60

Gln Gly Arg Val Thr Met Thr Ala Asp Arg Ser Ile Ser Thr Ala Tyr
65                  70                  75                  80

Met Glu Leu Ser Arg Leu Arg Ser Asp Asp Ala Ala Val Tyr Tyr Cys
                85                  90                  95

Ala Arg Thr Tyr Asp Gly Tyr Pro Tyr Ala Met Asp Val Trp Gly Gln
            100                 105                 110

Gly Thr Thr Val Thr Val Ser Ser
        115                 120
```

<210> SEQ ID NO 122
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 122

Gln Val Gln Leu Val Gln Ser Gly Ala Glu Val Val Lys Pro Gly Ala
1               5                   10                  15

Ser Val Lys Leu Ser Cys Lys Ala Ser Gly Asp Thr Phe Thr Asp Phe
            20                  25                  30

Glu Ile His Trp Val Lys Gln Ala Pro Gly Gln Gly Leu Glu Trp Ile
        35                  40                  45

Gly Asp Ile Asp Pro Glu Thr Gly Gly Thr Ala Tyr Asn Gln Lys Phe
    50                  55                  60

Gln Gly Arg Ala Thr Leu Thr Ala Asp Arg Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Thr Val Thr Val Ser Ser
        115                 120

<210> SEQ ID NO 123
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 124
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Asn Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
                100                 105                 110

<210> SEQ ID NO 125
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
                100                 105                 110

<210> SEQ ID NO 126
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Tyr Ala Ser Thr Arg Glu Ser Gly Val

```
                50                  55                  60
Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Arg Thr Phe Gly Gly Gly Thr Lys Leu Glu Ile Lys
                100                 105                 110
```

<210> SEQ ID NO 127
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Asp Ile Val Met Thr Gln Ser Pro Ser Ser Leu Ala Val Ser Leu Gly
 1                   5                  10                  15

Glu Arg Val Thr Met Asn Cys Lys Ser Ser Gln Ser Leu Leu Tyr Ser
                 20                  25                  30

Asn Asn Gln Lys Asn Tyr Leu Ala Trp Tyr Gln Gln Lys Pro Gly Gln
                 35                  40                  45

Ser Pro Lys Leu Leu Ile Tyr Trp Ala Ser Thr Arg Glu Ser Gly Val
                 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Arg Thr Phe Gly Gly Gly Thr Lys Leu Glu Ile Lys
                100                 105                 110
```

<210> SEQ ID NO 128
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 128

```
Asp Ile Val Met Thr Gln Ser Pro Leu Ser Leu Pro Val Thr Val Gly
 1                   5                  10                  15

Glu Pro Val Ser Ile Ser Cys Arg Ser Ser Gln Ser Leu Leu His Ser
                 20                  25                  30

Asn Asn Gln Lys Asn Tyr Leu Ala Trp Tyr Leu Gln Lys Pro Gly Gln
                 35                  40                  45

Ser Pro Gln Leu Leu Ile Tyr Trp Gly Ser Thr Arg Ala Ser Gly Val
                 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Tyr Tyr Ser Tyr Arg Thr Phe Gly Gly Gly Thr Lys Leu Glu Ile Lys
                100                 105                 110
```

<210> SEQ ID NO 129

```
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129
```

Asp Ile Val Met Thr Gln Ser Pro Leu Ser Leu Pro Val Thr Val Gly
1               5                   10                  15

Glu Pro Val Ser Ile Ser Cys Arg Ser Ser Gln Ser Leu Leu Tyr Ser
                20                  25                  30

Asn Asn Gln Lys Asn Tyr Leu Ala Trp Tyr Leu Gln Lys Pro Gly Gln
            35                  40                  45

Ser Pro Gln Leu Leu Ile Tyr Trp Gly Ser Thr Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

```
<210> SEQ ID NO 130
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130
```

Asp Ile Val Met Thr Gln Ser Pro Leu Ser Leu Ala Val Thr Val Gly
1               5                   10                  15

Glu Lys Val Ser Ile Ser Cys Arg Ser Ser Gln Ser Leu Leu Tyr Ser
                20                  25                  30

Asn Asn Gln Lys Asn Tyr Leu Ala Trp Tyr Gln Gln Lys Pro Gly Gln
            35                  40                  45

Ser Pro Lys Leu Leu Ile Tyr Trp Gly Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Arg Val Glu Ala Glu Asp Val Gly Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

```
<210> SEQ ID NO 131
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131
```

Asp Ile Gln Met Thr Gln Ser Pro Ser Ser Leu Ser Val Ser Val Gly
1               5                   10                  15

Asp Arg Val Thr Met Thr Cys Arg Ala Ser Gln Gly Ile Ser Tyr Ser
            20                  25                  30

Asn Asn Gln Lys Asn Tyr Leu Ala Trp Tyr Gln Lys Pro Gly Lys
        35                  40                  45

Ser Pro Lys Leu Leu Ile Tyr Trp Ala Ser Thr Arg Gln Ser Gly Val
 50                  55                  60

Pro Ser Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 132
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Asp Ile Gln Met Thr Gln Ser Pro Ser Ser Leu Ser Val Ser Val Gly
1               5                   10                  15

Asp Arg Val Thr Met Thr Cys Arg Ser Ser Gln Ser Leu Leu Tyr Ser
            20                  25                  30

Asn Asn Gln Lys Asn Tyr Leu Ala Trp Tyr Gln Lys Pro Gly Lys
        35                  40                  45

Ser Pro Lys Leu Leu Ile Tyr Trp Ala Ser Thr Arg Gln Ser Gly Val
 50                  55                  60

Pro Ser Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 133
<211> LENGTH: 806
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
 50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val

```
            85                  90                  95
Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
                195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Arg Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
                500                 505                 510
```

-continued

```
Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
        530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Gly Leu Asp
                565                 570                 575

Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
                740                 745                 750

Thr Val Thr Ser Thr Asp Glu Tyr Leu Asp Leu Ser Ala Pro Phe Glu
            755                 760                 765

Gln Tyr Ser Pro Gly Gly Gln Asp Thr Pro Ser Ser Ser Ser Ser Gly
        770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 134
<211> LENGTH: 223
<212> TYPE: PRT
<213> ORGANISM: Homo sapiens

<400> SEQUENCE: 134

Asp Thr Gly Val Asp Thr Gly Ala Pro Tyr Trp Thr Arg Pro Glu Arg
1               5                   10                  15

Met Asp Lys Lys Leu Leu Ala Val Pro Ala Ala Asn Thr Val Arg Phe
                20                  25                  30

Arg Cys Pro Ala Ala Gly Asn Pro Thr Pro Ser Ile Ser Trp Leu Lys
            35                  40                  45

Asn Gly Arg Glu Phe Arg Gly Glu His Arg Ile Gly Gly Ile Lys Leu
        50                  55                  60

Arg His Gln Gln Trp Ser Leu Val Met Glu Ser Val Val Pro Ser Asp
```

```
                65                  70                  75                  80
Arg Gly Asn Tyr Thr Cys Val Val Glu Asn Lys Phe Gly Ser Ile Arg
                    85                  90                  95

Gln Thr Tyr Thr Leu Asp Val Leu Glu Arg Ser Pro His Arg Pro Ile
                100                 105                 110

Leu Gln Ala Gly Leu Pro Ala Asn Gln Thr Ala Val Leu Gly Ser Asp
            115                 120                 125

Val Glu Phe His Cys Lys Val Tyr Ser Asp Ala Gln Pro His Ile Gln
        130                 135                 140

Trp Leu Lys His Val Glu Val Asn Gly Ser Lys Val Gly Pro Asp Gly
145                 150                 155                 160

Thr Pro Tyr Val Thr Val Leu Lys Thr Ala Gly Ala Asn Thr Thr Asp
                165                 170                 175

Lys Glu Leu Glu Val Leu Ser Leu His Asn Val Thr Phe Glu Asp Ala
                180                 185                 190

Gly Glu Tyr Thr Cys Leu Ala Gly Asn Ser Ile Gly Phe Ser His His
            195                 200                 205

Ser Ala Trp Leu Val Val Leu Pro Ala Glu Glu Glu Leu Val Glu
        210                 215                 220

<210> SEQ ID NO 135
<211> LENGTH: 806
<212> TYPE: PRT
<213> ORGANISM: Homo sapiens

<400> SEQUENCE: 135

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220
```

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
        260                 265                 270

Phe His Cys Lys Val Tyr Ser Asp Ala Gln Pro His Ile Gln Trp Leu
    275                 280                 285

Lys His Val Glu Val Asn Gly Ser Lys Val Gly Pro Asp Gly Thr Pro
290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
            325                 330                 335

Tyr Thr Cys Leu Ala Gly Asn Ser Ile Gly Phe Ser His His Ser Ala
        340                 345                 350

Trp Leu Val Val Leu Pro Ala Glu Glu Leu Val Glu Ala Asp Glu
    355                 360                 365

Ala Gly Ser Val Tyr Ala Gly Ile Leu Ser Tyr Gly Val Gly Phe Phe
370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
            405                 410                 415

Phe Pro Leu Lys Arg Gln Val Ser Leu Glu Ser Asn Ala Ser Met Ser
        420                 425                 430

Ser Asn Thr Pro Leu Val Arg Ile Ala Arg Leu Ser Ser Gly Glu Gly
    435                 440                 445

Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
        500                 505                 510

Asp Ala Thr Asp Lys Asp Leu Ser Asp Leu Val Ser Glu Met Glu Met
    515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
            565                 570                 575

Tyr Ser Phe Asp Thr Cys Lys Pro Pro Glu Glu Gln Leu Thr Phe Lys
        580                 585                 590

Asp Leu Val Ser Cys Ala Tyr Gln Val Ala Arg Gly Met Glu Tyr Leu
    595                 600                 605

Ala Ser Gln Lys Cys Ile His Arg Asp Leu Ala Ala Arg Asn Val Leu
610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu

|     |     |     |     | 645 |     |     |     | 650 |     |     |     | 655 |     |     |
| --- | --- | --- | --- | --- | --- | --- | --- | --- | --- | --- | --- | --- | --- | --- |
| Pro | Val | Lys | Trp | Met | Ala | Pro | Glu | Ala | Leu | Phe | Asp | Arg | Val | Tyr | Thr |
|     |     |     | 660 |     |     |     |     | 665 |     |     |     | 670 |     |     |     |
| His | Gln | Ser | Asp | Val | Trp | Ser | Phe | Gly | Val | Leu | Leu | Trp | Glu | Ile | Phe |
|     |     |     | 675 |     |     |     |     | 680 |     |     |     | 685 |     |     |     |
| Thr | Leu | Gly | Gly | Ser | Pro | Tyr | Pro | Gly | Ile | Pro | Val | Glu | Glu | Leu | Phe |
|     | 690 |     |     |     |     | 695 |     |     |     |     | 700 |     |     |     |     |
| Lys | Leu | Leu | Lys | Glu | Gly | His | Arg | Met | Asp | Lys | Pro | Ala | Asn | Cys | Thr |
| 705 |     |     |     |     | 710 |     |     |     |     | 715 |     |     |     |     | 720 |
| His | Asp | Leu | Tyr | Met | Ile | Met | Arg | Glu | Cys | Trp | His | Ala | Ala | Pro | Ser |
|     |     |     |     | 725 |     |     |     |     | 730 |     |     |     |     | 735 |     |
| Gln | Arg | Pro | Thr | Phe | Lys | Gln | Leu | Val | Glu | Asp | Leu | Asp | Arg | Val | Leu |
|     |     |     | 740 |     |     |     |     | 745 |     |     |     | 750 |     |     |     |
| Thr | Val | Thr | Ser | Thr | Asp | Glu | Tyr | Leu | Asp | Leu | Ser | Ala | Pro | Phe | Glu |
|     |     |     | 755 |     |     |     |     | 760 |     |     |     | 765 |     |     |     |
| Gln | Tyr | Ser | Pro | Gly | Gly | Gln | Asp | Thr | Pro | Ser | Ser | Ser | Ser | Ser | Gly |
|     |     |     | 770 |     |     |     |     | 775 |     |     |     | 780 |     |     |     |
| Asp | Asp | Ser | Val | Phe | Ala | His | Asp | Leu | Leu | Pro | Pro | Ala | Pro | Pro | Ser |
| 785 |     |     |     |     | 790 |     |     |     |     | 795 |     |     |     |     | 800 |
| Ser | Gly | Gly | Ser | Arg | Thr |
|     |     |     |     | 805 |     |

<210> SEQ ID NO 136
<211> LENGTH: 2421
<212> TYPE: DNA
<213> ORGANISM: Macaca fascicularis

<400> SEQUENCE: 136

| atgggcgccc | ctgcctgcgc | cctcgcgctc | tgcgtggcag | tggccatcgt | ggccggcgcc | 60 |
| tcctcggagt | ccttggggac | ggagcagcgc | gtcgtgggc | gagtggcaga | agtgtccggc | 120 |
| ccggagccca | gccagcagga | gcagttggtc | ttcggcagcg | gggacgctgt | ggagctgagc | 180 |
| tgtccccgc | ccggggggtgg | tcccatgggg | cccactgtct | gggtcaagga | tggcgcaggg | 240 |
| ctggtgccct | cggagcgtgt | cctggtgggg | ccccagcggc | tgcaggtgct | gaatgcctcc | 300 |
| cacgaggact | ctggggccta | cagctgccgg | cagcggctca | cacagctcgt | actgtgccac | 360 |
| ttcagtgtgc | gggtgacaga | tgctccatcc | tcgggagatg | acgaagacgg | ggaggacgag | 420 |
| gctgaggaca | caggtgtgga | cacaggggcc | ccttactgga | ctcggcccga | gcggatggac | 480 |
| aagaagctgc | tggctgtgcc | ggccgccaac | accgtccgct | tccgctgccc | ggctgccggc | 540 |
| aaccccactc | cctccatctc | ctggctgaag | aatggcaagg | agttccgcgg | cgagcaccgc | 600 |
| attggcggca | tcaagcttcg | gcaccagcag | tggagcctgg | tcatggaaag | cgtggtgccc | 660 |
| tcggaccgcg | gcaactacac | ctgcgtggtg | gagaacaagt | ttggcagcat | ccggcagaca | 720 |
| tacacgctgg | acgtgctgga | gcgctccccg | caccggccca | tcctgcaggc | ggggctgccg | 780 |
| gccaaccaga | cggcggtgct | gggcagcgat | gtggagtttc | actgcaaggt | gtacagtgat | 840 |
| gcgcagcccc | acatccagtg | gctcaagcac | gtggaggtga | atggcagcaa | ggtgggcccc | 900 |
| gacggcacac | cctacgtcac | cgtgctcaag | acgcgggcg | ctaataccac | cgacaaggag | 960 |
| ctagaggttc | tgtccttgca | caacgtcacc | tttgaggacg | ccggggagta | cacctgcctg | 1020 |
| gcgggcaatt | ctattgggtt | ttcccatcac | tctgcgtggc | tcgtggtgct | gccagctgag | 1080 |
| gaggagctgg | tggaggctga | cgaggcgggc | agtgtgtacg | caggcatcct | cagctacggg | 1140 |
| gtgggcttct | tcctgttcat | cctggtggtg | gcggctgtga | cgctctgccg | cctgcgcagc | 1200 |

```
acccccaaga aaggcctggg ctcccccacc gtgcacaaga tctcccgctt cccactcaag   1260
cgacaggtgt ccctggagtc caacgcgtcc atgagctcca acacaccgct ggtgcgcatc   1320
gcaaggctgt cctcagggga gggtcccaca ctggccaatg tctccgagct tgagctgcct   1380
gctgacccca aatgggagct gtctcgggcc cggctgaccc tgggcaagcc ccttggggag   1440
ggctgctttg gccaggtggt catggcggag gctatcggca ttgacaagga ccgggccgcc   1500
aagcctgtca ccgtagccgt gaagatgctg aaagatgatg ccactgacaa ggacctgtca   1560
gacctggtgt ctgagatgga gatgatgaag atgattggga aacacaagaa cattatcaac   1620
ctgctgggcg cctgcacgca gggcgggccc ctgtacgtgc tggtggagta cgcggccaag   1680
ggcaacctga gggagtttct gcgggcgcgg cggcccccgg gcctggacta ctccttcgac   1740
acctgcaagc cgcctgagga gcagctcacc ttcaaggacc tggtgtcctg tgcctaccag   1800
gtggcccgag gcatggagta cctcgcctcc cagaagtgca tccacaggga cctggctgct   1860
cgaaatgtgc tggtgaccga ggacaacgtg atgaagatcg cagacttcgg gctggcccgc   1920
gacgtgcaca accttgacta ctacaagaag acaaccaacg gccggctgcc cgtgaagtgg   1980
atggcgcctg aggccctgtt tgaccgagtc tacacccacc agagtgacgt ctggtccttt   2040
ggggtcctgc tctgggagat cttcacgctg gggggctctc cgtaccccgg catccctgtg   2100
gaggagctct tcaagctgct gaaggagggt caccggatgg acaagccggc caactgcaca   2160
cacgacctgt acatgatcat gcgggagtgc tggcatgctg cgccctccca gaggcccacc   2220
ttcaagcagc tggtggagga cctggaccgt gtcctcactg tgacgtccac cgacgagtac   2280
ctggacctgt cagcgccctt cgagcagtac tcccccggcg gccaggacac cccgagctcc   2340
agctcctcag gggatgactc cgtgtttgcc cacgacctgc tgccccggc cccacccagc   2400 agtgggggct cgcggacgtg a                                            2421
```

<210> SEQ ID NO 137

<400> SEQUENCE: 137

000

<210> SEQ ID NO 138
<211> LENGTH: 806
<212> TYPE: PRT
<213> ORGANISM: Macaca fascicularis

<400> SEQUENCE: 138

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Val Ala Glu Val Ser Gly Pro Glu Pro Ser Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Ala Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110
```

```
Leu Thr Gln Leu Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Lys Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
370                 375                 380

Leu Phe Ile Leu Val Val Ala Ala Val Thr Leu Cys Arg Leu Arg Ser
385                 390                 395                 400

Thr Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
```

```
            530                 535                 540
Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 139
<211> LENGTH: 806
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Val Ala Glu Val Ser Gly Pro Glu Pro Ser Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Ala Gly
65                  70                  75                  80
```

-continued

```
Leu Val Pro Ser Glu Arg Val Leu Val Gly Pro Gln Arg Leu Gln Val
                 85                  90                  95
Leu Asn Ala Ser His Glu Asp Ser Gly Ala Tyr Ser Cys Arg Gln Arg
                100                 105                 110
Leu Thr Gln Leu Val Leu Cys His Phe Ser Val Arg Val Thr Asp Ala
            115                 120                 125
Pro Ser Ser Gly Asp Asp Glu Asp Gly Glu Asp Glu Ala Glu Asp Thr
        130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
                180                 185                 190
Lys Glu Phe Arg Gly Glu His Arg Ile Gly Gly Ile Lys Leu Arg His
            195                 200                 205
Gln Gln Trp Ser Leu Val Met Glu Ser Val Val Pro Ser Asp Arg Gly
        210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
        290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Glu Leu Val Glu Ala Asp Glu
        355                 360                 365
Ala Gly Ser Val Tyr Ala Gly Ile Leu Ser Tyr Arg Val Gly Phe Phe
    370                 375                 380
Leu Phe Ile Leu Val Val Ala Ala Val Thr Leu Cys Arg Leu Arg Ser
385                 390                 395                 400
Thr Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
```

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 140
<211> LENGTH: 390
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Gly Gly Leu Asn Asp Ile Phe Glu Ala Gln Lys Ile Glu Trp His Glu
1               5                   10                  15

His His His His His His Glu Asp Gln Val Asp Pro Arg Leu Ile Asp
                20                  25                  30

Gly Lys Ile Gln Pro Glu Pro Glu Ser Leu Gly Thr Glu Gln Arg Val

```
                35                  40                  45
Val Gly Arg Ala Ala Glu Val Pro Gly Pro Glu Pro Gly Gln Gln Glu
 50                  55                  60
Gln Leu Val Phe Gly Ser Gly Asp Ala Val Glu Leu Ser Cys Pro Pro
 65                  70                  75                  80
Pro Gly Gly Gly Pro Met Gly Pro Thr Val Trp Val Lys Asp Gly Thr
                 85                  90                  95
Gly Leu Val Pro Ser Glu Arg Val Leu Val Gly Pro Gln Arg Leu Gln
                100                 105                 110
Val Leu Asn Ala Ser His Glu Asp Ser Gly Ala Tyr Ser Cys Arg Gln
            115                 120                 125
Arg Leu Thr Gln Arg Val Leu Cys His Phe Ser Val Arg Val Thr Asp
        130                 135                 140
Ala Pro Ser Ser Gly Asp Asp Glu Asp Gly Glu Asp Glu Ala Glu Asp
145                 150                 155                 160
Thr Gly Val Asp Thr Gly Ala Pro Tyr Trp Thr Arg Pro Glu Arg Met
                165                 170                 175
Asp Lys Lys Leu Leu Ala Val Pro Ala Ala Asn Thr Val Arg Phe Arg
                180                 185                 190
Cys Pro Ala Ala Gly Asn Pro Thr Pro Ser Ile Ser Trp Leu Lys Asn
            195                 200                 205
Gly Arg Glu Phe Arg Gly Glu His Arg Ile Gly Gly Ile Lys Leu Arg
        210                 215                 220
His Gln Gln Trp Ser Leu Val Met Glu Ser Val Val Pro Ser Asp Arg
225                 230                 235                 240
Gly Asn Tyr Thr Cys Val Val Glu Asn Lys Phe Gly Ser Ile Arg Gln
                245                 250                 255
Thr Tyr Thr Leu Asp Val Leu Glu Arg Ser Pro His Arg Pro Ile Leu
                260                 265                 270
Gln Ala Gly Leu Pro Ala Asn Gln Thr Ala Val Leu Gly Ser Asp Val
            275                 280                 285
Glu Phe His Cys Lys Val Tyr Ser Asp Ala Gln Pro His Ile Gln Trp
        290                 295                 300
Leu Lys His Val Glu Val Asn Gly Ser Lys Val Gly Pro Asp Gly Thr
305                 310                 315                 320
Pro Tyr Val Thr Val Leu Lys Thr Ala Gly Ala Asn Thr Thr Asp Lys
                325                 330                 335
Glu Leu Glu Val Leu Ser Leu His Asn Val Thr Phe Glu Asp Ala Gly
                340                 345                 350
Glu Tyr Thr Cys Leu Ala Gly Asn Ser Ile Gly Phe Ser His His Ser
            355                 360                 365
Ala Trp Leu Val Val Leu Pro Ala Glu Glu Leu Val Glu Ala Asp
        370                 375                 380
Glu Ala Gly Ser Ala Ser
385                 390

<210> SEQ ID NO 141
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141
```

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 142
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 143
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 144
<211> LENGTH: 214
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 144

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 145
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110
```

```
Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 146
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Phe Cys Leu Gln Tyr Asp Asn Leu Leu Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 147
<211> LENGTH: 221
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147
```

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Val Thr Thr Tyr Asn Gln Lys Phe
50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

```
<210> SEQ ID NO 148
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148
```

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Gly
                20                  25                  30

Val Ala Trp Tyr Gln Gln Lys Pro Gly Gln Ser Pro Gln Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Tyr Ile Leu Thr Ile Arg Ser Val Gln Ala
65                  70                  75                  80

Glu Asp Leu Ala Leu Tyr Tyr Cys Gln Gln His Tyr Ser Thr Pro Leu

```
                     85                  90                  95
Thr Phe Gly Ala Gly Thr Lys Leu Glu Leu Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 149
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Gln Val Gln Leu Gln Gln Ser Gly Ala Glu Leu Val Arg Pro Gly Ala
1               5                   10                  15
Ser Val Thr Leu Ser Cys Lys Ala Ser Gly Ser Thr Phe Ser Asp Phe
            20                  25                  30
Glu Ile His Trp Val Lys Gln Thr Pro Val His Gly Leu Glu Trp Ile
        35                  40                  45
Gly Gly Ile Asp Pro Glu Thr Gly Gly Thr Ala Tyr Asn Gln Lys Phe
    50                  55                  60
Lys Gly Lys Ala Ile Leu Thr Ala Asp Arg Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Thr Arg Asn Tyr Asp Gly Tyr Ser Gln Thr Met Asp Tyr Trp Gly Gln
                100                 105                 110
Gly Thr Ser Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys
        210                 215                 220
```

<210> SEQ ID NO 150
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Met Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 151
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

```
Lys Gly Lys Ala Ile Leu Thr Ala Val Lys Ser Ser Thr Ala Tyr
 65                  70                  75                  80

Met Gly Leu Arg Ser Leu Thr Ser Glu Asp Ser Ala Val Tyr Tyr Cys
                 85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 152
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Ser
65                  70                  75                  80

Ile Ser Ser Val Gln Thr Glu Asp Leu Ala Val Tyr Tyr Cys His Gln
                85                  90                  95

Tyr Leu Ser Ser Tyr Thr Phe Gly Gly Gly Thr Arg Leu Glu Met Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

Pro Val Thr Lys Ser Phe Asn Arg Gly Glu Cys
    210                 215

<210> SEQ ID NO 153
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 154
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Tyr Ala Ser Thr Arg Glu Ser Gly Val
    50                  55                  60

Pro Asp Arg Phe Ser Gly Ser Gly Ser Gly Thr Asp Phe Thr Leu Thr
65              70                  75                  80

Ile Ser Ser Val Gln Ala Glu Asp Val Ala Val Tyr Tyr Cys Gln Gln
                    85                  90                  95

Tyr Tyr Ser Tyr Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 155
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65              70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 156
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 157
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="D"
<220> FEATURE:
<221> NAME/KEY: VARIANT
<222> LOCATION: (7)..(7)

```
<223> OTHER INFORMATION: /replace="Y"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 157

Gly Tyr Thr Phe Thr Asp Phe Glu
1               5

<210> SEQ ID NO 158
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="S"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 158

Ile Asp Pro Glu Thr Gly Gly Thr
1               5

<210> SEQ ID NO 159
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="V"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 159

Ile Asn Pro Asn Asn Gly Gly Thr
1               5

<210> SEQ ID NO 160
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="E"
<220> FEATURE:
<221> NAME/KEY: SITE
<222> LOCATION: (1)..(8)
```

```
<223> OTHER INFORMATION: /note="Variant residues given in the sequence
      have no preference with respect to those in the annotations
      for variant positions"

<400> SEQUENCE: 160

Val Asp Pro Glu Thr Gly Gly Thr
1               5

<210> SEQ ID NO 161
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="N"
<220> FEATURE:
<221> NAME/KEY: VARIANT
<222> LOCATION: (5)..(5)
<223> OTHER INFORMATION: /replace="E"
<220> FEATURE:
<221> NAME/KEY: VARIANT
<222> LOCATION: (8)..(8)
<223> OTHER INFORMATION: /replace="P"
<220> FEATURE:
<221> NAME/KEY: VARIANT
<222> LOCATION: (9)..(9)
<223> OTHER INFORMATION: /replace="R" or "Y"
<220> FEATURE:
<221> NAME/KEY: VARIANT
<222> LOCATION: (10)..(10)
<223> OTHER INFORMATION: /replace="A"
<220> FEATURE:
<221> NAME/KEY: VARIANT
<222> LOCATION: (11)..(11)
<223> OTHER INFORMATION: /replace="M"
<220> FEATURE:
<221> NAME/KEY: SITE
<222> LOCATION: (1)..(13)
<223> OTHER INFORMATION: /note="Variant residues given in the sequence
      have no preference with respect to those in the annotations
      for variant positions"

<400> SEQUENCE: 161

Thr Arg Thr Tyr Asp Gly Tyr Ser Gln Thr Phe Asp Tyr
1               5                   10

<210> SEQ ID NO 162
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="V"
<220> FEATURE:
<221> NAME/KEY: VARIANT
<222> LOCATION: (7)..(7)
<223> OTHER INFORMATION: /replace="D" or "S"
<220> FEATURE:
<221> NAME/KEY: VARIANT
<222> LOCATION: (9)..(9)
<223> OTHER INFORMATION: /replace="N"
<220> FEATURE:
<221> NAME/KEY: SITE
<222> LOCATION: (1)..(12)
<223> OTHER INFORMATION: /note="Variant residues given in the sequence
``` have no preference with respect to those in the annotations
for variant positions"

<400> SEQUENCE: 162

Gln Ser Leu Leu Tyr Ser Asn Asn Gln Lys Asn Tyr
1               5                  10

<210> SEQ ID NO 163
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Y" or "F"
<220> FEATURE:
<221> NAME/KEY: SITE
<222> LOCATION: (1)..(3)
<223> OTHER INFORMATION: /note="Variant residues given in the sequence
      have no preference with respect to those in the annotations
      for variant positions"

<400> SEQUENCE: 163

Trp Ala Ser
1

<210> SEQ ID NO 164
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
            180                 185                 190
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220
```

<210> SEQ ID NO 165
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser
    210                 215                 220
```

<210> SEQ ID NO 166
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30
```

```
Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
 65              70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser
            210                 215                 220

<210> SEQ ID NO 167
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Glu Val Gln Leu Gln Gln Ser Gly Pro Asp Leu Val Lys Pro Gly Ala
 1               5                  10                  15

Ser Val Lys Ile Ser Cys Lys Ala Ser Gly Tyr Thr Val Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Thr Thr Ala Tyr
 65              70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160
```

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser
    210                 215                 220

<210> SEQ ID NO 168
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220

<210> SEQ ID NO 169
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Gln Val Gln Leu Gln Gln Ser Gly Ala Glu Leu Val Arg Pro Gly Ala

```
1               5                   10                  15
Ser Val Thr Leu Ser Cys Lys Ala Ser Gly Ser Thr Phe Thr Asp Phe
                20                  25                  30

Glu Ile His Trp Val Lys Gln Thr Pro Val His Gly Leu Glu Trp Ile
                35                  40                  45

Gly Ala Ile Asp Pro Glu Thr Gly Gly Thr Ala Tyr Asn Gln Lys Phe
        50                  55                  60

Lys Gly Lys Ala Ile Leu Thr Ala Val Lys Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser
            210                 215                 220
```

<210> SEQ ID NO 170
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 170

```
Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Trp Ile
                35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220
```

<210> SEQ ID NO 171
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 171

```
Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220
```

<210> SEQ ID NO 172
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 172

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220

<210> SEQ ID NO 173
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val

```
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys
        210                 215                 220

<210> SEQ ID NO 174
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Asp Tyr
            20                  25                  30
Asn Met His Trp Val Lys Gln Ser His Gly Lys Ser Leu Glu Trp Ile
        35                  40                  45
Gly Tyr Ile Asn Pro Asn Asn Gly Gly Thr Arg Tyr Asn Gln Lys Phe
    50                  55                  60
Lys Gly Lys Ala Thr Leu Thr Val Asn Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Arg Glu Arg Asp Tyr Asp Gly Ala Met Asp Tyr Trp Gly Gln Gly
            100                 105                 110
Thr Ser Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys
    210                 215                 220

<210> SEQ ID NO 175
<211> LENGTH: 220
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 175

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys
    210                 215                 220

<210> SEQ ID NO 176
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys
            210                 215

<210> SEQ ID NO 177
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 177

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
        50                  55                  60

Lys Gly Lys Ala Ile Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys
            210                 215                 220

-continued

<210> SEQ ID NO 178
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 178

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Val Lys Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys
    210                 215                 220

<210> SEQ ID NO 179
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 179

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

```
Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys
        210                 215                 220
```

<210> SEQ ID NO 180
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

```
Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

Pro Ser Asn Thr Lys Val Asp Lys Lys Val Glu Pro Lys
            210                 215                 220

<210> SEQ ID NO 181
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys
    210                 215                 220

<210> SEQ ID NO 182
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe

```
                50                  55                  60
Arg Gly Arg Ala Met Leu Thr Ala Asp Arg Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Thr Tyr Asp Gly Tyr Pro Ala Met Asp Tyr Trp Gly Gln
                100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro
            210                 215                 220

<210> SEQ ID NO 183
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Glu Val Gln Leu Gln Gln Ser Gly Pro Glu Leu Val Lys Pro Gly Ala
  1                 5                  10                  15

Ser Val Lys Met Ser Cys Lys Ala Ser Gly Tyr Thr Phe Thr Asp Tyr
                 20                  25                  30

Asn Met His Trp Val Lys Gln Ser His Gly Lys Ser Leu Glu Trp Ile
             35                  40                  45

Gly Tyr Ile Asn Pro Asn Asn Gly Gly Thr Arg Tyr Asn Gln Lys Phe
 50                  55                  60

Lys Gly Lys Ala Thr Leu Thr Val Asn Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Arg Asp Tyr Asp Gly Ala Met Asp Tyr Trp Gly Gln Gly
                100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro
        210                 215
```

<210> SEQ ID NO 184
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro
        210                 215
```

<210> SEQ ID NO 185
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30
```

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
 50                  55                  60

Lys Asp Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro
    210                 215

<210> SEQ ID NO 186
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
 50                  55                  60

Lys Gly Lys Ala Ile Leu Thr Ala Asp Arg Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val

```
                        165                 170                 175

Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro
        210                 215                 220

<210> SEQ ID NO 187
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Val Lys Ser Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 188
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

Glu Val Gln Leu Val Gln Ser Gly Ala Glu Val Lys Lys Pro Gly Ala
1               5                   10                  15
```

```
Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro
            210                 215                 220

<210> SEQ ID NO 189
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 190
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 191
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 191

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu
    210                 215

<210> SEQ ID NO 192
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 192

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu
        210                 215

<210> SEQ ID NO 193
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 193

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu
        210                 215

<210> SEQ ID NO 194
<211> LENGTH: 217
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 194

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Val Thr Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu
    210                 215

<210> SEQ ID NO 195
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
                20                  25                  30

Glu Ile His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
        50                  55                  60

Lys Gly Lys Ala Ile Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
```

```
              100                 105                 110
Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu
            210                 215
```

<210> SEQ ID NO 196
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 196

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Lys Phe
50                  55                  60

Lys Gly Lys Ala Ile Leu Thr Ala Val Lys Ser Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu
            210                 215
```

<210> SEQ ID NO 197

<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 197

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu
    210                 215

<210> SEQ ID NO 198
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 198

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
            85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu
            210                 215

<210> SEQ ID NO 199
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
            35                  40                  45

Gly Asp Val Asp Pro Glu Thr Gly Gly Thr Ala Tyr Ala Glu Lys Phe
50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
            85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu

<210> SEQ ID NO 200
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 200

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val
    210                 215

<210> SEQ ID NO 201
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 201

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215

<210> SEQ ID NO 202
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Ser His Gly Lys Ser Leu Gln Trp Ile
            35                  40                  45

Gly Tyr Ile Asn Pro Asn Asn Gly Gly Thr Asn Tyr Asn Gln Asn Phe
        50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
        195                 200                 205

Ser Asn Thr Lys Val Asp Lys Lys Val
    210                 215

<210> SEQ ID NO 203
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val
    210                 215

<210> SEQ ID NO 204
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
```

```
            35                  40                  45
Gly Gly Ile Asp Pro Glu Thr Gly Gly Thr Ala Tyr Asn Gln Lys Phe
         50                  55                  60

Lys Gly Lys Ala Ile Leu Thr Ala Asp Arg Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Asn Tyr Asp Gly Tyr Ser Gln Thr Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val
    210                 215

<210> SEQ ID NO 205
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Val Lys Ser Ser Ser Thr Ala Tyr
 65                  70                  75                  80

Met Gly Leu Arg Ser Leu Thr Ser Glu Asp Ser Ala Val Tyr Tyr Cys
                 85                  90                  95

Thr Arg Asn Tyr Asp Gly Tyr Ser Arg Thr Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val
        210                 215

<210> SEQ ID NO 206
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Ala Pro Gly Lys Gly Leu Glu Trp Ile
        35                  40                  45

Gly Asp Val Asp Pro Glu Thr Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val
        210                 215

<210> SEQ ID NO 207
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Glu Val Gln Leu Val Gln Ser Gly Ala Glu Val Lys Lys Pro Gly Ala
1               5                   10                  15
```

-continued

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val
210                 215

<210> SEQ ID NO 208
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
            35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser

```
                 145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val
            210                 215

<210> SEQ ID NO 209
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys
            210                 215

<210> SEQ ID NO 210
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Thr Arg Tyr Asn Gln Lys Phe
50                  55                  60

Lys Gly Lys Ala Thr Leu Thr Val Asn Lys Ser Ser Thr Ala Tyr
65              70                  75                  80

Met Glu Leu Arg Ser Leu Thr Ser Glu Asp Ser Ala Val Tyr Tyr Cys
            85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys
210                 215

<210> SEQ ID NO 211
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Thr Asn Tyr Asn Gln Asn Phe
50                  55                  60

Lys Asp Lys Ala Thr Leu Thr Val Asn Lys Ser Ser Thr Ala Tyr
65              70                  75                  80

Met Glu Leu Arg Ser Leu Thr Ser Glu Asp Ser Ala Val Tyr Tyr Cys
            85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
            115                 120                 125

-continued

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys
    210                 215

<210> SEQ ID NO 212
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Val Thr Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys
    210                 215

<210> SEQ ID NO 213
<211> LENGTH: 217
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic polypeptide"

<400> SEQUENCE: 213

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Thr Ala Tyr Asn Gln Lys Phe
    50                  55                  60

Lys Gly Lys Ala Ile Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys
    210                 215

<210> SEQ ID NO 214
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Val Lys Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys
    210                 215

<210> SEQ ID NO 215
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 215

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys
    210                 215

<210> SEQ ID NO 216
<211> LENGTH: 217

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 216

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys
        210                 215

<210> SEQ ID NO 217
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Tyr Ile
            35                  40                  45

Gly Asp Val Asp Pro Glu Thr Gly Gly Thr Ala Tyr Ala Glu Lys Phe
        50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys

```
                      85                  90                  95

Thr Arg Thr Tyr Asp Gly Tyr Pro Tyr Ala Phe Asp Tyr Tyr Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys
    210                 215

<210> SEQ ID NO 218
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys
    210                 215
```

<210> SEQ ID NO 219
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 219

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys
    210                 215
```

<210> SEQ ID NO 220
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 220

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60
```

```
Lys Asp Lys Ala Thr Leu Thr Val Asn Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys
    210                 215

<210> SEQ ID NO 221
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

Asn Thr Lys Val Asp Lys
            210

<210> SEQ ID NO 222
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys
    210                 215

<210> SEQ ID NO 223
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

```
Gly Ala Ile Asp Pro Glu Thr Gly Thr Ala Tyr Asn Gln Lys Phe
    50                  55                  60

Lys Gly Lys Ala Ile Leu Thr Ala Val Lys Ser Ser Thr Ala Tyr
 65                  70                  75                  80

Met Gly Leu Arg Ser Leu Thr Ser Glu Asp Ser Ala Val Tyr Tyr Cys
                 85                  90                  95

Thr Arg Asn Tyr Asp Gly Tyr Ser Arg Thr Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys
    210                 215

<210> SEQ ID NO 224
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys
        210                 215

<210> SEQ ID NO 225
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 225

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys
        210                 215

<210> SEQ ID NO 226
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe

```
            20                  25                  30
Glu Ile His Trp Val Gln Gln Ala Pro Gly Lys Gly Leu Glu Tyr Ile
            35                  40                  45
Gly Asp Val Asp Pro Glu Thr Gly Gly Thr Ala Tyr Ala Glu Lys Phe
 50                  55                  60
Gln Gly Arg Ala Thr Leu Thr Ala Asp Arg Ser Thr Asp Thr Ala Tyr
 65                  70                  75                  80
Leu Glu Leu Ser Ser Leu Arg Ser Glu Asp Thr Ala Val Tyr Tyr Cys
                85                  90                  95
Thr Arg Thr Tyr Asp Gly Tyr Pro Tyr Ala Phe Asp Tyr Tyr Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
                195                 200                 205
Pro Ser Asn Thr Lys Val Asp Lys
        210                 215

<210> SEQ ID NO 227
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Gln Val Gln Leu Gln Gln Ser Gly Ala Glu Leu Val Arg Pro Gly Ala
 1               5                  10                  15
Ser Val Thr Leu Ser Cys Lys Ala Ser Gly Asp Thr Phe Thr Asp Phe
            20                  25                  30
Glu Ile His Trp Val Lys Gln Thr Pro Val His Gly Leu Glu Trp Ile
            35                  40                  45
Gly Asp Ile Asp Pro Glu Thr Gly Gly Thr Ala Tyr Asn Gln Lys Phe
 50                  55                  60
Arg Gly Arg Ala Met Leu Thr Ala Asp Arg Ser Ser Thr Ala Tyr
 65                  70                  75                  80
Met Glu Leu Arg Ser Leu Thr Ser Glu Asp Ser Ala Val Tyr Tyr Cys
                85                  90                  95
Thr Arg Thr Tyr Asp Gly Tyr Pro Tyr Ala Met Asp Tyr Trp Gly Gln
                100                 105                 110
Gly Thr Ser Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro
225                 230
```

<210> SEQ ID NO 228
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 228

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro
225
```

<210> SEQ ID NO 229
<211> LENGTH: 229
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 229

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro
225

<210> SEQ ID NO 230
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
```

```
            85                  90                  95
Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro
225

<210> SEQ ID NO 231
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

```
Pro Ser Asn Thr Lys Val Asp Lys Lys Val Glu Pro Lys Ser Cys Asp
    210                 215                 220

Lys Thr His Thr Cys Pro
225                 230

<210> SEQ ID NO 232
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 232

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Val Lys Ser Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro
225                 230

<210> SEQ ID NO 233
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 233

Glu Val Gln Leu Val Gln Ser Gly Ala Glu Val Lys Lys Pro Gly Ala
1               5                   10                  15
```

```
Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Met Glu Leu Ser Ser Leu Arg Ser Glu Asp Thr Ala Val Tyr Tyr Cys
             85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro
225                 230

<210> SEQ ID NO 234
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 234

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
             85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
```

```
              130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro
225                 230

<210> SEQ ID NO 235
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Gln Ala Pro Gly Lys Gly Leu Glu Tyr Ile
            35                  40                  45

Gly Asp Val Asp Pro Glu Thr Gly Gly Thr Ala Tyr Ala Glu Lys Phe
50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro
225                 230

<210> SEQ ID NO 236
```

```
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 236

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
                20                  25                  30

Glu Ile His Trp Val Lys Gln Thr Pro Val His Gly Leu Glu Trp Ile
            35                  40                  45

Gly Asp Ile Asp Pro Glu Thr Gly Gly Thr Ala Tyr Asn Gln Lys Phe
50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys
225

<210> SEQ ID NO 237
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Asn Pro Asn Asn Gly Gly Thr Arg Tyr Asn Gln Lys Phe
50                  55                  60
```

```
Lys Gly Lys Ala Thr Leu Thr Val Asn Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Arg Asp Tyr Asp Gly Ala Met Asp Tyr Trp Gly Gln Gly
                100                 105                 110

Thr Ser Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys
225

<210> SEQ ID NO 238
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Ser His Gly Lys Ser Leu Gln Trp Ile
                35                  40                  45

Gly Tyr Ile Asn Pro Asn Asn Gly Gly Thr Asn Tyr Asn Gln Asn Phe
            50                  55                  60

Lys Asp Lys Ala Thr Leu Thr Val Asn Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Arg Asp Tyr Asp Gly Ser Met Asp Phe Trp Gly Gln Gly
                100                 105                 110

Thr Ser Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

180                 185                 190
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys
225

<210> SEQ ID NO 239
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys
225

<210> SEQ ID NO 240
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
                20                  25                  30

Glu Ile His Trp Val Lys Gln Thr Pro Val His Gly Leu Glu Trp Ile
            35                  40                  45

Gly Gly Ile Asp Pro Glu Thr Gly Thr Ala Tyr Asn Gln Lys Phe
    50                  55                  60

Lys Gly Lys Ala Ile Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys
225

<210> SEQ ID NO 241
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
                20                  25                  30

Glu Ile His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Val Lys Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
                100                 105                 110

```
Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys
225

<210> SEQ ID NO 242
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys
```

```
<210> SEQ ID NO 243
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243
```

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Ala Pro Gly Lys Gly Leu Glu Trp Ile
            35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys
225

```
<210> SEQ ID NO 244
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244
```

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
                20                  25                  30

Glu Ile His Trp Val Gln Ala Pro Gly Lys Gly Leu Glu Tyr Ile
            35                  40                  45

Gly Asp Val Asp Pro Glu Thr Gly Thr Ala Tyr Ala Glu Lys Phe
            50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys
225

<210> SEQ ID NO 245
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Gln Val Gln Leu Gln Gln Ser Gly Ala Glu Leu Val Arg Pro Gly Ala
 1               5                  10                  15

Ser Val Thr Leu Ser Cys Lys Ala Ser Gly Asp Thr Phe Thr Asp Phe
                20                  25                  30

Glu Ile His Trp Val Lys Gln Thr Pro Val His Gly Leu Glu Trp Ile
            35                  40                  45

Gly Asp Ile Asp Pro Glu Thr Gly Thr Ala Tyr Asn Gln Lys Phe
            50                  55                  60

Arg Gly Arg Ala Met Leu Thr Ala Asp Arg Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

-continued

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
         180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
         210                 215                 220

Lys Thr His Thr
225

<210> SEQ ID NO 246
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 247
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 247

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 248
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 248

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

```
Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr
225
```

<210> SEQ ID NO 249
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
50                  55                  60

Lys Gly Lys Ala Ile Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205
```

```
Pro Ser Asn Thr Lys Val Asp Lys Lys Val Glu Pro Lys Ser Cys Asp
            210                 215                 220

Lys Thr His Thr
225

<210> SEQ ID NO 250
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 250

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Thr Ala Tyr Asn Gln Lys Phe
50                  55                  60

Lys Gly Lys Ala Ile Leu Thr Ala Val Lys Ser Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
            210                 215                 220

Lys Thr His Thr
225

<210> SEQ ID NO 251
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
```

```
                    20                  25                  30
Glu Ile His Trp Val Gln Gln Ala Pro Gly Lys Gly Leu Glu Trp Ile
                35                  40                  45
Gly Asp Val Asp Pro Glu Thr Gly Gly Thr Ala Tyr Ala Glu Lys Phe
             50                  55                  60
Gln Gly Arg Ala Thr Leu Thr Ala Asp Arg Ser Thr Asp Thr Ala Tyr
 65                  70                  75                  80
Met Glu Leu Ser Ser Leu Arg Ser Glu Asp Thr Ala Val Tyr Tyr Cys
                 85                  90                  95
Thr Arg Thr Tyr Asp Gly Tyr Pro Tyr Ala Phe Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr
225

<210> SEQ ID NO 252
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Glu Val Gln Leu Val Gln Ser Gly Ala Glu Val Lys Lys Pro Gly Ala
 1               5                  10                  15
Thr Val Lys Leu Ser Cys Lys Ala Ser Gly Asp Thr Phe Thr Asp Phe
                20                  25                  30
Glu Ile His Trp Val Gln Gln Ala Pro Gly Lys Gly Leu Glu Trp Ile
                35                  40                  45
Gly Asp Val Asp Pro Glu Thr Gly Gly Thr Ala Tyr Ala Glu Lys Phe
             50                  55                  60
Gln Gly Arg Ala Thr Leu Thr Ala Asp Arg Ser Thr Asp Thr Ala Tyr
 65                  70                  75                  80
Leu Glu Leu Ser Ser Leu Arg Ser Glu Asp Thr Ala Val Tyr Tyr Cys
                 85                  90                  95
Thr Arg Thr Tyr Asp Gly Tyr Pro Tyr Ala Phe Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225

<210> SEQ ID NO 253
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225

<210> SEQ ID NO 254
<211> LENGTH: 227
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His
225

<210> SEQ ID NO 255
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 255

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr

```
                  65                  70                  75                  80
Met Glu Leu Arg Ser Leu Thr Ser Glu Asp Ser Ala Val Tyr Tyr Cys
                        85                  90                  95

Ala Arg Glu Arg Asp Tyr Asp Gly Ala Met Asp Tyr Trp Gly Gln Gly
                    100                 105                 110

Thr Ser Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His
225

<210> SEQ ID NO 256
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                        85                  90                  95

Ala Arg Glu Arg Asp Tyr Asp Gly Ser Met Asp Phe Trp Gly Gln Gly
                    100                 105                 110

Thr Ser Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190
```

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His
225

<210> SEQ ID NO 257
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His
225

<210> SEQ ID NO 258
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 258

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
                20                  25                  30

Glu Ile His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
50                  55                  60

Lys Gly Lys Ala Ile Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His
225

<210> SEQ ID NO 259
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
                20                  25                  30

Glu Ile His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Lys Phe
50                  55                  60

Lys Gly Lys Ala Ile Leu Thr Ala Val Lys Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
                100                 105                 110

Gly Thr Ser Val Thr Val Ser Ser Ala Ser Thr Lys Gly Pro Ser Val

```
                115                 120                 125
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His
225

<210> SEQ ID NO 260
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 260

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His
225
```

<210> SEQ ID NO 261
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 261

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His
225

<210> SEQ ID NO 262
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 262

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

```
Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His
225

<210> SEQ ID NO 263
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 263

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
                20                  25                  30

Glu Ile His Trp Val Lys Gln Thr Pro Val His Gly Leu Glu Trp Ile
            35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
                100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr
225

<210> SEQ ID NO 264
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 264

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr
225

<210> SEQ ID NO 265
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 265

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr
225

<210> SEQ ID NO 266
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 266

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

```
Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220
```

<210> SEQ ID NO 267
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 267

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr
```

<210> SEQ ID NO 268
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 268

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Thr Ala Tyr Asn Gln Lys Phe
    50                  55                  60

Lys Gly Lys Ala Ile Leu Thr Ala Val Lys Ser Ser Thr Ala Tyr
65                  70                  75                  80

Met Gly Leu Arg Ser Leu Thr Ser Glu Asp Ser Ala Val Tyr Tyr Cys
                85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr
225

<210> SEQ ID NO 269
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 269

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Thr Ala Tyr Ala Glu Lys Phe
            50                  55                  60

Gln Gly Arg Ala Thr Leu Thr Ala Asp Arg Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr
225

<210> SEQ ID NO 270
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 270

Glu Val Gln Leu Val Gln Ser Gly Ala Glu Val Lys Lys Pro Gly Ala
 1               5                  10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
             35                 40                  45

Gly Asp Val Asp Pro Glu Thr Gly Thr Ala Tyr Ala Glu Lys Phe
            50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr
225

<210> SEQ ID NO 271
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 271

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr
225

<210> SEQ ID NO 272
<211> LENGTH: 225
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 272

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Thr Tyr Asp Gly Tyr Pro Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys
225

<210> SEQ ID NO 273
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 273

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

<210> SEQ ID NO 274
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 274

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

-continued

<210> SEQ ID NO 275
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 275

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys
    210                 215                 220

<210> SEQ ID NO 276
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Arg Ser Ser Ser Thr Ala Tyr

```
            65                  70                  75                  80
Met Glu Leu Arg Ser Leu Thr Ser Glu Asp Ser Ala Val Tyr Tyr Cys
                    85                  90                  95

Thr Arg Asn Tyr Asp Gly Tyr Ser Gln Thr Met Asp Tyr Trp Gly Gln
                100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys
225

<210> SEQ ID NO 277
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Phe
                20                  25                  30

Glu Ile His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Lys Phe
        50                  55                  60

Lys Gly Lys Ala Ile Leu Thr Ala Val Lys Ser Ser Ser Thr Ala Tyr
65                  70                  75                  80

Met Gly Leu Arg Ser Leu Thr Ser Glu Asp Ser Ala Val Tyr Tyr Cys
                    85                  90                  95

Thr Arg Asn Tyr Asp Gly Tyr Ser Arg Thr Met Asp Tyr Trp Gly Gln
                100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys
225

<210> SEQ ID NO 278
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 278

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Ala Pro Gly Lys Gly Leu Glu Trp Ile
        35                  40                  45

Gly Asp Val Asp Pro Glu Thr Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys
225

<210> SEQ ID NO 279
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 279
```

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
            35                  40                  45

Gly Asp Val Asp Pro Glu Thr Gly Gly Thr Ala Tyr Ala Glu Lys Phe
50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys
225

<210> SEQ ID NO 280
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 280

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
            35                  40                  45

Gly Asp Val Asp Pro Glu Thr Gly Gly Thr Ala Tyr Ala Glu Lys Phe
50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Tyr Gly Gln
            100                 105                 110

Gly Thr Leu Val Thr Val Ser Ser Ala Ser Thr Lys Gly Pro Ser Val 115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys
225

<210> SEQ ID NO 281
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 281

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Arg Thr Tyr Asp Gly Tyr Pro Tyr Ala Met Asp Tyr Trp Gly Gln
        100                 105                 110

Gly Thr Ser Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

<210> SEQ ID NO 282

<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 282

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Arg Tyr Asn Gln Lys Phe
    50                  55                  60

Lys Gly Lys Ala Thr Leu Thr Val Asn Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Asp Tyr Asp Gly Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp
    210                 215                 220
```

<210> SEQ ID NO 283
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 283

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Gln Trp Ile
        35                  40                  45

Gly Tyr Ile Asn Pro Asn Asn Gly Gly Thr Asn Tyr Asn Gln Asn Phe
    50                  55                  60

Lys Asp Lys Ala Thr Leu Thr Val Asn Lys Ser Ser Thr Thr Ala Tyr
65                  70                  75                  80
```

```
Met Glu Leu Arg Ser Leu Thr Ser Glu Asp Ser Ala Val Tyr Tyr Cys
                 85                  90                  95

Ala Arg Glu Arg Asp Tyr Asp Gly Ser Met Asp Phe Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp
    210                 215                 220

<210> SEQ ID NO 284
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 284

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Val Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Val Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Glu Asp Phe Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp
```

-continued

```
            210                 215                 220
```

<210> SEQ ID NO 285
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 285

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Ser Asp Phe
            20                  25                  30

Glu Ile His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asn Tyr Asp Gly Tyr Ser Gln Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

<210> SEQ ID NO 286
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 286

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Ser Thr Phe Thr Asp Phe
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60
```

```
Lys Gly Lys Ala Ile Leu Thr Ala Val Lys Ser Ser Thr Ala Tyr
 65                  70                  75                  80

Met Gly Leu Arg Ser Leu Thr Ser Glu Asp Ser Ala Val Tyr Tyr Cys
                 85                  90                  95

Thr Arg Asn Tyr Asp Gly Tyr Ser Arg Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

<210> SEQ ID NO 287
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 287

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Trp Ile
        35                  40                  45

Gly Asp Val Asp Pro Glu Thr Gly Gly Thr Ala Tyr Ala Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

<210> SEQ ID NO 288
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Ala Pro Gly Lys Gly Leu Glu Trp Ile
        35                  40                  45

Gly Asp Val Asp Pro Glu Thr Gly Gly Thr Ala Tyr Ala Glu Lys Phe
50                  55                  60

Gln Gly Arg Ala Thr Leu Thr Ala Asp Arg Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Arg Thr Tyr Asp Gly Tyr Pro Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

<210> SEQ ID NO 289
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 289

Glu Val Gln Leu Val Gln Ser Gly Ala Glu Val Lys Lys Pro Gly Ala
1               5                   10                  15

Thr Val Lys Leu Ser Cys Lys Ala Ser Gly Asp Thr Phe Thr Asp Phe
            20                  25                  30

Glu Ile His Trp Val Gln Gln Ala Pro Gly Lys Gly Leu Glu Tyr Ile
```

```
                35                  40                  45
Gly Asp Val Asp Pro Glu Thr Gly Gly Thr Ala Tyr Ala Glu Lys Phe
 50                  55                  60

Gln Gly Arg Ala Thr Leu Thr Ala Asp Arg Ser Thr Asp Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Thr Tyr Asp Gly Tyr Pro Tyr Ala Phe Asp Tyr Tyr Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

<210> SEQ ID NO 290
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="S"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 290

His Gln Tyr Leu Ser Pro Tyr Thr
 1               5

<210> SEQ ID NO 291
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 291

Gln Val Gln Leu Gln Gln Ser Gly Ala Glu Leu Val Arg Pro Gly Ala
 1               5                  10                  15

Ser Val Thr Leu Ser Cys Lys Ala Ser Gly Asp Thr Phe Thr Asp Phe
                 20                  25                  30

Glu Ile His Trp Val Lys Gln Thr Pro Val His Gly Leu Glu Trp Ile
```

```
                35                  40                  45
Gly Asp Ile Asp Pro Glu Thr Gly Gly Thr Ala Tyr Asn Gln Lys Phe
 50                  55                  60

Arg Gly Arg Ala Met Leu Thr Ala Asp Arg Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Thr Tyr Asp Gly Tyr Pro Tyr Ala Met Asp Tyr Trp Gly Gln
                100                 105                 110

Gly Thr Ser Val Thr Val Ser Ser Ala Lys Thr Thr Ala Pro Ser Val
                115                 120                 125

Tyr Pro Leu Ala Pro Val Cys Gly Asp Thr Thr Gly Ser Ser Val Thr
                130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
                180                 185                 190

Ser Thr Trp Pro Ser Gln Ser Ile Thr Cys Asn Val Ala His Pro Ala
                195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Val Ala Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
                260                 265                 270

Pro Asp Val Gln Ile Ser Trp Phe Val Asn Asn Val Glu Val His Thr
                275                 280                 285

Ala Gln Thr Gln Thr His Arg Glu Asp Tyr Asn Ser Thr Leu Arg Val
                290                 295                 300

Val Ser Ala Leu Pro Ile Gln His Gln Asp Trp Met Ser Gly Lys Glu
305                 310                 315                 320

Phe Lys Cys Lys Val Asn Asn Lys Gly Leu Pro Ser Ser Ile Glu Arg
                325                 330                 335

Thr Ile Ser Lys Pro Lys Gly Ser Val Arg Ala Pro Gln Val Tyr Val
                340                 345                 350

Leu Pro Pro Pro Glu Glu Glu Met Thr Lys Lys Gln Val Thr Leu Thr
                355                 360                 365

Cys Met Val Thr Asp Phe Met Pro Glu Asp Ile Tyr Val Glu Trp Thr
                370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
                435                 440                 445

Lys
```

```
<210> SEQ ID NO 292
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 292

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 293
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 293

Gln Val Gln Leu Gln Gln Ser Gly Ala Glu Leu Val Arg Pro Gly Ala
1               5                   10                  15

Ser Val Thr Leu Ser Cys Lys Ala Ser Gly Asp Thr Phe Thr Asp Phe
            20                  25                  30

Glu Ile His Trp Val Lys Gln Thr Pro Val His Gly Leu Glu Trp Ile
        35                  40                  45

Gly Asp Ile Asp Pro Glu Thr Gly Gly Thr Ala Tyr Asn Gln Lys Phe
    50                  55                  60

Arg Gly Arg Ala Met Leu Thr Ala Asp Arg Ser Ser Ser Thr Ala Tyr
```

```
              65                  70                  75                  80
        Met Glu Leu Arg Ser Leu Thr Ser Glu Asp Ser Ala Val Tyr Tyr Cys
                            85                  90                  95

Thr Arg Thr Tyr Asp Gly Tyr Pro Tyr Ala Met Asp Tyr Trp Gly Gln
                        100                 105                 110

Gly Thr Ser Val Thr Val Ser Ala Lys Thr Thr Ala Pro Ser Val
                    115                 120                 125

Tyr Pro Leu Ala Pro Val Cys Gly Asp Thr Thr Gly Ser Ser Val Thr
                130                 135                 140

Leu Gly Cys Leu Val Lys Gly Tyr Phe Pro Glu Pro Val Thr Leu Thr
        145                 150                 155                 160

Trp Asn Ser Gly Ser Leu Ser Ser Gly Val His Thr Phe Pro Ala Val
                        165                 170                 175

Leu Gln Ser Asp Leu Tyr Thr Leu Ser Ser Ser Val Thr Val Thr Ser
                    180                 185                 190

Ser Thr Trp Pro Ser Gln Ser Ile Thr Cys Asn Val Ala His Pro Ala
                    195                 200                 205

Ser Ser Thr Lys Val Asp Lys Lys Ile
                    210                 215

<210> SEQ ID NO 294
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 294

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205
```

```
Pro Ile Val Lys Ser Phe Asn Arg Asn Glu Cys
    210                 215
```

<210> SEQ ID NO 295
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

```
Gly Asp Thr Phe Thr Asp Tyr Glu
1               5
```

<210> SEQ ID NO 296
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

```
Gly Tyr Thr Phe Thr Asp Phe Glu
1               5
```

<210> SEQ ID NO 297
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

```
Val Asp Pro Glu Thr Gly Gly Thr
1               5
```

<210> SEQ ID NO 298
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

```
Ile Asp Pro Glu Thr Gly Ser Thr
1               5
```

<210> SEQ ID NO 299
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

```
Val Glu Pro Glu Thr Gly Gly Thr
1               5
```

<210> SEQ ID NO 300
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Thr Arg Thr Tyr Glu Gly Tyr Pro Tyr Ala Met Asp Tyr
1               5                   10

<210> SEQ ID NO 301
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Thr Arg Thr Tyr Asp Gly Tyr Pro Tyr Ala Phe Asp Tyr
1               5                   10

<210> SEQ ID NO 302
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Gln Ser Val Leu Tyr Ser Asn Asn Asn Lys Asn Tyr
1               5                   10

<210> SEQ ID NO 303
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Tyr Ala Ser
1

<210> SEQ ID NO 304
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Phe Ala Ser
1

<210> SEQ ID NO 305
<211> LENGTH: 13
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Thr Arg Asn Tyr Asp Gly Tyr Ser Gln Thr Phe Asp Tyr
1               5                   10

<210> SEQ ID NO 306
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Gln Ser Val Leu Tyr Ser Asp Asn Gln Lys Asn Tyr
1               5                   10

<210> SEQ ID NO 307
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Thr Arg Asn Tyr Asp Gly Tyr Ser Arg Thr Phe Asp Tyr
1               5                   10

<210> SEQ ID NO 308
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (11)..(11)
<223> OTHER INFORMATION: /replace="F"
<220> FEATURE:
<221> NAME/KEY: SITE
<222> LOCATION: (1)..(13)
<223> OTHER INFORMATION: /note="Variant residues given in the sequence
      have no preference with respect to those in the annotations
      for variant positions"

<400> SEQUENCE: 308

Thr Arg Asn Tyr Asp Gly Tyr Ser Gln Thr Met Asp Tyr
1               5                   10

<210> SEQ ID NO 309
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="D"
```

```
<220> FEATURE:
<221> NAME/KEY: SITE
<222> LOCATION: (1)..(12)
<223> OTHER INFORMATION: /note="Variant residues given in the sequence
      have no preference with respect to those in the annotations
      for variant positions"

<400> SEQUENCE: 309

Gln Ser Val Leu Tyr Ser Ser Asn Gln Lys Asn Tyr
1               5                   10

<210> SEQ ID NO 310
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Ala Arg Thr Tyr Asp Gly Tyr Pro Tyr Ala Met Asp Tyr
1               5                   10

<210> SEQ ID NO 311
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ala Arg Thr Tyr Asp Gly Tyr Pro Tyr Ala Met Asp Val
1               5                   10

<210> SEQ ID NO 312
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Ile Asp Pro Glu Ser Gly Gly Thr
1               5

<210> SEQ ID NO 313
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Ile Glu Pro Glu Ser Gly Gly Thr
1               5

<210> SEQ ID NO 314
<211> LENGTH: 8
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 314

His Gln Tyr Leu Ser Pro Tyr Thr
1               5

<210> SEQ ID NO 315
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Gln Ser Val Leu Tyr Ser Asn Asn Gln Lys Asn Tyr
1               5                   10

<210> SEQ ID NO 316
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Trp Gly Ser
1

<210> SEQ ID NO 317
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Gln Ser Leu Leu His Ser Asn Asn Gln Lys Asn Tyr
1               5                   10

<210> SEQ ID NO 318
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49

-continued

```
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 318

Gln Val Gln Leu Val Gln Ser Gly Ala Glu Val Lys Pro Gly Ala
1               5                   10                  15

Ser Val Lys Val Ser Cys Lys Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Ala Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Ala Tyr Asn Gln
        130                 135                 140

Lys Phe Gln Gly Arg Val Thr Ile Thr Ala Asp Lys Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa
            210                 215                 220

Xaa Xaa Xaa Trp Gly Gln Gly Thr Leu Val Thr Val Ser Ser
225                 230                 235

<210> SEQ ID NO 319
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
```

```
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 319

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Ala Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Lys Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235

<210> SEQ ID NO 320
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
```

```
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 320

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Ala Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Lys Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235

<210> SEQ ID NO 321
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
```

```
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 321
```

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Ala Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Lys Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235

```
<210> SEQ ID NO 322
<211> LENGTH: 238
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 322

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Gly Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Arg Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235
```

-continued

```
<210> SEQ ID NO 323
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 323

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Gly Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Arg Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220
```

```
Xaa Xaa Xaa Trp Gly Gln Gly Thr Leu Val Thr Val Ser Ser
225                 230                 235
```

<210> SEQ ID NO 324
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 324

```
Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Arg Ser Thr Ser Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190
```

```
Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235

<210> SEQ ID NO 325
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 325

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Ile His Trp Val Arg Gln
65                  70                  75                  80

Ala Pro Gly Gln Gly Leu Glu Trp Ile Gly Gly Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Ala Tyr Asn Gln
    130                 135                 140

Lys Phe Gln Gly Arg Val Thr Ile Thr Ala Asp Arg Ser Thr Ser Thr
145                 150                 155                 160

Ala Tyr Met Glu Leu Ser Ser Leu Arg Ser Glu Asp Thr Ala Val Tyr
```

-continued

```
                165                 170                 175

Tyr Cys Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235

<210> SEQ ID NO 326
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 326

Glu Val Gln Leu Val Gln Ser Gly Ala Glu Val Lys Lys Pro Gly Ala
1               5                   10                  15

Thr Val Lys Leu Ser Cys Lys Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Ile His Trp Val Gln Gln
65                  70                  75                  80

Ala Pro Gly Lys Gly Leu Glu Trp Ile Gly Asp Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Ala Tyr Ala Glu
    130                 135                 140
```

```
Lys Phe Gln Gly Arg Ala Thr Leu Thr Ala Asp Arg Ser Thr Asp Thr
145                 150                 155                 160

Ala Tyr Met Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235

<210> SEQ ID NO 327
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 327

Glu Val Gln Leu Val Gln Ser Gly Ala Glu Val Lys Lys Pro Gly Ala
1               5                   10                  15

Thr Val Lys Leu Ser Cys Lys Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Ile His Trp Val Gln Gln
65                  70                  75                  80

Ala Pro Gly Lys Gly Leu Glu Trp Ile Gly Asp Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110
```

```
Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Ala Tyr Ala Glu
    130                 135                 140

Lys Phe Gln Gly Arg Ala Thr Leu Thr Ala Asp Arg Ser Thr Asp Thr
145                 150                 155                 160

Ala Tyr Leu Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa
    210                 215                 220

Xaa Xaa Xaa Trp Gly Gln Gly Thr Leu Val Thr Val Ser Ser
225                 230                 235
```

```
<210> SEQ ID NO 328
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(74)
<223> OTHER INFORMATION: Any naturally occurring amino acid
<220> FEATURE:
<221> NAME/KEY: SITE
<222> LOCATION: (26)..(74)
<223> OTHER INFORMATION: /note="This sequence may encompass 3-49
      residues"
<220> FEATURE:
<221> NAME/KEY: MOD_RES
<222> LOCATION: (92)..(140)
<223> OTHER INFORMATION: Any naturally occurring amino acid
<220> FEATURE:
<221> NAME/KEY: SITE
<222> LOCATION: (92)..(140)
<223> OTHER INFORMATION: /note="This sequence may encompass 3-49
      residues"
<220> FEATURE:
<221> NAME/KEY: MOD_RES
<222> LOCATION: (179)..(227)
<223> OTHER INFORMATION: Any naturally occurring amino acid
<220> FEATURE:
<221> NAME/KEY: SITE
<222> LOCATION: (179)..(227)
<223> OTHER INFORMATION: /note="This sequence may encompass 3-49
      residues"

<400> SEQUENCE: 328

Glu Val Gln Leu Val Gln Ser Gly Ala Glu Val Lys Lys Pro Gly Ala
1               5                   10                  15

Thr Val Lys Leu Ser Cys Lys Ala Ser Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Ile His Trp Val Gln Gln
65                  70                  75                  80

Ala Pro Gly Lys Gly Leu Glu Trp Ile Gly Asp Xaa Xaa Xaa Xaa Xaa
```

-continued

```
                 85                  90                  95
Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Ala Tyr Ala Glu
        130                 135                 140

Lys Phe Gln Gly Arg Ala Thr Leu Thr Ala Asp Arg Ser Thr Asp Thr
145                 150                 155                 160

Ala Tyr Leu Glu Leu Ser Ser Leu Arg Ser Glu Asp Thr Ala Val Tyr
                165                 170                 175

Tyr Cys Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa
        210                 215                 220

Xaa Xaa Xaa Trp Gly Gln Gly Thr Leu Val Thr Val Ser Ser
225                 230                 235
```

<210> SEQ ID NO 329
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49 residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49 residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49 residues"

<400> SEQUENCE: 329

```
Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60
```

```
Xaa Xaa Xaa Xaa Xaa Xaa Xaa Xaa Xaa Xaa Leu Ala Trp Tyr Gln
 65                  70                  75                  80

Gln Lys Pro Gly Gln Ser Pro Lys Leu Leu Ile Tyr Xaa Xaa Xaa
                 85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa
    210                 215                 220

Xaa Xaa Phe Gly Gln Gly Thr Lys Leu Glu Ile Lys
225                 230                 235

<210> SEQ ID NO 330
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 330

Asp Ile Val Met Thr Gln Ser Pro Asp Ser Leu Ala Val Ser Leu Gly
 1               5                  10                  15

Glu Arg Val Thr Ile Asn Cys Lys Ser Ser Xaa Xaa Xaa Xaa Xaa
             20                  25                  30
```

```
Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa
        210                 215                 220

Xaa Xaa Phe Gly Gln Gly Thr Lys Leu Glu Ile Lys
225                 230                 235

<210> SEQ ID NO 331
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 331

Asp Ile Val Met Thr Gln Ser Pro Asp Ser Leu Ala Val Ser Leu Gly
```

```
                1               5                  10                 15
Glu Arg Val Thr Ile Asn Cys Lys Ser Ser Xaa Xaa Xaa Xaa Xaa
                20                  25                 30

Xaa Xaa Xaa Xaa Xaa Xaa Xaa Xaa Xaa Xaa Xaa Xaa Xaa Xaa Xaa
                35                  40                 45

Xaa Xaa Xaa Xaa Xaa Xaa Xaa Xaa Xaa Xaa Xaa Xaa Xaa Xaa Xaa
                50                  55                 60

Xaa Xaa Xaa Xaa Xaa Xaa Xaa Xaa Xaa Xaa Leu Ala Trp Tyr Gln
65                  70                  75                 80

Gln Lys Pro Gly Gln Ser Pro Lys Leu Leu Ile Tyr Xaa Xaa Xaa Xaa
                85                  90                 95

Xaa Xaa Xaa Xaa Xaa Xaa Xaa Xaa Xaa Xaa Xaa Xaa Xaa Xaa Xaa
                100                 105                110

Xaa Xaa Xaa Xaa Xaa Xaa Xaa Xaa Xaa Xaa Xaa Xaa Xaa Xaa Xaa
                115                 120                125

Xaa Xaa Xaa Xaa Xaa Xaa Xaa Xaa Xaa Xaa Xaa Xaa Thr Arg Glu
                130                 135                140

Ser Gly Val Pro Asp Arg Phe Ser Gly Ser Gly Ser Gly Thr Asp Phe
145                 150                 155                160

Thr Leu Thr Ile Ser Ser Leu Gln Ala Glu Asp Val Ala Val Tyr Tyr
                165                 170                175

Cys Xaa Xaa Xaa Xaa Xaa Xaa Xaa Xaa Xaa Xaa Xaa Xaa Xaa Xaa
                180                 185                190

Xaa Xaa Xaa Xaa Xaa Xaa Xaa Xaa Xaa Xaa Xaa Xaa Xaa Xaa Xaa
                195                 200                205

Xaa Xaa Xaa Xaa Xaa Xaa Xaa Xaa Xaa Xaa Xaa Xaa Xaa Xaa Xaa
                210                 215                220

Xaa Xaa Phe Gly Gln Gly Thr Lys Leu Glu Ile Lys
225                 230                 235

<210> SEQ ID NO 332
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
``` residues"

<400> SEQUENCE: 332

Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa
    210                 215                 220

Xaa Xaa Phe Gly Gln Gly Thr Lys Leu Glu Ile Lys
225                 230                 235

<210> SEQ ID NO 333
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)

<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 333

```
Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
        210                 215                 220

Xaa Xaa Phe Gly Gln Gly Thr Lys Leu Glu Ile Lys
225                 230                 235
```

<210> SEQ ID NO 334
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)

<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 334

Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Phe Gly Gln Gly Thr Lys Leu Glu Ile Lys
225                 230                 235

<210> SEQ ID NO 335
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES -continued

```
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 335

Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Thr Arg Glu
130                 135                 140

Ser Gly Val Pro Asp Arg Phe Ser Gly Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Phe Gly Gln Gly Thr Lys Leu Glu Ile Lys
225                 230                 235

<210> SEQ ID NO 336
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
```

```
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 336

Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Thr Arg Glu
130                 135                 140

Ser Gly Val Pro Asp Arg Phe Ser Gly Ser Gly Ser Gly Thr Asp Phe
145                 150                 155                 160

Thr Leu Thr Ile Ser Ser Leu Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Phe Gly Gln Gly Thr Lys Leu Glu Ile Lys
225                 230                 235

<210> SEQ ID NO 337
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
```

```
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 337

Asp Ile Val Met Thr Gln Ser Pro Asp Ser Leu Ala Val Ser Leu Gly
1               5                   10                  15

Glu Arg Ala Thr Ile Asn Cys Lys Ser Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Leu Ala Trp Tyr Gln Gln
65                  70                  75                  80

Lys Pro Gly Gln Ser Pro Lys Leu Leu Ile Tyr Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Val Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Phe Gly Gly Gly Thr Lys Val Glu Ile Lys
225                 230                 235

<210> SEQ ID NO 338
<211> LENGTH: 236
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 338

Asp Ile Val Met Thr Gln Ser Pro Asp Ser Leu Ala Val Ser Leu Gly
1               5                   10                  15

Glu Arg Ala Thr Ile Asn Cys Lys Ser Ser Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Val Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Phe Gly Gly Gly Thr Lys Val Glu Ile Lys
225                 230                 235
```

```
<210> SEQ ID NO 339
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (27)..(75)
<223> OTHER INFORMATION: Any naturally occurring amino acid
<220> FEATURE:
<221> NAME/KEY: SITE
<222> LOCATION: (27)..(75)
<223> OTHER INFORMATION: /note="This sequence may encompass 3-49
      residues"
<220> FEATURE:
<221> NAME/KEY: MOD_RES
<222> LOCATION: (93)..(141)
<223> OTHER INFORMATION: Any naturally occurring amino acid
<220> FEATURE:
<221> NAME/KEY: SITE
<222> LOCATION: (93)..(141)
<223> OTHER INFORMATION: /note="This sequence may encompass 3-49
      residues"
<220> FEATURE:
<221> NAME/KEY: MOD_RES
<222> LOCATION: (178)..(226)
<223> OTHER INFORMATION: Any naturally occurring amino acid
<220> FEATURE:
<221> NAME/KEY: SITE
<222> LOCATION: (178)..(226)
<223> OTHER INFORMATION: /note="This sequence may encompass 3-49
      residues"

<400> SEQUENCE: 339

Asp Ile Val Met Thr Gln Ser Pro Asp Ser Leu Ala Val Ser Leu Gly
1               5                   10                  15

Glu Arg Val Thr Ile Asn Cys Lys Ser Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Leu Ala Trp Tyr Gln
65                  70                  75                  80

Gln Lys Pro Gly Gln Ser Pro Lys Leu Leu Ile Tyr Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Thr Arg Glu
    130                 135                 140

Ser Gly Val Pro Asp Arg Phe Ser Gly Ser Gly Ser Gly Thr Asp Phe
145                 150                 155                 160

Thr Leu Thr Ile Ser Ser Val Gln Ala Glu Asp Val Ala Val Tyr Tyr
                165                 170                 175

Cys Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
```

```
                  210                 215                 220
Xaa Xaa Phe Gly Gly Gly Thr Lys Leu Glu Ile Lys
225                 230                 235

<210> SEQ ID NO 340
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Ile His Trp Val Gln Gln Ala Pro Gly Lys Gly Leu Glu Trp Ile Gly
1               5                   10                  15

Asp

<210> SEQ ID NO 341
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 341

Ala Tyr Ala Glu Lys Phe Gln Gly Arg Ala Thr Leu Thr Ala Asp Arg
1               5                   10                  15

Ser Thr Asp Thr Ala Tyr Met Glu Leu Ser Ser Leu Arg Ser Glu Asp
            20                  25                  30

Thr Ala Val Tyr Tyr Cys
        35

<210> SEQ ID NO 342
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Trp Gly Gln Gly Thr Leu Val Thr Val Ser Ser
1               5                   10

<210> SEQ ID NO 343
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Gln Ser Val Leu Tyr Ser Ser Asn Asn Lys Asn Tyr
1               5                   10

<210> SEQ ID NO 344
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 344

Gln Gly Ile Ser Tyr Ser Asn Asn Gln Lys Asn Tyr
1               5                   10
```

FGFR3 ANTIBODIES AND METHODS OF USE

RELATED APPLICATION

This application claims the benefit of priority of U.S. Provisional Application No. 63/068,575, filed Aug. 21, 2020, the content of which is incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Aug. 20, 2021, is named 720722_SA9-231_ST25.txt and is 545,959 bytes in size.

FIELD OF THE INVENTION

This disclosure relates to compositions of anti-fibroblast growth factor receptor 3 (anti-FGFR3) antigen-binding proteins or antigen-binding fragments thereof, such as antibodies and fragments thereof, and methods of using the same.

BACKGROUND

Fibroblast growth factor receptor 3 (FGFR3) is a protein involved, in part, in the negative regulation of bone development, being highly expressed in growth plate chondrocytes (Sarabipour et al. Biochim Biophys Acta. 1858(7 Pt A): 1436-1442. 2016). FGFR3 is a single-pass membrane receptor tyrosine kinase with 3 Ig-like domains (D1-D3). Binding of FGFR3 to an FGFR3-ligand, such as FGF18, triggers ligand-dependent receptor dimerization which leads to tyrosine kinase activation and downstream signal transduction. This signaling cascade regulates, among other things, chondrocyte proliferation and differentiation.

FGFR3 is a member of the fibroblast growth factor receptor family, which also includes FGFR1, FGFR2, and FGFR4. Each member of the receptor family is a single-pass membrane receptor tyrosine kinase and shares the feature of 3 Ig-like domains. Moreover, each member of the receptor family possesses a high degree of homology with the other members. Strategies to develop FGFR3-specific inhibitors have proven challenging for this reason. Nonetheless, it is important to develop FGFR3-specific inhibitors that do not cross-react with other fibroblast growth factor receptor family members to avoid unwanted side effects in the treatment of an FGFR3-mediate disease or disorder.

Accordingly, there is a need in the art to identify antigen-binding proteins or antigen-binding fragments thereof, that achieve effective inhibition of FGFR3 activity. Such antigen-binding proteins or antigen-binding fragments thereof may be useful in the treatment of FGFR3-mediated diseases and disorders.

SUMMARY

Disclosed herein are anti-FGFR3 antigen-binding proteins or antigen-binding fragments thereof, such as antibodies and antigen-binding fragments thereof. The antigen-binding proteins or antigen-binding fragments thereof, such as anti-FGFR3 antibodies and antigen-binding fragments thereof of the disclosure are suitable for treating FGFR3-mediated diseases and disorders.

In one aspect, the disclosure provides an antigen-binding protein or antigen-binding fragment thereof that specifically binds to fibroblast growth factor receptor 3 (FGFR3), comprising an antibody heavy chain variable (VH) domain and an antibody light chain variable (VL) domain, wherein: (a) the VH domain comprises a CDR-H1 sequence comprising the amino acid sequence of $GX^1TFTDX^2E$ (SEQ ID NO: 157), wherein $X^1$ comprises or consists of Y or D and $X^2$ comprises or consists of F or Y; a CDR-H2 sequence comprising the amino acid sequence of $IDPETGX^3T$ (SEQ ID NO: 158), wherein $X^3$ comprises or consists of G or S; or CDR-H2 sequence comprising the amino acid sequence of $INPNNGX^4T$ (SEQ ID NO: 159), wherein $X^4$ comprises or consists of G or V; or CDR-H2 sequence comprising the amino acid sequence of $VX^5PETGGT$ (SEQ ID NO: 160), wherein $X^5$ comprises or consists of D or E; a CDR-H3 sequence comprising the amino acid sequence of $TRX^6YX^7GYX^8X^9X^{10}X^{11}DY$ (SEQ ID NO: 161), wherein $X^6$ comprises or consists of T or N, $X^7$ comprises D or E, $X^8$ comprises or consists of S or P, $X^9$ comprises or consists of Q, R, or Y, $X^{10}$ comprises or consists of T or A, $X^{11}$ comprises or consists of F or M; and the VL domain comprises a CDR-L1 sequence comprising the amino acid sequence of QS $X^{12}$LYS $X^{13}$N $X^{14}$KNY (SEQ ID NO: 162), wherein $X^{12}$ comprises or consists of L or V, $X^{13}$ comprises or consists of N, D, or S, and $X^{14}$ comprises or consists of Q or N; a CDR-L2 sequence comprising the amino acid sequence of $X^{15}AS$ (SEQ ID NO: 163), wherein $X^{15}$ comprises or consists of W, Y, or F; a CDR-L3 sequence comprising the amino acid sequence of QQYYSYRT (SEQ ID NO: 75), LQYDNLLWT (SEQ ID NO: 81), or HQYLSX$^{16}$YT (SEQ ID NO: 290) wherein $X^{16}$ comprises or consists of P or S; (b) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGAMDY (SEQ ID NO: 78); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87); (c) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGSMDF (SEQ ID NO: 84); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87); (d) the VH domain comprises a CDR-H1 sequence comprising the amino acid sequence of GYTVTDYY (SEQ ID NO: 88); a CDR-H2 sequence comprising the amino acid sequence of INPNNGVT (SEQ ID NO: 89); a CDR-H3 sequence comprising the amino acid sequence of AREEDFDGFDY (SEQ ID NO: 90); and the VL domain comprises a CDR-L1 sequence comprising the amino acid sequence of QDVSTG (SEQ ID NO: 91); a CDR-L2 sequence comprising the amino acid sequence of WAS (SEQ ID NOs: 74, 92, 98 and 104); a CDR-L3 sequence comprising the amino acid sequence of QQHYSTPLT (SEQ ID NO: 93); (e) the VH domain comprises a CDR-H1 sequence comprising the amino acid sequence of GSTFSDFE (SEQ ID NO: 94); a CDR-H2 sequence comprising the amino acid sequence of IDPETGGT (SEQ ID NOs: 71, 95, and 101); a CDR-H3 sequence comprising the amino acid sequence of TRNYDGYSQTX$^{17}$DY (SEQ ID NO: 308), wherein X$^{17}$ comprises M or F; and the VL domain comprises a CDR-L1 sequence comprising the amino acid sequence of QSVLYSX$^{18}$NQKNY (SEQ ID NO: 309), wherein X$^{18}$ comprises S or D; a CDR-L2 sequence comprising the amino acid sequence of WAS (SEQ ID NOs: 74, 92, 98 and 104); a CDR-L3 sequence comprising the amino acid sequence of or HQYLSSYT (SEQ ID NOs: 99 and 105); or (f) the VH domain comprises a CDR-H1 sequence comprising the amino acid sequence of GSTFTDFE (SEQ ID NO: 100); a CDR-H2 sequence comprising the amino acid sequence of IDPETGGT (SEQ ID NOs: 71, 95, and 101); a CDR-H3 sequence comprising the amino acid sequence of TRNYDGYSQTX$^{17}$DY (SEQ ID NO: 308), wherein X$^{17}$ comprises M or F; and the VL domain comprises a CDR-L1 sequence comprising the amino acid sequence of QSVLYSX$^{18}$NQKNY (SEQ ID NO: 309), wherein X$^{18}$ comprises S or D; a CDR-L2 sequence comprising the amino acid sequence of WAS (SEQ ID NOs: 74, 92, 98 and 104); a CDR-L3 sequence comprising the amino acid sequence of or HQYLSSYT (SEQ ID NOs: 99 and 105).

In certain embodiments, (a) the VH domain comprises a CDR-H1 sequence comprising the amino acid sequence of GDTFTDFE (SEQ ID NO: 70), GDTFTDYE (SEQ ID NO: 295), or GYTFTDFE (SEQ ID NO: 296); a CDR-H2 sequence comprising the amino acid sequence of IDPETGGT (SEQ ID NOs: 71, 95, and 101), VDPETGGT (SEQ ID NO: 297), IDPETGST (SEQ ID NO: 298), or VEPETGGT (SEQ ID NO: 299); a CDR-H3 sequence comprising the amino acid sequence of TRTYDGYPYAMDY (SEQ ID NO: 72), TRTYEGYPYAMDY (SEQ ID NO: 300), or TRTYDGYPYAFDY (SEQ ID NO: 301); and the VL domain comprises a CDR-L1 sequence comprising the amino acid sequence of QSLLYSNNQKNY (SEQ ID NO: 73), QSVLYSNNNKNY (SEQ ID NO: 302), or QSVLYSDNQKNY (SEQ ID NO: 306); a CDR-L2 sequence comprising the amino acid sequence of WAS (SEQ ID NOs: 74, 92, 98, and 104), YAS (SEQ ID NO: 303), or FAS (SEQ ID NO: 304); a CDR-L3 sequence comprising the amino acid sequence of QQYYSYRT (SEQ ID NO: 75); (b) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGAMDY (SEQ ID NO: 78); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87); (c) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGSMDF (SEQ ID NO: 84); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87); (d) the VH domain comprises a CDR-H1 sequence comprising the amino acid sequence of GYTVTDYY (SEQ ID NO: 88); a CDR-H2 sequence comprising the amino acid sequence of INPNNGVT (SEQ ID NO: 89); a CDR-H3 sequence comprising the amino acid sequence of AREEDFDGFDY (SEQ ID NO: 90); and the VL domain comprises a CDR-L1 sequence comprising the amino acid sequence of QDVSTG (SEQ ID NO: 91); a CDR-L2 sequence comprising the amino acid sequence of WAS (SEQ ID NOs: 74, 92, 98, and 104); a CDR-L3 sequence comprising the amino acid sequence of QQHYSTPLT (SEQ ID NO: 93); (e) the VH domain comprises a CDR-H1 sequence comprising the amino acid sequence of GSTFSDFE (SEQ ID NO: 94); a CDR-H2 sequence comprising the amino acid sequence of IDPETGGT (SEQ ID NOs: 71, 95, and 101); a CDR-H3 sequence comprising the amino acid sequence of TRNYDGYSQTMDY (SEQ ID NO: 96) or TRNYDGYSQTFDY (SEQ ID NO: 305); and the VL domain comprises a CDR-L1 sequence comprising the amino acid sequence of QSVLYSSNQKNY (SEQ ID NOs: 97 and 103) or QSVLYSDNQKNY (SEQ ID NO: 306); a CDR-L2 sequence comprising the amino acid sequence of WAS (SEQ ID NOs: 74, 92, 98, and 104); a CDR-L3 sequence comprising the amino acid sequence of or HQYLSSYT (SEQ ID NOs: 99 and 105); or (f) the VH domain comprises a CDR-H1 sequence comprising the amino acid sequence of GSTFTDFE (SEQ ID NO: 100); a CDR-H2 sequence comprising the amino acid sequence of IDPETGGT (SEQ ID NOs: 71, 95, and 101); a CDR-H3 sequence comprising the amino acid sequence of TRNYDGYSRTMDY (SEQ ID NO: 102) or TRNYDGYSRTFDY (SEQ ID NO: 307); and the VL domain comprises a CDR-L1 sequence comprising the amino acid sequence of QSVLYSSNQKNY (SEQ ID NOs: 97 and 103) or QSVLYSDNQKNY (SEQ ID NO: 306); a CDR-L2 sequence comprising the amino acid sequence of WAS (SEQ ID NOs: 74, 92, 98, and 104); a CDR-L3 sequence comprising the amino acid sequence of or HQYLSSYT (SEQ ID NOs: 99 and 105).

In certain embodiments, (a) the VH domain comprises the amino acid sequence selected from the group consisting of: SEQ ID NO: 6, SEQ ID NO: 18, SEQ ID NO: 106, SEQ ID NO: 107, SEQ ID NO: 108, SEQ ID NO: 10, SEQ ID NO: 110, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 57, and SEQ ID NO: 58; and the VL domain comprises the amino acid sequence selected from the group consisting of: SEQ ID NO: 7, SEQ ID NO: 19, SEQ ID NO: 112, SEQ ID NO: 113, SEQ ID NO: 114, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 60, and SEQ ID NO: 61; (b) the VH domain comprises the amino acid sequence of SEQ ID NO: 8; and the VL domain comprises the amino acid sequence of SEQ ID NO: 9; (c) the VH domain comprises the amino acid sequence of SEQ ID NO: 10; and the VL domain comprises the amino acid sequence of SEQ ID NO: 11; (d) the VH domain comprises the amino acid sequence of SEQ ID NO: 12; and the VL domain comprises the amino acid sequence of SEQ ID NO: 13; (e) the VH domain comprises the amino acid sequence selected from the group consisting of: SEQ ID NO: 14, SEQ ID NO: 20, SEQ ID NO: 21, SEQ ID NO: 22, and SEQ ID NO: 23; and the VL domain comprises the amino acid sequence selected from the group consisting of: SEQ ID NO: 15, SEQ ID NO: 24, SEQ ID NO: 25, SEQ ID NO: 26, and SEQ ID NO: 27;

(f) the VH domain comprises the amino acid sequence selected from the group consisting of: SEQ ID NO: 16, SEQ ID NO: 28, SEQ ID NO: 29, SEQ ID NO: 30, and SEQ ID NO: 31; the VL domain comprises the amino acid sequence selected from the group consisting of: SEQ ID NO: 17, SEQ ID NO: 32, SEQ ID NO: 33, SEQ ID NO: 34, and SEQ ID NO: 35.

In certain embodiments, the antibody heavy chain comprises the amino acid sequence of SEQ ID NO: 63 or 65, and the antibody light chain comprises the amino acid sequence of SEQ ID NO: 67 or 69.

In certain embodiments, the VH domain is at least about 90% identical or at least about 95% identical to the amino acid sequence of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 21, SEQ ID NO: 22, SEQ ID NO: 23, SEQ ID NO: 28, SEQ ID NO: 29, SEQ ID NO: 30, SEQ ID NO: 31, SEQ ID NO: 56, SEQ ID NO: 57, SEQ ID NO: 58, SEQ ID NO: 63, SEQ ID NO: 65, SEQ ID NO: 106, SEQ ID NO: 107, SEQ ID NO: 108, SEQ ID NO: 109, SEQ ID NO: 110, SEQ ID NO: 111, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, and wherein the VL domain is at least about 90% identical or at least about 95% identical to the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 24, SEQ ID NO: 25, SEQ ID NO: 26, SEQ ID NO: 27, SEQ ID NO: 32, SEQ ID NO: 33, SEQ ID NO: 34, SEQ ID NO: 35, SEQ ID NO: 59, SEQ ID NO: 60, SEQ ID NO: 61, SEQ ID NO: 67, SEQ ID NO: 69, SEQ ID NO: 112, SEQ ID NO: 113, SEQ ID NO: 114, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, or SEQ ID NO: 132.

In certain embodiments, the antigen binding protein or fragment thereof of comprises an antibody heavy chain at least about 90% identical or at least about 95% identical to the amino acid sequence of SEQ ID NO: 63 or 65, and an antibody light chain at least about 90% identical or at least about 95% identical to the amino acid sequence of SEQ ID NO: 67 or 69.

In certain embodiments, (a) the VH domain comprises a CDR-H1 sequence comprising the amino acid sequence of GDTFTDFE (SEQ ID NO: 70), a CDR-H2 sequence comprising the amino acid sequence of IDPETGGT (SEQ ID NO: 71), and a CDR-H3 sequence comprising the amino acid sequence of TRTYDGYPYAMDY (SEQ ID NO: 72); and (b) the VL domain comprises a CDR-L1 sequence comprising the amino acid sequence of QSLLYSNNQKNY (SEQ ID NO: 73), a CDR-L2 sequence comprising the amino acid sequence of WAS (SEQ ID NO: 74), and a CDR-L3 sequence comprising the amino acid sequence of QQYYSYRT (SEQ ID NO: 75). In some embodiments thereof, the VH domain comprises the amino acid sequence of SEQ ID NO: 6, and the VL domain comprises the amino acid sequence of SEQ ID NO: 7.

In certain embodiments, (a) the VH domain comprises a CDR-H1 sequence comprising the amino acid sequence of GYTFTDYN (SEQ ID NO: 76), a CDR-H2 sequence comprising the amino acid sequence of INPNNGGT (SEQ ID NO: 77), and a CDR-H3 sequence comprising the amino acid sequence of ARERDYDGAMDY (SEQ ID NO: 78); and (b) the VL domain comprises a CDR-L1 sequence comprising the amino acid sequence of QDINKF (SEQ ID NO: 79), a CDR-L2 sequence comprising the amino acid sequence of YTS (SEQ ID NO: 80), and a CDR-L3 sequence comprising the amino acid sequence of LQYDNLLWT (SEQ ID NO: 81).

In certain embodiments, the VH domain comprises the amino acid sequence of SEQ ID NO: 8, and the VL domain comprises the amino acid sequence of SEQ ID NO: 9.

In certain embodiments, (a) the VH domain comprises a CDR-H1 sequence comprising the amino acid sequence of GYTFTDYN (SEQ ID NO: 82), a CDR-H2 sequence comprising the amino acid sequence of INPNNGGT (SEQ ID NO: 83), and a CDR-H3 sequence comprising the amino acid sequence of ARERDYDGSMDF (SEQ ID NO: 84); and (b) the VL domain comprises a CDR-L1 sequence comprising the amino acid sequence of QDINKF (SEQ ID NO: 85), a CDR-L2 sequence comprising the amino acid sequence of YTS (SEQ ID NO: 86), and a CDR-L3 sequence comprising the amino acid sequence of LQYDNLLWT (SEQ ID NO: 87).

In certain embodiments, the VH domain comprises the amino acid sequence of SEQ ID NO: 10, and the VL domain comprises the amino acid sequence of SEQ ID NO: 11.

In certain embodiments, (a) the VH domain comprises a CDR-H1 sequence comprising the amino acid sequence of GYTVTDYY (SEQ ID NO: 88), a CDR-H2 sequence comprising the amino acid sequence of INPNNGVT (SEQ ID NO: 89), and a CDR-H3 sequence comprising the amino acid sequence of AREEDFDGFDY (SEQ ID NO: 90); and (b) the VL domain comprises a CDR-L1 sequence comprising the amino acid sequence of QDVSTG (SEQ ID NO: 91), a CDR-L2 sequence comprising the amino acid sequence of WAS (SEQ ID NO: 92), and a CDR-L3 sequence comprising the amino acid sequence of QQHYSTPLT (SEQ ID NO: 93).

In certain embodiments, the VH domain comprises the amino acid sequence of SEQ ID NO: 12, and the VL domain comprises the amino acid sequence of SEQ ID NO: 13.

In certain embodiments, (a) the VH domain comprises a CDR-H1 sequence comprising the amino acid sequence of GSTFSDFE (SEQ ID NO: 94), a CDR-H2 sequence comprising the amino acid sequence of IDPETGGT (SEQ ID NO: 95), and a CDR-H3 sequence comprising the amino acid sequence of TRNYDGYSQTMDY (SEQ ID NO: 96); and (b) the VL domain comprises a CDR-L1 sequence comprising the amino acid sequence of QSVLYSSNQKNY (SEQ ID NO: 97), a CDR-L2 sequence comprising the amino acid sequence of WAS (SEQ ID NO: 98), and a CDR-L3 sequence comprising the amino acid sequence of HQYLSSYT (SEQ ID NO: 99).

In certain embodiments, the VH domain comprises the amino acid sequence of SEQ ID NO: 14, and the VL domain comprises the amino acid sequence of SEQ ID NO: 15.

In certain embodiments, (a) the VH domain comprises a CDR-H1 sequence comprising the amino acid sequence of GSTFTDFE (SEQ ID NO: 100), a CDR-H2 sequence comprising the amino acid sequence of IDPETGGT (SEQ ID NO: 101), and a CDR-H3 sequence comprising the amino acid sequence of TRNYDGYSRTMDY (SEQ ID NO: 102); and (b) the VL domain comprises a CDR-L1 sequence comprising the amino acid sequence of QSVLYSSNQKNY (SEQ ID NO: 103), a CDR-L2 sequence comprising the amino acid sequence of WAS (SEQ ID NO: 104), and a CDR-L3 sequence comprising the amino acid sequence of HQYLSSYT (SEQ ID NO: 105).

In certain embodiments, the VH domain comprises the amino acid sequence of SEQ ID NO: 16, and the VL domain comprises the amino acid sequence of SEQ ID NO: 17.

In certain embodiments, (a) the VH domain comprises a CDR-H1 sequence comprising the amino acid sequence of GDTFTDFE (SEQ ID NO: 70), a CDR-H2 sequence comprising the amino acid sequence of VDPETGGT (SEQ ID NO: 297), and a CDR-H3 sequence comprising the amino acid sequence of TRTYDGYPYAFDY (SEQ ID NO: 301); and (b) the VL domain comprises a CDR-L1 sequence comprising the amino acid sequence of QSVLYSNNNKNY (SEQ ID NO: 302), a CDR-L2 sequence comprising the amino acid sequence of WAS (SEQ ID NOs: 74, 92, 98, 104), and a CDR-L3 sequence comprising the amino acid sequence of QQYYSYRT (SEQ ID NO: 75).

In certain embodiments, the VH domain comprises the amino acid sequence of SEQ ID NO: 57, and the VL domain comprises the amino acid sequence of SEQ ID NO: 19 or 59.

In certain embodiments, the antibody heavy chain comprises the amino acid sequence of SEQ ID NO: 63, and the antibody light chain comprises the amino acid sequence of SEQ ID NO: 67.

In certain embodiments, (a) the VH domain comprises a CDR-H1 sequence comprising the amino acid sequence of GDTFTDFE (SEQ ID NO: 70), a CDR-H2 sequence comprising the amino acid sequence of VDPETGGT (SEQ ID NO: 297), and a CDR-H3 sequence comprising the amino acid sequence of TRTYDGYPYAFDY (SEQ ID NO: 301); and (b) the VL domain comprises a CDR-L1 sequence comprising the amino acid sequence of QSVLYSDNQKNY (SEQ ID NO: 306), a CDR-L2 sequence comprising the amino acid sequence of FAS (SEQ ID NO: 304), and a CDR-L3 sequence comprising the amino acid sequence of QQYYSYRT (SEQ ID NO: 75).

In certain embodiments, the VH domain comprises the amino acid sequence of SEQ ID NO: 57, and the VL domain comprises the amino acid sequence of SEQ ID NO: 61.

In certain embodiments, the antibody heavy chain comprises the amino acid sequence of SEQ ID NO: 65, and the antibody light chain comprises the amino acid sequence of SEQ ID NO: 67.

In certain embodiments, the antigen binding protein or antigen-binding binding fragment thereof binds a human FGFR3 polypeptide comprising the amino acid sequence of SEQ ID NO: 133.

In certain embodiments, the antigen binding protein or antigen-binding fragment thereof binds a human FGFR3 polypeptide comprising the amino acid sequence of SEQ ID NO: 134.

In certain embodiments, the antigen binding protein or antigen-binding fragment thereof binds a region of human FGFR3 polypeptide comprising the amino acids D143 through L163 of SEQ ID NO: 133.

In certain embodiments, the antigen binding protein or antigen-binding fragment thereof binds a region of human FGFR3 polypeptide comprising the amino acids D143 through N170 of SEQ ID NO: 133.

In certain embodiments, the antigen binding protein or antigen-binding fragment thereof binds a region of human FGFR3 polypeptide comprising the amino acids D143 through D160 and G197 through L213 of SEQ ID NO: 133.

In certain embodiments, the antigen binding protein or antigen-binding binding fragment thereof is a chimeric or humanized antibody or antigen-binding binding fragment thereof.

In certain embodiments, the antigen binding protein or antigen-binding binding fragment thereof is a human antibody or antigen-binding binding fragment thereof.

In certain embodiments, the antigen binding protein or antigen-binding binding fragment thereof is a monoclonal antibody or antigen-binding binding fragment thereof.

In certain embodiments, the antigen binding protein or antigen-binding binding fragment thereof comprises one or more full-length antibody heavy chains comprising an Fc region.

In certain embodiments, the Fc region is a human IgG1 Fc region.

In certain embodiments, the antigen binding protein or antigen-binding binding fragment thereof comprises an antibody F(ab), F(ab')2, Fab'-SH, Fv, or scFv fragment.

In certain embodiments, the antigen binding protein or antigen-binding binding fragment thereof comprises an antibody F(ab) fragment.

In certain embodiments, the antibody F(ab) fragment comprises SEQ ID NO: 56 and the first about 100 amino acids of SEQ ID NO: 54.

In certain embodiments, the antibody F(ab) fragment comprises SEQ ID NO: 57 and the first about 100 amino acids of SEQ ID NO: 54.

In certain embodiments, the antibody F(ab) fragment comprises SEQ ID NO: 58 and the first about 100 amino acids of SEQ ID NO: 54.

In certain embodiments, the antibody F(ab) fragment heavy chain comprises the amino acid sequence of SEQ ID NO: 141 and the antibody F(ab) fragment light chain comprises the amino acid sequence of SEQ ID NO: 142.

In certain embodiments, the antibody F(ab) fragment heavy chain comprises the amino acid sequence of SEQ ID NO: 143 and the antibody F(ab) fragment light chain comprises the amino acid sequence of SEQ ID NO: 144.

In certain embodiments, the antibody F(ab) fragment heavy chain comprises the amino acid sequence of SEQ ID NO: 145 and the antibody F(ab) fragment light chain comprises the amino acid sequence of SEQ ID NO: 146.

In certain embodiments, the antibody F(ab) fragment heavy chain comprises the amino acid sequence of SEQ ID NO: 147 and the antibody F(ab) fragment light chain comprises the amino acid sequence of SEQ ID NO: 148.

In certain embodiments, the antibody F(ab) fragment heavy chain comprises the amino acid sequence of SEQ ID NO: 149 and the antibody F(ab) fragment light chain comprises the amino acid sequence of SEQ ID NO: 150.

In certain embodiments, the antibody F(ab) fragment heavy chain comprises the amino acid sequence of SEQ ID NO: 151 and the antibody F(ab) fragment light chain comprises the amino acid sequence of SEQ ID NO: 152.

In certain embodiments, the antibody F(ab) fragment heavy chain comprises the amino acid sequence of SEQ ID NO: 153 and the antibody F(ab) fragment light chain comprises the amino acid sequence of SEQ ID NO: 67.

In certain embodiments, the antibody F(ab) fragment heavy chain comprises the amino acid sequence of SEQ ID NO: 153 and the antibody F(ab) fragment light chain comprises the amino acid sequence of SEQ ID NO: 154.

In certain embodiments, the antibody F(ab) fragment heavy chain comprises the amino acid sequence of SEQ ID NO: 153 and the antibody F(ab) fragment light chain comprises the amino acid sequence of SEQ ID NO: 69.

In certain embodiments, the antibody F(ab) fragment heavy chain comprises the amino acid sequence of SEQ ID NO: 155 and the antibody F(ab) fragment light chain comprises the amino acid sequence of SEQ ID NO: 67.

In certain embodiments, the antibody F(ab) fragment heavy chain comprises the amino acid sequence of SEQ ID NO: 155 and the antibody F(ab) fragment light chain comprises the amino acid sequence of SEQ ID NO: 154.

In certain embodiments, the antibody F(ab) fragment heavy chain comprises the amino acid sequence of SEQ ID NO: 155 and the antibody F(ab) fragment light chain comprises the amino acid sequence of SEQ ID NO: 69.

In certain embodiments, the antibody F(ab) fragment heavy chain comprises the amino acid sequence of SEQ ID NO: 156 and the antibody F(ab) fragment light chain comprises the amino acid sequence of SEQ ID NO: 67.

In certain embodiments, the antibody F(ab) fragment heavy chain comprises the amino acid sequence of SEQ ID NO: 156 and the antibody F(ab) fragment light chain comprises the amino acid sequence of SEQ ID NO: 154.

In certain embodiments, the antibody F(ab) fragment heavy chain comprises the amino acid sequence of SEQ ID NO: 156 and the antibody F(ab) fragment light chain comprises the amino acid sequence of SEQ ID NO: 69.

In certain embodiments, the antigen binding protein or antigen-binding binding fragment thereof comprises cross-reactivity to mouse and cynomolgus FGFR3.

In certain embodiments, the antigen binding or antigen-binding binding fragment thereof protein does not bind to one or more of FGFR1, FGFR2, and FGFR4.

In certain embodiments, the antigen binding protein or antigen-binding binding fragment thereof does not bind to each of FGFR1, FGFR2, and FGFR4.

In certain embodiments, the antigen binding protein or antigen-binding binding fragment thereof binds to each of FGFR1, FGFR2, and FGFR4 with an affinity of 100 µM or greater.

In certain embodiments, the antigen binding protein or antigen-binding binding fragment thereof binds human FGFR3 with an equilibrium dissociation constant (KD) of 10 nM or less.

In certain embodiments, the antigen binding protein or antigen-binding binding fragment thereof binds human FGFR3 with an off rate (Kd) of $10^{-4}$ or greater.

In certain embodiments, the antigen binding protein or antigen-binding binding fragment thereof inhibits ligand-induced FGFR3 dimerization with $IC_{50}$ of 5 µg/ml or less.

In certain embodiments, the antigen binding protein or antigen-binding binding fragment thereof inhibits FGFR3 receptor activation and downstream signaling with $IC_{50}$ of 5 µg/ml or less.

In certain embodiments, the antigen binding protein or antigen-binding binding fragment thereof inhibits the activity of an $FGFR3^{G380R}$ mutant.

In certain embodiments, the antigen binding protein or antigen-binding fragment thereof is capable of penetrating a bone growth plate.

In certain embodiments, the antigen binding protein or antigen-binding fragment thereof is capable of decreasing binding of FGFR3 and its ligand in a bone growth plate.

In another aspect, the disclosure provides a pharmaceutical composition comprising the antigen binding protein or antigen-binding fragment thereof recited above, and a pharmaceutically acceptable carrier.

In another aspect, the disclosure provides an isolated nucleic acid molecule encoding the antigen binding protein or antigen-binding fragment thereof recited above.

In another aspect, the disclosure provides an expression vector comprising the nucleic acid molecule recited above.

In another aspect, the disclosure provides a host cell comprising the expression vector recited above.

In another aspect, the disclosure provides a method for treating a FGFR3-mediated disease or disorder in a subject, comprising administering to a subject in need thereof the antigen binding protein or antigen-binding fragment thereof recited above.

In certain embodiments, the FGFR3-mediated disease or disorder is achondroplasia.

In certain embodiments, the achondroplasia is $FGFR3^{G380R+}$ achondroplasia.

In certain embodiments, the subject suffering from achondroplasia comprises one or more symptoms selected from the group consisting of shortened proximal limbs, brachydactyly, large head with prominent forehead frontal bossing, small midface with a flattened nasal bridge, spinal kyphosis, spinal lordosis, varus, valgus, ear infections, sleep apnea, and hydrocephalus.

In certain embodiments, the FGFR3-mediated disease or disorder is cancer.

In certain embodiments, the cancer is bladder cancer melanoma, urothelial cancer, and endometrial cancer.

In one aspect, the disclosure provides a method for treating achondroplasia in a subject, comprising administering to a subject in need thereof an antigen-binding protein fragment that specifically binds to FGFR3, wherein the antigen binding protein fragment does not bind to one or more of FGFR1, FGFR2, and FGFR4.

In one aspect, the disclosure provides a method for inhibiting one or both of FGFR3 activity and expression in a bone growth plate of a subject, comprising administering to a subject an antigen-binding protein fragment that specifically binds to FGFR3, wherein the antigen binding protein fragment does not bind to one or more of FGFR1, FGFR2, and FGFR4.

In one aspect, the disclosure provides an antigen-binding protein or antigen-binding fragment thereof that specifically binds to fibroblast growth factor receptor 3 (FGFR3), comprising an antibody heavy chain variable (VH) domain and an antibody light chain variable (VL) domain, wherein the antigen binding protein binds a human FGFR3 polypeptide comprising the amino acid sequence of SEQ ID NO: 134.

In certain embodiments, the antigen binding protein binds a region of human FGFR3 polypeptide comprising the amino acids D143 through L163 of SEQ ID NO: 133.

In certain embodiments, the antigen binding protein or antigen-binding binding fragment thereof binds a region of human FGFR3 polypeptide comprising the amino acids D143 through N170 of SEQ ID NO: 133.

In certain embodiments, the antigen binding protein or antigen-binding binding fragment thereof binds a region of human FGFR3 polypeptide comprising the amino acids D143 through D160 and G197 through L213 of SEQ ID NO: 133.

In one aspect, the disclosure provides an antigen-binding protein or antigen-binding fragment thereof with binding specificity to a fibroblast growth factor receptor 3 (FGFR3) epitope, comprising an antibody heavy chain variable (VH) domain and an antibody light chain variable (VL) domain, wherein the antigen binding protein or antigen-binding binding fragment thereof competes for binding to FGFR3 with an antibody comprising VH/VL domain amino acid sequence pairs selected from the group consisting of: SEQ ID NO: 6/SEQ ID NO: 7, SEQ ID NO: 8/SEQ ID NO: 9, SEQ ID NO: 10/SEQ ID NO: 11, SEQ ID NO: 12/SEQ ID NO: 13, SEQ ID NO: 14/SEQ ID NO: 15, and SEQ ID NO: 16/SEQ ID NO: 17.

In certain embodiments, the antigen binding protein or antigen-binding binding fragment thereof is a chimeric or humanized antibody or antigen-binding binding fragment thereof.

In certain embodiments, the antigen binding protein or antigen-binding binding fragment thereof is a human antibody or antigen-binding binding fragment thereof.

In certain embodiments, the antigen binding protein or antigen-binding binding fragment thereof is a monoclonal antibody or antigen-binding binding fragment thereof.

In certain embodiments, the antigen binding protein or antigen-binding binding fragment thereof comprises one or more full-length antibody heavy chains comprising an Fc region.

In certain embodiments, the Fc region is a human IgG1 Fc region.

In certain embodiments, the antigen binding protein or antigen-binding binding fragment thereof comprises an antibody F(ab), F(ab')2, Fab'-SH, Fv, or scFv fragment.

In certain embodiments, the antigen binding protein or antigen-binding binding fragment thereof comprises an antibody F(ab) fragment.

In certain embodiments, the antibody F(ab) fragment comprises SEQ ID NO: 56 and the first about 100 amino acids of SEQ ID NO: 54.

In certain embodiments, the antibody F(ab) fragment comprises a heavy chain comprising SEQ ID NO: 57 and the first about 100 amino acids of SEQ ID NO: 54.

In certain embodiments, the antibody F(ab) fragment comprises a heavy chain comprising SEQ ID NO: 58 and the first about 100 amino acids of SEQ ID NO: 54.

In certain embodiments, the antibody F(ab) fragment heavy chain comprises the amino acid sequence of SEQ ID NO: 141, 164, 173, 182, 191, 200, 209, 218, 227, 236, 245, 254, 263, 272, or 281, and the antibody F(ab) fragment light chain comprises the amino acid sequence of SEQ ID NO: 142.

In certain embodiments, the antibody F(ab) fragment heavy chain comprises the amino acid sequence of SEQ ID NO: 143, 165, 174, 183, 192, 201, 210, 219, 228, 237, 246, 255, 264, 273, or 282, and the antibody F(ab) fragment light chain comprises the amino acid sequence of SEQ ID NO: 144.

In certain embodiments, the antibody F(ab) fragment heavy chain comprises the amino acid sequence of SEQ ID NO: 145, 166, 175, 184, 193, 202, 211, 220, 229, 238, 247, 256, 265, 274, or 283, and the antibody F(ab) fragment light chain comprises the amino acid sequence of SEQ ID NO: 146.

In certain embodiments, the antibody F(ab) fragment heavy chain comprises the amino acid sequence of SEQ ID NO: 147, 167, 176, 185, 194, 203, 212, 221, 230, 239, 248, 257, 266, 275, or 284, and the antibody F(ab) fragment light chain comprises the amino acid sequence of SEQ ID NO: 148.

In certain embodiments, the antibody F(ab) fragment heavy chain comprises the amino acid sequence of SEQ ID NO: 149, 168, 177, 186, 195, 204, 213, 222, 231, 240, 249, 258, 267, 276, or 285, and the antibody F(ab) fragment light chain comprises the amino acid sequence of SEQ ID NO: 150.

In certain embodiments, the antibody F(ab) fragment heavy chain comprises the amino acid sequence of SEQ ID NO: 151, 169, 178, 187, 196, 205, 214, 223, 232, 241, 250, 259, 268, 277, or 286, and the antibody F(ab) fragment light chain comprises the amino acid sequence of SEQ ID NO: 152.

In certain embodiments, the antibody F(ab) fragment heavy chain comprises the amino acid sequence of SEQ ID NO: 153, 170, 179, 188, 197, 206, 215, 224, 233, 242, 251, 260, 269, 278, or 287, and the antibody F(ab) fragment light chain comprises the amino acid sequence of SEQ ID NO: 67.

In certain embodiments, the antibody F(ab) fragment heavy chain comprises the amino acid sequence of SEQ ID NO: 153, 170, 179, 188, 197, 206, 215, 224, 233, 242, 251, 260, 269, 278, or 287, and the antibody F(ab) fragment light chain comprises the amino acid sequence of SEQ ID NO: 154.

In certain embodiments, the antibody F(ab) fragment heavy chain comprises the amino acid sequence of SEQ ID NO: 153, 170, 179, 188, 197, 206, 215, 224, 233, 242, 251, 260, 269, 278, or 287, and the antibody F(ab) fragment light chain comprises the amino acid sequence of SEQ ID NO: 69.

In certain embodiments, the antibody F(ab) fragment heavy chain comprises the amino acid sequence of SEQ ID NO: 155, 171, 180, 189, 198, 207, 216, 225, 234, 243, 252, 261, 270, 279, or 288, and the antibody F(ab) fragment light chain comprises the amino acid sequence of SEQ ID NO: 67.

In certain embodiments, the antibody F(ab) fragment heavy chain comprises the amino acid sequence of SEQ ID NO: 155, 171, 180, 189, 198, 207, 216, 225, 234, 243, 252, 261, 270, 279, or 288, and the antibody F(ab) fragment light chain comprises the amino acid sequence of SEQ ID NO: 154.

In certain embodiments, the antibody F(ab) fragment heavy chain comprises the amino acid sequence of SEQ ID NO: 155, 171, 180, 189, 198, 207, 216, 225, 234, 243, 252, 261, 270, 279, or 288, and the antibody F(ab) fragment light chain comprises the amino acid sequence of SEQ ID NO: 69.

In certain embodiments, the antibody F(ab) fragment heavy chain comprises the amino acid sequence of SEQ ID NO: 156, 172, 181, 190, 199, 208, 217, 226, 235, 244, 253, 262, 271, 280, or 289, and the antibody F(ab) fragment light chain comprises the amino acid sequence of SEQ ID NO: 67.

In certain embodiments, the antibody F(ab) fragment heavy chain comprises the amino acid sequence of SEQ ID NO: 156, 172, 181, 190, 199, 208, 217, 226, 235, 244, 253, 262, 271, 280, or 289, and the antibody F(ab) fragment light chain comprises the amino acid sequence of SEQ ID NO: 154.

In certain embodiments, the antibody F(ab) fragment heavy chain comprises the amino acid sequence of SEQ ID NO: 156, 172, 181, 190, 199, 208, 217, 226, 235, 244, 253, 262, 271, 280, or 289, and the antibody F(ab) fragment light chain comprises the amino acid sequence of SEQ ID NO: 69.

In certain embodiments, the antigen binding protein or antigen-binding binding fragment thereof comprises has cross-reactivity to mouse and cynomolgus FGFR3.

In certain embodiments, the antigen binding or antigen-binding binding fragment thereof protein does not bind to one or more of FGFR1, FGFR2, and FGFR4.

In certain embodiments, the antigen binding protein or antigen-binding binding fragment thereof does not bind to each of FGFR1, FGFR2, and FGFR4.

In certain embodiments, the antigen binding protein or antigen-binding binding fragment thereof binds to each of FGFR1, FGFR2, and FGFR4 with an affinity equilibrium dissociation constant (KD) of 100 µM or greater.

In certain embodiments, the antigen binding protein or antigen-binding binding fragment thereof binds human FGFR3 with an equilibrium dissociation constant (KD) of 10 nM or less.

In certain embodiments, the antigen binding protein or antigen-binding binding fragment thereof binds human FGFR3 with an off rate (Kd) of 10' or greater.

In certain embodiments, the antigen binding protein or antigen-binding binding fragment thereof inhibits ligand-induced FGFR3 dimerization with $IC_{50}$ of 5 µg/ml or less.

In certain embodiments, the antigen binding protein or antigen-binding binding fragment thereof inhibits FGFR3 receptor activation and downstream signaling with $IC_{50}$ of 5 µg/ml or less.

In certain embodiments, the antigen binding protein or antigen-binding binding fragment thereof inhibits the activity of an $FGFR3^{G380R}$ mutant.

In certain embodiments, the antigen binding protein or antigen-binding binding fragment thereof is capable of penetrating a bone growth plate.

In certain embodiments, the antigen binding protein or antigen-binding binding fragment thereof is capable of decreasing the binding of FGFR3 with its ligand in a bone growth plate. In certain embodiments, the antigen binding protein or antigen-binding binding fragment thereof is capable of decreasing the kinase activity of FGFR3 in a bone growth plate.

Also provided is a pharmaceutical composition comprising the antigen binding protein or antigen-binding fragment thereof as described herein. In certain embodiments, the pharmaceutical composition comprises a pharmaceutically acceptable carrier.

Also provided is an isolated nucleic acid molecule encoding the antigen binding protein or antigen-binding fragment thereof as described herein. Also provided is an expression cassette comprising said nucleic acid molecule. Also provided is an expression vector comprising the isolated nucleic acid molecule. Further provided is a host cell comprising the expression vector, the expression cassette or the nucleic acid molecule.

Further provided is a method for treating a FGFR3-mediated disease or disorder in a subject. In certain embodiments, the method comprises administering to a subject in need thereof the antigen binding protein or antigen-binding fragment thereof as described herein. In certain embodiments, the FGFR3-mediated disease or disorder is achondroplasia. In certain embodiments, the achondroplasia is $FGFR3^{G380R+}$ achondroplasia.

In certain embodiments, the FGFR3-mediated disease or disorder is cancer.

In certain embodiments, the cancer is bladder cancer melanoma, urothelial cancer, and endometrial cancer.

Also provided is a method for treating achondroplasia in a subject. In certain embodiments, the method comprises administering to a subject in need thereof an antigen-binding protein fragment that specifically binds to FGFR3, wherein the antigen binding protein fragment does not bind to one or more of FGFR1, FGFR2, and FGFR4.

Also provided is a method for inhibiting one or both of FGFR3 activity and expression in a bone growth plate of a subject. In certain embodiments, the method comprises administering to a subject an antigen-binding protein fragment that specifically binds to FGFR3, wherein the antigen binding protein fragment does not bind to one or more of FGFR1, FGFR2, and FGFR4.

In certain embodiments, the subject is a child. In certain embodiments, the child is an infant. In certain embodiments, the infant is a newborn.

Also provided is a method for preventing or alleviating one or more symptoms of achondroplasia in a subject. In certain embodiments, the method comprises administering to the subject an antigen-binding protein or an antigen-binding protein fragment thereof that specifically binds to FGFR3, wherein the antigen binding protein fragment does not bind to one or more of FGFR1, FGFR2, and FGFR4.

BRIEF DESCRIPTION OF THE DRAWINGS

The foregoing and other features and advantages of the present disclosure will be more fully understood from the following detailed description of illustrative embodiments taken in conjunction with the accompanying drawings. The patent or application file contains at least one drawing executed in color. Copies of this patent or patent application publication with color drawing(s) will be provided to the Office upon request and payment of the necessary fee.

FIG. 6 depicts an alignment of anti-FGFR3 antibodies KC18, KE63, and KE94.

FIG. 7 depicts an alignment of anti-FGFR3 antibody KC18_Hu18 with variants. Mutations of Hu18 residues are highlighted green or red.

FIG. 10A depicts inhibition effect of KC18 as a full-length antibody (KC18), a Fab fragment (Kc18 Fab), a one-armed, monovalent antibody (MetMab), and a PEGylated Fab fragment (PEG) in WT cells. FIG. 10B depicts inhibition effect of KC18 as a full-length antibody (IgG), a Fab fragment, a one-armed, monovalent antibody (MetMab), and a PEGylated Fab fragment (PEG) in Ach cells. FIG. 10C depicts KC18 fab fragments with half-life extension moieties using a human albumin nanobody conjugate (KC18 Fab-HLE), with and without human serum albumin (HSA) or mouse serum albumin (MSA). Erk phosphorylation was measured in an HTRF assay and compared to an isotype control (Iso).

DETAILED DESCRIPTION

Figure 1:
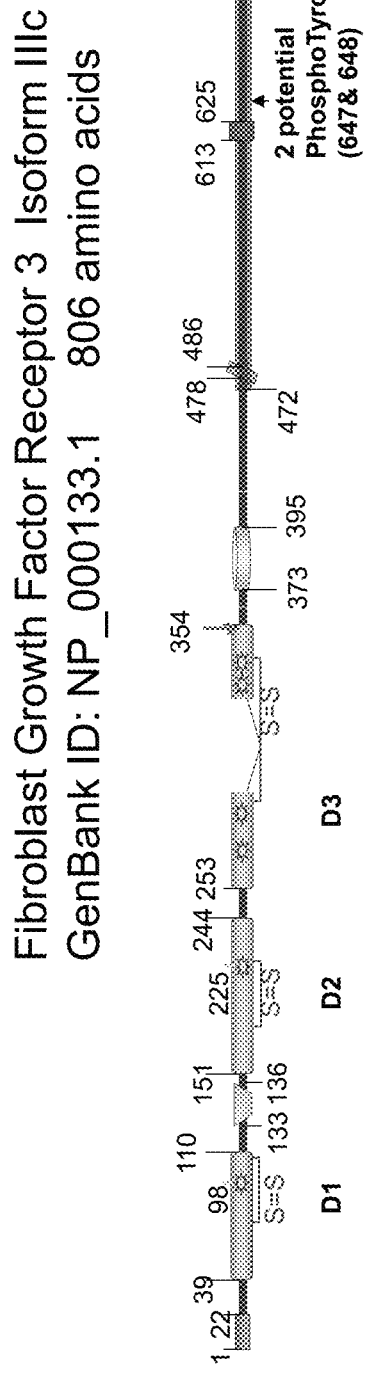
FIG. 1 schematically depicts fibroblast growth factor receptor 3 (FGFR3) isoform IIIc.
Figure 1:
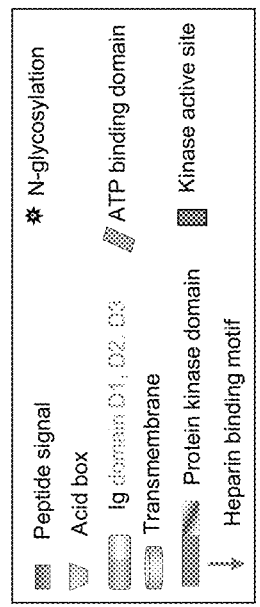

Antigen-binding proteins or antigen-binding fragments thereof are provided. Methods of inhibiting one or more FGFR3 activities, and methods of treating FGFR3-mediated diseases and disorders are also provided.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the disclosure may be more readily understood, certain terms are first defined.

Fibroblast Growth Factor Receptor 3 (FGFR3)

As used herein, the term "FGFR3" or "fibroblast growth factor receptor 3" or "CD333" refers to the FGFR3 protein encoded by the FGFR3 gene. FGFR3 belongs to a family of fibroblast growth factor receptors that also includes FGFR1, FGFR2, and FGFR4. Like the other fibroblast growth factor receptor family members, FGFR3 is a single-pass membrane receptor tyrosine kinase with 3 Ig-like domains (D1, D2, and D3). Ligand dependent receptor dimerization leads to tyrosine kinase activation and downstream signal transduction. FGFR3 undergoes alternative splicing leading to several isoforms, including isoform IIIb and isoform IIIc. IIIb and IIIc arise from alternative splicing of exons 8 and 9. IIb and IIc have identical Ig1 (D1) and Ig2 (D2) domains, but vary in the Ig3 (D3) domain. It is FGFR3 IIc that is the major FGFR3 isoform in chondrocytes and mediates the anabolic effects of the FGFR3 ligand, FGF18, in articular cartilage. The structure and function of FGFR3 is described in further detail in Olsen et al. (PNAS. 101(4): 935-940. 2004), incorporated herein by reference in its entirety for all purposes.

The human FGFR3 isoform IIIc amino acid sequence is recited below.

(SEQ ID NO: 135)
MGAPACALALCVAVAIVAGASSESLGTEQRVVGRAAEVPGPEPGQQEQLV

FGSGDAVELSCPPPGGGPMGPTVWVKDGTGLVPSERVLVGPQRLQVLNAS

HEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHR

IGGIKLRHQQWSLVMESVVPSDRGNYTCVVENKFGSIRQTYTLDVLERSP

HRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHH

SAWLVVLPAEEELVEADEAGSVYAGILSYGVGFFLFILVVAAVTLCRLRS

PPKKGLGSPTVHKISRFPLKRQVSLESNASMSSNTPLVRIARLSSGEGPT

LANVSELELPADPKWELSRARLTLGKPLGEGCFGQVVMAEAIGIDKDRAA

KPVTVAVKMLKDDATDKDLSDLVSEMEMMKMIGKHKNIINLLGACTQGGP

LYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKK

TTNGRLPVKWMAPEALFDRVYTHQSDVWSFGVLLWEIFTLGGSPYPGIPV

EELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPS

SGGSRT

Mutations in FGFR3 can lead to certain undesired conditions. A G380R mutation in the transmembrane domain of FGFR3 is associated with 98% of all achondroplasia cases. FGFR3 with a G380R mutation can be referred to as FGFR3$^{G380R}$ and the sequence of the human FGFR3$^{G380R}$ isoform IIIc is recited below.

(SEQ ID NO: 133)
MGAPACALALCVAVAIVAGASSESLGTEQRVVGRAAEVPGPEPGQQEQLV

FGSGDAVELSCPPPGGGPMGPTVWVKDGTGLVPSERVLVGPQRLQVLNAS

HEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHR

IGGIKLRHQQWSLVMESVVPSDRGNYTCVVENKFGSIRQTYTLDVLERSP

HRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHH

SAWLVVLPAEEELVEADEAGSVYAGILSYRVGFFLFILVVAAVTLCRLRS

PPKKGLGSPTVHKISRFPLKRQVSLESNASMSSNTPLVRIARLSSGEGPT

LANVSELELPADPKWELSRARLTLGKPLGEGCFGQVVMAEAIGIDKDRAA

KPVTVAVKMLKDDATDKDLSDLVSEMEMMKMIGKHKNIINLLGACTQGGP

LYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKK

TTNGRLPVKWMAPEALFDRVYTHQSDVWSFGVLLWEIFTLGGSPYPGIPV

EELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPS

SGGSRT

Antigen-Binding Proteins

As used herein, the term "antibody" or "antigen-binding protein" refers to an immunoglobulin molecule that specifically binds to, or is immunologically reactive with an antigen or epitope (e.g., a FGFR3 antigen or epitope), and includes both polyclonal and monoclonal antibodies, as well as functional antibody fragments thereof, including but not limited to fragment antigen-binding (Fab) fragments, F(ab')2 fragments, Fab' fragments, Fv fragments, recombinant IgG (rIgG) fragments, single chain variable fragments (scFv) and single domain antibodies (e.g., sdAb, sdFv, nanobody) fragments. The term "antibody" includes genetically engineered or otherwise modified forms of immunoglobulins, such as intrabodies, peptibodies, chimeric antibodies, fully human antibodies, humanized antibodies, meditope-enabled antibodies, heteroconjugate antibodies (e.g., bispecific antibodies, diabodies, triabodies, tetrabodies, tandem di-scFv, tandem tri-scFv) and the like. Unless otherwise stated, the term "antibody" should be understood to encompass functional antibody fragments thereof. As used herein, the term "functional antibody fragment" refers to an antibody fragment having at least 80%, at least 85%, at least 90%, or at least 95% affinity as the antibody of interest from which the fragment is derived from.

As used herein, the term "complementarity determining region" or "CDR" refers to sequences of amino acids within antibody variable regions, which confer antigen specificity and binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" or "FR" are known in the art to refer to the non-CDR portions of the variable regions of the heavy and light chains. In general, there are four FRs in each heavy chain variable region (FR-H1, FR-H2, FR-H3, and FR-H4), and four FRs in each light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745. ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, (AHo numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

A "CDR" or "complementary determining region," or individual specified CDRs (e.g., "CDR-H1," "CDR-H2," "CDR-H3"), of a given antibody or region thereof, such as a variable region thereof, should be understood to encompass a (or the specific) complementary determining region as defined by any of the known schemes. Likewise, an "FR" or "framework region," or individual specified FRs (e.g., "FR-H1," "FR-H2") of a given antibody or region thereof, such as a variable region thereof, should be understood to encompass a (or the specific) framework region as defined by any of the known schemes. In some instances, the scheme for identification of a particular CDR or FR is specified, such as the CDR as defined by the IMGT, Kabat, Chothia, AbM, or Contact method. In other cases, the particular amino acid sequence of a CDR or FR is given. Unless otherwise specified, all particular CDR amino acid sequences mentioned in the disclosure are IMGT CDRs. However, alternative CDRs defined by other schemes are also encompassed by the present disclosure, such as those determined by abYsis Key Annotation (Website: abysis.org/abysis/sequence_input/key_annotation/key_annotation.cgi).

As used herein, the term "specifically binds," "specifically binding," "binding specificity" or "specifically recognized" refers that an antigen binding protein or antigen-binding fragment thereof that exhibits appreciable affinity for an antigen (e.g., an FGFR3 antigen) and does not exhibit significant cross reactivity to a target that is not an FGFR3 protein. As used herein, the term "affinity" refers to the strength of the interaction between an antigen binding protein or antigen-binding fragment thereof antigen binding site and the epitope to which it binds. As readily understood by those skilled in the art, an antigen binding protein affinity may be reported as a dissociation constant (KD) in molarity (M). The antigen binding protein or antigen-binding fragment thereof of the disclosure have KD values in the range of about $10^{-6}$ M to about $10^{-12}$ M (i.e., low micromolar to picomolar range), about $10^{-7}$ M to $10^{-11}$ M, about $10^{-8}$ M to about $10^{-10}$ M, about $10^{-9}$ M. In certain embodiments, the antigen binding protein or antigen-binding fragment thereof has a binding affinity of about $10^{-6}$ M, $10^{-7}$ M, $10^{-8}$ M, $10^{-9}$ M, $10^{-10}$ M, $10^{-11}$ M, or $10^{-12}$ M. In certain embodiments, the antigen binding protein or antigen-binding fragment thereof has a binding affinity of about $10^{-7}$ M to about $10^{-9}$ M (nanomolar range).

Specific binding can be determined according to any art-recognized means for determining such binding. In some embodiments, specific binding is determined by competitive binding assays (e.g. ELISA) or Biacore assays. In certain embodiments, the assay is conducted at about 20° C., 25° C., 30° C., or 37° C.

Anti-FGFR3 Antigen-Binding Proteins

In one aspect, the disclosure provides antigen binding proteins and antigen-binding fragments thereof with binding specificity to FGFR3.

Exemplary anti-FGFR3 antigen binding protein and antigen-binding fragment thereof CDRs are recited below in Table 1 and Table 4. Exemplary anti-FGFR3 antigen binding protein and antigen-binding fragment thereof variable heavy (VH) and variable light (VL) domains are recited below in Table 3, Table 8, Table 9, and Table 13. Exemplary anti-FGFR3 antigen binding protein full length heavy and light chains are recited below in Table 14.

TABLE 1

Antibody Heavy chain and Light chain CDR regions

| VH Chain ID | HCDR1-IMGT | HCDR2-IMGT | HCDR3-IMGT |
|---|---|---|---|
| KC18_VH | GDTFTDFE (SEQ ID NO: 70) | IDPETGGT (SEQ ID NO: 71) | TRTYDGYPYAMDY (SEQ ID NO: 72) |
| KE35_VH | GYTFTDYN (SEQ ID NO: 76) | INPNNGGT (SEQ ID NO: 77) | ARERDYDGAMDY (SEQ ID NO: 78) |
| KE42_VH | GYTFTDYN (SEQ ID NO: 82) | INPNNGGT (SEQ ID NO: 83) | ARERDYDGSMDF (SEQ ID NO: 84) |
| KE58_VH | GYTVTDYY (SEQ ID NO: 88) | INPNNGVT (SEQ ID NO: 89) | AREEDFDGFDY (SEQ ID NO: 90) |
| KE63_VH | GSTFSDEE (SEQ ID NO: 94) | IDPETGGT (SEQ ID NO: 95) | TRNYDGYSQTMDY (SEQ ID NO: 96) |
| KE94_VH | GSTFTDEE (SEQ ID NO: 100) | IDPETGGT (SEQ ID NO: 101) | TRNYDGYSRTMDY (SEQ ID NO: 102) |
| KC18_Hu18_VH | GDTFTDFE (SEQ ID NO: 70) | VDPETGGT (SEQ ID NO: 297) | TRTYDGYPYAFDY (SEQ ID NO: 301) |
| KC18Hrw1 | GDTFTDFE (SEQ ID NO: 70) | IDPETGST (SEQ ID NO: 298) | TRTYDGYPYAMDY (SEQ ID NO: 72) |
| KC18Hrw2 | GDTFTDYE (SEQ ID NO: 295) | IDPETGST (SEQ ID NO: 298) | TRTYDGYPYAMDY (SEQ ID NO: 72) |
| KC18Hrw3 | GDTFTDYE (SEQ ID NO: 295) | IDPETGST (SEQ ID NO: 298) | TRTYDGYPYAMDY (SEQ ID NO: 72) |
| KC18HV1-69rw2 | GDTFTDFE (SEQ ID NO: 70) | VDPETGGT (SEQ ID NO: 297) | TRTYDGYPYAMDY (SEQ ID NO: 72) |
| KC18HV1-69rw3 | GDTFTDFE (SEQ ID NO: 70) | VDPETGGT (SEQ ID NO: 297) | TRTYEGYPYAMDY (SEQ ID NO: 300) |
| KC18HV1-69rw4 | GDTFTDFE (SEQ ID NO: 70) | VDPETGGT (SEQ ID NO: 297) | TRTYDGYPYAFDY (SEQ ID NO: 301) |
| KC18_CL_VH1 | GDTFTDFE (SEQ ID NO: 70) | IDPETGGT (SEQ ID NO: 95) | ARTYDGYPYAMDY (SEQ ID NO: 310) |
| KC18_CL_VH1b | GYTFTDFE (SEQ ID NO: 296) | VDPETGGT (SEQ ID NO: 297) | ARTYDGYPYAMDY (SEQ ID NO: 310) |
| KC18_CL_VH1c | GYTFTDFE (SEQ ID NO: 296) | VEPETGGT (SEQ ID NO: 299) | ARTYDGYPYAMDV (SEQ ID NO: 311) |
| KC18_CL_VH2 | GDTFTDFE (SEQ ID NO: 70) | IDPETGGT (SEQ ID NO: 95) | TRTYDGYPYAMDY (SEQ ID NO: 72) |
| KC18_CL_VH3 | GDTFTDFE (SEQ ID NO: 70) | IDPESGGT (SEQ ID NO: 312) | ARTYDGYPYAMDY (SEQ ID NO: 310) |
| KC18_CL_VH3b | GYTFTDFE (SEQ ID NO: 296) | IDPESGGT (SEQ ID NO: 312) | ARTYDGYPYAMDY (SEQ ID NO: 310) |

TABLE 1-continued

Antibody Heavy chain and Light chain CDR regions

| | | | |
|---|---|---|---|
| KC18_CL_VH3c | GYTFTDFE (SEQ ID NO: 296) | IEPESGGT (SEQ ID NO: 313) | ARTYDGYPYAMDV (SEQ ID NO: 311) |
| KC18_CL_VH4 | GDTFTDFE (SEQ ID NO: 70) | IDPETGGT (SEQ ID NO: 95) | TRTYDGYPYAMDY (SEQ ID NO: 72) |
| KC18_VH_6 | GDTFTDFE (SEQ ID NO: 70) | VDPETGGT (SEQ ID NO: 297) | TRTYDGYPYAFDY (SEQ ID NO: 301) |
| KC18_VH_15 | GDTFTDFE (SEQ ID NO: 70) | VDPETGGT (SEQ ID NO: 297) | TRTYDGYPYAFDY (SEQ ID NO: 301) |
| KC18_VH_16 | GDTFTDFE (SEQ ID NO: 70) | VDPETGGT (SEQ ID NO: 297) | TRTYDGYPYAFDY (SEQ ID NO: 301) |
| KE63_Hu01 VH | GSTFSDEE (SEQ ID NO: 94) | IDPETGGT (SEQ ID NO: 95) | TRNYDGYSQTFDY (SEQ ID NO: 305) |
| KE63_Hu02 VH | GSTFSDEE (SEQ ID NO: 94) | IDPETGGT (SEQ ID NO: 95) | TRNYDGYSQTFDY (SEQ ID NO: 305) |
| KE63_Hu03 VH | GSTFSDEE (SEQ ID NO: 94) | IDPETGGT (SEQ ID NO: 95) | TRNYDGYSQTFDY (SEQ ID NO: 305) |
| KE63_Hu04 VH | GSTFSDEE (SEQ ID NO: 94) | IDPETGGT (SEQ ID NO: 95) | TRNYDGYSQTFDY (SEQ ID NO: 305) |
| KE94_Hu01 VH | GSTFTDEE (SEQ ID NO: 100) | IDPETGGT (SEQ ID NO: 101) | TRNYDGYSRTFDY (SEQ ID NO: 307) |
| KE94_Hu02 VH | GSTFTDEE (SEQ ID NO: 100) | IDPETGGT (SEQ ID NO: 101) | TRNYDGYSRTFDY (SEQ ID NO: 307) |
| KE94_Hu03 VH | GSTFTDEE (SEQ ID NO: 100) | IDPETGGT (SEQ ID NO: 101) | TRNYDGYSRTFDY (SEQ ID NO: 307) |
| KE94_Hu04 VH | GSTFTDEE (SEQ ID NO: 100) | IDPETGGT (SEQ ID NO: 101) | TRNYDGYSRTFDY (SEQ ID NO: 307) |

LIGHT Chain

| VL Chain ID | LCDR1-IMGT | LCDR2-IMGT | LCDR3-IMGT |
|---|---|---|---|
| KC18_VL | QSLLYSNNQKNY (SEQ ID NO: 73) | WAS (SEQ ID NO: 74) | QQYYSYRT (SEQ ID NO: 75) |
| KE35_VL | QDINKF (SEQ ID NO: 79) | YTS (SEQ ID NO: 80) | LQYDNLLWT (SEQ ID NO: 81) |
| KE42_VL | QDINKF (SEQ ID NO: 85) | YTS (SEQ ID NO: 86) | LQYDNLLWT (SEQ ID NO: 87) |
| KE58_VL | QDVSTG (SEQ ID NO: 91) | WAS (SEQ ID NO: 92) | QQHYSTPLT (SEQ ID NO: 93) |
| KE63_VL | QSVLYSSNQKNY (SEQ ID NO: 97) | WAS (SEQ ID NO: 98) | HQYLSSYT (SEQ ID NO: 99) |
| KE94_VL | QSVLYSSNQKNY (SEQ ID NO: 103) | WAS (SEQ ID NO: 104) | HQYLSSYT (SEQ ID NO: 105) |
| KC18_Hu18 VL | QSVLYSNNNKNY (SEQ ID NO: 302) | WAS (SEQ ID NO: 74) | QQYYSYRT (SEQ ID NO: 75) |
| KC18Lrw1 | QSLLYSNNQKNY (SEQ ID NO: 73) | WAS (SEQ ID NO: 74) | QQYYSYRT (SEQ ID NO: 75) |
| KC18Lrw2 | QSVLYSSNNKNY (SEQ ID NO: X) | WAS (SEQ ID NO: 74) | QQYYSYRT (SEQ ID NO: 75) |
| KC18Lrw3 | QSVLYSNNNKNY (SEQ ID NO: 302) | WAS (SEQ ID NO: 74) | QQYYSYRT (SEQ ID NO: 75) |
| KC18_CL_VL1 | QSVLYSSNQKNY (SEQ ID NO: 97) | WAS (SEQ ID NO: 74) | QQYYSYRT (SEQ ID NO: 75) |

TABLE 1-continued

Antibody Heavy chain and Light chain CDR regions

| | | | |
|---|---|---|---|
| KC18_CL_VL1b | QSVLYSNNQKNY (SEQ ID NO: 315) | WAS (SEQ ID NO: 74) | QQYYSYRT (SEQ ID NO: 75) |
| KC18_CL_VL1c | QSVLYSSNQKNY (SEQ ID NO: 97) | WAS (SEQ ID NO: 74) | QQYYSYRT (SEQ ID NO: 75) |
| KC18_CL_VL1d | QSVLYSSNQKNY (SEQ ID NO: 97) | YAS (SEQ ID NO: 303) | QQYYSYRT (SEQ ID NO: 75) |
| KC18_CL_VL2 | QSLLYSNNQKNY (SEQ ID NO: 73) | WAS (SEQ ID NO: 74) | QQYYSYRT (SEQ ID NO: 75) |
| KC18_CL_VL3 | QSLLHSNNQKNY (SEQ ID NO: 317) | WGS (SEQ ID NO: 316) | QQYYSYRT (SEQ ID NO: 75) |
| KC18_CL_VL3b | QSLLYSNNQKNY (SEQ ID NO: 73) | WGS (SEQ ID NO: 316) | QQYYSYRT (SEQ ID NO: 75) |
| KC18_CL_VL4 | QSLLYSNNQKNY (SEQ ID NO: 73) | WGS (SEQ ID NO: 316) | QQYYSYRT (SEQ ID NO: 75) |
| KC18_CL_VL5 | QGISYSNNQKNY (SEQ ID NO: X) | WAS (SEQ ID NO: 74) | QQYYSYRT (SEQ ID NO: 75) |
| KC18_CL_VL6 | QSLLYSNNQKNY (SEQ ID NO: 73) | WAS (SEQ ID NO: 74) | QQYYSYRT (SEQ ID NO: 75) |
| KC18_VL_3 | QSVLYSNNNKNY (SEQ ID NO: 302) | WAS (SEQ ID NO: 74) | QQYYSYRT (SEQ ID NO: 75) |
| KC18_VL_14 | QSVLYSDNQKNY (SEQ ID NO: 306) | YAS (SEQ ID NO: 303) | QQYYSYRT (SEQ ID NO: 75) |
| KC18_VL_15 | QSVLYSDNQKNY (SEQ ID NO: 306) | FAS (SEQ ID NO: 304) | QQYYSYRT (SEQ ID NO: 75) |
| KE63_Hu01 VL | QSVLYSSNQKNY (SEQ ID NO: 97) | WAS (SEQ ID NO: 98) | HQYLSSYT (SEQ ID NO: 99) |
| KE63_Hu02 VL | QSVLYSSNQKNY (SEQ ID NO: 97) | WAS (SEQ ID NO: 98) | HQYLSPYT (SEQ ID NO: 314) |
| KE63_Hu03 VL | QSVLYSDNQKNY (SEQ ID NO: 306) | YAS (SEQ ID NO: 303) | HQYLSPYT (SEQ ID NO: 314) |
| KE63_Hu04 VL | QSVLYSDNQKNY (SEQ ID NO: 306) | FAS (SEQ ID NO: 304) | HQYLSPYT (SEQ ID NO: 314) |
| KE94_Hu01 VL | QSVLYSSNQKNY (SEQ ID NO: 97) | WAS (SEQ ID NO: 104) | HQYLSSYT (SEQ ID NO: 105) |
| KE94_Hu02 VL | QSVLYSSNQKNY (SEQ ID NO: 97) | WAS (SEQ ID NO: 104) | HQYLSPYT (SEQ ID NO: 314) |
| KE94_Hu03 VL | QSVLYSDNQKNY (SEQ ID NO: 306) | YAS (SEQ ID NO: 303) | HQYLSPYT (SEQ ID NO: 314) |
| KE94_Hu04 VL | QSVLYSDNQKNY (SEQ ID NO: 306) | FAS (SEQ ID NO: 304) | HQYLSPYT (SEQ ID NO: 314) |

In certain embodiments, the anti-FGFR3 antigen binding proteins and antigen-binding fragments thereof comprise an antibody heavy chain variable (VH) domain comprising a CDR-H1 sequence, a CDR-H2 sequence, and a CDR-H3 sequence. The CDR-H1 sequence comprises the amino acid sequence of GX$^1$TFTDX$^2$E (SEQ ID NO: 157), wherein X$^1$ comprises Y or D and X$^2$ comprises F or Y; the CDR-H2 sequence comprises the amino acid sequence of IDPETGX$^3$T (SEQ ID NO: 158), wherein X$^3$ comprises G or S; or CDR-H2 sequence comprising the amino acid sequence of INPNNGX$^4$T (SEQ ID NO: 159), wherein X$^4$ comprises G or V; or CDR-H2 sequence comprising the amino acid sequence of VX$^5$PETGGT (SEQ ID NO: 160), wherein X$^5$ comprises D or E; and the CDR-H3 sequence comprises the amino acid sequence of TRX$^6$YX$^7$GYX$^8$X$^9$X$^{10}$X$^{11}$DY (SEQ ID NO: 161), wherein X$^6$ comprises T or N, X$^7$ comprises D or E, X$^8$ comprises S or P, X$^9$ comprises Q, R, or Y, X$^{10}$ comprises T or A, X$^{11}$ comprises F or M.

In certain embodiments, the anti-FGFR3 antigen binding proteins and antigen-binding fragments thereof comprise an antibody light chain variable (VL) domain comprising a CDR-L1 sequence, a CDR-L2 sequence, and a CDR-L3 sequence. The CDR-L1 sequence comprises the amino acid sequence of QS X$^{12}$LYS X$^{13}$N X$^{14}$KNY (SEQ ID NO: 162), wherein X$^{12}$ comprises L or V, X$^{13}$ comprises N, D, or S, and X$^{14}$ comprises Q or N; the CDR-L2 sequence comprises the amino acid sequence of X$^{15}$AS (SEQ ID NO: 163), wherein $X^{15}$ comprises W, Y, or F; and the CDR-L3 sequence comprises the amino acid sequence of QQYYSYRT (SEQ ID NO: 75), LQYDNLLWT (SEQ ID NO: 81), or HQYLSX$^{16}$YT (SEQ ID NO: 290), wherein $X^{16}$ comprises P or S.

In one aspect, the disclosure provides an antigen-binding protein or fragment thereof that specifically binds to fibroblast growth factor receptor 3 (FGFR3), comprising an antibody heavy chain variable (VH) domain and an antibody light chain variable (VL) domain, wherein:

(a) the VH domain comprises a CDR-H1 sequence comprising the amino acid sequence of GX$^1$TFTDX$^2$E (SEQ ID NO: 157), wherein $X^1$ comprises Y or D and $X^2$ comprises F or Y; a CDR-H2 sequence comprising the amino acid sequence of IDPETGX$^3$T (SEQ ID NO: 158), wherein $X^3$ comprises G or S; or CDR-H2 sequence comprising the amino acid sequence of INPNNGX$^4$T (SEQ ID NO: 159), wherein $X^4$ comprises G or V; or CDR-H2 sequence comprising the amino acid sequence of VX$^5$PETGGT (SEQ ID NO: 160), wherein $X^5$ comprises D or E; a CDR-H3 sequence comprising the amino acid sequence of TRX$^6$YX$^7$GYX$^8$X$^9$X$^{10}$X$^{11}$DY (SEQ ID NO: 161), wherein $X^6$ comprises T or N, $X^7$ comprises D or E, $X^8$ comprises S or P, $X^9$ comprises Q, R, or Y, $X^{10}$ comprises T or A, $X^{11}$ comprises F or M; and the VL domain comprises a CDR-L1 sequence comprising the amino acid sequence of QS X$^{12}$LYS X$^{13}$N X$^{14}$KNY (SEQ ID NO: 162), wherein $X^{12}$ comprises L or V, $X^{13}$ comprises N, D, or S, and $X^{14}$ comprises Q or N; a CDR-L2 sequence comprising the amino acid sequence of X$^{15}$AS (SEQ ID NO: 163), wherein $X^{15}$ comprises W, Y, or F; a CDR-L3 sequence comprising the amino acid sequence of QQYYSYRT (SEQ ID NO: 75), LQYDNLLWT (SEQ ID NO: 81), or HQYLSX$^{16}$YT (SEQ ID NO: 290) wherein $X^{16}$ comprises P or S;

(b) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGAMDY (SEQ ID NO: 78); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87);

(c) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGSMDF (SEQ ID NO: 84); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87);

(d) the VH domain comprises a CDR-H1 sequence comprising the amino acid sequence of GYTVTDYY (SEQ ID NO: 88); a CDR-H2 sequence comprising the amino acid sequence of INPNNGVT (SEQ ID NO: 89); a CDR-H3 sequence comprising the amino acid sequence of AREEDFDGFDY (SEQ ID NO: 90); and the VL domain comprises a CDR-L1 sequence comprising the amino acid sequence of QDVSTG (SEQ ID NO: 91); a CDR-L2 sequence comprising the amino acid sequence of WAS (SEQ ID NOs: 74, 92, 98, and 104); a CDR-L3 sequence comprising the amino acid sequence of QQHYSTPLT (SEQ ID NO: 93);

(e) the VH domain comprises a CDR-H1 sequence comprising the amino acid sequence of GSTFSDFE (SEQ ID NO: 94); a CDR-H2 sequence comprising the amino acid sequence of IDPETGGT (SEQ ID NOs: 71, 95, and 101); a CDR-H3 sequence comprising the amino acid sequence of TRNYDGYSQTX$^{17}$DY (SEQ ID NO: 308), wherein $X^{17}$ comprises M or F; and the VL domain comprises a CDR-L1 sequence comprising the amino acid sequence of QSVLYSX$^{18}$NQKNY (SEQ ID NO: 309), wherein $X^{18}$ comprises S or D; a CDR-L2 sequence comprising the amino acid sequence of WAS (SEQ ID NOs: 74, 92, 98, and 104); a CDR-L3 sequence comprising the amino acid sequence of or HQYLSSYT (SEQ ID NOs: 99 and 105); or (f) the VH domain comprises a CDR-H1 sequence comprising the amino acid sequence of GSTFTDFE (SEQ ID NO: 100); a CDR-H2 sequence comprising the amino acid sequence of IDPETGGT (SEQ ID NOs: 71, 95, and 101); a CDR-H3 sequence comprising the amino acid sequence of TRNYDGYSQTX$^{17}$DY (SEQ ID NO: 308), wherein $X^{17}$ comprises M or F; and the VL domain comprises a CDR-L1 sequence comprising the amino acid sequence of QSVLYSX$^{18}$NQKNY (SEQ ID NO: 309), wherein $X^{18}$ comprises S or D; a CDR-L2 sequence comprising the amino acid sequence of WAS (SEQ ID NOs: 74, 92, 98, and 104); a CDR-L3 sequence comprising the amino acid sequence of HQYLSSYT (SEQ ID NOs: 99 and 105).

In certain embodiments, the antigen binding protein or fragment thereof comprises a VH domain and a VL domain, wherein:

(a) the VH domain comprises a CDR-H1 sequence comprising the amino acid sequence of GDTFTDFE (SEQ ID NO: 70), GDTFTDYE (SEQ ID NO: 295), or GYTFTDFE (SEQ ID NO: 296); a CDR-H2 sequence comprising the amino acid sequence of IDPETGGT (SEQ ID NOs: 71, 95, and 101), VDPETGGT (SEQ ID NO: 297), IDPETGST (SEQ ID NO: 298), or VEPETGGT (SEQ ID NO: 299); a CDR-H3 sequence comprising the amino acid sequence of TRTYDGYPYAMDY (SEQ ID NO: 72), TRTYEGYPYAMDY (SEQ ID NO: 300), or TRTYDGYPYAFDY (SEQ ID NO: 301); and the VL domain comprises a CDR-L1 sequence comprising the amino acid sequence of QSLLYSNNQKNY (SEQ ID NO: 73), QSVLYSNNNKNY (SEQ ID NO: 302), or QSVLYSDNQKNY (SEQ ID NO: 306); a CDR-L2 sequence comprising the amino acid sequence of WAS (SEQ ID NOs: 74, 92, 98, and 104), YAS (SEQ ID NO: 303), or FAS (SEQ ID NO: 304); a CDR-L3 sequence comprising the amino acid sequence of QQYYSYRT (SEQ ID NO: 75);

(b) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGAMDY (SEQ ID NO: 78); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87);

(c) the VH domain comprises a CDR-H1 sequence comprising the amino acid sequence of GYTFTDYN (SEQ ID NOs: 76 and 82); a CDR-H2 sequence comprising the amino acid sequence of INPNNGGT (SEQ ID NOs: 77 and 83); a CDR-H3 sequence comprising the amino acid sequence of ARERDYDGSMDF (SEQ ID NO: 84); and the VL domain comprises a CDR-L1 sequence comprising the amino acid sequence of QDINKF (SEQ ID NOs: 79 and 85); a CDR-L2 sequence comprising the amino acid sequence of YTS (SEQ ID NOs: 80 and 86); a CDR-L3 sequence comprising the amino acid sequence of LQYDNLLWT (SEQ ID NOs: 81 and 87);

(d) the VH domain comprises a CDR-H1 sequence comprising the amino acid sequence of GYTVTDYY (SEQ ID NO: 88); a CDR-H2 sequence comprising the amino acid sequence of INPNNGVT (SEQ ID NO: 89); a CDR-H3 sequence comprising the amino acid sequence of AREEDFDGFDY (SEQ ID NO: 90); and the VL domain comprises a CDR-L1 sequence comprising the amino acid sequence of QDVSTG (SEQ ID NO: 91); a CDR-L2 sequence comprising the amino acid sequence of WAS (SEQ ID NOs: 74, 92, 98, 104); a CDR-L3 sequence comprising the amino acid sequence of QQHYSTPLT (SEQ ID NO: 93);

(e) the VH domain comprises a CDR-H1 sequence comprising the amino acid sequence of GSTFSDFE (SEQ ID NO: 94); a CDR-H2 sequence comprising the amino acid sequence of IDPETGGT (SEQ ID NOs: 71, 95, and 101); a CDR-H3 sequence comprising the amino acid sequence of TRNYDGYSQTMDY (SEQ ID NO: 96) or TRNYDGYSQTFDY (SEQ ID NO: 305); and the VL domain comprises a CDR-L1 sequence comprising the amino acid sequence of QSVLYSSNQKNY(SEQ ID NOs: 97 and 103) or QSVLYSDNQKNY (SEQ ID NO: 306); a CDR-L2 sequence comprising the amino acid sequence of WAS (SEQ ID NOs: 74, 92, 98, and 104); a CDR-L3 sequence comprising the amino acid sequence of or HQYLSSYT (SEQ ID NOs: 99 and 105); or (f) the VH domain comprises a CDR-H1 sequence comprising the amino acid sequence of GSTFTDFE (SEQ ID NO: 100); a CDR-H2 sequence comprising the amino acid sequence of IDPETGGT (SEQ ID NOs: 71, 95, and 101); a CDR-H3 sequence comprising the amino acid sequence of TRNYDGYSRTMDY (SEQ ID NO: 102) or TRNYDGYSRTFDY (SEQ ID NO: 307); and the VL domain comprises a CDR-L1 sequence comprising the amino acid sequence of QSVLYSSNQKNY(SEQ ID NOs: 97 and 103) or QSVLYSDNQKNY (SEQ ID NO: 306); a CDR-L2 sequence comprising the amino acid sequence of WAS (SEQ ID NOs: 74, 92, 98, 104); a CDR-L3 sequence comprising the amino acid sequence of or HQYLSSYT (SEQ ID NOs: 99 and 105).

In certain embodiments, the FGFR3 antigen binding proteins and antigen-binding fragments thereof comprise one VH domain and one VL domain recited in Table 3, 8, 9, or 13. In certain embodiments, exemplary antigen-binding proteins or antigen-binding fragments thereof are provided:

TABLE 1.1

Heavy chains and light chains of exemplary antigen-binding proteins or antigen-binding fragments

| No. | Heavy Chain | Light Chain |
|---|---|---|
| 1 | SEQ ID NO: 6 | SEQ ID NO: 7 |
| 2 | SEQ ID NO: 6 | SEQ ID NO: 9 |
| 3 | SEQ ID NO: 6 | SEQ ID NO: 11 |
| 4 | SEQ ID NO: 6 | SEQ ID NO: 13 |
| 5 | SEQ ID NO: 6 | SEQ ID NO: 15 |
| 6 | SEQ ID NO: 6 | SEQ ID NO: 17 |
| 7 | SEQ ID NO: 8 | SEQ ID NO: 7 |

TABLE 1.1-continued

Heavy chains and light chains of exemplary antigen-binding proteins or antigen-binding fragments

| No. | Heavy Chain | Light Chain |
|---|---|---|
| 8 | SEQ ID NO: 8 | SEQ ID NO: 9 |
| 9 | SEQ ID NO: 8 | SEQ ID NO: 11 |
| 10 | SEQ ID NO: 8 | SEQ ID NO: 13 |
| 11 | SEQ ID NO: 8 | SEQ ID NO: 15 |
| 12 | SEQ ID NO: 8 | SEQ ID NO: 17 |
| 13 | SEQ ID NO: 10 | SEQ ID NO: 7 |
| 14 | SEQ ID NO: 10 | SEQ ID NO: 9 |
| 15 | SEQ ID NO: 10 | SEQ ID NO: 11 |
| 16 | SEQ ID NO: 10 | SEQ ID NO: 13 |
| 17 | SEQ ID NO: 10 | SEQ ID NO: 15 |
| 18 | SEQ ID NO: 10 | SEQ ID NO: 17 |
| 19 | SEQ ID NO: 12 | SEQ ID NO: 7 |
| 20 | SEQ ID NO: 12 | SEQ ID NO: 9 |
| 21 | SEQ ID NO: 12 | SEQ ID NO: 11 |
| 22 | SEQ ID NO: 12 | SEQ ID NO: 13 |
| 23 | SEQ ID NO: 12 | SEQ ID NO: 15 |
| 24 | SEQ ID NO: 12 | SEQ ID NO: 17 |
| 25 | SEQ ID NO: 14 | SEQ ID NO: 7 |
| 26 | SEQ ID NO: 14 | SEQ ID NO: 9 |
| 27 | SEQ ID NO: 14 | SEQ ID NO: 11 |
| 28 | SEQ ID NO: 14 | SEQ ID NO: 13 |
| 29 | SEQ ID NO: 14 | SEQ ID NO: 15 |
| 30 | SEQ ID NO: 14 | SEQ ID NO: 17 |
| 31 | SEQ ID NO: 18 | SEQ ID NO: 19 |
| 32 | SEQ ID NO: 18 | SEQ ID NO: 24 |
| 33 | SEQ ID NO: 18 | SEQ ID NO: 25 |
| 34 | SEQ ID NO: 18 | SEQ ID NO: 26 |
| 35 | SEQ ID NO: 18 | SEQ ID NO: 27 |
| 36 | SEQ ID NO: 18 | SEQ ID NO: 32 |
| 37 | SEQ ID NO: 18 | SEQ ID NO: 33 |
| 38 | SEQ ID NO: 18 | SEQ ID NO: 34 |
| 39 | SEQ ID NO: 18 | SEQ ID NO: 35 |
| 40 | SEQ ID NO: 18 | SEQ ID NO: 59 |
| 41 | SEQ ID NO: 18 | SEQ ID NO: 60 |
| 42 | SEQ ID NO: 18 | SEQ ID NO: 61 |
| 43 | SEQ ID NO: 18 | SEQ ID NO: 67 |
| 44 | SEQ ID NO: 18 | SEQ ID NO: 69 |
| 45 | SEQ ID NO: 18 | SEQ ID NO: 112 |
| 46 | SEQ ID NO: 18 | SEQ ID NO: 113 |
| 47 | SEQ ID NO: 18 | SEQ ID NO: 114 |
| 48 | SEQ ID NO: 18 | SEQ ID NO: 123 |
| 49 | SEQ ID NO: 18 | SEQ ID NO: 124 |
| 50 | SEQ ID NO: 18 | SEQ ID NO: 125 |
| 51 | SEQ ID NO: 18 | SEQ ID NO: 126 |
| 52 | SEQ ID NO: 18 | SEQ ID NO: 127 |
| 53 | SEQ ID NO: 18 | SEQ ID NO: 128 |
| 54 | SEQ ID NO: 18 | SEQ ID NO: 129 |
| 55 | SEQ ID NO: 18 | SEQ ID NO: 130 |
| 56 | SEQ ID NO: 18 | SEQ ID NO: 131 |
| 57 | SEQ ID NO: 18 | SEQ ID NO: 132 |
| 58 | SEQ ID NO: 20 | SEQ ID NO: 19 |
| 59 | SEQ ID NO: 20 | SEQ ID NO: 24 |
| 60 | SEQ ID NO: 20 | SEQ ID NO: 25 |
| 61 | SEQ ID NO: 20 | SEQ ID NO: 26 |
| 62 | SEQ ID NO: 20 | SEQ ID NO: 27 |
| 63 | SEQ ID NO: 20 | SEQ ID NO: 32 |
| 64 | SEQ ID NO: 20 | SEQ ID NO: 33 |
| 65 | SEQ ID NO: 20 | SEQ ID NO: 34 |
| 66 | SEQ ID NO: 20 | SEQ ID NO: 35 |
| 67 | SEQ ID NO: 20 | SEQ ID NO: 59 |
| 68 | SEQ ID NO: 20 | SEQ ID NO: 60 |
| 69 | SEQ ID NO: 20 | SEQ ID NO: 61 |
| 70 | SEQ ID NO: 20 | SEQ ID NO: 67 |
| 71 | SEQ ID NO: 20 | SEQ ID NO: 69 |
| 72 | SEQ ID NO: 20 | SEQ ID NO: 112 |
| 73 | SEQ ID NO: 20 | SEQ ID NO: 113 |
| 74 | SEQ ID NO: 20 | SEQ ID NO: 114 |
| 75 | SEQ ID NO: 20 | SEQ ID NO: 123 |
| 76 | SEQ ID NO: 20 | SEQ ID NO: 124 |
| 77 | SEQ ID NO: 20 | SEQ ID NO: 125 |
| 78 | SEQ ID NO: 20 | SEQ ID NO: 126 |
| 79 | SEQ ID NO: 20 | SEQ ID NO: 127 |
| 80 | SEQ ID NO: 20 | SEQ ID NO: 128 |
| 81 | SEQ ID NO: 20 | SEQ ID NO: 129 |
| 82 | SEQ ID NO: 20 | SEQ ID NO: 130 |

TABLE 1.1-continued

Heavy chains and light chains of exemplary antigen-binding proteins or antigen-binding fragments

| No. | Heavy Chain | Light Chain |
|---|---|---|
| 83 | SEQ ID NO: 20 | SEQ ID NO: 131 |
| 84 | SEQ ID NO: 20 | SEQ ID NO: 132 |
| 85 | SEQ ID NO: 21 | SEQ ID NO: 19 |
| 86 | SEQ ID NO: 21 | SEQ ID NO: 24 |
| 87 | SEQ ID NO: 21 | SEQ ID NO: 25 |
| 88 | SEQ ID NO: 21 | SEQ ID NO: 26 |
| 89 | SEQ ID NO: 21 | SEQ ID NO: 27 |
| 90 | SEQ ID NO: 21 | SEQ ID NO: 32 |
| 91 | SEQ ID NO: 21 | SEQ ID NO: 33 |
| 92 | SEQ ID NO: 21 | SEQ ID NO: 34 |
| 93 | SEQ ID NO: 21 | SEQ ID NO: 35 |
| 94 | SEQ ID NO: 21 | SEQ ID NO: 59 |
| 95 | SEQ ID NO: 21 | SEQ ID NO: 60 |
| 96 | SEQ ID NO: 21 | SEQ ID NO: 61 |
| 97 | SEQ ID NO: 21 | SEQ ID NO: 67 |
| 98 | SEQ ID NO: 21 | SEQ ID NO: 69 |
| 99 | SEQ ID NO: 21 | SEQ ID NO: 112 |
| 100 | SEQ ID NO: 21 | SEQ ID NO: 113 |
| 101 | SEQ ID NO: 21 | SEQ ID NO: 114 |
| 102 | SEQ ID NO: 21 | SEQ ID NO: 123 |
| 103 | SEQ ID NO: 21 | SEQ ID NO: 124 |
| 104 | SEQ ID NO: 21 | SEQ ID NO: 125 |
| 105 | SEQ ID NO: 21 | SEQ ID NO: 126 |
| 106 | SEQ ID NO: 21 | SEQ ID NO: 127 |
| 107 | SEQ ID NO: 21 | SEQ ID NO: 128 |
| 108 | SEQ ID NO: 21 | SEQ ID NO: 129 |
| 109 | SEQ ID NO: 21 | SEQ ID NO: 130 |
| 110 | SEQ ID NO: 21 | SEQ ID NO: 131 |
| 111 | SEQ ID NO: 21 | SEQ ID NO: 132 |
| 112 | SEQ ID NO: 22 | SEQ ID NO: 19 |
| 113 | SEQ ID NO: 22 | SEQ ID NO: 24 |
| 114 | SEQ ID NO: 22 | SEQ ID NO: 25 |
| 115 | SEQ ID NO: 22 | SEQ ID NO: 26 |
| 116 | SEQ ID NO: 22 | SEQ ID NO: 27 |
| 117 | SEQ ID NO: 22 | SEQ ID NO: 32 |
| 118 | SEQ ID NO: 22 | SEQ ID NO: 33 |
| 119 | SEQ ID NO: 22 | SEQ ID NO: 34 |
| 120 | SEQ ID NO: 22 | SEQ ID NO: 35 |
| 121 | SEQ ID NO: 22 | SEQ ID NO: 59 |
| 122 | SEQ ID NO: 22 | SEQ ID NO: 60 |
| 123 | SEQ ID NO: 22 | SEQ ID NO: 61 |
| 124 | SEQ ID NO: 22 | SEQ ID NO: 67 |
| 125 | SEQ ID NO: 22 | SEQ ID NO: 69 |
| 126 | SEQ ID NO: 22 | SEQ ID NO: 112 |
| 127 | SEQ ID NO: 22 | SEQ ID NO: 113 |
| 128 | SEQ ID NO: 22 | SEQ ID NO: 114 |
| 129 | SEQ ID NO: 22 | SEQ ID NO: 123 |
| 130 | SEQ ID NO: 22 | SEQ ID NO: 124 |
| 131 | SEQ ID NO: 22 | SEQ ID NO: 125 |
| 132 | SEQ ID NO: 22 | SEQ ID NO: 126 |
| 133 | SEQ ID NO: 22 | SEQ ID NO: 127 |
| 134 | SEQ ID NO: 22 | SEQ ID NO: 128 |
| 135 | SEQ ID NO: 22 | SEQ ID NO: 129 |
| 136 | SEQ ID NO: 22 | SEQ ID NO: 130 |
| 137 | SEQ ID NO: 22 | SEQ ID NO: 131 |
| 138 | SEQ ID NO: 22 | SEQ ID NO: 132 |
| 139 | SEQ ID NO: 23 | SEQ ID NO: 19 |
| 140 | SEQ ID NO: 23 | SEQ ID NO: 24 |
| 141 | SEQ ID NO: 23 | SEQ ID NO: 25 |
| 142 | SEQ ID NO: 23 | SEQ ID NO: 26 |
| 143 | SEQ ID NO: 23 | SEQ ID NO: 27 |
| 144 | SEQ ID NO: 23 | SEQ ID NO: 32 |
| 145 | SEQ ID NO: 23 | SEQ ID NO: 33 |
| 146 | SEQ ID NO: 23 | SEQ ID NO: 34 |
| 147 | SEQ ID NO: 23 | SEQ ID NO: 35 |
| 148 | SEQ ID NO: 23 | SEQ ID NO: 59 |
| 149 | SEQ ID NO: 23 | SEQ ID NO: 60 |
| 150 | SEQ ID NO: 23 | SEQ ID NO: 61 |
| 151 | SEQ ID NO: 23 | SEQ ID NO: 67 |
| 152 | SEQ ID NO: 23 | SEQ ID NO: 69 |
| 153 | SEQ ID NO: 23 | SEQ ID NO: 112 |
| 154 | SEQ ID NO: 23 | SEQ ID NO: 113 |
| 155 | SEQ ID NO: 23 | SEQ ID NO: 114 |
| 156 | SEQ ID NO: 23 | SEQ ID NO: 123 |
| 157 | SEQ ID NO: 23 | SEQ ID NO: 124 |
| 158 | SEQ ID NO: 23 | SEQ ID NO: 125 |
| 159 | SEQ ID NO: 23 | SEQ ID NO: 126 |
| 160 | SEQ ID NO: 23 | SEQ ID NO: 127 |
| 161 | SEQ ID NO: 23 | SEQ ID NO: 128 |
| 162 | SEQ ID NO: 23 | SEQ ID NO: 129 |
| 163 | SEQ ID NO: 23 | SEQ ID NO: 130 |
| 164 | SEQ ID NO: 23 | SEQ ID NO: 131 |
| 165 | SEQ ID NO: 23 | SEQ ID NO: 132 |
| 166 | SEQ ID NO: 28 | SEQ ID NO: 19 |
| 167 | SEQ ID NO: 28 | SEQ ID NO: 24 |
| 168 | SEQ ID NO: 28 | SEQ ID NO: 25 |
| 169 | SEQ ID NO: 28 | SEQ ID NO: 26 |
| 170 | SEQ ID NO: 28 | SEQ ID NO: 27 |
| 171 | SEQ ID NO: 28 | SEQ ID NO: 32 |
| 172 | SEQ ID NO: 28 | SEQ ID NO: 33 |
| 173 | SEQ ID NO: 28 | SEQ ID NO: 34 |
| 174 | SEQ ID NO: 28 | SEQ ID NO: 35 |
| 175 | SEQ ID NO: 28 | SEQ ID NO: 59 |
| 176 | SEQ ID NO: 28 | SEQ ID NO: 60 |
| 177 | SEQ ID NO: 28 | SEQ ID NO: 61 |
| 178 | SEQ ID NO: 28 | SEQ ID NO: 67 |
| 179 | SEQ ID NO: 28 | SEQ ID NO: 69 |
| 180 | SEQ ID NO: 28 | SEQ ID NO: 112 |
| 181 | SEQ ID NO: 28 | SEQ ID NO: 113 |
| 182 | SEQ ID NO: 28 | SEQ ID NO: 114 |
| 183 | SEQ ID NO: 28 | SEQ ID NO: 123 |
| 184 | SEQ ID NO: 28 | SEQ ID NO: 124 |
| 185 | SEQ ID NO: 28 | SEQ ID NO: 125 |
| 186 | SEQ ID NO: 28 | SEQ ID NO: 126 |
| 187 | SEQ ID NO: 28 | SEQ ID NO: 127 |
| 188 | SEQ ID NO: 28 | SEQ ID NO: 128 |
| 189 | SEQ ID NO: 28 | SEQ ID NO: 129 |
| 190 | SEQ ID NO: 28 | SEQ ID NO: 130 |
| 191 | SEQ ID NO: 28 | SEQ ID NO: 131 |
| 192 | SEQ ID NO: 28 | SEQ ID NO: 132 |
| 193 | SEQ ID NO: 29 | SEQ ID NO: 19 |
| 194 | SEQ ID NO: 29 | SEQ ID NO: 24 |
| 195 | SEQ ID NO: 29 | SEQ ID NO: 25 |
| 196 | SEQ ID NO: 29 | SEQ ID NO: 26 |
| 197 | SEQ ID NO: 29 | SEQ ID NO: 27 |
| 198 | SEQ ID NO: 29 | SEQ ID NO: 32 |
| 199 | SEQ ID NO: 29 | SEQ ID NO: 33 |
| 200 | SEQ ID NO: 29 | SEQ ID NO: 34 |
| 201 | SEQ ID NO: 29 | SEQ ID NO: 35 |
| 202 | SEQ ID NO: 29 | SEQ ID NO: 59 |
| 203 | SEQ ID NO: 29 | SEQ ID NO: 60 |
| 204 | SEQ ID NO: 29 | SEQ ID NO: 61 |
| 205 | SEQ ID NO: 29 | SEQ ID NO: 67 |
| 206 | SEQ ID NO: 29 | SEQ ID NO: 69 |
| 207 | SEQ ID NO: 29 | SEQ ID NO: 112 |
| 208 | SEQ ID NO: 29 | SEQ ID NO: 113 |
| 209 | SEQ ID NO: 29 | SEQ ID NO: 114 |
| 210 | SEQ ID NO: 29 | SEQ ID NO: 123 |
| 211 | SEQ ID NO: 29 | SEQ ID NO: 124 |
| 212 | SEQ ID NO: 29 | SEQ ID NO: 125 |
| 213 | SEQ ID NO: 29 | SEQ ID NO: 126 |
| 214 | SEQ ID NO: 29 | SEQ ID NO: 127 |
| 215 | SEQ ID NO: 29 | SEQ ID NO: 128 |
| 216 | SEQ ID NO: 29 | SEQ ID NO: 129 |
| 217 | SEQ ID NO: 29 | SEQ ID NO: 130 |
| 218 | SEQ ID NO: 29 | SEQ ID NO: 131 |
| 219 | SEQ ID NO: 29 | SEQ ID NO: 132 |
| 220 | SEQ ID NO: 30 | SEQ ID NO: 19 |
| 221 | SEQ ID NO: 30 | SEQ ID NO: 24 |
| 222 | SEQ ID NO: 30 | SEQ ID NO: 25 |
| 223 | SEQ ID NO: 30 | SEQ ID NO: 26 |
| 224 | SEQ ID NO: 30 | SEQ ID NO: 27 |
| 225 | SEQ ID NO: 30 | SEQ ID NO: 32 |
| 226 | SEQ ID NO: 30 | SEQ ID NO: 33 |
| 227 | SEQ ID NO: 30 | SEQ ID NO: 34 |
| 228 | SEQ ID NO: 30 | SEQ ID NO: 35 |
| 229 | SEQ ID NO: 30 | SEQ ID NO: 59 |
| 230 | SEQ ID NO: 30 | SEQ ID NO: 60 |
| 231 | SEQ ID NO: 30 | SEQ ID NO: 61 |
| 232 | SEQ ID NO: 30 | SEQ ID NO: 67 |

TABLE 1.1-continued

Heavy chains and light chains of exemplary antigen-binding proteins or antigen-binding fragments

| No. | Heavy Chain | Light Chain |
|---|---|---|
| 233 | SEQ ID NO: 30 | SEQ ID NO: 69 |
| 234 | SEQ ID NO: 30 | SEQ ID NO: 112 |
| 235 | SEQ ID NO: 30 | SEQ ID NO: 113 |
| 236 | SEQ ID NO: 30 | SEQ ID NO: 114 |
| 237 | SEQ ID NO: 30 | SEQ ID NO: 123 |
| 238 | SEQ ID NO: 30 | SEQ ID NO: 124 |
| 239 | SEQ ID NO: 30 | SEQ ID NO: 125 |
| 240 | SEQ ID NO: 30 | SEQ ID NO: 126 |
| 241 | SEQ ID NO: 30 | SEQ ID NO: 127 |
| 242 | SEQ ID NO: 30 | SEQ ID NO: 128 |
| 243 | SEQ ID NO: 30 | SEQ ID NO: 129 |
| 244 | SEQ ID NO: 30 | SEQ ID NO: 130 |
| 245 | SEQ ID NO: 30 | SEQ ID NO: 131 |
| 246 | SEQ ID NO: 30 | SEQ ID NO: 132 |
| 247 | SEQ ID NO: 31 | SEQ ID NO: 19 |
| 248 | SEQ ID NO: 31 | SEQ ID NO: 24 |
| 249 | SEQ ID NO: 31 | SEQ ID NO: 25 |
| 250 | SEQ ID NO: 31 | SEQ ID NO: 26 |
| 251 | SEQ ID NO: 31 | SEQ ID NO: 27 |
| 252 | SEQ ID NO: 31 | SEQ ID NO: 32 |
| 253 | SEQ ID NO: 31 | SEQ ID NO: 33 |
| 254 | SEQ ID NO: 31 | SEQ ID NO: 34 |
| 255 | SEQ ID NO: 31 | SEQ ID NO: 35 |
| 256 | SEQ ID NO: 31 | SEQ ID NO: 59 |
| 257 | SEQ ID NO: 31 | SEQ ID NO: 60 |
| 258 | SEQ ID NO: 31 | SEQ ID NO: 61 |
| 259 | SEQ ID NO: 31 | SEQ ID NO: 67 |
| 260 | SEQ ID NO: 31 | SEQ ID NO: 69 |
| 261 | SEQ ID NO: 31 | SEQ ID NO: 112 |
| 262 | SEQ ID NO: 31 | SEQ ID NO: 113 |
| 263 | SEQ ID NO: 31 | SEQ ID NO: 114 |
| 264 | SEQ ID NO: 31 | SEQ ID NO: 123 |
| 265 | SEQ ID NO: 31 | SEQ ID NO: 124 |
| 266 | SEQ ID NO: 31 | SEQ ID NO: 125 |
| 267 | SEQ ID NO: 31 | SEQ ID NO: 126 |
| 268 | SEQ ID NO: 31 | SEQ ID NO: 127 |
| 269 | SEQ ID NO: 31 | SEQ ID NO: 128 |
| 270 | SEQ ID NO: 31 | SEQ ID NO: 129 |
| 271 | SEQ ID NO: 31 | SEQ ID NO: 130 |
| 272 | SEQ ID NO: 31 | SEQ ID NO: 131 |
| 273 | SEQ ID NO: 31 | SEQ ID NO: 132 |
| 274 | SEQ ID NO: 56 | SEQ ID NO: 19 |
| 275 | SEQ ID NO: 56 | SEQ ID NO: 24 |
| 276 | SEQ ID NO: 56 | SEQ ID NO: 25 |
| 277 | SEQ ID NO: 56 | SEQ ID NO: 26 |
| 278 | SEQ ID NO: 56 | SEQ ID NO: 27 |
| 279 | SEQ ID NO: 56 | SEQ ID NO: 32 |
| 280 | SEQ ID NO: 56 | SEQ ID NO: 33 |
| 281 | SEQ ID NO: 56 | SEQ ID NO: 34 |
| 282 | SEQ ID NO: 56 | SEQ ID NO: 35 |
| 283 | SEQ ID NO: 56 | SEQ ID NO: 59 |
| 284 | SEQ ID NO: 56 | SEQ ID NO: 60 |
| 285 | SEQ ID NO: 56 | SEQ ID NO: 61 |
| 286 | SEQ ID NO: 56 | SEQ ID NO: 67 |
| 287 | SEQ ID NO: 56 | SEQ ID NO: 69 |
| 288 | SEQ ID NO: 56 | SEQ ID NO: 112 |
| 289 | SEQ ID NO: 56 | SEQ ID NO: 113 |
| 290 | SEQ ID NO: 56 | SEQ ID NO: 114 |
| 291 | SEQ ID NO: 56 | SEQ ID NO: 123 |
| 292 | SEQ ID NO: 56 | SEQ ID NO: 124 |
| 293 | SEQ ID NO: 56 | SEQ ID NO: 125 |
| 294 | SEQ ID NO: 56 | SEQ ID NO: 126 |
| 295 | SEQ ID NO: 56 | SEQ ID NO: 127 |
| 296 | SEQ ID NO: 56 | SEQ ID NO: 128 |
| 297 | SEQ ID NO: 56 | SEQ ID NO: 129 |
| 298 | SEQ ID NO: 56 | SEQ ID NO: 130 |
| 299 | SEQ ID NO: 56 | SEQ ID NO: 131 |
| 300 | SEQ ID NO: 56 | SEQ ID NO: 132 |
| 301 | SEQ ID NO: 57 | SEQ ID NO: 19 |
| 302 | SEQ ID NO: 57 | SEQ ID NO: 24 |
| 303 | SEQ ID NO: 57 | SEQ ID NO: 25 |
| 304 | SEQ ID NO: 57 | SEQ ID NO: 26 |
| 305 | SEQ ID NO: 57 | SEQ ID NO: 27 |
| 306 | SEQ ID NO: 57 | SEQ ID NO: 32 |
| 307 | SEQ ID NO: 57 | SEQ ID NO: 33 |
| 308 | SEQ ID NO: 57 | SEQ ID NO: 34 |
| 309 | SEQ ID NO: 57 | SEQ ID NO: 35 |
| 310 | SEQ ID NO: 57 | SEQ ID NO: 59 |
| 311 | SEQ ID NO: 57 | SEQ ID NO: 60 |
| 312 | SEQ ID NO: 57 | SEQ ID NO: 61 |
| 313 | SEQ ID NO: 57 | SEQ ID NO: 67 |
| 314 | SEQ ID NO: 57 | SEQ ID NO: 69 |
| 315 | SEQ ID NO: 57 | SEQ ID NO: 112 |
| 316 | SEQ ID NO: 57 | SEQ ID NO: 113 |
| 317 | SEQ ID NO: 57 | SEQ ID NO: 114 |
| 318 | SEQ ID NO: 57 | SEQ ID NO: 123 |
| 319 | SEQ ID NO: 57 | SEQ ID NO: 124 |
| 320 | SEQ ID NO: 57 | SEQ ID NO: 125 |
| 321 | SEQ ID NO: 57 | SEQ ID NO: 126 |
| 322 | SEQ ID NO: 57 | SEQ ID NO: 127 |
| 323 | SEQ ID NO: 57 | SEQ ID NO: 128 |
| 324 | SEQ ID NO: 57 | SEQ ID NO: 129 |
| 325 | SEQ ID NO: 57 | SEQ ID NO: 130 |
| 326 | SEQ ID NO: 57 | SEQ ID NO: 131 |
| 327 | SEQ ID NO: 57 | SEQ ID NO: 132 |
| 328 | SEQ ID NO: 58 | SEQ ID NO: 19 |
| 329 | SEQ ID NO: 58 | SEQ ID NO: 24 |
| 330 | SEQ ID NO: 58 | SEQ ID NO: 25 |
| 331 | SEQ ID NO: 58 | SEQ ID NO: 26 |
| 332 | SEQ ID NO: 58 | SEQ ID NO: 27 |
| 333 | SEQ ID NO: 58 | SEQ ID NO: 32 |
| 334 | SEQ ID NO: 58 | SEQ ID NO: 33 |
| 335 | SEQ ID NO: 58 | SEQ ID NO: 34 |
| 336 | SEQ ID NO: 58 | SEQ ID NO: 35 |
| 337 | SEQ ID NO: 58 | SEQ ID NO: 59 |
| 338 | SEQ ID NO: 58 | SEQ ID NO: 60 |
| 339 | SEQ ID NO: 58 | SEQ ID NO: 61 |
| 340 | SEQ ID NO: 58 | SEQ ID NO: 67 |
| 341 | SEQ ID NO: 58 | SEQ ID NO: 69 |
| 342 | SEQ ID NO: 58 | SEQ ID NO: 112 |
| 343 | SEQ ID NO: 58 | SEQ ID NO: 113 |
| 344 | SEQ ID NO: 58 | SEQ ID NO: 114 |
| 345 | SEQ ID NO: 58 | SEQ ID NO: 123 |
| 346 | SEQ ID NO: 58 | SEQ ID NO: 124 |
| 347 | SEQ ID NO: 58 | SEQ ID NO: 125 |
| 348 | SEQ ID NO: 58 | SEQ ID NO: 126 |
| 349 | SEQ ID NO: 58 | SEQ ID NO: 127 |
| 350 | SEQ ID NO: 58 | SEQ ID NO: 128 |
| 351 | SEQ ID NO: 58 | SEQ ID NO: 129 |
| 352 | SEQ ID NO: 58 | SEQ ID NO: 130 |
| 353 | SEQ ID NO: 58 | SEQ ID NO: 131 |
| 354 | SEQ ID NO: 58 | SEQ ID NO: 132 |
| 355 | SEQ ID NO: 63 | SEQ ID NO: 19 |
| 356 | SEQ ID NO: 63 | SEQ ID NO: 24 |
| 357 | SEQ ID NO: 63 | SEQ ID NO: 25 |
| 358 | SEQ ID NO: 63 | SEQ ID NO: 26 |
| 359 | SEQ ID NO: 63 | SEQ ID NO: 27 |
| 360 | SEQ ID NO: 63 | SEQ ID NO: 32 |
| 361 | SEQ ID NO: 63 | SEQ ID NO: 33 |
| 362 | SEQ ID NO: 63 | SEQ ID NO: 34 |
| 363 | SEQ ID NO: 63 | SEQ ID NO: 35 |
| 364 | SEQ ID NO: 63 | SEQ ID NO: 59 |
| 365 | SEQ ID NO: 63 | SEQ ID NO: 60 |
| 366 | SEQ ID NO: 63 | SEQ ID NO: 61 |
| 367 | SEQ ID NO: 63 | SEQ ID NO: 67 |
| 368 | SEQ ID NO: 63 | SEQ ID NO: 69 |
| 369 | SEQ ID NO: 63 | SEQ ID NO: 112 |
| 370 | SEQ ID NO: 63 | SEQ ID NO: 113 |
| 371 | SEQ ID NO: 63 | SEQ ID NO: 114 |
| 372 | SEQ ID NO: 63 | SEQ ID NO: 123 |
| 373 | SEQ ID NO: 63 | SEQ ID NO: 124 |
| 374 | SEQ ID NO: 63 | SEQ ID NO: 125 |
| 375 | SEQ ID NO: 63 | SEQ ID NO: 126 |
| 376 | SEQ ID NO: 63 | SEQ ID NO: 127 |
| 377 | SEQ ID NO: 63 | SEQ ID NO: 128 |
| 378 | SEQ ID NO: 63 | SEQ ID NO: 129 |
| 379 | SEQ ID NO: 63 | SEQ ID NO: 130 |
| 380 | SEQ ID NO: 63 | SEQ ID NO: 131 |
| 381 | SEQ ID NO: 63 | SEQ ID NO: 132 |
| 382 | SEQ ID NO: 65 | SEQ ID NO: 19 |

TABLE 1.1-continued

Heavy chains and light chains of exemplary antigen-binding proteins or antigen-binding fragments

| No. | Heavy Chain | Light Chain |
|---|---|---|
| 383 | SEQ ID NO: 65 | SEQ ID NO: 24 |
| 384 | SEQ ID NO: 65 | SEQ ID NO: 25 |
| 385 | SEQ ID NO: 65 | SEQ ID NO: 26 |
| 386 | SEQ ID NO: 65 | SEQ ID NO: 27 |
| 387 | SEQ ID NO: 65 | SEQ ID NO: 32 |
| 388 | SEQ ID NO: 65 | SEQ ID NO: 33 |
| 389 | SEQ ID NO: 65 | SEQ ID NO: 34 |
| 390 | SEQ ID NO: 65 | SEQ ID NO: 35 |
| 391 | SEQ ID NO: 65 | SEQ ID NO: 59 |
| 392 | SEQ ID NO: 65 | SEQ ID NO: 60 |
| 393 | SEQ ID NO: 65 | SEQ ID NO: 61 |
| 394 | SEQ ID NO: 65 | SEQ ID NO: 67 |
| 395 | SEQ ID NO: 65 | SEQ ID NO: 69 |
| 396 | SEQ ID NO: 65 | SEQ ID NO: 112 |
| 397 | SEQ ID NO: 65 | SEQ ID NO: 113 |
| 398 | SEQ ID NO: 65 | SEQ ID NO: 114 |
| 399 | SEQ ID NO: 65 | SEQ ID NO: 123 |
| 400 | SEQ ID NO: 65 | SEQ ID NO: 124 |
| 401 | SEQ ID NO: 65 | SEQ ID NO: 125 |
| 402 | SEQ ID NO: 65 | SEQ ID NO: 126 |
| 403 | SEQ ID NO: 65 | SEQ ID NO: 127 |
| 404 | SEQ ID NO: 65 | SEQ ID NO: 128 |
| 405 | SEQ ID NO: 65 | SEQ ID NO: 129 |
| 406 | SEQ ID NO: 65 | SEQ ID NO: 130 |
| 407 | SEQ ID NO: 65 | SEQ ID NO: 131 |
| 408 | SEQ ID NO: 65 | SEQ ID NO: 132 |
| 409 | SEQ ID NO: 106 | SEQ ID NO: 19 |
| 410 | SEQ ID NO: 106 | SEQ ID NO: 24 |
| 411 | SEQ ID NO: 106 | SEQ ID NO: 25 |
| 412 | SEQ ID NO: 106 | SEQ ID NO: 26 |
| 413 | SEQ ID NO: 106 | SEQ ID NO: 27 |
| 414 | SEQ ID NO: 106 | SEQ ID NO: 32 |
| 415 | SEQ ID NO: 106 | SEQ ID NO: 33 |
| 416 | SEQ ID NO: 106 | SEQ ID NO: 34 |
| 417 | SEQ ID NO: 106 | SEQ ID NO: 35 |
| 418 | SEQ ID NO: 106 | SEQ ID NO: 59 |
| 419 | SEQ ID NO: 106 | SEQ ID NO: 60 |
| 420 | SEQ ID NO: 106 | SEQ ID NO: 61 |
| 421 | SEQ ID NO: 106 | SEQ ID NO: 67 |
| 422 | SEQ ID NO: 106 | SEQ ID NO: 69 |
| 423 | SEQ ID NO: 106 | SEQ ID NO: 112 |
| 424 | SEQ ID NO: 106 | SEQ ID NO: 113 |
| 425 | SEQ ID NO: 106 | SEQ ID NO: 114 |
| 426 | SEQ ID NO: 106 | SEQ ID NO: 123 |
| 427 | SEQ ID NO: 106 | SEQ ID NO: 124 |
| 428 | SEQ ID NO: 106 | SEQ ID NO: 125 |
| 429 | SEQ ID NO: 106 | SEQ ID NO: 126 |
| 430 | SEQ ID NO: 106 | SEQ ID NO: 127 |
| 431 | SEQ ID NO: 106 | SEQ ID NO: 128 |
| 432 | SEQ ID NO: 106 | SEQ ID NO: 129 |
| 433 | SEQ ID NO: 106 | SEQ ID NO: 130 |
| 434 | SEQ ID NO: 106 | SEQ ID NO: 131 |
| 435 | SEQ ID NO: 106 | SEQ ID NO: 132 |
| 436 | SEQ ID NO: 107 | SEQ ID NO: 19 |
| 437 | SEQ ID NO: 107 | SEQ ID NO: 24 |
| 438 | SEQ ID NO: 107 | SEQ ID NO: 25 |
| 439 | SEQ ID NO: 107 | SEQ ID NO: 26 |
| 440 | SEQ ID NO: 107 | SEQ ID NO: 27 |
| 441 | SEQ ID NO: 107 | SEQ ID NO: 32 |
| 442 | SEQ ID NO: 107 | SEQ ID NO: 33 |
| 443 | SEQ ID NO: 107 | SEQ ID NO: 34 |
| 444 | SEQ ID NO: 107 | SEQ ID NO: 35 |
| 445 | SEQ ID NO: 107 | SEQ ID NO: 59 |
| 446 | SEQ ID NO: 107 | SEQ ID NO: 60 |
| 447 | SEQ ID NO: 107 | SEQ ID NO: 61 |
| 448 | SEQ ID NO: 107 | SEQ ID NO: 67 |
| 449 | SEQ ID NO: 107 | SEQ ID NO: 69 |
| 450 | SEQ ID NO: 107 | SEQ ID NO: 112 |
| 451 | SEQ ID NO: 107 | SEQ ID NO: 113 |
| 452 | SEQ ID NO: 107 | SEQ ID NO: 114 |
| 453 | SEQ ID NO: 107 | SEQ ID NO: 123 |
| 454 | SEQ ID NO: 107 | SEQ ID NO: 124 |
| 455 | SEQ ID NO: 107 | SEQ ID NO: 125 |
| 456 | SEQ ID NO: 107 | SEQ ID NO: 126 |
| 457 | SEQ ID NO: 107 | SEQ ID NO: 127 |
| 458 | SEQ ID NO: 107 | SEQ ID NO: 128 |
| 459 | SEQ ID NO: 107 | SEQ ID NO: 129 |
| 460 | SEQ ID NO: 107 | SEQ ID NO: 130 |
| 461 | SEQ ID NO: 107 | SEQ ID NO: 131 |
| 462 | SEQ ID NO: 107 | SEQ ID NO: 132 |
| 463 | SEQ ID NO: 108 | SEQ ID NO: 19 |
| 464 | SEQ ID NO: 108 | SEQ ID NO: 24 |
| 465 | SEQ ID NO: 108 | SEQ ID NO: 25 |
| 466 | SEQ ID NO: 108 | SEQ ID NO: 26 |
| 467 | SEQ ID NO: 108 | SEQ ID NO: 27 |
| 468 | SEQ ID NO: 108 | SEQ ID NO: 32 |
| 469 | SEQ ID NO: 108 | SEQ ID NO: 33 |
| 470 | SEQ ID NO: 108 | SEQ ID NO: 34 |
| 471 | SEQ ID NO: 108 | SEQ ID NO: 35 |
| 472 | SEQ ID NO: 108 | SEQ ID NO: 59 |
| 473 | SEQ ID NO: 108 | SEQ ID NO: 60 |
| 474 | SEQ ID NO: 108 | SEQ ID NO: 61 |
| 475 | SEQ ID NO: 108 | SEQ ID NO: 67 |
| 476 | SEQ ID NO: 108 | SEQ ID NO: 69 |
| 477 | SEQ ID NO: 108 | SEQ ID NO: 112 |
| 478 | SEQ ID NO: 108 | SEQ ID NO: 113 |
| 479 | SEQ ID NO: 108 | SEQ ID NO: 114 |
| 480 | SEQ ID NO: 108 | SEQ ID NO: 123 |
| 481 | SEQ ID NO: 108 | SEQ ID NO: 124 |
| 482 | SEQ ID NO: 108 | SEQ ID NO: 125 |
| 483 | SEQ ID NO: 108 | SEQ ID NO: 126 |
| 484 | SEQ ID NO: 108 | SEQ ID NO: 127 |
| 485 | SEQ ID NO: 108 | SEQ ID NO: 128 |
| 486 | SEQ ID NO: 108 | SEQ ID NO: 129 |
| 487 | SEQ ID NO: 108 | SEQ ID NO: 130 |
| 488 | SEQ ID NO: 108 | SEQ ID NO: 131 |
| 489 | SEQ ID NO: 108 | SEQ ID NO: 132 |
| 490 | SEQ ID NO: 109 | SEQ ID NO: 19 |
| 491 | SEQ ID NO: 109 | SEQ ID NO: 24 |
| 492 | SEQ ID NO: 109 | SEQ ID NO: 25 |
| 493 | SEQ ID NO: 109 | SEQ ID NO: 26 |
| 494 | SEQ ID NO: 109 | SEQ ID NO: 27 |
| 495 | SEQ ID NO: 109 | SEQ ID NO: 32 |
| 496 | SEQ ID NO: 109 | SEQ ID NO: 33 |
| 497 | SEQ ID NO: 109 | SEQ ID NO: 34 |
| 498 | SEQ ID NO: 109 | SEQ ID NO: 35 |
| 499 | SEQ ID NO: 109 | SEQ ID NO: 59 |
| 500 | SEQ ID NO: 109 | SEQ ID NO: 60 |
| 501 | SEQ ID NO: 109 | SEQ ID NO: 61 |
| 502 | SEQ ID NO: 109 | SEQ ID NO: 67 |
| 503 | SEQ ID NO: 109 | SEQ ID NO: 69 |
| 504 | SEQ ID NO: 109 | SEQ ID NO: 112 |
| 505 | SEQ ID NO: 109 | SEQ ID NO: 113 |
| 506 | SEQ ID NO: 109 | SEQ ID NO: 114 |
| 507 | SEQ ID NO: 109 | SEQ ID NO: 123 |
| 508 | SEQ ID NO: 109 | SEQ ID NO: 124 |
| 509 | SEQ ID NO: 109 | SEQ ID NO: 125 |
| 510 | SEQ ID NO: 109 | SEQ ID NO: 126 |
| 511 | SEQ ID NO: 109 | SEQ ID NO: 127 |
| 512 | SEQ ID NO: 109 | SEQ ID NO: 128 |
| 513 | SEQ ID NO: 109 | SEQ ID NO: 129 |
| 514 | SEQ ID NO: 109 | SEQ ID NO: 130 |
| 515 | SEQ ID NO: 109 | SEQ ID NO: 131 |
| 516 | SEQ ID NO: 109 | SEQ ID NO: 132 |
| 517 | SEQ ID NO: 110 | SEQ ID NO: 19 |
| 518 | SEQ ID NO: 110 | SEQ ID NO: 24 |
| 519 | SEQ ID NO: 110 | SEQ ID NO: 25 |
| 520 | SEQ ID NO: 110 | SEQ ID NO: 26 |
| 521 | SEQ ID NO: 110 | SEQ ID NO: 27 |
| 522 | SEQ ID NO: 110 | SEQ ID NO: 32 |
| 523 | SEQ ID NO: 110 | SEQ ID NO: 33 |
| 524 | SEQ ID NO: 110 | SEQ ID NO: 34 |
| 525 | SEQ ID NO: 110 | SEQ ID NO: 35 |
| 526 | SEQ ID NO: 110 | SEQ ID NO: 59 |
| 527 | SEQ ID NO: 110 | SEQ ID NO: 60 |
| 528 | SEQ ID NO: 110 | SEQ ID NO: 61 |
| 529 | SEQ ID NO: 110 | SEQ ID NO: 67 |
| 530 | SEQ ID NO: 110 | SEQ ID NO: 69 |
| 531 | SEQ ID NO: 110 | SEQ ID NO: 112 |
| 532 | SEQ ID NO: 110 | SEQ ID NO: 113 |

TABLE 1.1-continued

Heavy chains and light chains of exemplary antigen-binding proteins or antigen-binding fragments

| No. | Heavy Chain | Light Chain |
|-----|-------------|-------------|
| 533 | SEQ ID NO: 110 | SEQ ID NO: 114 |
| 534 | SEQ ID NO: 110 | SEQ ID NO: 123 |
| 535 | SEQ ID NO: 110 | SEQ ID NO: 124 |
| 536 | SEQ ID NO: 110 | SEQ ID NO: 125 |
| 537 | SEQ ID NO: 110 | SEQ ID NO: 126 |
| 538 | SEQ ID NO: 110 | SEQ ID NO: 127 |
| 539 | SEQ ID NO: 110 | SEQ ID NO: 128 |
| 540 | SEQ ID NO: 110 | SEQ ID NO: 129 |
| 541 | SEQ ID NO: 110 | SEQ ID NO: 130 |
| 542 | SEQ ID NO: 110 | SEQ ID NO: 131 |
| 543 | SEQ ID NO: 111 | SEQ ID NO: 132 |
| 544 | SEQ ID NO: 111 | SEQ ID NO: 19 |
| 545 | SEQ ID NO: 111 | SEQ ID NO: 24 |
| 546 | SEQ ID NO: 111 | SEQ ID NO: 25 |
| 547 | SEQ ID NO: 111 | SEQ ID NO: 26 |
| 548 | SEQ ID NO: 111 | SEQ ID NO: 27 |
| 549 | SEQ ID NO: 111 | SEQ ID NO: 32 |
| 550 | SEQ ID NO: 111 | SEQ ID NO: 33 |
| 551 | SEQ ID NO: 111 | SEQ ID NO: 34 |
| 552 | SEQ ID NO: 111 | SEQ ID NO: 35 |
| 553 | SEQ ID NO: 111 | SEQ ID NO: 59 |
| 554 | SEQ ID NO: 111 | SEQ ID NO: 60 |
| 555 | SEQ ID NO: 111 | SEQ ID NO: 61 |
| 556 | SEQ ID NO: 111 | SEQ ID NO: 67 |
| 557 | SEQ ID NO: 111 | SEQ ID NO: 69 |
| 558 | SEQ ID NO: 111 | SEQ ID NO: 112 |
| 559 | SEQ ID NO: 111 | SEQ ID NO: 113 |
| 560 | SEQ ID NO: 111 | SEQ ID NO: 114 |
| 561 | SEQ ID NO: 111 | SEQ ID NO: 123 |
| 562 | SEQ ID NO: 111 | SEQ ID NO: 124 |
| 563 | SEQ ID NO: 111 | SEQ ID NO: 125 |
| 564 | SEQ ID NO: 111 | SEQ ID NO: 126 |
| 565 | SEQ ID NO: 111 | SEQ ID NO: 127 |
| 566 | SEQ ID NO: 111 | SEQ ID NO: 128 |
| 567 | SEQ ID NO: 111 | SEQ ID NO: 129 |
| 568 | SEQ ID NO: 111 | SEQ ID NO: 130 |
| 569 | SEQ ID NO: 111 | SEQ ID NO: 131 |
| 570 | SEQ ID NO: 111 | SEQ ID NO: 132 |
| 571 | SEQ ID NO: 115 | SEQ ID NO: 19 |
| 572 | SEQ ID NO: 115 | SEQ ID NO: 24 |
| 573 | SEQ ID NO: 115 | SEQ ID NO: 25 |
| 574 | SEQ ID NO: 115 | SEQ ID NO: 26 |
| 575 | SEQ ID NO: 115 | SEQ ID NO: 27 |
| 576 | SEQ ID NO: 115 | SEQ ID NO: 32 |
| 577 | SEQ ID NO: 115 | SEQ ID NO: 33 |
| 578 | SEQ ID NO: 115 | SEQ ID NO: 34 |
| 579 | SEQ ID NO: 115 | SEQ ID NO: 35 |
| 580 | SEQ ID NO: 115 | SEQ ID NO: 59 |
| 581 | SEQ ID NO: 115 | SEQ ID NO: 60 |
| 582 | SEQ ID NO: 115 | SEQ ID NO: 61 |
| 583 | SEQ ID NO: 115 | SEQ ID NO: 67 |
| 584 | SEQ ID NO: 115 | SEQ ID NO: 69 |
| 585 | SEQ ID NO: 115 | SEQ ID NO: 112 |
| 586 | SEQ ID NO: 115 | SEQ ID NO: 113 |
| 587 | SEQ ID NO: 115 | SEQ ID NO: 114 |
| 588 | SEQ ID NO: 115 | SEQ ID NO: 123 |
| 589 | SEQ ID NO: 115 | SEQ ID NO: 124 |
| 590 | SEQ ID NO: 115 | SEQ ID NO: 125 |
| 591 | SEQ ID NO: 115 | SEQ ID NO: 126 |
| 592 | SEQ ID NO: 115 | SEQ ID NO: 127 |
| 593 | SEQ ID NO: 115 | SEQ ID NO: 128 |
| 594 | SEQ ID NO: 115 | SEQ ID NO: 129 |
| 595 | SEQ ID NO: 115 | SEQ ID NO: 130 |
| 596 | SEQ ID NO: 115 | SEQ ID NO: 131 |
| 597 | SEQ ID NO: 115 | SEQ ID NO: 132 |
| 598 | SEQ ID NO: 116 | SEQ ID NO: 19 |
| 599 | SEQ ID NO: 116 | SEQ ID NO: 24 |
| 600 | SEQ ID NO: 116 | SEQ ID NO: 25 |
| 601 | SEQ ID NO: 116 | SEQ ID NO: 26 |
| 602 | SEQ ID NO: 116 | SEQ ID NO: 27 |
| 603 | SEQ ID NO: 116 | SEQ ID NO: 32 |
| 604 | SEQ ID NO: 116 | SEQ ID NO: 33 |
| 605 | SEQ ID NO: 116 | SEQ ID NO: 34 |
| 606 | SEQ ID NO: 116 | SEQ ID NO: 35 |
| 607 | SEQ ID NO: 116 | SEQ ID NO: 59 |
| 608 | SEQ ID NO: 116 | SEQ ID NO: 60 |
| 609 | SEQ ID NO: 116 | SEQ ID NO: 61 |
| 610 | SEQ ID NO: 116 | SEQ ID NO: 67 |
| 611 | SEQ ID NO: 116 | SEQ ID NO: 69 |
| 612 | SEQ ID NO: 116 | SEQ ID NO: 112 |
| 613 | SEQ ID NO: 116 | SEQ ID NO: 113 |
| 614 | SEQ ID NO: 116 | SEQ ID NO: 114 |
| 615 | SEQ ID NO: 116 | SEQ ID NO: 123 |
| 616 | SEQ ID NO: 116 | SEQ ID NO: 124 |
| 617 | SEQ ID NO: 116 | SEQ ID NO: 125 |
| 618 | SEQ ID NO: 116 | SEQ ID NO: 126 |
| 619 | SEQ ID NO: 116 | SEQ ID NO: 127 |
| 620 | SEQ ID NO: 116 | SEQ ID NO: 128 |
| 621 | SEQ ID NO: 116 | SEQ ID NO: 129 |
| 622 | SEQ ID NO: 116 | SEQ ID NO: 130 |
| 623 | SEQ ID NO: 116 | SEQ ID NO: 131 |
| 624 | SEQ ID NO: 116 | SEQ ID NO: 132 |
| 625 | SEQ ID NO: 117 | SEQ ID NO: 19 |
| 626 | SEQ ID NO: 117 | SEQ ID NO: 24 |
| 627 | SEQ ID NO: 117 | SEQ ID NO: 25 |
| 628 | SEQ ID NO: 117 | SEQ ID NO: 26 |
| 629 | SEQ ID NO: 117 | SEQ ID NO: 27 |
| 630 | SEQ ID NO: 117 | SEQ ID NO: 32 |
| 631 | SEQ ID NO: 117 | SEQ ID NO: 33 |
| 632 | SEQ ID NO: 117 | SEQ ID NO: 34 |
| 633 | SEQ ID NO: 117 | SEQ ID NO: 35 |
| 634 | SEQ ID NO: 117 | SEQ ID NO: 59 |
| 635 | SEQ ID NO: 117 | SEQ ID NO: 60 |
| 636 | SEQ ID NO: 117 | SEQ ID NO: 61 |
| 637 | SEQ ID NO: 117 | SEQ ID NO: 67 |
| 638 | SEQ ID NO: 117 | SEQ ID NO: 69 |
| 639 | SEQ ID NO: 117 | SEQ ID NO: 112 |
| 640 | SEQ ID NO: 117 | SEQ ID NO: 113 |
| 641 | SEQ ID NO: 117 | SEQ ID NO: 114 |
| 642 | SEQ ID NO: 117 | SEQ ID NO: 123 |
| 643 | SEQ ID NO: 117 | SEQ ID NO: 124 |
| 644 | SEQ ID NO: 117 | SEQ ID NO: 125 |
| 645 | SEQ ID NO: 117 | SEQ ID NO: 126 |
| 646 | SEQ ID NO: 117 | SEQ ID NO: 127 |
| 647 | SEQ ID NO: 117 | SEQ ID NO: 128 |
| 648 | SEQ ID NO: 117 | SEQ ID NO: 129 |
| 649 | SEQ ID NO: 117 | SEQ ID NO: 130 |
| 650 | SEQ ID NO: 117 | SEQ ID NO: 131 |
| 651 | SEQ ID NO: 117 | SEQ ID NO: 132 |
| 652 | SEQ ID NO: 118 | SEQ ID NO: 19 |
| 653 | SEQ ID NO: 118 | SEQ ID NO: 24 |
| 654 | SEQ ID NO: 118 | SEQ ID NO: 25 |
| 655 | SEQ ID NO: 118 | SEQ ID NO: 26 |
| 656 | SEQ ID NO: 118 | SEQ ID NO: 27 |
| 657 | SEQ ID NO: 118 | SEQ ID NO: 32 |
| 658 | SEQ ID NO: 118 | SEQ ID NO: 33 |
| 659 | SEQ ID NO: 118 | SEQ ID NO: 34 |
| 660 | SEQ ID NO: 118 | SEQ ID NO: 35 |
| 661 | SEQ ID NO: 118 | SEQ ID NO: 59 |
| 662 | SEQ ID NO: 118 | SEQ ID NO: 60 |
| 663 | SEQ ID NO: 118 | SEQ ID NO: 61 |
| 664 | SEQ ID NO: 118 | SEQ ID NO: 67 |
| 665 | SEQ ID NO: 118 | SEQ ID NO: 69 |
| 666 | SEQ ID NO: 118 | SEQ ID NO: 112 |
| 667 | SEQ ID NO: 118 | SEQ ID NO: 113 |
| 668 | SEQ ID NO: 118 | SEQ ID NO: 114 |
| 669 | SEQ ID NO: 118 | SEQ ID NO: 123 |
| 670 | SEQ ID NO: 118 | SEQ ID NO: 124 |
| 671 | SEQ ID NO: 118 | SEQ ID NO: 125 |
| 672 | SEQ ID NO: 118 | SEQ ID NO: 126 |
| 673 | SEQ ID NO: 118 | SEQ ID NO: 127 |
| 674 | SEQ ID NO: 118 | SEQ ID NO: 128 |
| 675 | SEQ ID NO: 118 | SEQ ID NO: 129 |
| 676 | SEQ ID NO: 118 | SEQ ID NO: 130 |
| 677 | SEQ ID NO: 118 | SEQ ID NO: 131 |
| 678 | SEQ ID NO: 118 | SEQ ID NO: 132 |
| 679 | SEQ ID NO: 119 | SEQ ID NO: 19 |
| 680 | SEQ ID NO: 119 | SEQ ID NO: 24 |
| 681 | SEQ ID NO: 119 | SEQ ID NO: 25 |
| 682 | SEQ ID NO: 119 | SEQ ID NO: 26 |

TABLE 1.1-continued

Heavy chains and light chains of exemplary antigen-binding proteins or antigen-binding fragments

| No. | Heavy Chain | Light Chain |
|---|---|---|
| 683 | SEQ ID NO: 119 | SEQ ID NO: 27 |
| 684 | SEQ ID NO: 119 | SEQ ID NO: 32 |
| 685 | SEQ ID NO: 119 | SEQ ID NO: 33 |
| 686 | SEQ ID NO: 119 | SEQ ID NO: 34 |
| 687 | SEQ ID NO: 119 | SEQ ID NO: 35 |
| 688 | SEQ ID NO: 119 | SEQ ID NO: 59 |
| 689 | SEQ ID NO: 119 | SEQ ID NO: 60 |
| 690 | SEQ ID NO: 119 | SEQ ID NO: 61 |
| 691 | SEQ ID NO: 119 | SEQ ID NO: 67 |
| 692 | SEQ ID NO: 119 | SEQ ID NO: 69 |
| 693 | SEQ ID NO: 119 | SEQ ID NO: 112 |
| 694 | SEQ ID NO: 119 | SEQ ID NO: 113 |
| 695 | SEQ ID NO: 119 | SEQ ID NO: 114 |
| 696 | SEQ ID NO: 119 | SEQ ID NO: 123 |
| 697 | SEQ ID NO: 119 | SEQ ID NO: 124 |
| 698 | SEQ ID NO: 119 | SEQ ID NO: 125 |
| 699 | SEQ ID NO: 119 | SEQ ID NO: 126 |
| 700 | SEQ ID NO: 119 | SEQ ID NO: 127 |
| 701 | SEQ ID NO: 119 | SEQ ID NO: 128 |
| 702 | SEQ ID NO: 119 | SEQ ID NO: 129 |
| 703 | SEQ ID NO: 119 | SEQ ID NO: 130 |
| 704 | SEQ ID NO: 119 | SEQ ID NO: 131 |
| 705 | SEQ ID NO: 119 | SEQ ID NO: 132 |
| 706 | SEQ ID NO: 120 | SEQ ID NO: 19 |
| 707 | SEQ ID NO: 120 | SEQ ID NO: 24 |
| 708 | SEQ ID NO: 120 | SEQ ID NO: 25 |
| 709 | SEQ ID NO: 120 | SEQ ID NO: 26 |
| 710 | SEQ ID NO: 120 | SEQ ID NO: 27 |
| 711 | SEQ ID NO: 120 | SEQ ID NO: 32 |
| 712 | SEQ ID NO: 120 | SEQ ID NO: 33 |
| 713 | SEQ ID NO: 120 | SEQ ID NO: 34 |
| 714 | SEQ ID NO: 120 | SEQ ID NO: 35 |
| 715 | SEQ ID NO: 120 | SEQ ID NO: 59 |
| 716 | SEQ ID NO: 120 | SEQ ID NO: 60 |
| 717 | SEQ ID NO: 120 | SEQ ID NO: 61 |
| 718 | SEQ ID NO: 120 | SEQ ID NO: 67 |
| 719 | SEQ ID NO: 120 | SEQ ID NO: 69 |
| 720 | SEQ ID NO: 120 | SEQ ID NO: 112 |
| 721 | SEQ ID NO: 120 | SEQ ID NO: 113 |
| 722 | SEQ ID NO: 120 | SEQ ID NO: 114 |
| 723 | SEQ ID NO: 120 | SEQ ID NO: 123 |
| 724 | SEQ ID NO: 120 | SEQ ID NO: 124 |
| 725 | SEQ ID NO: 120 | SEQ ID NO: 125 |
| 726 | SEQ ID NO: 120 | SEQ ID NO: 126 |
| 727 | SEQ ID NO: 120 | SEQ ID NO: 127 |
| 728 | SEQ ID NO: 120 | SEQ ID NO: 128 |
| 729 | SEQ ID NO: 120 | SEQ ID NO: 129 |
| 730 | SEQ ID NO: 120 | SEQ ID NO: 130 |
| 731 | SEQ ID NO: 120 | SEQ ID NO: 131 |
| 732 | SEQ ID NO: 120 | SEQ ID NO: 132 |
| 733 | SEQ ID NO: 121 | SEQ ID NO: 19 |
| 734 | SEQ ID NO: 121 | SEQ ID NO: 24 |
| 735 | SEQ ID NO: 121 | SEQ ID NO: 25 |
| 736 | SEQ ID NO: 121 | SEQ ID NO: 26 |
| 737 | SEQ ID NO: 121 | SEQ ID NO: 27 |
| 738 | SEQ ID NO: 121 | SEQ ID NO: 32 |
| 739 | SEQ ID NO: 121 | SEQ ID NO: 33 |
| 740 | SEQ ID NO: 121 | SEQ ID NO: 34 |
| 741 | SEQ ID NO: 121 | SEQ ID NO: 35 |
| 742 | SEQ ID NO: 121 | SEQ ID NO: 59 |
| 743 | SEQ ID NO: 121 | SEQ ID NO: 60 |
| 744 | SEQ ID NO: 121 | SEQ ID NO: 61 |
| 745 | SEQ ID NO: 121 | SEQ ID NO: 67 |
| 746 | SEQ ID NO: 121 | SEQ ID NO: 69 |
| 747 | SEQ ID NO: 121 | SEQ ID NO: 112 |
| 748 | SEQ ID NO: 121 | SEQ ID NO: 113 |
| 749 | SEQ ID NO: 121 | SEQ ID NO: 114 |
| 750 | SEQ ID NO: 121 | SEQ ID NO: 123 |
| 751 | SEQ ID NO: 121 | SEQ ID NO: 124 |
| 752 | SEQ ID NO: 121 | SEQ ID NO: 125 |
| 753 | SEQ ID NO: 121 | SEQ ID NO: 126 |
| 754 | SEQ ID NO: 121 | SEQ ID NO: 127 |
| 755 | SEQ ID NO: 121 | SEQ ID NO: 128 |
| 756 | SEQ ID NO: 121 | SEQ ID NO: 129 |
| 757 | SEQ ID NO: 121 | SEQ ID NO: 130 |
| 758 | SEQ ID NO: 121 | SEQ ID NO: 131 |
| 759 | SEQ ID NO: 121 | SEQ ID NO: 132 |
| 760 | SEQ ID NO: 122 | SEQ ID NO: 19 |
| 761 | SEQ ID NO: 122 | SEQ ID NO: 24 |
| 762 | SEQ ID NO: 122 | SEQ ID NO: 25 |
| 763 | SEQ ID NO: 122 | SEQ ID NO: 26 |
| 764 | SEQ ID NO: 122 | SEQ ID NO: 27 |
| 765 | SEQ ID NO: 122 | SEQ ID NO: 32 |
| 766 | SEQ ID NO: 122 | SEQ ID NO: 33 |
| 767 | SEQ ID NO: 122 | SEQ ID NO: 34 |
| 768 | SEQ ID NO: 122 | SEQ ID NO: 35 |
| 769 | SEQ ID NO: 122 | SEQ ID NO: 59 |
| 770 | SEQ ID NO: 122 | SEQ ID NO: 60 |
| 771 | SEQ ID NO: 122 | SEQ ID NO: 61 |
| 772 | SEQ ID NO: 122 | SEQ ID NO: 67 |
| 773 | SEQ ID NO: 122 | SEQ ID NO: 69 |
| 774 | SEQ ID NO: 122 | SEQ ID NO: 112 |
| 775 | SEQ ID NO: 122 | SEQ ID NO: 113 |
| 776 | SEQ ID NO: 122 | SEQ ID NO: 114 |
| 777 | SEQ ID NO: 122 | SEQ ID NO: 123 |
| 778 | SEQ ID NO: 122 | SEQ ID NO: 124 |
| 779 | SEQ ID NO: 122 | SEQ ID NO: 125 |
| 780 | SEQ ID NO: 122 | SEQ ID NO: 126 |
| 781 | SEQ ID NO: 122 | SEQ ID NO: 127 |
| 782 | SEQ ID NO: 122 | SEQ ID NO: 128 |
| 783 | SEQ ID NO: 122 | SEQ ID NO: 129 |
| 784 | SEQ ID NO: 122 | SEQ ID NO: 130 |
| 785 | SEQ ID NO: 122 | SEQ ID NO: 131 |
| 786 | SEQ ID NO: 122 | SEQ ID NO: 132 |
| 787 | SEQ ID NO: 141 | SEQ ID NO: 142 |
| 788 | SEQ ID NO: 143 | SEQ ID NO: 142 |
| 789 | SEQ ID NO: 145 | SEQ ID NO: 142 |
| 790 | SEQ ID NO: 147 | SEQ ID NO: 142 |
| 791 | SEQ ID NO: 149 | SEQ ID NO: 142 |
| 792 | SEQ ID NO: 151 | SEQ ID NO: 142 |
| 793 | SEQ ID NO: 153 | SEQ ID NO: 142 |
| 794 | SEQ ID NO: 155 | SEQ ID NO: 142 |
| 795 | SEQ ID NO: 156 | SEQ ID NO: 142 |
| 796 | SEQ ID NO: 164 | SEQ ID NO: 142 |
| 797 | SEQ ID NO: 165 | SEQ ID NO: 142 |
| 798 | SEQ ID NO: 166 | SEQ ID NO: 142 |
| 799 | SEQ ID NO: 167 | SEQ ID NO: 142 |
| 800 | SEQ ID NO: 168 | SEQ ID NO: 142 |
| 801 | SEQ ID NO: 169 | SEQ ID NO: 142 |
| 802 | SEQ ID NO: 170 | SEQ ID NO: 142 |
| 803 | SEQ ID NO: 171 | SEQ ID NO: 142 |
| 804 | SEQ ID NO: 172 | SEQ ID NO: 142 |
| 805 | SEQ ID NO: 173 | SEQ ID NO: 142 |
| 806 | SEQ ID NO: 174 | SEQ ID NO: 142 |
| 807 | SEQ ID NO: 175 | SEQ ID NO: 142 |
| 808 | SEQ ID NO: 176 | SEQ ID NO: 142 |
| 809 | SEQ ID NO: 177 | SEQ ID NO: 142 |
| 810 | SEQ ID NO: 178 | SEQ ID NO: 142 |
| 811 | SEQ ID NO: 179 | SEQ ID NO: 142 |
| 812 | SEQ ID NO: 180 | SEQ ID NO: 142 |
| 813 | SEQ ID NO: 181 | SEQ ID NO: 142 |
| 814 | SEQ ID NO: 182 | SEQ ID NO: 142 |
| 815 | SEQ ID NO: 183 | SEQ ID NO: 142 |
| 816 | SEQ ID NO: 184 | SEQ ID NO: 142 |
| 817 | SEQ ID NO: 185 | SEQ ID NO: 142 |
| 818 | SEQ ID NO: 186 | SEQ ID NO: 142 |
| 819 | SEQ ID NO: 187 | SEQ ID NO: 142 |
| 820 | SEQ ID NO: 188 | SEQ ID NO: 142 |
| 821 | SEQ ID NO: 189 | SEQ ID NO: 142 |
| 822 | SEQ ID NO: 190 | SEQ ID NO: 142 |
| 823 | SEQ ID NO: 191 | SEQ ID NO: 142 |
| 824 | SEQ ID NO: 192 | SEQ ID NO: 142 |
| 825 | SEQ ID NO: 193 | SEQ ID NO: 142 |
| 826 | SEQ ID NO: 194 | SEQ ID NO: 142 |
| 827 | SEQ ID NO: 195 | SEQ ID NO: 142 |
| 828 | SEQ ID NO: 196 | SEQ ID NO: 142 |
| 829 | SEQ ID NO: 197 | SEQ ID NO: 142 |
| 830 | SEQ ID NO: 198 | SEQ ID NO: 142 |
| 831 | SEQ ID NO: 199 | SEQ ID NO: 142 |
| 832 | SEQ ID NO: 200 | SEQ ID NO: 142 |

TABLE 1.1-continued

Heavy chains and light chains of exemplary antigen-binding proteins or antigen-binding fragments

| No. | Heavy Chain | Light Chain |
|---|---|---|
| 833 | SEQ ID NO: 201 | SEQ ID NO: 142 |
| 834 | SEQ ID NO: 202 | SEQ ID NO: 142 |
| 835 | SEQ ID NO: 203 | SEQ ID NO: 142 |
| 836 | SEQ ID NO: 204 | SEQ ID NO: 142 |
| 837 | SEQ ID NO: 205 | SEQ ID NO: 142 |
| 838 | SEQ ID NO: 206 | SEQ ID NO: 142 |
| 839 | SEQ ID NO: 207 | SEQ ID NO: 142 |
| 840 | SEQ ID NO: 208 | SEQ ID NO: 142 |
| 841 | SEQ ID NO: 209 | SEQ ID NO: 142 |
| 842 | SEQ ID NO: 210 | SEQ ID NO: 142 |
| 843 | SEQ ID NO: 211 | SEQ ID NO: 142 |
| 844 | SEQ ID NO: 212 | SEQ ID NO: 142 |
| 845 | SEQ ID NO: 213 | SEQ ID NO: 142 |
| 846 | SEQ ID NO: 214 | SEQ ID NO: 142 |
| 847 | SEQ ID NO: 215 | SEQ ID NO: 142 |
| 848 | SEQ ID NO: 216 | SEQ ID NO: 142 |
| 849 | SEQ ID NO: 217 | SEQ ID NO: 142 |
| 850 | SEQ ID NO: 218 | SEQ ID NO: 142 |
| 851 | SEQ ID NO: 219 | SEQ ID NO: 142 |
| 852 | SEQ ID NO: 220 | SEQ ID NO: 142 |
| 853 | SEQ ID NO: 221 | SEQ ID NO: 142 |
| 854 | SEQ ID NO: 222 | SEQ ID NO: 142 |
| 855 | SEQ ID NO: 223 | SEQ ID NO: 142 |
| 856 | SEQ ID NO: 224 | SEQ ID NO: 142 |
| 857 | SEQ ID NO: 225 | SEQ ID NO: 142 |
| 858 | SEQ ID NO: 226 | SEQ ID NO: 142 |
| 859 | SEQ ID NO: 227 | SEQ ID NO: 142 |
| 860 | SEQ ID NO: 228 | SEQ ID NO: 142 |
| 861 | SEQ ID NO: 229 | SEQ ID NO: 142 |
| 862 | SEQ ID NO: 230 | SEQ ID NO: 142 |
| 863 | SEQ ID NO: 231 | SEQ ID NO: 142 |
| 864 | SEQ ID NO: 232 | SEQ ID NO: 142 |
| 865 | SEQ ID NO: 233 | SEQ ID NO: 142 |
| 866 | SEQ ID NO: 234 | SEQ ID NO: 142 |
| 867 | SEQ ID NO: 235 | SEQ ID NO: 142 |
| 868 | SEQ ID NO: 236 | SEQ ID NO: 142 |
| 869 | SEQ ID NO: 237 | SEQ ID NO: 142 |
| 870 | SEQ ID NO: 238 | SEQ ID NO: 142 |
| 871 | SEQ ID NO: 239 | SEQ ID NO: 142 |
| 872 | SEQ ID NO: 240 | SEQ ID NO: 142 |
| 873 | SEQ ID NO: 241 | SEQ ID NO: 142 |
| 874 | SEQ ID NO: 242 | SEQ ID NO: 142 |
| 875 | SEQ ID NO: 243 | SEQ ID NO: 142 |
| 876 | SEQ ID NO: 244 | SEQ ID NO: 142 |
| 877 | SEQ ID NO: 245 | SEQ ID NO: 142 |
| 878 | SEQ ID NO: 246 | SEQ ID NO: 142 |
| 879 | SEQ ID NO: 247 | SEQ ID NO: 142 |
| 880 | SEQ ID NO: 248 | SEQ ID NO: 142 |
| 881 | SEQ ID NO: 249 | SEQ ID NO: 142 |
| 882 | SEQ ID NO: 250 | SEQ ID NO: 142 |
| 883 | SEQ ID NO: 251 | SEQ ID NO: 142 |
| 884 | SEQ ID NO: 252 | SEQ ID NO: 142 |
| 885 | SEQ ID NO: 253 | SEQ ID NO: 142 |
| 886 | SEQ ID NO: 254 | SEQ ID NO: 142 |
| 887 | SEQ ID NO: 255 | SEQ ID NO: 142 |
| 888 | SEQ ID NO: 256 | SEQ ID NO: 142 |
| 889 | SEQ ID NO: 257 | SEQ ID NO: 142 |
| 890 | SEQ ID NO: 258 | SEQ ID NO: 142 |
| 891 | SEQ ID NO: 259 | SEQ ID NO: 142 |
| 892 | SEQ ID NO: 260 | SEQ ID NO: 142 |
| 893 | SEQ ID NO: 261 | SEQ ID NO: 142 |
| 894 | SEQ ID NO: 262 | SEQ ID NO: 142 |
| 895 | SEQ ID NO: 263 | SEQ ID NO: 142 |
| 896 | SEQ ID NO: 264 | SEQ ID NO: 142 |
| 897 | SEQ ID NO: 265 | SEQ ID NO: 142 |
| 898 | SEQ ID NO: 266 | SEQ ID NO: 142 |
| 899 | SEQ ID NO: 267 | SEQ ID NO: 142 |
| 900 | SEQ ID NO: 268 | SEQ ID NO: 142 |
| 901 | SEQ ID NO: 269 | SEQ ID NO: 142 |
| 902 | SEQ ID NO: 270 | SEQ ID NO: 142 |
| 903 | SEQ ID NO: 271 | SEQ ID NO: 142 |
| 904 | SEQ ID NO: 272 | SEQ ID NO: 142 |
| 905 | SEQ ID NO: 273 | SEQ ID NO: 142 |
| 906 | SEQ ID NO: 274 | SEQ ID NO: 142 |
| 907 | SEQ ID NO: 275 | SEQ ID NO: 142 |
| 908 | SEQ ID NO: 276 | SEQ ID NO: 142 |
| 909 | SEQ ID NO: 277 | SEQ ID NO: 142 |
| 910 | SEQ ID NO: 278 | SEQ ID NO: 142 |
| 911 | SEQ ID NO: 279 | SEQ ID NO: 142 |
| 912 | SEQ ID NO: 280 | SEQ ID NO: 142 |
| 913 | SEQ ID NO: 281 | SEQ ID NO: 142 |
| 914 | SEQ ID NO: 282 | SEQ ID NO: 142 |
| 915 | SEQ ID NO: 283 | SEQ ID NO: 142 |
| 916 | SEQ ID NO: 284 | SEQ ID NO: 142 |
| 917 | SEQ ID NO: 285 | SEQ ID NO: 142 |
| 918 | SEQ ID NO: 286 | SEQ ID NO: 142 |
| 919 | SEQ ID NO: 287 | SEQ ID NO: 142 |
| 920 | SEQ ID NO: 288 | SEQ ID NO: 142 |
| 921 | SEQ ID NO: 289 | SEQ ID NO: 142 |
| 922 | SEQ ID NO: 141 | SEQ ID NO: 144 |
| 923 | SEQ ID NO: 143 | SEQ ID NO: 144 |
| 924 | SEQ ID NO: 145 | SEQ ID NO: 144 |
| 925 | SEQ ID NO: 147 | SEQ ID NO: 144 |
| 926 | SEQ ID NO: 149 | SEQ ID NO: 144 |
| 927 | SEQ ID NO: 151 | SEQ ID NO: 144 |
| 928 | SEQ ID NO: 153 | SEQ ID NO: 144 |
| 929 | SEQ ID NO: 155 | SEQ ID NO: 144 |
| 930 | SEQ ID NO: 156 | SEQ ID NO: 144 |
| 931 | SEQ ID NO: 164 | SEQ ID NO: 144 |
| 932 | SEQ ID NO: 165 | SEQ ID NO: 144 |
| 933 | SEQ ID NO: 166 | SEQ ID NO: 144 |
| 934 | SEQ ID NO: 167 | SEQ ID NO: 144 |
| 935 | SEQ ID NO: 168 | SEQ ID NO: 144 |
| 936 | SEQ ID NO: 169 | SEQ ID NO: 144 |
| 937 | SEQ ID NO: 170 | SEQ ID NO: 144 |
| 938 | SEQ ID NO: 171 | SEQ ID NO: 144 |
| 939 | SEQ ID NO: 172 | SEQ ID NO: 144 |
| 940 | SEQ ID NO: 173 | SEQ ID NO: 144 |
| 941 | SEQ ID NO: 174 | SEQ ID NO: 144 |
| 942 | SEQ ID NO: 175 | SEQ ID NO: 144 |
| 943 | SEQ ID NO: 176 | SEQ ID NO: 144 |
| 944 | SEQ ID NO: 177 | SEQ ID NO: 144 |
| 945 | SEQ ID NO: 178 | SEQ ID NO: 144 |
| 946 | SEQ ID NO: 179 | SEQ ID NO: 144 |
| 947 | SEQ ID NO: 180 | SEQ ID NO: 144 |
| 948 | SEQ ID NO: 181 | SEQ ID NO: 144 |
| 949 | SEQ ID NO: 182 | SEQ ID NO: 144 |
| 950 | SEQ ID NO: 183 | SEQ ID NO: 144 |
| 951 | SEQ ID NO: 184 | SEQ ID NO: 144 |
| 952 | SEQ ID NO: 185 | SEQ ID NO: 144 |
| 953 | SEQ ID NO: 186 | SEQ ID NO: 144 |
| 954 | SEQ ID NO: 187 | SEQ ID NO: 144 |
| 955 | SEQ ID NO: 188 | SEQ ID NO: 144 |
| 956 | SEQ ID NO: 189 | SEQ ID NO: 144 |
| 957 | SEQ ID NO: 190 | SEQ ID NO: 144 |
| 958 | SEQ ID NO: 191 | SEQ ID NO: 144 |
| 959 | SEQ ID NO: 192 | SEQ ID NO: 144 |
| 960 | SEQ ID NO: 193 | SEQ ID NO: 144 |
| 961 | SEQ ID NO: 194 | SEQ ID NO: 144 |
| 962 | SEQ ID NO: 195 | SEQ ID NO: 144 |
| 963 | SEQ ID NO: 196 | SEQ ID NO: 144 |
| 964 | SEQ ID NO: 197 | SEQ ID NO: 144 |
| 965 | SEQ ID NO: 198 | SEQ ID NO: 144 |
| 966 | SEQ ID NO: 199 | SEQ ID NO: 144 |
| 967 | SEQ ID NO: 200 | SEQ ID NO: 144 |
| 968 | SEQ ID NO: 201 | SEQ ID NO: 144 |
| 969 | SEQ ID NO: 202 | SEQ ID NO: 144 |
| 970 | SEQ ID NO: 203 | SEQ ID NO: 144 |
| 971 | SEQ ID NO: 204 | SEQ ID NO: 144 |
| 972 | SEQ ID NO: 205 | SEQ ID NO: 144 |
| 973 | SEQ ID NO: 206 | SEQ ID NO: 144 |
| 974 | SEQ ID NO: 207 | SEQ ID NO: 144 |
| 975 | SEQ ID NO: 208 | SEQ ID NO: 144 |
| 976 | SEQ ID NO: 209 | SEQ ID NO: 144 |
| 977 | SEQ ID NO: 210 | SEQ ID NO: 144 |
| 978 | SEQ ID NO: 211 | SEQ ID NO: 144 |
| 979 | SEQ ID NO: 212 | SEQ ID NO: 144 |
| 980 | SEQ ID NO: 213 | SEQ ID NO: 144 |
| 981 | SEQ ID NO: 214 | SEQ ID NO: 144 |
| 982 | SEQ ID NO: 215 | SEQ ID NO: 144 |

TABLE 1.1-continued

Heavy chains and light chains of exemplary antigen-binding proteins or antigen-binding fragments

| No. | Heavy Chain | Light Chain |
|---|---|---|
| 983 | SEQ ID NO: 216 | SEQ ID NO: 144 |
| 984 | SEQ ID NO: 217 | SEQ ID NO: 144 |
| 985 | SEQ ID NO: 218 | SEQ ID NO: 144 |
| 986 | SEQ ID NO: 219 | SEQ ID NO: 144 |
| 987 | SEQ ID NO: 220 | SEQ ID NO: 144 |
| 988 | SEQ ID NO: 221 | SEQ ID NO: 144 |
| 989 | SEQ ID NO: 222 | SEQ ID NO: 144 |
| 990 | SEQ ID NO: 223 | SEQ ID NO: 144 |
| 991 | SEQ ID NO: 224 | SEQ ID NO: 144 |
| 992 | SEQ ID NO: 225 | SEQ ID NO: 144 |
| 993 | SEQ ID NO: 226 | SEQ ID NO: 144 |
| 994 | SEQ ID NO: 227 | SEQ ID NO: 144 |
| 995 | SEQ ID NO: 228 | SEQ ID NO: 144 |
| 996 | SEQ ID NO: 229 | SEQ ID NO: 144 |
| 997 | SEQ ID NO: 230 | SEQ ID NO: 144 |
| 998 | SEQ ID NO: 231 | SEQ ID NO: 144 |
| 999 | SEQ ID NO: 232 | SEQ ID NO: 144 |
| 1000 | SEQ ID NO: 233 | SEQ ID NO: 144 |
| 1001 | SEQ ID NO: 234 | SEQ ID NO: 144 |
| 1002 | SEQ ID NO: 235 | SEQ ID NO: 144 |
| 1003 | SEQ ID NO: 236 | SEQ ID NO: 144 |
| 1004 | SEQ ID NO: 237 | SEQ ID NO: 144 |
| 1005 | SEQ ID NO: 238 | SEQ ID NO: 144 |
| 1006 | SEQ ID NO: 239 | SEQ ID NO: 144 |
| 1007 | SEQ ID NO: 240 | SEQ ID NO: 144 |
| 1008 | SEQ ID NO: 241 | SEQ ID NO: 144 |
| 1009 | SEQ ID NO: 242 | SEQ ID NO: 144 |
| 1010 | SEQ ID NO: 243 | SEQ ID NO: 144 |
| 1011 | SEQ ID NO: 244 | SEQ ID NO: 144 |
| 1012 | SEQ ID NO: 245 | SEQ ID NO: 144 |
| 1013 | SEQ ID NO: 246 | SEQ ID NO: 144 |
| 1014 | SEQ ID NO: 247 | SEQ ID NO: 144 |
| 1015 | SEQ ID NO: 248 | SEQ ID NO: 144 |
| 1016 | SEQ ID NO: 249 | SEQ ID NO: 144 |
| 1017 | SEQ ID NO: 250 | SEQ ID NO: 144 |
| 1018 | SEQ ID NO: 251 | SEQ ID NO: 144 |
| 1019 | SEQ ID NO: 252 | SEQ ID NO: 144 |
| 1020 | SEQ ID NO: 253 | SEQ ID NO: 144 |
| 1021 | SEQ ID NO: 254 | SEQ ID NO: 144 |
| 1022 | SEQ ID NO: 255 | SEQ ID NO: 144 |
| 1023 | SEQ ID NO: 256 | SEQ ID NO: 144 |
| 1024 | SEQ ID NO: 257 | SEQ ID NO: 144 |
| 1025 | SEQ ID NO: 258 | SEQ ID NO: 144 |
| 1026 | SEQ ID NO: 259 | SEQ ID NO: 144 |
| 1027 | SEQ ID NO: 260 | SEQ ID NO: 144 |
| 1028 | SEQ ID NO: 261 | SEQ ID NO: 144 |
| 1029 | SEQ ID NO: 262 | SEQ ID NO: 144 |
| 1030 | SEQ ID NO: 263 | SEQ ID NO: 144 |
| 1031 | SEQ ID NO: 264 | SEQ ID NO: 144 |
| 1032 | SEQ ID NO: 265 | SEQ ID NO: 144 |
| 1033 | SEQ ID NO: 266 | SEQ ID NO: 144 |
| 1034 | SEQ ID NO: 267 | SEQ ID NO: 144 |
| 1035 | SEQ ID NO: 268 | SEQ ID NO: 144 |
| 1036 | SEQ ID NO: 269 | SEQ ID NO: 144 |
| 1037 | SEQ ID NO: 270 | SEQ ID NO: 144 |
| 1038 | SEQ ID NO: 271 | SEQ ID NO: 144 |
| 1039 | SEQ ID NO: 272 | SEQ ID NO: 144 |
| 1040 | SEQ ID NO: 273 | SEQ ID NO: 144 |
| 1041 | SEQ ID NO: 274 | SEQ ID NO: 144 |
| 1042 | SEQ ID NO: 275 | SEQ ID NO: 144 |
| 1043 | SEQ ID NO: 276 | SEQ ID NO: 144 |
| 1044 | SEQ ID NO: 277 | SEQ ID NO: 144 |
| 1045 | SEQ ID NO: 278 | SEQ ID NO: 144 |
| 1046 | SEQ ID NO: 279 | SEQ ID NO: 144 |
| 1047 | SEQ ID NO: 280 | SEQ ID NO: 144 |
| 1048 | SEQ ID NO: 281 | SEQ ID NO: 144 |
| 1049 | SEQ ID NO: 282 | SEQ ID NO: 144 |
| 1050 | SEQ ID NO: 283 | SEQ ID NO: 144 |
| 1051 | SEQ ID NO: 284 | SEQ ID NO: 144 |
| 1052 | SEQ ID NO: 285 | SEQ ID NO: 144 |
| 1053 | SEQ ID NO: 286 | SEQ ID NO: 144 |
| 1054 | SEQ ID NO: 287 | SEQ ID NO: 144 |
| 1055 | SEQ ID NO: 288 | SEQ ID NO: 144 |
| 1056 | SEQ ID NO: 289 | SEQ ID NO: 144 |
| 1057 | SEQ ID NO: 141 | SEQ ID NO: 146 |
| 1058 | SEQ ID NO: 143 | SEQ ID NO: 146 |
| 1059 | SEQ ID NO: 145 | SEQ ID NO: 146 |
| 1060 | SEQ ID NO: 147 | SEQ ID NO: 146 |
| 1061 | SEQ ID NO: 149 | SEQ ID NO: 146 |
| 1062 | SEQ ID NO: 151 | SEQ ID NO: 146 |
| 1063 | SEQ ID NO: 153 | SEQ ID NO: 146 |
| 1064 | SEQ ID NO: 155 | SEQ ID NO: 146 |
| 1065 | SEQ ID NO: 156 | SEQ ID NO: 146 |
| 1066 | SEQ ID NO: 164 | SEQ ID NO: 146 |
| 1067 | SEQ ID NO: 165 | SEQ ID NO: 146 |
| 1068 | SEQ ID NO: 166 | SEQ ID NO: 146 |
| 1069 | SEQ ID NO: 167 | SEQ ID NO: 146 |
| 1070 | SEQ ID NO: 168 | SEQ ID NO: 146 |
| 1071 | SEQ ID NO: 169 | SEQ ID NO: 146 |
| 1072 | SEQ ID NO: 170 | SEQ ID NO: 146 |
| 1073 | SEQ ID NO: 171 | SEQ ID NO: 146 |
| 1074 | SEQ ID NO: 172 | SEQ ID NO: 146 |
| 1075 | SEQ ID NO: 173 | SEQ ID NO: 146 |
| 1076 | SEQ ID NO: 174 | SEQ ID NO: 146 |
| 1077 | SEQ ID NO: 175 | SEQ ID NO: 146 |
| 1078 | SEQ ID NO: 176 | SEQ ID NO: 146 |
| 1079 | SEQ ID NO: 177 | SEQ ID NO: 146 |
| 1080 | SEQ ID NO: 178 | SEQ ID NO: 146 |
| 1081 | SEQ ID NO: 179 | SEQ ID NO: 146 |
| 1082 | SEQ ID NO: 180 | SEQ ID NO: 146 |
| 1083 | SEQ ID NO: 181 | SEQ ID NO: 146 |
| 1084 | SEQ ID NO: 182 | SEQ ID NO: 146 |
| 1085 | SEQ ID NO: 183 | SEQ ID NO: 146 |
| 1086 | SEQ ID NO: 184 | SEQ ID NO: 146 |
| 1087 | SEQ ID NO: 185 | SEQ ID NO: 146 |
| 1088 | SEQ ID NO: 186 | SEQ ID NO: 146 |
| 1089 | SEQ ID NO: 187 | SEQ ID NO: 146 |
| 1090 | SEQ ID NO: 188 | SEQ ID NO: 146 |
| 1091 | SEQ ID NO: 189 | SEQ ID NO: 146 |
| 1092 | SEQ ID NO: 190 | SEQ ID NO: 146 |
| 1093 | SEQ ID NO: 191 | SEQ ID NO: 146 |
| 1094 | SEQ ID NO: 192 | SEQ ID NO: 146 |
| 1095 | SEQ ID NO: 193 | SEQ ID NO: 146 |
| 1096 | SEQ ID NO: 194 | SEQ ID NO: 146 |
| 1097 | SEQ ID NO: 195 | SEQ ID NO: 146 |
| 1098 | SEQ ID NO: 196 | SEQ ID NO: 146 |
| 1099 | SEQ ID NO: 197 | SEQ ID NO: 146 |
| 1100 | SEQ ID NO: 198 | SEQ ID NO: 146 |
| 1101 | SEQ ID NO: 199 | SEQ ID NO: 146 |
| 1102 | SEQ ID NO: 200 | SEQ ID NO: 146 |
| 1103 | SEQ ID NO: 201 | SEQ ID NO: 146 |
| 1104 | SEQ ID NO: 202 | SEQ ID NO: 146 |
| 1105 | SEQ ID NO: 203 | SEQ ID NO: 146 |
| 1106 | SEQ ID NO: 204 | SEQ ID NO: 146 |
| 1107 | SEQ ID NO: 205 | SEQ ID NO: 146 |
| 1108 | SEQ ID NO: 206 | SEQ ID NO: 146 |
| 1109 | SEQ ID NO: 207 | SEQ ID NO: 146 |
| 1110 | SEQ ID NO: 208 | SEQ ID NO: 146 |
| 1111 | SEQ ID NO: 209 | SEQ ID NO: 146 |
| 1112 | SEQ ID NO: 210 | SEQ ID NO: 146 |
| 1113 | SEQ ID NO: 211 | SEQ ID NO: 146 |
| 1114 | SEQ ID NO: 212 | SEQ ID NO: 146 |
| 1115 | SEQ ID NO: 213 | SEQ ID NO: 146 |
| 1116 | SEQ ID NO: 214 | SEQ ID NO: 146 |
| 1117 | SEQ ID NO: 215 | SEQ ID NO: 146 |
| 1118 | SEQ ID NO: 216 | SEQ ID NO: 146 |
| 1119 | SEQ ID NO: 217 | SEQ ID NO: 146 |
| 1120 | SEQ ID NO: 218 | SEQ ID NO: 146 |
| 1121 | SEQ ID NO: 219 | SEQ ID NO: 146 |
| 1122 | SEQ ID NO: 220 | SEQ ID NO: 146 |
| 1123 | SEQ ID NO: 221 | SEQ ID NO: 146 |
| 1124 | SEQ ID NO: 222 | SEQ ID NO: 146 |
| 1125 | SEQ ID NO: 223 | SEQ ID NO: 146 |
| 1126 | SEQ ID NO: 224 | SEQ ID NO: 146 |
| 1127 | SEQ ID NO: 225 | SEQ ID NO: 146 |
| 1128 | SEQ ID NO: 226 | SEQ ID NO: 146 |
| 1129 | SEQ ID NO: 227 | SEQ ID NO: 146 |
| 1130 | SEQ ID NO: 228 | SEQ ID NO: 146 |
| 1131 | SEQ ID NO: 229 | SEQ ID NO: 146 |
| 1132 | SEQ ID NO: 230 | SEQ ID NO: 146 |

TABLE 1.1-continued

Heavy chains and light chains of exemplary antigen-binding proteins or antigen-binding fragments

| No. | Heavy Chain | Light Chain |
|---|---|---|
| 1133 | SEQ ID NO: 231 | SEQ ID NO: 146 |
| 1134 | SEQ ID NO: 232 | SEQ ID NO: 146 |
| 1135 | SEQ ID NO: 233 | SEQ ID NO: 146 |
| 1136 | SEQ ID NO: 234 | SEQ ID NO: 146 |
| 1137 | SEQ ID NO: 235 | SEQ ID NO: 146 |
| 1138 | SEQ ID NO: 236 | SEQ ID NO: 146 |
| 1139 | SEQ ID NO: 237 | SEQ ID NO: 146 |
| 1140 | SEQ ID NO: 238 | SEQ ID NO: 146 |
| 1141 | SEQ ID NO: 239 | SEQ ID NO: 146 |
| 1142 | SEQ ID NO: 240 | SEQ ID NO: 146 |
| 1143 | SEQ ID NO: 241 | SEQ ID NO: 146 |
| 1144 | SEQ ID NO: 242 | SEQ ID NO: 146 |
| 1145 | SEQ ID NO: 243 | SEQ ID NO: 146 |
| 1146 | SEQ ID NO: 244 | SEQ ID NO: 146 |
| 1147 | SEQ ID NO: 245 | SEQ ID NO: 146 |
| 1148 | SEQ ID NO: 246 | SEQ ID NO: 146 |
| 1149 | SEQ ID NO: 247 | SEQ ID NO: 146 |
| 1150 | SEQ ID NO: 248 | SEQ ID NO: 146 |
| 1151 | SEQ ID NO: 249 | SEQ ID NO: 146 |
| 1152 | SEQ ID NO: 250 | SEQ ID NO: 146 |
| 1153 | SEQ ID NO: 251 | SEQ ID NO: 146 |
| 1154 | SEQ ID NO: 252 | SEQ ID NO: 146 |
| 1155 | SEQ ID NO: 253 | SEQ ID NO: 146 |
| 1156 | SEQ ID NO: 254 | SEQ ID NO: 146 |
| 1157 | SEQ ID NO: 255 | SEQ ID NO: 146 |
| 1158 | SEQ ID NO: 256 | SEQ ID NO: 146 |
| 1159 | SEQ ID NO: 257 | SEQ ID NO: 146 |
| 1160 | SEQ ID NO: 258 | SEQ ID NO: 146 |
| 1161 | SEQ ID NO: 259 | SEQ ID NO: 146 |
| 1162 | SEQ ID NO: 260 | SEQ ID NO: 146 |
| 1163 | SEQ ID NO: 261 | SEQ ID NO: 146 |
| 1164 | SEQ ID NO: 262 | SEQ ID NO: 146 |
| 1165 | SEQ ID NO: 263 | SEQ ID NO: 146 |
| 1166 | SEQ ID NO: 264 | SEQ ID NO: 146 |
| 1167 | SEQ ID NO: 265 | SEQ ID NO: 146 |
| 1168 | SEQ ID NO: 266 | SEQ ID NO: 146 |
| 1169 | SEQ ID NO: 267 | SEQ ID NO: 146 |
| 1170 | SEQ ID NO: 268 | SEQ ID NO: 146 |
| 1171 | SEQ ID NO: 269 | SEQ ID NO: 146 |
| 1172 | SEQ ID NO: 270 | SEQ ID NO: 146 |
| 1173 | SEQ ID NO: 271 | SEQ ID NO: 146 |
| 1174 | SEQ ID NO: 272 | SEQ ID NO: 146 |
| 1175 | SEQ ID NO: 273 | SEQ ID NO: 146 |
| 1176 | SEQ ID NO: 274 | SEQ ID NO: 146 |
| 1177 | SEQ ID NO: 275 | SEQ ID NO: 146 |
| 1178 | SEQ ID NO: 276 | SEQ ID NO: 146 |
| 1179 | SEQ ID NO: 277 | SEQ ID NO: 146 |
| 1180 | SEQ ID NO: 278 | SEQ ID NO: 146 |
| 1181 | SEQ ID NO: 279 | SEQ ID NO: 146 |
| 1182 | SEQ ID NO: 280 | SEQ ID NO: 146 |
| 1183 | SEQ ID NO: 281 | SEQ ID NO: 146 |
| 1184 | SEQ ID NO: 282 | SEQ ID NO: 146 |
| 1185 | SEQ ID NO: 283 | SEQ ID NO: 146 |
| 1186 | SEQ ID NO: 284 | SEQ ID NO: 146 |
| 1187 | SEQ ID NO: 285 | SEQ ID NO: 146 |
| 1188 | SEQ ID NO: 286 | SEQ ID NO: 146 |
| 1189 | SEQ ID NO: 287 | SEQ ID NO: 146 |
| 1190 | SEQ ID NO: 288 | SEQ ID NO: 146 |
| 1191 | SEQ ID NO: 289 | SEQ ID NO: 146 |
| 1192 | SEQ ID NO: 141 | SEQ ID NO: 148 |
| 1193 | SEQ ID NO: 143 | SEQ ID NO: 148 |
| 1194 | SEQ ID NO: 145 | SEQ ID NO: 148 |
| 1195 | SEQ ID NO: 147 | SEQ ID NO: 148 |
| 1196 | SEQ ID NO: 149 | SEQ ID NO: 148 |
| 1197 | SEQ ID NO: 151 | SEQ ID NO: 148 |
| 1198 | SEQ ID NO: 153 | SEQ ID NO: 148 |
| 1199 | SEQ ID NO: 155 | SEQ ID NO: 148 |
| 1200 | SEQ ID NO: 156 | SEQ ID NO: 148 |
| 1201 | SEQ ID NO: 164 | SEQ ID NO: 148 |
| 1202 | SEQ ID NO: 165 | SEQ ID NO: 148 |
| 1203 | SEQ ID NO: 166 | SEQ ID NO: 148 |
| 1204 | SEQ ID NO: 167 | SEQ ID NO: 148 |
| 1205 | SEQ ID NO: 168 | SEQ ID NO: 148 |
| 1206 | SEQ ID NO: 169 | SEQ ID NO: 148 |
| 1207 | SEQ ID NO: 170 | SEQ ID NO: 148 |
| 1208 | SEQ ID NO: 171 | SEQ ID NO: 148 |
| 1209 | SEQ ID NO: 172 | SEQ ID NO: 148 |
| 1210 | SEQ ID NO: 173 | SEQ ID NO: 148 |
| 1211 | SEQ ID NO: 174 | SEQ ID NO: 148 |
| 1212 | SEQ ID NO: 175 | SEQ ID NO: 148 |
| 1213 | SEQ ID NO: 176 | SEQ ID NO: 148 |
| 1214 | SEQ ID NO: 177 | SEQ ID NO: 148 |
| 1215 | SEQ ID NO: 178 | SEQ ID NO: 148 |
| 1216 | SEQ ID NO: 179 | SEQ ID NO: 148 |
| 1217 | SEQ ID NO: 180 | SEQ ID NO: 148 |
| 1218 | SEQ ID NO: 181 | SEQ ID NO: 148 |
| 1219 | SEQ ID NO: 182 | SEQ ID NO: 148 |
| 1220 | SEQ ID NO: 183 | SEQ ID NO: 148 |
| 1221 | SEQ ID NO: 184 | SEQ ID NO: 148 |
| 1222 | SEQ ID NO: 185 | SEQ ID NO: 148 |
| 1223 | SEQ ID NO: 186 | SEQ ID NO: 148 |
| 1224 | SEQ ID NO: 187 | SEQ ID NO: 148 |
| 1225 | SEQ ID NO: 188 | SEQ ID NO: 148 |
| 1226 | SEQ ID NO: 189 | SEQ ID NO: 148 |
| 1227 | SEQ ID NO: 190 | SEQ ID NO: 148 |
| 1228 | SEQ ID NO: 191 | SEQ ID NO: 148 |
| 1229 | SEQ ID NO: 192 | SEQ ID NO: 148 |
| 1230 | SEQ ID NO: 193 | SEQ ID NO: 148 |
| 1231 | SEQ ID NO: 194 | SEQ ID NO: 148 |
| 1232 | SEQ ID NO: 195 | SEQ ID NO: 148 |
| 1233 | SEQ ID NO: 196 | SEQ ID NO: 148 |
| 1234 | SEQ ID NO: 197 | SEQ ID NO: 148 |
| 1235 | SEQ ID NO: 198 | SEQ ID NO: 148 |
| 1236 | SEQ ID NO: 199 | SEQ ID NO: 148 |
| 1237 | SEQ ID NO: 200 | SEQ ID NO: 148 |
| 1238 | SEQ ID NO: 201 | SEQ ID NO: 148 |
| 1239 | SEQ ID NO: 202 | SEQ ID NO: 148 |
| 1240 | SEQ ID NO: 203 | SEQ ID NO: 148 |
| 1241 | SEQ ID NO: 204 | SEQ ID NO: 148 |
| 1242 | SEQ ID NO: 205 | SEQ ID NO: 148 |
| 1243 | SEQ ID NO: 206 | SEQ ID NO: 148 |
| 1244 | SEQ ID NO: 207 | SEQ ID NO: 148 |
| 1245 | SEQ ID NO: 208 | SEQ ID NO: 148 |
| 1246 | SEQ ID NO: 209 | SEQ ID NO: 148 |
| 1247 | SEQ ID NO: 210 | SEQ ID NO: 148 |
| 1248 | SEQ ID NO: 211 | SEQ ID NO: 148 |
| 1249 | SEQ ID NO: 212 | SEQ ID NO: 148 |
| 1250 | SEQ ID NO: 213 | SEQ ID NO: 148 |
| 1251 | SEQ ID NO: 214 | SEQ ID NO: 148 |
| 1252 | SEQ ID NO: 215 | SEQ ID NO: 148 |
| 1253 | SEQ ID NO: 216 | SEQ ID NO: 148 |
| 1254 | SEQ ID NO: 217 | SEQ ID NO: 148 |
| 1255 | SEQ ID NO: 218 | SEQ ID NO: 148 |
| 1256 | SEQ ID NO: 219 | SEQ ID NO: 148 |
| 1257 | SEQ ID NO: 220 | SEQ ID NO: 148 |
| 1258 | SEQ ID NO: 221 | SEQ ID NO: 148 |
| 1259 | SEQ ID NO: 222 | SEQ ID NO: 148 |
| 1260 | SEQ ID NO: 223 | SEQ ID NO: 148 |
| 1261 | SEQ ID NO: 224 | SEQ ID NO: 148 |
| 1262 | SEQ ID NO: 225 | SEQ ID NO: 148 |
| 1263 | SEQ ID NO: 226 | SEQ ID NO: 148 |
| 1264 | SEQ ID NO: 227 | SEQ ID NO: 148 |
| 1265 | SEQ ID NO: 228 | SEQ ID NO: 148 |
| 1266 | SEQ ID NO: 229 | SEQ ID NO: 148 |
| 1267 | SEQ ID NO: 230 | SEQ ID NO: 148 |
| 1268 | SEQ ID NO: 231 | SEQ ID NO: 148 |
| 1269 | SEQ ID NO: 232 | SEQ ID NO: 148 |
| 1270 | SEQ ID NO: 233 | SEQ ID NO: 148 |
| 1271 | SEQ ID NO: 234 | SEQ ID NO: 148 |
| 1272 | SEQ ID NO: 235 | SEQ ID NO: 148 |
| 1273 | SEQ ID NO: 236 | SEQ ID NO: 148 |
| 1274 | SEQ ID NO: 237 | SEQ ID NO: 148 |
| 1275 | SEQ ID NO: 238 | SEQ ID NO: 148 |
| 1276 | SEQ ID NO: 239 | SEQ ID NO: 148 |
| 1277 | SEQ ID NO: 240 | SEQ ID NO: 148 |
| 1278 | SEQ ID NO: 241 | SEQ ID NO: 148 |
| 1279 | SEQ ID NO: 242 | SEQ ID NO: 148 |
| 1280 | SEQ ID NO: 243 | SEQ ID NO: 148 |
| 1281 | SEQ ID NO: 244 | SEQ ID NO: 148 |
| 1282 | SEQ ID NO: 245 | SEQ ID NO: 148 |

TABLE 1.1-continued

Heavy chains and light chains of exemplary antigen-binding proteins or antigen-binding fragments

| No. | Heavy Chain | Light Chain |
|---|---|---|
| 1283 | SEQ ID NO: 246 | SEQ ID NO: 148 |
| 1284 | SEQ ID NO: 247 | SEQ ID NO: 148 |
| 1285 | SEQ ID NO: 248 | SEQ ID NO: 148 |
| 1286 | SEQ ID NO: 249 | SEQ ID NO: 148 |
| 1287 | SEQ ID NO: 250 | SEQ ID NO: 148 |
| 1288 | SEQ ID NO: 251 | SEQ ID NO: 148 |
| 1289 | SEQ ID NO: 252 | SEQ ID NO: 148 |
| 1290 | SEQ ID NO: 253 | SEQ ID NO: 148 |
| 1291 | SEQ ID NO: 254 | SEQ ID NO: 148 |
| 1292 | SEQ ID NO: 255 | SEQ ID NO: 148 |
| 1293 | SEQ ID NO: 256 | SEQ ID NO: 148 |
| 1294 | SEQ ID NO: 257 | SEQ ID NO: 148 |
| 1295 | SEQ ID NO: 258 | SEQ ID NO: 148 |
| 1296 | SEQ ID NO: 259 | SEQ ID NO: 148 |
| 1297 | SEQ ID NO: 260 | SEQ ID NO: 148 |
| 1298 | SEQ ID NO: 261 | SEQ ID NO: 148 |
| 1299 | SEQ ID NO: 262 | SEQ ID NO: 148 |
| 1300 | SEQ ID NO: 263 | SEQ ID NO: 148 |
| 1301 | SEQ ID NO: 264 | SEQ ID NO: 148 |
| 1302 | SEQ ID NO: 265 | SEQ ID NO: 148 |
| 1303 | SEQ ID NO: 266 | SEQ ID NO: 148 |
| 1304 | SEQ ID NO: 267 | SEQ ID NO: 148 |
| 1305 | SEQ ID NO: 268 | SEQ ID NO: 148 |
| 1306 | SEQ ID NO: 269 | SEQ ID NO: 148 |
| 1307 | SEQ ID NO: 270 | SEQ ID NO: 148 |
| 1308 | SEQ ID NO: 271 | SEQ ID NO: 148 |
| 1309 | SEQ ID NO: 272 | SEQ ID NO: 148 |
| 1310 | SEQ ID NO: 273 | SEQ ID NO: 148 |
| 1311 | SEQ ID NO: 274 | SEQ ID NO: 148 |
| 1312 | SEQ ID NO: 275 | SEQ ID NO: 148 |
| 1313 | SEQ ID NO: 276 | SEQ ID NO: 148 |
| 1314 | SEQ ID NO: 277 | SEQ ID NO: 148 |
| 1315 | SEQ ID NO: 278 | SEQ ID NO: 148 |
| 1316 | SEQ ID NO: 279 | SEQ ID NO: 148 |
| 1317 | SEQ ID NO: 280 | SEQ ID NO: 148 |
| 1318 | SEQ ID NO: 281 | SEQ ID NO: 148 |
| 1319 | SEQ ID NO: 282 | SEQ ID NO: 148 |
| 1320 | SEQ ID NO: 283 | SEQ ID NO: 148 |
| 1321 | SEQ ID NO: 284 | SEQ ID NO: 148 |
| 1322 | SEQ ID NO: 285 | SEQ ID NO: 148 |
| 1323 | SEQ ID NO: 286 | SEQ ID NO: 148 |
| 1324 | SEQ ID NO: 287 | SEQ ID NO: 148 |
| 1325 | SEQ ID NO: 288 | SEQ ID NO: 148 |
| 1326 | SEQ ID NO: 289 | SEQ ID NO: 148 |
| 1327 | SEQ ID NO: 141 | SEQ ID NO: 150 |
| 1328 | SEQ ID NO: 143 | SEQ ID NO: 150 |
| 1329 | SEQ ID NO: 145 | SEQ ID NO: 150 |
| 1330 | SEQ ID NO: 147 | SEQ ID NO: 150 |
| 1331 | SEQ ID NO: 149 | SEQ ID NO: 150 |
| 1332 | SEQ ID NO: 151 | SEQ ID NO: 150 |
| 1333 | SEQ ID NO: 153 | SEQ ID NO: 150 |
| 1334 | SEQ ID NO: 155 | SEQ ID NO: 150 |
| 1335 | SEQ ID NO: 156 | SEQ ID NO: 150 |
| 1336 | SEQ ID NO: 164 | SEQ ID NO: 150 |
| 1337 | SEQ ID NO: 165 | SEQ ID NO: 150 |
| 1338 | SEQ ID NO: 166 | SEQ ID NO: 150 |
| 1339 | SEQ ID NO: 167 | SEQ ID NO: 150 |
| 1340 | SEQ ID NO: 168 | SEQ ID NO: 150 |
| 1341 | SEQ ID NO: 169 | SEQ ID NO: 150 |
| 1342 | SEQ ID NO: 170 | SEQ ID NO: 150 |
| 1343 | SEQ ID NO: 171 | SEQ ID NO: 150 |
| 1344 | SEQ ID NO: 172 | SEQ ID NO: 150 |
| 1345 | SEQ ID NO: 173 | SEQ ID NO: 150 |
| 1346 | SEQ ID NO: 174 | SEQ ID NO: 150 |
| 1347 | SEQ ID NO: 175 | SEQ ID NO: 150 |
| 1348 | SEQ ID NO: 176 | SEQ ID NO: 150 |
| 1349 | SEQ ID NO: 177 | SEQ ID NO: 150 |
| 1350 | SEQ ID NO: 178 | SEQ ID NO: 150 |
| 1351 | SEQ ID NO: 179 | SEQ ID NO: 150 |
| 1352 | SEQ ID NO: 180 | SEQ ID NO: 150 |
| 1353 | SEQ ID NO: 181 | SEQ ID NO: 150 |
| 1354 | SEQ ID NO: 182 | SEQ ID NO: 150 |
| 1355 | SEQ ID NO: 183 | SEQ ID NO: 150 |
| 1356 | SEQ ID NO: 184 | SEQ ID NO: 150 |
| 1357 | SEQ ID NO: 185 | SEQ ID NO: 150 |
| 1358 | SEQ ID NO: 186 | SEQ ID NO: 150 |
| 1359 | SEQ ID NO: 187 | SEQ ID NO: 150 |
| 1360 | SEQ ID NO: 188 | SEQ ID NO: 150 |
| 1361 | SEQ ID NO: 189 | SEQ ID NO: 150 |
| 1362 | SEQ ID NO: 190 | SEQ ID NO: 150 |
| 1363 | SEQ ID NO: 191 | SEQ ID NO: 150 |
| 1364 | SEQ ID NO: 192 | SEQ ID NO: 150 |
| 1365 | SEQ ID NO: 193 | SEQ ID NO: 150 |
| 1366 | SEQ ID NO: 194 | SEQ ID NO: 150 |
| 1367 | SEQ ID NO: 195 | SEQ ID NO: 150 |
| 1368 | SEQ ID NO: 196 | SEQ ID NO: 150 |
| 1369 | SEQ ID NO: 197 | SEQ ID NO: 150 |
| 1370 | SEQ ID NO: 198 | SEQ ID NO: 150 |
| 1371 | SEQ ID NO: 199 | SEQ ID NO: 150 |
| 1372 | SEQ ID NO: 200 | SEQ ID NO: 150 |
| 1373 | SEQ ID NO: 201 | SEQ ID NO: 150 |
| 1374 | SEQ ID NO: 202 | SEQ ID NO: 150 |
| 1375 | SEQ ID NO: 203 | SEQ ID NO: 150 |
| 1376 | SEQ ID NO: 204 | SEQ ID NO: 150 |
| 1377 | SEQ ID NO: 205 | SEQ ID NO: 150 |
| 1378 | SEQ ID NO: 206 | SEQ ID NO: 150 |
| 1379 | SEQ ID NO: 207 | SEQ ID NO: 150 |
| 1380 | SEQ ID NO: 208 | SEQ ID NO: 150 |
| 1381 | SEQ ID NO: 209 | SEQ ID NO: 150 |
| 1382 | SEQ ID NO: 210 | SEQ ID NO: 150 |
| 1383 | SEQ ID NO: 211 | SEQ ID NO: 150 |
| 1384 | SEQ ID NO: 212 | SEQ ID NO: 150 |
| 1385 | SEQ ID NO: 213 | SEQ ID NO: 150 |
| 1386 | SEQ ID NO: 214 | SEQ ID NO: 150 |
| 1387 | SEQ ID NO: 215 | SEQ ID NO: 150 |
| 1388 | SEQ ID NO: 216 | SEQ ID NO: 150 |
| 1389 | SEQ ID NO: 217 | SEQ ID NO: 150 |
| 1390 | SEQ ID NO: 218 | SEQ ID NO: 150 |
| 1391 | SEQ ID NO: 219 | SEQ ID NO: 150 |
| 1392 | SEQ ID NO: 220 | SEQ ID NO: 150 |
| 1393 | SEQ ID NO: 221 | SEQ ID NO: 150 |
| 1394 | SEQ ID NO: 222 | SEQ ID NO: 150 |
| 1395 | SEQ ID NO: 223 | SEQ ID NO: 150 |
| 1396 | SEQ ID NO: 224 | SEQ ID NO: 150 |
| 1397 | SEQ ID NO: 225 | SEQ ID NO: 150 |
| 1398 | SEQ ID NO: 226 | SEQ ID NO: 150 |
| 1399 | SEQ ID NO: 227 | SEQ ID NO: 150 |
| 1400 | SEQ ID NO: 228 | SEQ ID NO: 150 |
| 1401 | SEQ ID NO: 229 | SEQ ID NO: 150 |
| 1402 | SEQ ID NO: 230 | SEQ ID NO: 150 |
| 1403 | SEQ ID NO: 231 | SEQ ID NO: 150 |
| 1404 | SEQ ID NO: 232 | SEQ ID NO: 150 |
| 1405 | SEQ ID NO: 233 | SEQ ID NO: 150 |
| 1406 | SEQ ID NO: 234 | SEQ ID NO: 150 |
| 1407 | SEQ ID NO: 235 | SEQ ID NO: 150 |
| 1408 | SEQ ID NO: 236 | SEQ ID NO: 150 |
| 1409 | SEQ ID NO: 237 | SEQ ID NO: 150 |
| 1410 | SEQ ID NO: 238 | SEQ ID NO: 150 |
| 1411 | SEQ ID NO: 239 | SEQ ID NO: 150 |
| 1412 | SEQ ID NO: 240 | SEQ ID NO: 150 |
| 1413 | SEQ ID NO: 241 | SEQ ID NO: 150 |
| 1414 | SEQ ID NO: 242 | SEQ ID NO: 150 |
| 1415 | SEQ ID NO: 243 | SEQ ID NO: 150 |
| 1416 | SEQ ID NO: 244 | SEQ ID NO: 150 |
| 1417 | SEQ ID NO: 245 | SEQ ID NO: 150 |
| 1418 | SEQ ID NO: 246 | SEQ ID NO: 150 |
| 1419 | SEQ ID NO: 247 | SEQ ID NO: 150 |
| 1420 | SEQ ID NO: 248 | SEQ ID NO: 150 |
| 1421 | SEQ ID NO: 249 | SEQ ID NO: 150 |
| 1422 | SEQ ID NO: 250 | SEQ ID NO: 150 |
| 1423 | SEQ ID NO: 251 | SEQ ID NO: 150 |
| 1424 | SEQ ID NO: 252 | SEQ ID NO: 150 |
| 1425 | SEQ ID NO: 253 | SEQ ID NO: 150 |
| 1426 | SEQ ID NO: 254 | SEQ ID NO: 150 |
| 1427 | SEQ ID NO: 255 | SEQ ID NO: 150 |
| 1428 | SEQ ID NO: 256 | SEQ ID NO: 150 |
| 1429 | SEQ ID NO: 257 | SEQ ID NO: 150 |
| 1430 | SEQ ID NO: 258 | SEQ ID NO: 150 |
| 1431 | SEQ ID NO: 259 | SEQ ID NO: 150 |
| 1432 | SEQ ID NO: 260 | SEQ ID NO: 150 |

TABLE 1.1-continued

Heavy chains and light chains of exemplary antigen-binding proteins or antigen-binding fragments

| No. | Heavy Chain | Light Chain |
|---|---|---|
| 1433 | SEQ ID NO: 261 | SEQ ID NO: 150 |
| 1434 | SEQ ID NO: 262 | SEQ ID NO: 150 |
| 1435 | SEQ ID NO: 263 | SEQ ID NO: 150 |
| 1436 | SEQ ID NO: 264 | SEQ ID NO: 150 |
| 1437 | SEQ ID NO: 265 | SEQ ID NO: 150 |
| 1438 | SEQ ID NO: 266 | SEQ ID NO: 150 |
| 1439 | SEQ ID NO: 267 | SEQ ID NO: 150 |
| 1440 | SEQ ID NO: 268 | SEQ ID NO: 150 |
| 1441 | SEQ ID NO: 269 | SEQ ID NO: 150 |
| 1442 | SEQ ID NO: 270 | SEQ ID NO: 150 |
| 1443 | SEQ ID NO: 271 | SEQ ID NO: 150 |
| 1444 | SEQ ID NO: 272 | SEQ ID NO: 150 |
| 1445 | SEQ ID NO: 273 | SEQ ID NO: 150 |
| 1446 | SEQ ID NO: 274 | SEQ ID NO: 150 |
| 1447 | SEQ ID NO: 275 | SEQ ID NO: 150 |
| 1448 | SEQ ID NO: 276 | SEQ ID NO: 150 |
| 1449 | SEQ ID NO: 277 | SEQ ID NO: 150 |
| 1450 | SEQ ID NO: 278 | SEQ ID NO: 150 |
| 1451 | SEQ ID NO: 279 | SEQ ID NO: 150 |
| 1452 | SEQ ID NO: 280 | SEQ ID NO: 150 |
| 1453 | SEQ ID NO: 281 | SEQ ID NO: 150 |
| 1454 | SEQ ID NO: 282 | SEQ ID NO: 150 |
| 1455 | SEQ ID NO: 283 | SEQ ID NO: 150 |
| 1456 | SEQ ID NO: 284 | SEQ ID NO: 150 |
| 1457 | SEQ ID NO: 285 | SEQ ID NO: 150 |
| 1458 | SEQ ID NO: 286 | SEQ ID NO: 150 |
| 1459 | SEQ ID NO: 287 | SEQ ID NO: 150 |
| 1460 | SEQ ID NO: 288 | SEQ ID NO: 150 |
| 1461 | SEQ ID NO: 289 | SEQ ID NO: 150 |
| 1462 | SEQ ID NO: 141 | SEQ ID NO: 152 |
| 1463 | SEQ ID NO: 143 | SEQ ID NO: 152 |
| 1464 | SEQ ID NO: 145 | SEQ ID NO: 152 |
| 1465 | SEQ ID NO: 147 | SEQ ID NO: 152 |
| 1466 | SEQ ID NO: 149 | SEQ ID NO: 152 |
| 1467 | SEQ ID NO: 151 | SEQ ID NO: 152 |
| 1468 | SEQ ID NO: 153 | SEQ ID NO: 152 |
| 1469 | SEQ ID NO: 155 | SEQ ID NO: 152 |
| 1470 | SEQ ID NO: 156 | SEQ ID NO: 152 |
| 1471 | SEQ ID NO: 164 | SEQ ID NO: 152 |
| 1472 | SEQ ID NO: 165 | SEQ ID NO: 152 |
| 1473 | SEQ ID NO: 166 | SEQ ID NO: 152 |
| 1474 | SEQ ID NO: 167 | SEQ ID NO: 152 |
| 1475 | SEQ ID NO: 168 | SEQ ID NO: 152 |
| 1476 | SEQ ID NO: 169 | SEQ ID NO: 152 |
| 1477 | SEQ ID NO: 170 | SEQ ID NO: 152 |
| 1478 | SEQ ID NO: 171 | SEQ ID NO: 152 |
| 1479 | SEQ ID NO: 172 | SEQ ID NO: 152 |
| 1480 | SEQ ID NO: 173 | SEQ ID NO: 152 |
| 1481 | SEQ ID NO: 174 | SEQ ID NO: 152 |
| 1482 | SEQ ID NO: 175 | SEQ ID NO: 152 |
| 1483 | SEQ ID NO: 176 | SEQ ID NO: 152 |
| 1484 | SEQ ID NO: 177 | SEQ ID NO: 152 |
| 1485 | SEQ ID NO: 178 | SEQ ID NO: 152 |
| 1486 | SEQ ID NO: 179 | SEQ ID NO: 152 |
| 1487 | SEQ ID NO: 180 | SEQ ID NO: 152 |
| 1488 | SEQ ID NO: 181 | SEQ ID NO: 152 |
| 1489 | SEQ ID NO: 182 | SEQ ID NO: 152 |
| 1490 | SEQ ID NO: 183 | SEQ ID NO: 152 |
| 1491 | SEQ ID NO: 184 | SEQ ID NO: 152 |
| 1492 | SEQ ID NO: 185 | SEQ ID NO: 152 |
| 1493 | SEQ ID NO: 186 | SEQ ID NO: 152 |
| 1494 | SEQ ID NO: 187 | SEQ ID NO: 152 |
| 1495 | SEQ ID NO: 188 | SEQ ID NO: 152 |
| 1496 | SEQ ID NO: 189 | SEQ ID NO: 152 |
| 1497 | SEQ ID NO: 190 | SEQ ID NO: 152 |
| 1498 | SEQ ID NO: 191 | SEQ ID NO: 152 |
| 1499 | SEQ ID NO: 192 | SEQ ID NO: 152 |
| 1500 | SEQ ID NO: 193 | SEQ ID NO: 152 |
| 1501 | SEQ ID NO: 194 | SEQ ID NO: 152 |
| 1502 | SEQ ID NO: 195 | SEQ ID NO: 152 |
| 1503 | SEQ ID NO: 196 | SEQ ID NO: 152 |
| 1504 | SEQ ID NO: 197 | SEQ ID NO: 152 |
| 1505 | SEQ ID NO: 198 | SEQ ID NO: 152 |
| 1506 | SEQ ID NO: 199 | SEQ ID NO: 152 |
| 1507 | SEQ ID NO: 200 | SEQ ID NO: 152 |
| 1508 | SEQ ID NO: 201 | SEQ ID NO: 152 |
| 1509 | SEQ ID NO: 202 | SEQ ID NO: 152 |
| 1510 | SEQ ID NO: 203 | SEQ ID NO: 152 |
| 1511 | SEQ ID NO: 204 | SEQ ID NO: 152 |
| 1512 | SEQ ID NO: 205 | SEQ ID NO: 152 |
| 1513 | SEQ ID NO: 206 | SEQ ID NO: 152 |
| 1514 | SEQ ID NO: 207 | SEQ ID NO: 152 |
| 1515 | SEQ ID NO: 208 | SEQ ID NO: 152 |
| 1516 | SEQ ID NO: 209 | SEQ ID NO: 152 |
| 1517 | SEQ ID NO: 210 | SEQ ID NO: 152 |
| 1518 | SEQ ID NO: 211 | SEQ ID NO: 152 |
| 1519 | SEQ ID NO: 212 | SEQ ID NO: 152 |
| 1520 | SEQ ID NO: 213 | SEQ ID NO: 152 |
| 1521 | SEQ ID NO: 214 | SEQ ID NO: 152 |
| 1522 | SEQ ID NO: 215 | SEQ ID NO: 152 |
| 1523 | SEQ ID NO: 216 | SEQ ID NO: 152 |
| 1524 | SEQ ID NO: 217 | SEQ ID NO: 152 |
| 1525 | SEQ ID NO: 218 | SEQ ID NO: 152 |
| 1526 | SEQ ID NO: 219 | SEQ ID NO: 152 |
| 1527 | SEQ ID NO: 220 | SEQ ID NO: 152 |
| 1528 | SEQ ID NO: 221 | SEQ ID NO: 152 |
| 1529 | SEQ ID NO: 222 | SEQ ID NO: 152 |
| 1530 | SEQ ID NO: 223 | SEQ ID NO: 152 |
| 1531 | SEQ ID NO: 224 | SEQ ID NO: 152 |
| 1532 | SEQ ID NO: 225 | SEQ ID NO: 152 |
| 1533 | SEQ ID NO: 226 | SEQ ID NO: 152 |
| 1534 | SEQ ID NO: 227 | SEQ ID NO: 152 |
| 1535 | SEQ ID NO: 228 | SEQ ID NO: 152 |
| 1536 | SEQ ID NO: 229 | SEQ ID NO: 152 |
| 1537 | SEQ ID NO: 230 | SEQ ID NO: 152 |
| 1538 | SEQ ID NO: 231 | SEQ ID NO: 152 |
| 1539 | SEQ ID NO: 232 | SEQ ID NO: 152 |
| 1540 | SEQ ID NO: 233 | SEQ ID NO: 152 |
| 1541 | SEQ ID NO: 234 | SEQ ID NO: 152 |
| 1542 | SEQ ID NO: 235 | SEQ ID NO: 152 |
| 1543 | SEQ ID NO: 236 | SEQ ID NO: 152 |
| 1544 | SEQ ID NO: 237 | SEQ ID NO: 152 |
| 1545 | SEQ ID NO: 238 | SEQ ID NO: 152 |
| 1546 | SEQ ID NO: 239 | SEQ ID NO: 152 |
| 1547 | SEQ ID NO: 240 | SEQ ID NO: 152 |
| 1548 | SEQ ID NO: 241 | SEQ ID NO: 152 |
| 1549 | SEQ ID NO: 242 | SEQ ID NO: 152 |
| 1550 | SEQ ID NO: 243 | SEQ ID NO: 152 |
| 1551 | SEQ ID NO: 244 | SEQ ID NO: 152 |
| 1552 | SEQ ID NO: 245 | SEQ ID NO: 152 |
| 1553 | SEQ ID NO: 246 | SEQ ID NO: 152 |
| 1554 | SEQ ID NO: 247 | SEQ ID NO: 152 |
| 1555 | SEQ ID NO: 248 | SEQ ID NO: 152 |
| 1556 | SEQ ID NO: 249 | SEQ ID NO: 152 |
| 1557 | SEQ ID NO: 250 | SEQ ID NO: 152 |
| 1558 | SEQ ID NO: 251 | SEQ ID NO: 152 |
| 1559 | SEQ ID NO: 252 | SEQ ID NO: 152 |
| 1560 | SEQ ID NO: 253 | SEQ ID NO: 152 |
| 1561 | SEQ ID NO: 254 | SEQ ID NO: 152 |
| 1562 | SEQ ID NO: 255 | SEQ ID NO: 152 |
| 1563 | SEQ ID NO: 256 | SEQ ID NO: 152 |
| 1564 | SEQ ID NO: 257 | SEQ ID NO: 152 |
| 1565 | SEQ ID NO: 258 | SEQ ID NO: 152 |
| 1566 | SEQ ID NO: 259 | SEQ ID NO: 152 |
| 1567 | SEQ ID NO: 260 | SEQ ID NO: 152 |
| 1568 | SEQ ID NO: 261 | SEQ ID NO: 152 |
| 1569 | SEQ ID NO: 262 | SEQ ID NO: 152 |
| 1570 | SEQ ID NO: 263 | SEQ ID NO: 152 |
| 1571 | SEQ ID NO: 264 | SEQ ID NO: 152 |
| 1572 | SEQ ID NO: 265 | SEQ ID NO: 152 |
| 1573 | SEQ ID NO: 266 | SEQ ID NO: 152 |
| 1574 | SEQ ID NO: 267 | SEQ ID NO: 152 |
| 1575 | SEQ ID NO: 268 | SEQ ID NO: 152 |
| 1576 | SEQ ID NO: 269 | SEQ ID NO: 152 |
| 1577 | SEQ ID NO: 270 | SEQ ID NO: 152 |
| 1578 | SEQ ID NO: 271 | SEQ ID NO: 152 |
| 1579 | SEQ ID NO: 272 | SEQ ID NO: 152 |
| 1580 | SEQ ID NO: 273 | SEQ ID NO: 152 |
| 1581 | SEQ ID NO: 274 | SEQ ID NO: 152 |
| 1582 | SEQ ID NO: 275 | SEQ ID NO: 152 |

TABLE 1.1-continued

Heavy chains and light chains of exemplary antigen-binding proteins or antigen-binding fragments

| No. | Heavy Chain | Light Chain |
|---|---|---|
| 1583 | SEQ ID NO: 276 | SEQ ID NO: 152 |
| 1584 | SEQ ID NO: 277 | SEQ ID NO: 152 |
| 1585 | SEQ ID NO: 278 | SEQ ID NO: 152 |
| 1586 | SEQ ID NO: 279 | SEQ ID NO: 152 |
| 1587 | SEQ ID NO: 280 | SEQ ID NO: 152 |
| 1588 | SEQ ID NO: 281 | SEQ ID NO: 152 |
| 1589 | SEQ ID NO: 282 | SEQ ID NO: 152 |
| 1590 | SEQ ID NO: 283 | SEQ ID NO: 152 |
| 1591 | SEQ ID NO: 284 | SEQ ID NO: 152 |
| 1592 | SEQ ID NO: 285 | SEQ ID NO: 152 |
| 1593 | SEQ ID NO: 286 | SEQ ID NO: 152 |
| 1594 | SEQ ID NO: 287 | SEQ ID NO: 152 |
| 1595 | SEQ ID NO: 288 | SEQ ID NO: 152 |
| 1596 | SEQ ID NO: 289 | SEQ ID NO: 152 |
| 1597 | SEQ ID NO: 141 | SEQ ID NO: 154 |
| 1598 | SEQ ID NO: 143 | SEQ ID NO: 154 |
| 1599 | SEQ ID NO: 145 | SEQ ID NO: 154 |
| 1600 | SEQ ID NO: 147 | SEQ ID NO: 154 |
| 1601 | SEQ ID NO: 149 | SEQ ID NO: 154 |
| 1602 | SEQ ID NO: 151 | SEQ ID NO: 154 |
| 1603 | SEQ ID NO: 153 | SEQ ID NO: 154 |
| 1604 | SEQ ID NO: 155 | SEQ ID NO: 154 |
| 1605 | SEQ ID NO: 156 | SEQ ID NO: 154 |
| 1606 | SEQ ID NO: 164 | SEQ ID NO: 154 |
| 1607 | SEQ ID NO: 165 | SEQ ID NO: 154 |
| 1608 | SEQ ID NO: 166 | SEQ ID NO: 154 |
| 1609 | SEQ ID NO: 167 | SEQ ID NO: 154 |
| 1610 | SEQ ID NO: 168 | SEQ ID NO: 154 |
| 1611 | SEQ ID NO: 169 | SEQ ID NO: 154 |
| 1612 | SEQ ID NO: 170 | SEQ ID NO: 154 |
| 1613 | SEQ ID NO: 171 | SEQ ID NO: 154 |
| 1614 | SEQ ID NO: 172 | SEQ ID NO: 154 |
| 1615 | SEQ ID NO: 173 | SEQ ID NO: 154 |
| 1616 | SEQ ID NO: 174 | SEQ ID NO: 154 |
| 1617 | SEQ ID NO: 175 | SEQ ID NO: 154 |
| 1618 | SEQ ID NO: 176 | SEQ ID NO: 154 |
| 1619 | SEQ ID NO: 177 | SEQ ID NO: 154 |
| 1620 | SEQ ID NO: 178 | SEQ ID NO: 154 |
| 1621 | SEQ ID NO: 179 | SEQ ID NO: 154 |
| 1622 | SEQ ID NO: 180 | SEQ ID NO: 154 |
| 1623 | SEQ ID NO: 181 | SEQ ID NO: 154 |
| 1624 | SEQ ID NO: 182 | SEQ ID NO: 154 |
| 1625 | SEQ ID NO: 183 | SEQ ID NO: 154 |
| 1626 | SEQ ID NO: 184 | SEQ ID NO: 154 |
| 1627 | SEQ ID NO: 185 | SEQ ID NO: 154 |
| 1628 | SEQ ID NO: 186 | SEQ ID NO: 154 |
| 1629 | SEQ ID NO: 187 | SEQ ID NO: 154 |
| 1630 | SEQ ID NO: 188 | SEQ ID NO: 154 |
| 1631 | SEQ ID NO: 189 | SEQ ID NO: 154 |
| 1632 | SEQ ID NO: 190 | SEQ ID NO: 154 |
| 1633 | SEQ ID NO: 191 | SEQ ID NO: 154 |
| 1634 | SEQ ID NO: 192 | SEQ ID NO: 154 |
| 1635 | SEQ ID NO: 193 | SEQ ID NO: 154 |
| 1636 | SEQ ID NO: 194 | SEQ ID NO: 154 |
| 1637 | SEQ ID NO: 195 | SEQ ID NO: 154 |
| 1638 | SEQ ID NO: 196 | SEQ ID NO: 154 |
| 1639 | SEQ ID NO: 197 | SEQ ID NO: 154 |
| 1640 | SEQ ID NO: 198 | SEQ ID NO: 154 |
| 1641 | SEQ ID NO: 199 | SEQ ID NO: 154 |
| 1642 | SEQ ID NO: 200 | SEQ ID NO: 154 |
| 1643 | SEQ ID NO: 201 | SEQ ID NO: 154 |
| 1644 | SEQ ID NO: 202 | SEQ ID NO: 154 |
| 1645 | SEQ ID NO: 203 | SEQ ID NO: 154 |
| 1646 | SEQ ID NO: 204 | SEQ ID NO: 154 |
| 1647 | SEQ ID NO: 205 | SEQ ID NO: 154 |
| 1648 | SEQ ID NO: 206 | SEQ ID NO: 154 |
| 1649 | SEQ ID NO: 207 | SEQ ID NO: 154 |
| 1650 | SEQ ID NO: 208 | SEQ ID NO: 154 |
| 1651 | SEQ ID NO: 209 | SEQ ID NO: 154 |
| 1652 | SEQ ID NO: 210 | SEQ ID NO: 154 |
| 1653 | SEQ ID NO: 211 | SEQ ID NO: 154 |
| 1654 | SEQ ID NO: 212 | SEQ ID NO: 154 |
| 1655 | SEQ ID NO: 213 | SEQ ID NO: 154 |
| 1656 | SEQ ID NO: 214 | SEQ ID NO: 154 |
| 1657 | SEQ ID NO: 215 | SEQ ID NO: 154 |
| 1658 | SEQ ID NO: 216 | SEQ ID NO: 154 |
| 1659 | SEQ ID NO: 217 | SEQ ID NO: 154 |
| 1660 | SEQ ID NO: 218 | SEQ ID NO: 154 |
| 1661 | SEQ ID NO: 219 | SEQ ID NO: 154 |
| 1662 | SEQ ID NO: 220 | SEQ ID NO: 154 |
| 1663 | SEQ ID NO: 221 | SEQ ID NO: 154 |
| 1664 | SEQ ID NO: 222 | SEQ ID NO: 154 |
| 1665 | SEQ ID NO: 223 | SEQ ID NO: 154 |
| 1666 | SEQ ID NO: 224 | SEQ ID NO: 154 |
| 1667 | SEQ ID NO: 225 | SEQ ID NO: 154 |
| 1668 | SEQ ID NO: 226 | SEQ ID NO: 154 |
| 1669 | SEQ ID NO: 227 | SEQ ID NO: 154 |
| 1670 | SEQ ID NO: 228 | SEQ ID NO: 154 |
| 1671 | SEQ ID NO: 229 | SEQ ID NO: 154 |
| 1672 | SEQ ID NO: 230 | SEQ ID NO: 154 |
| 1673 | SEQ ID NO: 231 | SEQ ID NO: 154 |
| 1674 | SEQ ID NO: 232 | SEQ ID NO: 154 |
| 1675 | SEQ ID NO: 233 | SEQ ID NO: 154 |
| 1676 | SEQ ID NO: 234 | SEQ ID NO: 154 |
| 1677 | SEQ ID NO: 235 | SEQ ID NO: 154 |
| 1678 | SEQ ID NO: 236 | SEQ ID NO: 154 |
| 1679 | SEQ ID NO: 237 | SEQ ID NO: 154 |
| 1680 | SEQ ID NO: 238 | SEQ ID NO: 154 |
| 1681 | SEQ ID NO: 239 | SEQ ID NO: 154 |
| 1682 | SEQ ID NO: 240 | SEQ ID NO: 154 |
| 1683 | SEQ ID NO: 241 | SEQ ID NO: 154 |
| 1684 | SEQ ID NO: 242 | SEQ ID NO: 154 |
| 1685 | SEQ ID NO: 243 | SEQ ID NO: 154 |
| 1686 | SEQ ID NO: 244 | SEQ ID NO: 154 |
| 1687 | SEQ ID NO: 245 | SEQ ID NO: 154 |
| 1688 | SEQ ID NO: 246 | SEQ ID NO: 154 |
| 1689 | SEQ ID NO: 247 | SEQ ID NO: 154 |
| 1690 | SEQ ID NO: 248 | SEQ ID NO: 154 |
| 1691 | SEQ ID NO: 249 | SEQ ID NO: 154 |
| 1692 | SEQ ID NO: 250 | SEQ ID NO: 154 |
| 1693 | SEQ ID NO: 251 | SEQ ID NO: 154 |
| 1694 | SEQ ID NO: 252 | SEQ ID NO: 154 |
| 1695 | SEQ ID NO: 253 | SEQ ID NO: 154 |
| 1696 | SEQ ID NO: 254 | SEQ ID NO: 154 |
| 1697 | SEQ ID NO: 255 | SEQ ID NO: 154 |
| 1698 | SEQ ID NO: 256 | SEQ ID NO: 154 |
| 1699 | SEQ ID NO: 257 | SEQ ID NO: 154 |
| 1700 | SEQ ID NO: 258 | SEQ ID NO: 154 |
| 1701 | SEQ ID NO: 259 | SEQ ID NO: 154 |
| 1702 | SEQ ID NO: 260 | SEQ ID NO: 154 |
| 1703 | SEQ ID NO: 261 | SEQ ID NO: 154 |
| 1704 | SEQ ID NO: 262 | SEQ ID NO: 154 |
| 1705 | SEQ ID NO: 263 | SEQ ID NO: 154 |
| 1706 | SEQ ID NO: 264 | SEQ ID NO: 154 |
| 1707 | SEQ ID NO: 265 | SEQ ID NO: 154 |
| 1708 | SEQ ID NO: 266 | SEQ ID NO: 154 |
| 1709 | SEQ ID NO: 267 | SEQ ID NO: 154 |
| 1710 | SEQ ID NO: 268 | SEQ ID NO: 154 |
| 1711 | SEQ ID NO: 269 | SEQ ID NO: 154 |
| 1712 | SEQ ID NO: 270 | SEQ ID NO: 154 |
| 1713 | SEQ ID NO: 271 | SEQ ID NO: 154 |
| 1714 | SEQ ID NO: 272 | SEQ ID NO: 154 |
| 1715 | SEQ ID NO: 273 | SEQ ID NO: 154 |
| 1716 | SEQ ID NO: 274 | SEQ ID NO: 154 |
| 1717 | SEQ ID NO: 275 | SEQ ID NO: 154 |
| 1718 | SEQ ID NO: 276 | SEQ ID NO: 154 |
| 1719 | SEQ ID NO: 277 | SEQ ID NO: 154 |
| 1720 | SEQ ID NO: 278 | SEQ ID NO: 154 |
| 1721 | SEQ ID NO: 279 | SEQ ID NO: 154 |
| 1722 | SEQ ID NO: 280 | SEQ ID NO: 154 |
| 1723 | SEQ ID NO: 281 | SEQ ID NO: 154 |
| 1724 | SEQ ID NO: 282 | SEQ ID NO: 154 |
| 1725 | SEQ ID NO: 283 | SEQ ID NO: 154 |
| 1726 | SEQ ID NO: 284 | SEQ ID NO: 154 |
| 1727 | SEQ ID NO: 285 | SEQ ID NO: 154 |
| 1728 | SEQ ID NO: 286 | SEQ ID NO: 154 |
| 1729 | SEQ ID NO: 287 | SEQ ID NO: 154 |
| 1730 | SEQ ID NO: 288 | SEQ ID NO: 154 |
| 1731 | SEQ ID NO: 289 | SEQ ID NO: 154 |

In certain embodiments, the anti-FGFR3 antigen binding protein or fragment thereof comprises a pair of heavy chain and light chain of Table 1.1 above.

In certain embodiments, the anti-FGFR3 antigen binding protein or fragment thereof comprises a VH domain and a VL domain, wherein:

(a) the VH domain comprises the amino acid sequence selected from the group consisting of: SEQ ID NO: 6, SEQ ID NO: 18, SEQ ID NO: 57, SEQ ID NO: 58, SEQ ID NO: 106, SEQ ID NO: 107, SEQ ID NO: 108, SEQ ID NO: 109, SEQ ID NO: 110, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122; and the VL domain comprises the amino acid sequence selected from the group consisting of: SEQ ID NO: 7, SEQ ID NO: 19, SEQ ID NO: 60, SEQ ID NO: 61SEQ ID NO: 112, SEQ ID NO: 113, SEQ ID NO: 114, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, and SEQ ID NO: 132;

(b) the VH domain comprises the amino acid sequence of SEQ ID NO: 8; and the VL domain comprises the amino acid sequence of SEQ ID NO: 9;

(c) the VH domain comprises the amino acid sequence of SEQ ID NO: 10; and the VL domain comprises the amino acid sequence of SEQ ID NO: 11;

(d) the VH domain comprises the amino acid sequence of SEQ ID NO: 12; and the VL domain comprises the amino acid sequence of SEQ ID NO: 13;

(e) the VH domain comprises the amino acid sequence selected from the group consisting of: SEQ ID NO: 14, SEQ ID NO: 20, SEQ ID NO: 21, SEQ ID NO: 22, and SEQ ID NO: 23; and the VL domain comprises the amino acid sequence selected from the group consisting of: SEQ ID NO: 15, SEQ ID NO: 24, SEQ ID NO: 25, SEQ ID NO: 26, and SEQ ID NO: 27;

(f) the VH domain comprises the amino acid sequence selected from the group consisting of: SEQ ID NO: 16, SEQ ID NO: 28, SEQ ID NO: 29, SEQ ID NO: 30, and SEQ ID NO: 31; the VL domain comprises the amino acid sequence selected from the group consisting of: SEQ ID NO: 17, SEQ ID NO: 32, SEQ ID NO: 33, SEQ ID NO: 34, and SEQ ID NO: 35.

In certain embodiments, the antibody heavy chain comprises the amino acid sequence of SEQ ID NO: 63 or 65, and the antibody light chain comprises the amino acid sequence of SEQ ID NO: 67 or 69.

Variants of the anti-FGFR3 antigen binding protein or fragment thereof as described herein are also provided. In certain embodiments, the VH domain of a variant is at least about 80%, at least at least about 81%, at least about 82%, at least about 83%, at least about 84%, at least about 85%, at least about 86%, at least about 87%, at least about 88%, at least about 89%, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the amino acid sequence of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 21, SEQ ID NO: 22, SEQ ID NO: 23, SEQ ID NO: 28, SEQ ID NO: 29, SEQ ID NO: 30, SEQ ID NO: 31, SEQ ID NO: 57, SEQ ID NO: 58, SEQ ID NO: 106, SEQ ID NO: 107, SEQ ID NO: 108, SEQ ID NO: 109, SEQ ID NO: 110, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, and the VL domain of the variant is at least about 80%, at least at least about 81%, at least about 82%, at least about 83%, at least about 84%, at least about 85%, at least about 86%, at least about 87%, at least about 88%, at least about 89%, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 24, SEQ ID NO: 25, SEQ ID NO: 26, SEQ ID NO: 27, SEQ ID NO: 32, SEQ ID NO: 33, SEQ ID NO: 34, SEQ ID NO: 35, SEQ ID NO: 60, SEQ ID NO: 61, SEQ ID NO: 112, SEQ ID NO: 113, SEQ ID NO: 114, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, or SEQ ID NO: 132. The amino acid sequence alignment for obtaining the identity can be any conventional amino acid sequence alignment tool, and the sequence alignment algorithms includes Needle-Wunsch algorithm, Smith-Waterman algorithm, or Karling & Altschul algorithm, but is not limited thereto; the amino acid sequence alignment tool includes BLAST (Basic Local Alignment Search Tool), BLAT (BLAST-like Alignment Tool), Grapped BLAST or FASTA, but is not limited thereto. In certain embodiments, the variant has all of the identical heavy chain CDRs and light chain CDRs of the anti-FGFR3 antigen binding protein or fragment thereof as described herein, with modifications in the constant region on the heavy chain and/or the light chain.

In certain embodiments, the anti-FGFR3 antigen binding protein or fragment thereof comprises an antibody heavy chain at least about 80%, at least at least about 81%, at least about 82%, at least about 83%, at least about 84%, at least about 85%, at least about 86%, at least about 87%, at least about 88%, at least about 89%, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the amino acid sequence of SEQ ID NO: 63 or 65, and an antibody light chain at least 80%, at least at least about 81%, at least about 82%, at least about 83%, at least about 84%, at least about 85%, at least about 86%, at least about 87%, at least about 88%, at least about 89%, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the amino acid sequence of SEQ ID NO: 67 or 69.

In certain embodiments, the anti-FGFR3 antigen binding protein or fragment thereof comprises a VH domain and a VL domain, wherein: (a) the VH domain comprises a CDR-H1 sequence comprising the amino acid sequence of GDTFTDFE (SEQ ID NO: 70), a CDR-H2 sequence comprising the amino acid sequence of VDPETGGT (SEQ ID NO: 297), and a CDR-H3 sequence comprising the amino acid sequence of TRTYDGYPYAFDY (SEQ ID NO: 301); and (b) the VL domain comprises a CDR-L1 sequence comprising the amino acid sequence of QSVLYSNNNKNY (SEQ ID NO: 302), a CDR-L2 sequence comprising the amino acid sequence of WAS (SEQ ID NOs: 74, 92, 98, and 104), and a CDR-L3 sequence comprising the amino acid sequence of QQYYSYRT (SEQ ID NO: 75).

In certain embodiments, the VH domain comprises the amino acid sequence of SEQ ID NO: 57, and the VL domain comprises the amino acid sequence of SEQ ID NO: 19 or 59.

In certain embodiments, the antibody heavy chain comprises the amino acid sequence of SEQ ID NO: 63, and the antibody light chain comprises the amino acid sequence of SEQ ID NO: 67. In certain embodiments, the antibody heavy chain comprises the amino acid sequence of SEQ ID NO: 65, and the antibody light chain comprises the amino acid sequence of SEQ ID NO: 69.

In certain embodiments, the anti-FGFR3 antigen binding protein or fragment thereof comprises a VH domain and a VL domain, wherein: (a) the VH domain comprises a CDR-H1 sequence comprising the amino acid sequence of GDTFTDFE (SEQ ID NO: 70), a CDR-H2 sequence comprising the amino acid sequence of VDPETGGT (SEQ ID NO: 297), and a CDR-H3 sequence comprising the amino acid sequence of TRTYDGYPYAFDY (SEQ ID NO: 301); and (b) the VL domain comprises a CDR-L1 sequence comprising the amino acid sequence of QSVLYSDNQKNY (SEQ ID NO: 306), a CDR-L2 sequence comprising the amino acid sequence of FAS (SEQ ID NO: 304), and a CDR-L3 sequence comprising the amino acid sequence of QQYYSYRT (SEQ ID NO: 75).

In certain embodiments, the VH domain comprises the amino acid sequence of SEQ ID NO: 57, and the VL domain comprises the amino acid sequence of SEQ ID NO: 61.

In certain embodiments, the antibody heavy chain comprises the amino acid sequence of SEQ ID NO: 65, and the antibody light chain comprises the amino acid sequence of SEQ ID NO: 67.

In certain embodiments, the anti-FGFR3 antigen binding proteins and antigen-binding fragments thereof of the disclosure comprise one or more sequences with at least about 80%, at least about 80%, at least about 85%, at least about 90%, at least about 95%, at least about 96%, at least about 97%, at least about 98%, at least about 99%, or 100% sequence identity to any of the sequences of Table 1, Table 3, Table 4, Table 8, Table 13, or Table 14, or protein sequences encoded by the nucleic acid sequences in Table 9.

Also provided herein are human framework regions for anti-FGFR3 antigen binding proteins and antigen-binding fragments thereof. Non-limiting examples of human framework regions are provided below.

TABLE 1.2

Human Framework regions of anti-FGFR3 antigen binding proteins and antigen-binding fragments thereof

| Framework type | Sequence | Note |
|---|---|---|
| Heavy chain | QVQLVQSGAEVKKPGASVKVSCKAS(X)$_{n1}$IHWVRQAP GQGLEWIGA(X)$_{n2}$AYNQKFQGRVTITADKSTSTAYMEL SSLRSEDTAVYYC(X)$_{n3}$WGQGTLVTVSS SEQ ID NO: 318 | X is any naturally occurring amino acid, and n1, n2, and n3 are numbers at least 3, and less than 50, each X can be the same or different amino acid as the amino acid next to it |
| Heavy chain | QVQLVQSGAEVKKPGASVKVSCKAS(X)$_{n1}$IHWVRQAP GQGLEWIGA(X)$_{n2}$AYNQKFQGRVTITADKSTSTAYMEL SSLRSEDTAVYYC(X)$_{n3}$WGQGTLVTVSS SEQ ID NO: 319 | |
| Heavy chain | QVQLVQSGAEVKKPGASVKVSCKAS(X)$_{n1}$IHWVRQAP GQGLEWIGA(X)$_{n2}$AYNQKFQGRVTITADKSTSTAYMEL SSLRSEDTAVYYC(X)$_{n3}$WGQGTLVTVSS SEQ ID NO: 320 | |
| Heavy chain | QVQLVQSGAEVKKPGASVKVSCKAS(X)$_{n1}$IHWVRQAP GQGLEWIGA(X)$_{n2}$AYNQKFQGRVTITADKSTSTAYMEL SSLRSEDTAVYYC(X)$_{n3}$WGQGTLVTVSS SEQ ID NO: 321 | |
| Heavy chain | QVQLVQSGAEVKKPGASVKVSCKAS(X)$_{n1}$IHWVRQAP GQGLEWIGG(X)$_{n2}$AYNQKFQGRVTITADRSTSTAYMEL SSLRSEDTAVYYC(X)$_{n3}$WGQGTLVTVSS SEQ ID NO: 322 | |
| Heavy chain | QVQLVQSGAEVKKPGASVKVSCKAS(X)$_{n1}$IHWVRQAP GQGLEWIGG(X)$_{n2}$AYNQKFQGRVTITADRSTSTAYMEL SSLRSEDTAVYYC(X)$_{n3}$WGQGTLVTVSS SEQ ID NO: 323 | |
| Heavy chain | QVQLVQSGAEVKKPGASVKVSCKAS(X)$_{n1}$IHWVRQAP GQGLEWIGG(X)$_{n2}$AYNQKFQGRVTITADRSTSTAYMEL SSLRSEDTAVYYC(X)$_{n3}$WGQGTLVTVSS SEQ ID NO: 324 | |
| Heavy chain | QVQLVQSGAEVKKPGASVKVSCKAS(X)$_{n1}$IHWVRQAP GQGLEWIGG(X)$_{n2}$AYNQKFQGRVTITADRSTSTAYMEL SSLRSEDTAVYYC(X)$_{n3}$WGQGTLVTVSS SEQ ID NO: 325 | |
| Heavy chain | EVQLVQSGAEVKKPGATVKLSCKAS(X)$_{n1}$IHWVQQAPG KGLEWIGD(X)$_{n2}$AYAEKFQGRATLTADRSTDTAYMELS SLRSEDTAVYYC(X)$_{n3}$WGQGTLVTVSS SEQ ID NO: 326 | |

TABLE 1.2-continued

Human Framework regions of anti-FGFR3 antigen binding
proteins and antigen-binding fragments thereof

| Framework type | Sequence | Note |
|---|---|---|
| Heavy chain | EVQLVQSGAEVKKPGATVKLSCKAS(X)$_{n1}$IHWVQQAPG<br>KGLEWIGD(X)$_{n2}$AYAEKFQGRATLTADRSTDTAYLELS<br>SLRSEDTAVYYC(X)$_{n3}$WGQGTLVTVSS<br>SEQ ID NO: 327 | |
| Heavy chain | EVQLVQSGAEVKKPGATVKLSCKAS(X)$_{n1}$IHWVQQAPG<br>KGLEWIGD(X)$_{n2}$AYAEKFQGRATLTADRSTDTAYLELS<br>SLRSEDTAVYYC(X)$_{n3}$WGQGTLVTVSS<br>SEQ ID NO: 328 | |
| Light chain | DIVMTQSPDSLAVSLGERVTINCKSS(X)$_{n1}$ILAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 329 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC$_{(X)n3}$FGQGTKLEIK<br>SEQ ID NO: 330 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 331 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 332 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 333 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 334 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 335 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSLQAE<br>DVAVYYC(X)$_{n3}$FGQGTKLEIK<br>SEQ ID NO: 336 | |
| Light chain | DIVMTQSPDSLAVSLGERATINCKSS(X)$_{n1}$LAWYQQKPG<br>QSPKLLIY(X)$_{n2}$TRESGVPDRFSGSGSGTDFTLTISSVQA<br>EDVAVYYC(X)$_{n3}$FGGGTKVEIK<br>SEQ ID NO: 337 | |
| Light chain | DIVMTQSPDSLAVSLGERATINCKSS(X)$_{n1}$LAWYQQKPG<br>QSPKLLIY(X)$_{n2}$TRESGVPDRFSGSGSGTDFTLTISSVQA<br>EDVAVYYC(X)n3FGGGTKVEIK<br>SEQ ID NO: 338 | |
| Light chain | DIVMTQSPDSLAVSLGERVTINCKSS(X)$_{n1}$LAWYQQKPG<br>QSPKLLIY(X)$_{n2}$TRESGVPDRFSGSGSGTDFTLTISSVQA<br>EDVAVYYC(X)$_{n3}$FGGGTKLEIK<br>SEQ ID NO: 339 | |

In some embodiments, the anti-FGFR3 antigen binding proteins and antigen-binding fragments comprise three heavy chain CDRs that bind to FGFR3, such as the three heavy chain CDRs of mouse antibody KC18, KE35, KE42, KE58, KE63, or KE94, and a human heavy chain variable region framework. In certain embodiments, the anti-FGFR3 antigen binding proteins and antigen-binding fragments further comprise three light chain CDRs that bind to FGFR3, such as the three light chain CDRs of mouse antibody KC18, KE35, KE42, KE58, KE63, or KE94, and a human light chain variable region framework. In certain embodiments, the human heavy chain variable region framework comprises any one of SEQ ID NOs: 318 to 328. In certain embodiments, the human light chain variable region framework comprises any one of SEQ ID NOs: 329 to 339. In certain embodiments, the human heavy chain variable region framework comprises a sequence having at least 80%, at least 81%, at least 82%, at least 83%, at least 84%, at least 85%, at least 86%, at least 87%, at least 88%, at least 89%, at least 91%, at least 92%, at least 93%, at least 94%, at least 95%, at least 96%, at least 97%, at least 98%, at least 99%, or more identity to any one of SEQ ID NOs: 318 to 328. In certain embodiments, the human light chain variable region framework comprises a sequence having at least 80%, at least 81%, at least 82%, at least 83%, at least 84%, at least 85%, at least 86%, at least 87%, at least 88%, at least 89%, at least 91%, at least 92%, at least 93%, at least 94%, at least 95%, at least 96%, at least 97%, at least 98%, at least 99%, or more identity to any one of SEQ ID NOs: 329 to 339. In certain embodiments, such anti-FGFR3 antigen binding proteins and antigen-binding fragments bind human FGFR3 with an equilibrium dissociation constant (KD) of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 9 nM or less, about 8 nM or less, about 7 nM or less, about 6 nM or less, about 5 nM or less, about 4 nM or less, about 3 nM or less, about 2.89 nM or less, about 2 nM or less, about 1.5 or less, about 1.4 or less, about 1.23 or less, about 1.2 or less, or about 1 nM or less, about 0.8 or less, or about 0.6 or less. "X nM or less" therein includes the embodiment "less than X nM". "Less" therein can mean e.g. to about 2.8 nM, to about 1.3 nM, to about 1.1 nM, to about 0.7 nM or to about 0.5 nM. These lower limits can be used to form ranges with any of the aforementioned upper limits, such as about 3 nM or <3 nM to about 2.8 nM, about 1.5 nM or <1.5 nM to about 1.3 nM, about 1.3 nM or <1.3 nM to about 1.1 nM, about 0.9 nM or <0.9 nM to about 0.7 nM, or about 0.7 nM or <0.7 nM to about 0.5 nM. "About X" therein can mean e.g. "X±5%", "X±4%", "X±4%", "X±3%", "X±2%", "X±1%" or "X±0.5%". In certain embodiments, the nM values are as obtained by a Surface Plasmon Resonance assay, such as the Biacore assay.

In certain embodiments, the anti-FGFR3 antigen binding proteins and antigen-binding fragments thereof of the disclosure are chimeric or humanized antibodies. In certain embodiments, the antigen binding protein is a humanized antibody.

In certain embodiments, the antigen binding protein is a monoclonal antibody.

In certain embodiments, the antigen binding protein comprises one or more full-length antibody heavy chains comprising an Fc region. In certain embodiments, the Fc region is a human IgG1 Fc region. In certain embodiments, the Fc region is a human IgG4 Fc region.

In certain embodiments, the antibody Fc region comprises one or more mutations that reduces Fc effector function. In certain embodiments, the one or more mutations reduces one or more of antibody dependent cellular cytotoxicity (ADCC), antibody dependent cellular phagocytosis (ADCP), or complement dependent cytotoxicity (CDC). In certain embodiments, the human IgG1 Fc region comprises a L234A and L235A mutation. In certain embodiments, the human IgG4 Fc region comprises a F234A and L235A mutation. These IgG1 and IgG4 mutations are also known as the "LALA" and "FALA" mutations, respectively, and are described in further detail in Xu et al. (Cell Immunol. 2000; 200:16-26). In certain embodiments, the human IgG4 Fc region comprises one or more stabilizing mutations, including, but limited to, mutations in the IgG4 hinge that reduce or prevent the formation of disulfide bonds and in vivo fab arm exchange (FAE). In certain embodiments, the human IgG4 Fc region comprises a S228P mutation. The IgG4 hinge mutation is described in further detail in Angal et al. (Mol. Immunol. 1993; 30:105-108). In certain embodiments, the human IgG4 Fc region comprises a S228P mutation and a L235A mutation. In certain embodiments, the human IgG1 Fc region comprises one or more mutations that alters antibody glycosylation. In certain embodiments, the human IgG1 Fc region comprises one or more of a S298N mutation, a T299A mutation, and a Y300S mutation. In certain embodiments, the human IgG1 Fc region comprises a S298N mutation, a T299A mutation, and a Y300S mutation. The Fc region amino acid positions referred to herein are based on EU antibody numbering.

In certain embodiments, the anti-FGFR3 antigen binding protein fragments of the disclosure comprise or consists of an antibody F(ab), F(ab')2, Fab'-SH, Fv, or scFv fragment. In certain embodiments, the antigen binding protein fragment comprises an antibody F(ab) fragment.

The antibody F(ab) fragment can be modified with one or more serum half-life extending moieties. In certain embodiments, the antibody F(ab) fragment is conjugated to an antigen binding protein with binding specificity to serum albumin. In certain embodiments, the antigen binding protein with binding specificity to serum albumin is a nanobody. In certain embodiments, the serum albumin is human serum albumin or mouse serum albumin.

In certain embodiments, the antibody F(ab) fragment comprises a heavy chain and a light chain. In certain embodiments, the heavy chain of the F(ab) fragment comprises a heavy chain variable region disclosed herewith, and a light chain variable region disclosed herewith. In certain embodiments, the heavy chain variable region comprises or consists of any one of SEQ ID NOs: 6, 8, 10, 12, 14, 16, 18, 20, 21, 22, 23, 28, 29, 30, 31, 56, 57, 58, 106, 107, 108, 109, 110, 111, 115, 116, 117, 118, 119, 120, 121, or 112, or a sequence having at least 90%, 91%, 92%, 93%, 94%, 95%, 96%, 97%, 98%, or at least 99% identity to any of SEQ ID NOs: 6, 8, 10, 12, 14, 16, 18, 20, 21, 22, 23, 28, 29, 30, 31, 56, 57, 58, 106, 107, 108, 109, 110, 111, 115, 116, 117, 118, 119, 120, 121, or 112. In certain embodiments, the light chain variable region comprises or consists of any one of SEQ ID NOs: 7, 9, 11, 13, 15, 17, 19, 24, 25, 26, 27, 32, 33, 34, 35, 59, 60, 61, 112, 113, 114, 123, 124, 125, 126, 127, 128, 129, 130, 131, or 132, or a or a sequence having at least 90%, 91%, 92%, 93%, 94%, 95%, 96%, 97%, 98%, or at least 99% identity to any of SEQ ID NOs: 7, 9, 11, 13, 15, 17, 19, 24, 25, 26, 27, 32, 33, 34, 35, 59, 60, 61, 112, 113, 114, 123, 124, 125, 126, 127, 128, 129, 130, 131, or 132.

In certain embodiments, the heavy chain of the F(ab) fragment comprises or consists of a heavy chain variable region disclosed herewith and a heavy chain constant region. In certain embodiments, the heavy chain constant region is derived from a human IgG1 Fc region, a human IgG2 Fc region, a human IgG3 Fc region, a human IgG4 Fc region, or a combination thereof. In certain embodiments, the heavy chain constant region is a fragment of a human IgG1 Fc region, a human IgG2 Fc region, a human IgG3 Fc region, a human IgG4 Fc region, or a combination thereof. In certain embodiments, the heavy chain constant region comprises or consists of the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 5, 36, 37, 38, 39, 40, 41, 44, 45, 46, 7, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or 300 amino acids of a human IgG Fc region, such as the human IgG1 Fc region (SEQ ID NO: 54).

In certain embodiments, the light chain of the F(ab) fragment comprises or consists of a light chain variable region disclosed herewith, and a light chain constant region. In certain embodiments, the light chain constant region is derived from a human kappa (κ) chain, a human lambda (λ) chain, or a combination thereof. In certain embodiments, the light chain constant region comprises or consists of a part of IgG1 light constant region. In certain embodiments, the part of the IgG1 light constant region comprises or consists of the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 5, 36, 37, 38, 39, 40, 41, 44, 45, 46, 7, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, or 107 amino acids of SEQ ID NO: 55.

In certain embodiments, the F(ab) fragment comprises one or more point mutations in the C-terminus to reduce anti-Fab antibody binding.

In certain embodiments, the antigen binding protein comprises cross-reactivity to one or both of mouse and cynomolgus FGFR3. In certain embodiments, the cynomolgus FGFR3 is encoded by SEQ ID NO: 136:

```
                                                  (SEQ ID NO: 136)
ATGGGCGCCCCTGCCTGCGCCCTCGCGCTCTGCGTGGCAGTGGCCATCGT

GGCCGGCGCCTCCTCGGAGTCCTTGGGGACGGAGCAGCGCGTCGTGGGGC

GAGTGGCAGAAGTGTCCGGCCCGGAGCCCAGCCAGCAGGAGCAGTTGGTC

TTCGGCAGCGGGGACGCTGTGGAGCTGAGCTGTCCCCCGCCCGGGGGTGG

TCCCATGGGGCCCACTGTCTGGGTCAAGGATGGCGCAGGGCTGGTGCCCT

CGGAGCGTGTCCTGGTGGGGCCCCAGCGGCTGCAGGTGCTGAATGCCTCC

CACGAGGACTCTGGGGCCTACAGCTGCCGGCAGCGGCTCACACAGCTCGT

ACTGTGCCACTTCAGTGTGCGGGTGACAGATGCTCCATCCTCGGGAGATG

ACGAAGACGGGGAGGACGAGGCTGAGGACACAGGTGTGGACACAGGGGCC

CCTTACTGGACTCGGCCCGAGCGGATGGACAAGAAGCTGCTGGCTGTGCC

GGCCGCCAACACCGTCCGCTTCCGCTGCCCGGCTGCCGGCAACCCCACTC

CCTCCATCTCCTGGCTGAAGAATGGCAAGGAGTTCCGCGGCGAGCACCGC

ATTGGCGGCATCAAGCTTCGGCACCAGCAGTGGAGCCTGGTCATGGAAAG

CGTGGTGCCCTCGGACCGCGGCAACTACACCTGCGTGGTGGAGAACAAGT

TTGGCAGCATCCGGCAGACATACACGCTGGACGTGCTGGAGCGCTCCCCG

CACCGGCCCATCCTGCAGGCGGGGCTGCCGGCCAACCAGACGGCGGTGCT

GGGCAGCGATGTGGAGTTTCACTGCAAGGTGTACAGTGATGCGCAGCCCC

ACATCCAGTGGCTCAAGCACGTGGAGGTGAATGGCAGCAAGGTGGGCCCC

GACGGCACACCCTACGTCACCGTGCTCAAGACGGCGGGCGCTAATACCAC

CGACAAGGAGCTAGAGGTTCTGTCCTTGCACAACGTCACCTTTGAGGACG

CCGGGGAGTACACCTGCCTGGCGGGCAATTCTATTGGGTTTTCCCATCAC

TCTGCGTGGCTCGTGGTGCTGCCAGCTGAGGAGGAGCTGGTGGAGGCTGA

CGAGGCGGGCAGTGTGTACGCAGGCATCCTCAGCTACGGGGTGGGCTTCT

TCCTGTTCATCCTGGTGGTGGCGGCTGTGACGCTCTGCCGCCTGCGCAGC

ACCCCCAAGAAGGGCCTGGGCTCCCCCACCGTGCACAAGATCTCCCGCTT

CCCACTCAAGCGACAGGTGTCCCTGGAGTCCAACGCGTCCATGAGCTCCA

ACACACCGCTGGTGCGCATCGCAAGGCTGTCCTCAGGGGAGGGTCCCACA

CTGGCCAATGTCTCCGAGCTTGAGCTGCCTGCTGACCCCAAATGGGAGCT

GTCTCGGGCCCGGCTGACCCTGGGCAAGCCCCTTGGGGAGGGCTGCTTTG

GCCAGGTGGTCATGGCGGAGGCTATCGGCATTGACAAGGACCGGGCCGCC

AAGCCTGTCACCGTAGCCGTGAAGATGCTGAAAGATGATGCCACTGACAA

GGACCTGTCAGACCTGGTGTCTGAGATGGAGATGATGAAGATGATTGGGA

AACACAAGAACATTATCAACCTGCTGGGCGCCTGCACGCAGGGCGGGCCC

CTGTACGTGCTGGTGGAGTACGCGGCCAAGGGCAACCTGAGGGAGTTTCT

GCGGGCGCGGCGGCCCCCGGGCCTGGACTACTCCTTCGACACCTGCAAGC

CGCCTGAGGAGCAGCTCACCTTCAAGGACCTGGTGTCCTGTGCCTACCAG

GTGGCCCGAGGCATGGAGTACCTCGCCTCCCAGAAGTGCATCCACAGGGA

CCTGGCTGCTCGAAATGTGCTGGTGACCGAGGACAACGTGATGAAGATCG

CAGACTTCGGGCTGGCCCGCGACGTGCACAACCTTGACTACTACAAGAAG

ACAACCAACGGCCGGCTGCCCGTGAAGTGGATGGCGCCTGAGGCCCTGTT

TGACCGAGTCTACACCCACCAGAGTGACGTCTGGTCCTTTGGGGTCCTGC

TCTGGGAGATCTTCACGCTGGGGGGCTCTCCGTACCCCGGCATCCCTGTG

GAGGAGCTCTTCAAGCTGCTGAAGGAGGGTCACCGGATGGACAAGCCGGC

CAACTGCACACACGACCTGTACATGATCATGCGGGAGTGCTGGCATGCTG

CGCCCTCCCAGAGGCCCACCTTCAAGCAGCTGGTGGAGGACCTGGACCGT

GTCCTCACTGTGACGTCCACCGACGAGTACCTGGACCTGTCAGCGCCCTT

CGAGCAGTACTCCCCCGGCGGCCAGGACACCCCGAGCTCCAGCTCCTCAG

GGGATGACTCCGTGTTTGCCCACGACCTGCTGCCCCGGCCCCACCCAGC

AGTGGGGGCTCGCGGACGTGA
```

In certain embodiments, the cynomolgus FGFR3 is the IIIc isoform, comprising SEQ ID NO: 138, or its mutated version comprising the G380R mutation (SEQ ID NO: 139):

(SEQ ID NO: 138)
MGAPACALALCVAVAIVAGASSESLGTEQRVVGRVAEVSGPEPSQQEQLV

FGSGDAVELSCPPPGGGPMGPTVWVKDGAGLVPSERVLVGPQRLQVLNAS

HEDSGAYSCRQRLTQLVLCHFSVRVTDAPSSGDDEDGEDEAEDTGVDTGA

PYWTRPERMDKKLLAVPAANTVRFRCPAAGNPTPSISWLKNGKEFRGEHR

IGGIKLRHQQWSLVMESVVPSDRGNYTCVVENKFGSIRQTYTLDVLERSP

HRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHH

SAWLVVLPAEEELVEADEAGSVYAGILSYGVGFFLFILVVAAVTLCRLRS

TPKKGLGSPTVHKISRFPLKRQVSLESNASMSSNTPLVRIARLSSGEGPT

LANVSELELPADPKWELSRARLTLGKPLGEGCFGQVVMAEAIGIDKDRAA

KPVTVAVKMLKDDATDKDLSDLVSEMEMMKMIGKHKNIINLLGACTQGGP

LYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKK

TTNGRLPVKWMAPEALFDRVYTHQSDVWSFGVLLWEIFTLGGSPYPGIPV

EELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPS

SGGSRT (SEQ ID NO: 139)
MGAPACALALCVAVAIVAGASSESLGTEQRVVGRVAEVSGPEPSQQEQLV

FGSGDAVELSCPPPGGGPMGPTVWVKDGAGLVPSERVLVGPQRLQVLNAS

HEDSGAYSCRQRLTQLVLCHFSVRVTDAPSSGDDEDGEDEAEDTGVDTGA

PYWTRPERMDKKLLAVPAANTVRFRCPAAGNPTPSISWLKNGKEFRGEHR

IGGIKLRHQQWSLVMESVVPSDRGNYTCVVENKFGSIRQTYTLDVLERSP

HRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHH

SAWLVVLPAEEELVEADEAGSVYAGILSYRVGFFLFILVVAAVTLCRLRS

TPKKGLGSPTVHKISRFPLKRQVSLESNASMSSNTPLVRIARLSSGEGPT

LANVSELELPADPKWELSRARLTLGKPLGEGCFGQVVMAEAIGIDKDRAA

KPVTVAVKMLKDDATDKDLSDLVSEMEMMKMIGKHKNIINLLGACTQGGP

LYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKK

TTNGRLPVKWMAPEALFDRVYTHQSDVWSFGVLLWEIFTLGGSPYPGIPV

EELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPS

SGGSRT

In certain embodiments, the antigen binding protein comprises binding specificity for FGFR3 isoform IIIb and/or isoform IIIc.

In certain embodiments, the antigen binding protein specifically binds to FGFR3, and does not bind to one or more of FGFR1, FGFR2, and FGFR4, or does not have detectable binding to one or more of FGFR1, FGFR2, and FGFR4. In certain embodiments, the antigen binding protein does not bind to each of FGFR1, FGFR2, and FGFR4, or does not have detectable binding to each of FGFR1, FGFR2, and FGFR4. In certain embodiments, the antigen binding protein binds to each of FGFR1, FGFR2, and FGFR4 with an affinity of about 100 μM, 500 μM, 1000 μM, or greater. In certain embodiments, the antigen binding protein does not bind to one or more of FGFR1, FGFR2, and FGFR4 over a background measurement, as determined by a Biacore affinity analysis.

In certain embodiments, the antigen binding protein binds human FGFR3 with an equilibrium dissociation constant (KD) of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 9 nM or less, about 8 nM or less, about 7 nM or less, about 6 nM or less, about 5 nM or less, about 4 nM or less, about 3 nM or less, about 2.89 nM or less, about 2 nM or less, about 1.5 or less, about 1.4 or less, about 1.23 or less, about 1.2 or less, or about 1 nM or less, about 0.8 or less, or about 0.6 or less. "X nM or less" therein includes the embodiment "less than X nM". "Less" therein can mean e.g. to about 2.8 nM, to about 1.3 nM, to about 1.1 nM, to about 0.7 nM or to about 0.5 nM. These lower limits can be used to form ranges with any of the aforementioned upper limits, such as about 3 nM or <3 nM to about 2.8 nM, about 1.5 nM or <1.5 nM to about 1.3 nM, about 1.3 nM or <1.3 nM to about 1.1 nM, about 0.9 nM or <0.9 nM to about 0.7 nM, or about 0.7 nM or <0.7 nM to about 0.5 nM. "About X" therein can mean e.g. "X±5%", "X±4%", "X±4%", "X±3%", "X±2%", "X±1%" or "X±0.5%". In certain embodiments, the nM values are as obtained by a Surface Plasmon Resonance assay, such as the Biacore assay. In certain embodiments, the Biacore assay is carried out at about 4° C., 10° C., 15° C., 20° C., 25° C., 30° C., or 37° C.

In certain embodiments, the antigen binding protein binds human FGFR3 with an off rate (Kd) of about $10^{-2}$ $s^{-1}$ or less, about $5\times10^{-3}$ $s^{-1}$ or less, about $2\times10^{-3}$ $s^{-1}$ or less, about $10^{-3}$ $s^{-1}$ or less, about $9\times10^{-4}$ $s^{-1}$ or less, about $8\times10^{-4}$ $s^{-1}$ or less, about $7\times10^{-4}$ $s^{-1}$ or less, about $6\times10^{-4}$ $s^{-1}$ or less, about $5\times10^{-4}$ $s^{-1}$ or less, about $4\times10^{-4}$ $s^{-1}$ or less, or about $3.5\times10^{-4}$ $s^{-1}$ or less. "Less" therein can mean e.g. to about $3\times10^{-4}$ $s^{-1}$. "About X" therein can mean e.g. "X±10%", "X±5%", "X±4%", "X±4%", "X±3%", "X±2%", "X±1%" or "X±0.5%".

In certain embodiments, the antigen binding protein inhibits ligand-induced FGFR3 dimerization with $IC_{50}$ of about 5 μg/ml or less, about 4 μg/ml or less, about 3 μg/ml or less, about 2 μg/ml or less, about 1 μg/ml or less, about 0.9 μg/ml or less, about 0.8 μg/ml or less, about 0.7 μg/ml or less, about 0.6 μg/ml or less, about 0.5 μg/ml or less, about 0.4 μg/ml or less, or about 0.3 μg/ml or less. "Less" therein can mean e.g. to about 0.25 μg/ml (or less, e.g. to about 0.2 μg/ml or about 0.1 μg/ml). "About X" therein can mean e.g. "X±10%", "X±5%", "X±4%", "X±4%", "X±3%", "X±2%", "X±1%" or "X±0.5%". In certain embodiments, the nM values are as obtained by a Homogenous Time-Resolved Fluorescence (HTRF) assay at about 4° C., 10° C., 15° C., 20° C., 25° C., 30° C., or 37° C.

In certain embodiments, the antigen binding protein inhibits FGFR3 receptor activation and downstream signaling with $IC_{50}$ of about 5 μg/ml or less, about 4 μg/ml or less, about 3 μg/ml or less, about 2 μg/ml or less, about 1 μg/ml or less, about 0.9 μg/ml or less, about 0.8 μg/ml or less, about 0.7 μg/ml or less, about 0.6 μg/ml or less, about 0.5 μg/ml or less, about 0.4 μg/ml or less, or about 0.3 μg/ml or less. "Less" therein can mean e.g. to about 0.25 μg/ml (or less, e.g. to about 0.2 μg/ml or about 0.1 μg/ml). About X" therein can mean e.g. "X±10%", "X±5%", "X±4%", "X±4%", "X±3%", "X±2%", "X±1%" or "X±0.5%".%". In certain embodiments, the nM values are as obtained by a homogenous time-resolved fluorescence (HTRF) assay.

Inhibition of FGFR3 receptor activation and downstream signaling can be determined by any means known in the art. In certain embodiments, inhibition of FGFR3 receptor activation and downstream signaling is measured by determining Erk phosphorylation. A decrease in Erk phosphorylation indicates inhibition of FGFR3 activation. Erk phosphorylation can be determined using a homogenous time-resolved fluorescence (HTRF) assay. In certain embodiments, the assay is performed in chondrocytes. In certain embodiments, the assay is performed in mouse primary rib chondrocytes.

In certain embodiments, the antigen binding protein inhibits the activity of an $FGFR3^{G380R}$ mutant. In certain embodiments, the antigen binding protein inhibits the activity of a human $FGFR3^{G380R}$ mutant, a mouse $FGFR3^{G380R}$ mutant, and/or a cynomolgus $FGFR3^{G380R}$ mutant. In certain embodiments, the human $FGFR3^{G380R}$ mutant is represented by the amino acid sequence set forth in SEQ ID NO: 133.

In certain embodiments, the antigen binding protein or fragment thereof is capable of penetrating a bone growth plate.

In certain embodiments, the antigen binding protein or fragment thereof is capable of decreasing the binding of FGFR3 with its ligand in a bone growth plate.

Anti-FGFR3 Antigen-Binding Protein Epitopes

In one aspect, the disclosure provides an antigen-binding protein or fragment thereof with binding specificity to a fibroblast growth factor receptor 3 (FGFR3) epitope, comprising an antibody heavy chain variable (VH) domain and an antibody light chain variable (VL) domain, wherein the antigen binding protein binds a human FGFR3 polypeptide comprising the amino acid sequence of SEQ ID NO: 134, recited below.

```
                                       (SEQ ID NO: 134)
DTGVDTGAPYWTRPERMDKKLLAVPAANTVRFRCPAAGNPTPSISWLKNG

REFRGEHRIGGIKLRHQQWSLVMESVVPSDRGNYTCVVENKFGSIRQTYT

LDVLERSPHRPILQAGLPANQTAVLGSDVEFHCKVYSDAQPHIQWLKHVE

VNGSKVGPDGTPYVTVLKTAGANTTDKELEVLSLHNVTFEDAGEYTCLAG

NSIGFSHHSAWLVVLPAEEELVE
```

In certain embodiments, the anti-FGFR3 antigen binding proteins and antigen-binding fragments thereof of the disclosure bind a human FGFR3 polypeptide comprising the amino acid sequence of SEQ ID NO: 134, recited above. The amino acid sequence recited above corresponds to the D2D3 region of FGFR3 isoform IIIc, specifically to amino acid D143 to E365 of FGFR3 isoform IIc.

In certain embodiments, the anti-FGFR3 antigen binding proteins and antigen-binding fragments thereof of the disclosure bind an epitope of human FGFR3 polypeptide comprising the N-terminus of the D2 region (amino acids D143 to L163) of SEQ ID NO: 133, shown above.

In certain embodiments, the anti-FGFR3 antigen binding proteins and antigen-binding fragments thereof of the disclosure bind an epitope of human FGFR3 polypeptide comprising the N-terminus of the D2 region (amino acids D143 to N170) of SEQ ID NO: 133, shown above.

In certain embodiments, the anti-FGFR3 antigen binding proteins and antigen-binding fragments thereof of the disclosure bind an epitope of human FGFR3 polypeptide comprising the N-terminus and middle of the D2 region (amino acids D143 to D160 and G197 to L213) of SEQ ID NO: 133, shown above.

In certain embodiments, the one or more epitopes of the anti-FGFR3 antigen binding proteins and antigen-binding fragments thereof of the disclosure are determined by hydrogen deuterium exchange (HDX) mass spectrometry. HDX is performed by measuring the amide hydrogen deuterium exchange on FGFR3 over time. HDX mass spectrometry is described in further detail in Pradzińska et al. (Amino Acids. 48: 2809-2820. 2016).

In certain embodiments, the anti-FGFR3 antigen binding proteins and antigen-binding fragments thereof of the disclosure compete with a reference binding protein for binding to the human FGFR3 polypeptide D2 region.

In one aspect, the disclosure provides an antigen-binding protein or fragment thereof with binding specificity to a fibroblast growth factor receptor 3 (FGFR3) epitope, comprising an antibody heavy chain variable (VH) domain and an antibody light chain variable (VL) domain, wherein the antigen binding protein competes for binding to FGFR3 with an antibody comprising VH/VL domain amino acid sequence pairs selected from the group consisting of: SEQ ID NO: 6/SEQ ID NO: 7, SEQ ID NO: 8/SEQ ID NO: 9, SEQ ID NO: 10/SEQ ID NO: 11, SEQ ID NO: 12/SEQ ID NO: 13, SEQ ID NO: 14/SEQ ID NO: 15, and SEQ ID NO: 16/SEQ ID NO: 17.

Expression of Antigen-Binding Proteins

In one aspect, polynucleotides encoding the binding proteins (e.g., antigen-binding proteins and antigen-binding fragments thereof) disclosed herein are provided. Methods of making binding proteins comprising expressing these polynucleotides are also provided.

Polynucleotides encoding the binding proteins disclosed herein are typically inserted in an expression vector for introduction into host cells that may be used to produce the desired quantity of the binding proteins. Accordingly, in certain aspects, the disclosure provides expression vectors comprising polynucleotides disclosed herein and host cells comprising these vectors and polynucleotides.

The term "vector" or "expression vector" is used herein to mean vectors used in accordance with the present disclosure as a vehicle for introducing into and expressing a desired gene in a cell. As known to those skilled in the art, such vectors may readily be selected from the group consisting of plasmids, phages, viruses and retroviruses. In general, vectors compatible with the disclosure will comprise a selection marker, appropriate restriction sites to facilitate cloning of the desired gene and the ability to enter and/or replicate in eukaryotic or prokaryotic cells.

Numerous expression vector systems may be employed for the purposes of this disclosure. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments, the cloned variable region genes are inserted into an expression vector along with the heavy and light chain constant region genes (e.g., human constant region genes) synthesized as discussed above.

In other embodiments, the binding proteins may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980, which is incorporated by reference herein in its entirety for all purposes. Those skilled in the art will appreciate that such expression systems may be used to effectively produce the full range of polypeptides disclosed in the instant application.

More generally, once a vector or DNA sequence encoding a binding protein, e.g. an antibody or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Plasmid introduction into the host can be by electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, from supernatant of lysed cells culture, or from the cell culture containing both the medium and the suspended cells.

In one embodiment, a host cell line used for antibody expression is of mammalian origin. Those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CV-1 (monkey kidney line), COS (a derivative of CV-1 with SV40 T antigen), R1610 (Chinese hamster fibroblast) BALBC/3T3 (mouse fibroblast), HEK (human kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (POTELLIGENT® cells) (Biowa, Princeton, N.J.)). In one embodiment, NSO cells may be used. CHO cells are particularly useful. Host cell lines are typically available from commercial services, e.g., the American Tissue Culture Collection, or from authors of published literature.

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the binding proteins featured in the disclosure can also be expressed in non-mammalian cells such as bacteria or yeast or plant cells. In this regard, it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the binding proteins can become part of inclusion bodies. In some embodiments, the binding proteins are then isolated, purified and assembled into functional molecules. In some embodiments, the binding proteins of the disclosure are expressed in a bacterial host cell. In some embodiments, the bacterial host cell is transformed with an expression vector comprising a nucleic acid molecule encoding a binding protein of the disclosure.

In addition to prokaryotes, eukaryotic microbes may also be used. *Saccharomyces cerevisiae*, or common baker's yeast, is the most commonly used among eukaryotic microbes, although a number of other strains are commonly available. For expression in *Saccharomyces*, the plasmid YRp7, for example (Stinchcomb et al., Nature, 282:39 (1979); Kingsman et al., Gene, 7:141 (1979); Tschemper et al., Gene, 10:157 (1980)), is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

Methods of Preparing/Administering Binding Proteins

Methods of preparing and administering binding proteins (e.g., antigen-binding proteins and antigen-binding fragments thereof disclosed herein) to a subject are also provided. The route of administration of the antigen binding proteins and antigen-binding fragments thereof of the current disclosure may be oral, parenteral, by inhalation or topical. The term parenteral as used herein includes intravenous, intraarterial, intraperitoneal, intramuscular, subcutaneous, rectal or vaginal administration. While all these forms of administration are clearly contemplated as being within the scope of the current disclosure, a form for administration would be a solution for injection, e.g. for intravenous or intraarterial injection or drip. Usually, a suitable pharmaceutical composition for injection may comprise a buffer, a surfactant, optionally a stabilizer agent, etc. However, in other methods compatible with the teachings herein, the modified antibodies can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Aqueous carriers include water, alcoholic/aqueous solutions, emulsions or suspensions, including saline and buffered media. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. Pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that syringability for injection exists. It should be stable under the conditions of manufacture and storage, and should also be preserved against the contaminating action of microorganisms, such as bacteria and fungi. The carrier can be a solvent or dispersion medium. The proper fluidity can be maintained, for example, by the use of a coating, by the maintenance of the required particle size in the case of dispersion and by the use of surfactants.

Prevention of the action of microorganisms can be achieved by various antibacterial and antifungal agents. Isotonic agents, for example, sugars, polyalcohols, may also be included in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a modified binding protein by itself or in combination with other active agents) in a required amount in an appropriate solvent with one or a combination of ingredients enumerated, followed by filtered sterilization. Generally, dispersions are prepared by incorporating the active compound into a sterile vehicle, which contains a basic dispersion medium and any required other ingredients. In the case of sterile powders for the preparation of sterile injectable solutions, methods of preparation typically include vacuum drying and freeze-drying, which yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit.

Effective doses of the compositions of the present disclosure, for the treatment of a disease or disorder vary depending upon many different factors, including means of administration, target site, physiological state of the subject, whether the subject is human or an animal, other medications administered, and whether treatment is prophylactic or therapeutic. Usually, the patient is a human, but non-human mammals including transgenic mammals can also be treated. Treatment dosages may be titrated to optimize safety and efficacy.

Binding proteins described herein can be administered on multiple occasions. Intervals between single dosages can be weekly, monthly or yearly. Intervals can also be irregular as indicated by measuring levels of binding protein or antigen in the subject. Alternatively, binding proteins can be administered as a sustained release formulation, in which case less frequent administration is required. For antibodies, dosage and frequency vary depending on the half-life of the antibody in the patient. In general, humanized antibodies show the longest half-life, followed by chimeric antibodies and non-human antibodies.

The dosage and frequency of administration can vary depending on whether the treatment is prophylactic or therapeutic. In prophylactic applications, compositions containing the present binding protein are administered to a subject not already in the disease state to enhance the subject's resistance. In terms of achondroplasia, a prophylactic treatment is understood as a method of preventing or alleviating one or more symptoms of the disorder. In terms of cancer, a prophylactic treatment is understood as a method of preventing the happening of cancer, or alleviating one or more symptoms of the cancer. Such an amount is defined to be a "prophylactic effective dose." In this use, the precise amounts again depend upon the subject's state of health and general immunity. In therapeutic applications, a relatively high dosage at relatively short intervals is sometimes required until progression of the disease is reduced or terminated, or until the patient shows partial or complete amelioration of disease symptoms. Thereafter, the patient can be administered a prophylactic regime.

Binding proteins described herein can optionally be administered in combination with other agents that are effective in treating the disorder or condition in need of treatment (e.g., prophylactic or therapeutic).

While the binding proteins may be administered as described immediately above, it must be emphasized that in other embodiments binding proteins may be administered to otherwise healthy subjects as a first line therapy. In such embodiments the binding proteins may be administered to subjects that have not, and are not, undergoing one or more other therapies, or subjects that have, or are undergoing one or more other therapies. As used herein, the administration of binding proteins, e.g. antibodies or fragments thereof, in conjunction or combination with an adjunct therapy means the sequential, simultaneous, coextensive, concurrent, concomitant, or contemporaneous administration or application of the therapy and the disclosed binding proteins. The administration or application of the various components of the combined therapeutic regimen may be timed to enhance the overall effectiveness of the treatment.

As previously discussed, the binding proteins of the present disclosure may be administered in a pharmaceutically effective amount for the in vivo treatment of mammalian disorders.

Pharmaceutical compositions in accordance with the present disclosure typically include a pharmaceutically acceptable, non-toxic, sterile carrier such as physiological saline, buffers, preservatives and the like. For the purposes of the instant application, a pharmaceutically effective amount of the binding protein that, shall be held to mean an amount sufficient to achieve effective binding to an antigen and to achieve a benefit, e.g., to ameliorate symptoms of a disease or disorder. Of course, the pharmaceutical compositions of the present disclosure may be administered in single or multiple doses to provide for a pharmaceutically effective amount of the antigen-binding protein or antigen-binding fragment thereof.

In keeping with the scope of the present disclosure, the antigen-binding protein or antigen-binding fragment thereof may be administered to a human or other animal in accordance with the methods of treatment herein in an amount sufficient to produce a therapeutic or prophylactic effect. The binding proteins of the disclosure can be administered to such human or other animal in a conventional dosage form prepared by combining the binding protein with a conventional pharmaceutically acceptable carrier or diluent according to known techniques. The form and character of the pharmaceutically acceptable carrier or diluent is dictated by the amount of active ingredient with which it is to be combined, the route of administration and other well-known variables. In some embodiments, a cocktail comprising one or more species of binding proteins described in the current disclosure may prove to be particularly effective.

Methods of Treatment and Inhibition of FGFR3 Activity

The anti-FGFR3 antigen binding proteins or fragments thereof are useful for the treatment of FGFR3-mediated diseases or disorders. As used herein, the term "FGFR3-mediated disease or disorder" refers to any disease or disorder that is the result of aberrant FGFR3 activity. In certain embodiments, the disease or disorder is caused by FGFR3 over activity or over expression. Non-limiting examples of FGFR3-mediated diseases or disorders include achondroplasia, hypochondroplasia, and cancer.

The anti-FGFR3 antigen binding proteins or fragments thereof are useful for the reduction of FGFR3 activity. As used herein, an "FGFR3 activity" refers to any signaling event associated with the dimerization of FGFR3 on the surface of a cell. The FGFR3 activity can be one or both of an extracellular activity and an intracellular activity. FGFR3 activities include, but are not limited to, FGFR3 dimerization, extracellular signal-regulated kinase (Erk) phosphorylation, mitogen-activated protein kinase kinase (MKK, MEK, or MAP2K) phosphorylation, FGFR3 cytoplasmic tyrosine kinase domain activity, and FGF ligand binding activity (e.g., FGF18 binding to FGFR3).

As used herein, the term "achondroplasia" refers to a genetic disorder caused by mutations in the FGFR3 gene that make the resulting protein overactive. The anti-FGFR3 antigen binding proteins or fragments thereof are useful for the reduction of one or more symptoms of achondroplasia. Achondroplasia symptoms include, but are not limited to, shortening of the proximal limbs, brachydactyly (i.e., short fingers and toes with trident hands), large head with prominent forehead frontal bossing, small midface with a flattened nasal bridge, spinal kyphosis (convex curvature) or lordosis (concave curvature), varus (i.e., bowleg) or valgus (i.e., knock knee, ear infections (due to Eustachian tube blockages)), sleep apnea (central or obstructive), and hydrocephalus. Achondroplasia may be diagnosed through the measurement of one or more of proximal limb length (e.g., femur and tibia length), finger and toe length, head circumference (e.g., skull length), and lumbar vertebrae length, although other anatomical measurements can be employed. Achondroplasia may be diagnosed through genetic testing to detect one or more mutations in the FGFR3 gene.

In one aspect, the disclosure provides a method for treating a FGFR3-mediated disease or disorder in a subject, comprising administering to a subject in need thereof the antigen binding protein or fragment thereof described herein.

As used herein, the term "subject," "patient," or "individual" refers to a human or non-human animal. The term "non-human animal" includes, but is not limited to, vertebrates such as non-human primates, sheep, dogs, cats, rabbits, ferrets, rodents such as mice, rats and guinea pigs, avian species (e.g., chickens), amphibians, and reptiles. In certain embodiments, the subject is a mammal such as a non-human primate, sheep, dog, cat, rabbit, ferret or rodent. In certain embodiments, the subject is a cynomolgus monkey. In certain embodiments, the subject is a human. In certain embodiments, the subject is a child. In certain embodiments, the subject is an adolescent.

In certain embodiments, the FGFR3-mediated disease or disorder is achondroplasia. In certain embodiments, the achondroplasia is $FGFR3^{G380R+}$ achondroplasia, meaning the subject to be treated contains the G380R mutation in its FGFR3 gene, either homozygous or heterozygous.

In certain embodiments, a subject diagnosed as having achondroplasia or risk of achondroplasia is treated with a binding protein disclosed herewith. In certain embodiments, the treatment leads to one or more effects selected from the group consisting of increased bone length (e.g., femur length and/or tibia length), increased bone diameter (e.g., femur diameter), increased growth plate volume (e.g., femur growth plate volume), increased vertebrae length, increased skull length, increased bone volume, increased skull volume, corrected vertebral abnormalities (e.g., increased Kyphosis Index), and improved bone age (e.g., more developed secondary ossification center), as compared to a control subject not receiving the treatment that is of the same development stage.

Accordingly, a method of improving one or more bone features in a subject is also provided. In certain embodiments, the method comprises administrating a binding protein or an antigen-binding fragment thereof disclosed herewith to a subject in need. In certain embodiments, the improved bone feature is selected from the group consisting of bone length (e.g., femur length or tibia length), bone diameter (e.g., femur diameter), growth plate volume, vertebrae length, skull length, bone volume, skull volume, Kyphosis Index, and improved bone age.

In certain embodiments, the FGFR3-mediated disease or disorder is cancer. In certain embodiments, the cancer is selected from the group consisting of bladder cancer, melanoma, urothelial cancer, and endometrial cancer.

In another aspect, the disclosure provides a method for treating achondroplasia in a subject, comprising administering to a subject in need thereof an antigen binding protein or an antigen-binding fragment thereof with binding specificity to an FGFR3 epitope, wherein the antigen binding protein or the antigen binding fragment thereof does not bind to one or more of FGFR1, FGFR2, and FGFR4.

In another aspect, the disclosure provides a method for inhibiting one or both of FGFR3 activity and expression in a bone growth plate of a subject, comprising administering to a subject an antigen binding protein or an antigen binding fragment thereof with binding specificity to an FGFR3 epitope, wherein the antigen binding protein fragment does not bind to one or more of FGFR1, FGFR2, and FGFR4. In certain embodiments, an FGFR3 antibody as described herewith is used.

Therapeutic and Prophylactic Uses

The disclosure provides therapeutic uses of its binding proteins or an antigen binding protein fragment thereof with binding specificity to an FGFR3 epitope, wherein the antigen binding protein fragment does not bind to one or more of FGFR1, FGFR2, and FGFR4) corresponding to the methods of treatment disclosed above. For instance, the disclosure provides a binding protein or the antigen binding protein fragment thereof as described herein for use in medicine. In some embodiments, it provides a binding protein, or an antigen binding protein fragment thereof as described herein for use as an FGFR3-activity inhibiting medicament. In some embodiments, it provides a binding protein, or an antigen binding protein fragment thereof as described herein for use in treating an FGFR3-mediated disorder. Examples of such disorders are given herein. In some embodiments, it provides a binding protein, or antigen binding protein fragment thereof as described herein for use in preventing one or more symptoms of achondroplasia, as exemplified above. In some embodiments, it provides a binding protein, or antigen binding protein fragment thereof as described herein for use in preventing cancer, as exemplified above. Embodiments described herein regarding methods of treatment, administration, subjects and all other aspects relevant to therapy and prevention also apply to these uses of binding proteins.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLE

Example 1—Generation of Anti-FGFR3 Antibodies

Generation of Immunogen

Anti-FGFR3 monoclonal antibodies were developed using 300.19 pre-B lymphoblast cells (ATCC, Manassas, Va.) transformed with DNA encoding full-length human FGFR3 (see FIG. 1, GenBank ID NP_000133.1, FGFR3 isoform IIIc) with the mutation G380R (SEQ ID NO: 133) which was expressed on the cell surface (FGFR3$^{G380R}$-300.19 cell). The FGFR3$^{G380R}$ open reading frame was subcloned into the pXL-MCS vector and transfected into 300.19 cells (Immunogen 1). Separately, DNA encoding the human FGFR3 extra cellular domain (ECD) protein (Immunogen 2) was subcloned into the pTT5 vector (Invitrogen), and was prepared using Expi293 cells (Invitrogen). FGFR3 extra cellular domain (ECD) protein (Immunogen 2):

```
                                        (SEQ ID NO: 140)
GGLNDIFEAQKIEWHEHHHHHHEDQVDPRLIDGKIQPEPESLGTEQRVVG

RAAEVPGPEPGQQEQLVFGSGDAVELSCPPPGGGPMGPTVWVKDGTGLVP

SERVLVGPQRLQVLNASHEDSGAYSCRQRLTQRVLCHFSVRVTDAPSSGD

DEDGEDEAEDTGVDTGAPYVVTRPERMDKKLLAVPAANTVRFRCPAAGNP

TPSISWLKNGREFRGEHRIGGIKLRHQQWSLVMESVVPSDRGNYTCVVEN

KFGSIRQTYTLDVLERSPHRPILQAGLPANQTAVLGSDVEFHCKVYSDAQ

PHIQWLKHVEVNGSKVGPDGTPYVTVLKTAGANTTDKELEVLSLHNVTFE

DAGEYTCLAGNSIGFSHHSAWLVVLPAEEELVEADEAGSAS
```

FGFR3 expression on FGFR3$^{G380R}$-300.19 cells was monitored and quantified by FACS analysis using the comparator antibody, GT184.6.1, described further in Yin et al. (Mol. Cancer Ther. 14(10): 2270-8. 2015). Anti-FGFR1 (MAB765), anti-FGFR2 (MAB6843), anti-FGFR3 (MAB766), and anti-FGFR4 (MAB6852) antibodies were used as negative controls (R&D Systems, Minneapolis, Minn.). The FGFR3 ECD protein was quantified using an enzyme-linked immunosorbent assay (ELISA) with the antibodies described further below.

The cells expressing FGFR3 were maintained at 37° C. under 5% $CO_2$ in RPMI (Gibco) supplemented with heat inactivated fetal bovine serum (FBS) (Hyclone). Cells were prepared for injection by substituting the above culture medium with phosphate buffered (Ca—Mg free) saline (CMF-PBS) supplemented with 5 mM EDTA and harvesting the cells in that buffer. The harvested cells were pelleted by centrifugation at 500×g for 5 minutes, washed once by resuspending the pellet in CMF-PBS and centrifuging as before, counted and adjusted to the appropriate volume (such as 5×10$^6$ cells in 0.2 ml) for injection by resuspending the cell pellet in CMF-PBS. The FGFR3 ECD protein was used to boost antibody titers in animals before sacrificing the mouse.

Cells were maintained in RPMI medium by seeding about 3-5×10$^5$ cells per ml in a T75 flask and grown for approximately 24-48 hours with selection antibiotic to eliminate the cells not carrying FGFR3 plasmid. Cell surface expression of FGFR3 on cells was verified by FACS analysis prior to use as an immunogen.

Generation of Anti-FGFR3 Antibodies—Hybridoma Strategy

Six eight-week old female FGFR3 KO (C57BL/6$^{mFGFR3-}$) mice from the Jackson Laboratory (Bar Harbor, Me.) were immunized with the FGFR3-transfected cells (Immunogen 1). Separately, wild-type Balb/c mice were immunized with the FGFR3 ECD protein described above (Immunogen 2). A group of mice were primed intraperitoneally on day 0 with FGFR3-expressing cells, FGFR3$^{G380R}$-300.19 cells, in PBS without adjuvants, administrated on days 14, 28, 42 and 56, followed by an intraperitoneal boost on day 77 with the FGFR3 ECD protein in PBS without adjuvants. Each injection was administrated with approximately 5×10$^6$ cells in a volume of 200 µl and 50 µg protein in a volume of 100 µl PBS. Immunizations were performed in two-week intervals and the IgG titer was evaluated by ELISA with FGFR3 ECD protein to assess immune response.

The mice were sacrificed for harvesting the spleen and placed in approximately 10 ml of pre-warmed serum-free DMEM (Hyclone) at 37° C. in a petri dish. The splenocytes were teased out of the capsule using forceps and transferred to a 15-ml conical tube. The cells were then washed three times with pre-warmed serum-free IMDM (Hyclone) and cells from multiple mice were pooled.

The fusion partner cell, FO B lymphoblasts (ATCC, Manassas, Va.), for the immunized spleen cells was established with a hypoxanthine/aminopterin/thymidine (HAT)-sensitive and IgG non-secreting myeloma cell line. Prior to the fusion, FO B lymphoblasts were maintained in IMDM medium supplemented with 10% FBS (37° C., 7% $CO_2$) ensuring that the cells were in logarithmic growth phase on the day of the fusion.

The fusion protocol was derived from Lerner (Yale J Biol Med, 1981, 54 (5) 387-402) and Gefter et al. (Somatic Cell Genet, 1977, 3 (2) 231-236). Before the fusion, the spleen cells and the logarithmic phase myeloma cells were washed three times with serum-free IMDM and counted. For each fusion, 1-1.5×10$^8$ spleen cells were mixed with 2-3×10$^7$ myeloma cells in a 50-ml conical polypropylene tube and cells were washed once with serum-free IMDM. The ratio of spleen cells to myeloma cells was 5:1. The tubes were centrifuged at 500×g for 10 minutes to pellet the cells. After aspiration of the supernatant, the pellets were gently resuspended by tapping the bottom of the tubes. The tubes were then placed in a beaker of 37° C. water. All subsequent fusion steps were carried out in the beaker of 37° C. water.

Next, 1 ml of polyethylene glycol 1500 (PEG) (Roche Applied Science, Indianapolis, Ind.) preheated to 37 C was slowly added to the cell pellet over the course of about 1 minute, while gently rocking the tube. The cells were incubated in the PEG for one minute followed by addition of 1 ml serum-free IMDM added dropwise to the pellet over the course of 30 seconds, and then 9 ml of serum-free IMDM were added to the pellet for one minute. The tube was then centrifuged at 500×g for 10 minutes at room temperature, and the supernatant was aspirated. The pellet was resuspended in 200 ml of filtered complete hybridoma production media, IMDM (Hyclone) supplemented with 10% FBS (Hyclone), 1× non-essential amino acid (Gibco), 1 mM sodium pyruvate (Gibco), 1× pen-strep (Gibco) and 1×HAT (Sigma). The resuspended cells were then seeded in ten 96-well flat-bottom microtiter plates, in a volume of about 200 µl/well. The plates were kept in an incubator at 37° C., 7% $CO_2$.

A primary hybridoma screen was designed to select hybridoma clones producing antibodies which recognized native FGFR3 epitopes. Supernatants from wells growing clones, typically on days $10^{-14}$ post-fusion, were incubated with Chinese hamster ovary (CHO) cells stably expressing FGFR3 (FGFR3-CHO). Antibody binding was detected by FACS using a fluorescently labeled goat anti-mouse secondary antibody. Clones were considered positive if labeled supernatant samples were greater than 10-fold over background in the FACS analysis. Selected positive clones were transferred to 24-well flat bottom plates and expanded for a second screen to confirm selection. Supernatants from 24-well plates were incubated with hFGFR3$^{G380R}$-300.19 cells and detected by a fluorescently labeled goat anti-mouse secondary antibody. More than 4,000 hybridomas were generated and screened by FACS assay described above. Only 25 clones were confirmed specific to FGFR3. Positive clones were expanded for purified antibody production, VH and VL gene sequencing and cryo-preservation.

Generation of Anti-FGFR3 Antibodies—Phage-Display Strategy

Three scFv phage libraries and two fab fragment phage libraries were screened, with 5 separate screening campaigns performed. A first campaign screened the scFv phage libraries against the hFGFR3 isoform IIIc dimer. 2,700 scFv antibodies were screened with only 13 antibodies identified as potential candidates. A second campaign screened fab and scFv libraries against the hFGFR3 isoform IIIc dimer. 1,940 antibodies were screened with only 13 antibodies identified as potential candidates. A third and fourth campaign screened fab and scFv libraries against the hFGFR3 isoform IIIc dimer, the hFGFR3 isoform IIIc his tagged monomer, and hFGFR3 isoform IIIc-expressing cells. 9,770 antibodies were screened with only 36 antibodies identified as potential candidates. A fifth campaign screened fab libraries against the hFGFR3 isoform IIIc monomer and mouse FGFR3 (mFGFR3) isoform IIIc monomer, and hFGFR3 isoform IIIc- and mFGFR3 isoform IIIc-expressing cells. 2,990 antibodies were screened with only 57 antibodies identified as potential candidates. Between the five screening campaigns, 17,400 antibodies were screened. Among those screened antibodies, only 48 were found to be cross-reactive between human, mouse, and cyno, and only 15 were found to block FGFR3 ligand binding.

FGFR family member proteins (human FGFR1α IIIb, FGFR1α IIIc, FGFR1β IIIb, FGFR1β IIIc, FGFR2α IIIc, FGFR2β IIIb, FGFR3 IIIb, FGFR3 IIIc, FGFR4; mouse FGFR3; and cynomolgus FGFR3 recombinant proteins) were purchased from R&D Systems (Minneapolis, Minn.) for identifying FGFR3 specific clones by ELISA. cDNA encoding the following proteins were all subcloned into the pTT5 vector (Invitrogen): partial ECD and chimeric ECD proteins of FGFR3; human D2D3 (hD2D3) and D3 (hD3) of human FGFR3; mouse D2D3 (mD2D3) and D3 (mD3) of mouse FGFR3; cynomolgus D2D3 (cyD2D3) and D3 (cyD3) of cynomolgus FGFR3; and hD1-cyD2D3 and hD1-mD2D3 recombinant proteins. Proteins were prepared by transient transfection using Lipofectamine 2000 (Invitrogen) in Expi293 cells (Invitrogen). Supernatants from the selected clones were incubated in 96-well plates coated with the recombinant FGFR proteins and detected with goat anti-mouse IgG horseradish peroxidase (Jackson Immunoresearch, West Grove, Pa.) followed by chemiluminescent detection.

Cell Based-Binding Assays for Anti-FGFR3 Antibodies

A cell-based binding assay was used to characterize the anti-FGFR3 antibodies generated above. Full-length human, mouse, and cynomolgus FGFR3 cDNAs were subcloned into different pcDNA 3.1 (Invitrogen) vectors and transfected into 300.19 cells (ATCC). The cDNA of FGFR3 Ig domains D2D3 was subcloned into pcDNA 3.1 and transfected into CHO (D2D3-CHO) (ATCC) cells. Full-length human FGFR3$^{G380R}$, mouse FGFR3, and cynomolgus FGFR3$^{G380R}$ cDNAs were also subcloned into different pcDNA 3.1 vectors. Stable cell lines expressing FGFR3 were generated by transfection of human FGFR3$^{G380R}$, mouse FGFR3, and cynomolgus FGFR3$^{G380R}$ cDNA plasmid constructs into CHO (hFGFR3$^{G380R}$-CHO and cyFGFR3$^{G380R}$-CHO) and human embryonic kidney (HEK, mFGFR3-HEK) (ATCC) cells using the Lipofectamine 2000 kit (Invitrogen). Cell lines were maintained in F-12K medium supplemented with 10% FBS for CHO cells and in DMEM supplemented with 10% FBS for HEK cells overnight, then cultured in the presence of geneticin (0.5 ml/ml) for 10-14 days. Isolated single colonies were picked and grown in separate wells until sufficient clonal cells were expanded. Stable clones resistant to geneticin and expressing high copies of FGFR3 protein were identified by FACS assay using GT184.6.1.

Cell-based antibody binding to wild-type FGFR3, mutant FGFR3, and D2D3 FGFR3 expressed on CHO and HEK cells was accessed by FACS analysis. Cells were incubated with anti-FGFR3 antibodies in 1% bovine serum albumin in PBS (BPBS). After three washes, the cells were incubated with a fluorescent-conjugated secondary antibody (Invitrogen).

The results indicated that several antibodies bind specifically to FGFR3 expressed on the cells. For example, clones KC18, KE35, KE42, KE58, KE63, and KE94, with mouse and human isotype controls as negative controls and GT184.6.1 as a positive control, were tested for binding to CHO, HEK and 300.19 cells transfected to express wild-type FGFR3, mutant FGFR3, and the ECD domain of FGFR3. All antibodies bound to the cells as described above, with similar binding profiles and titration kinetics. The negative control antibodies exhibited only background reactivities. The binding of anti-FGFR3 antibodies to mouse primary rib chondrocytes was also observed by FACS analysis.

The binding specificities of antibodies KC18, KE35, KE42, KE58, KE63, and KE94 were also tested using GT184.6.1 as positive control. Unlike GT184.6.1, which bound to both hFGFR2 and hFGFR3, KC18, KE35, KE42, KE58, KE63, and KE94 only bound to hFGFR3, indicating high FGFR3 specificities.

Biacore Affinity Analysis

The N-terminal ECD proteins of FGFR3 from human and mouse were produced with a terminal avidin tag and used in a forward format Biacore assay where proteins were immobilized on a Biacore chip and then the kinetics of antibody interaction with the proteins on the chip were determined. The proteins were immobilized on a Biacore chip for approximately 10,000 response units (RU). Then the antibodies were exposed to the chip for kinetic measurements, following the manufacturer's recommendations (GE Healthcare). Sensorgrams were fit to a 1:1 binding model and analyzed using double-reference subtraction by T200 Evaluation software (GE Healthcare). Affinities of the tested antibodies are shown in Table 2.

```
IgG1 3' Primer:
                                    (SEQ ID NO: 1)
5'-TATGCAAGGCTTACAACCACA-3'

IgG2b 3' Primer:
                                    (SEQ ID NO: 2)
5'-GTTAGGAGCTGGGCATTTGTGACACTCC-3'

IgG2c 3' Primer:
                                    (SEQ ID NO: 3)
5'-GTTAGGTGCTGGGCATTTGCATGGAGGACAGGG-3'

IgG3 3' Primer:
                                    (SEQ ID NO: 4)
5'-GTTTGGTGGGCATGAAGAACCCGGGG-3'
```

TABLE 2 anti-FGFR3 antibodies binding specificities and affinities

| FGFR3 antibodies | Selectivity | | | | Reactivity | | | |
|---|---|---|---|---|---|---|---|---|
| | FGFR1 | FGRF2 | FGFR3 | FGFR4 | hFGFR3IIIc | hFGFR3IIIb | mFGFR3 | cynoFGFR3 |
| KC18 | − | − | + | − | +++ | +++ | +++ | +++ |
| KE35 | − | − | + | − | +++ | +++ | +++ | +++ |
| KE42 | − | − | + | − | +++ | +++ | +++ | +++ |
| KE58 | − | − | + | − | +++ | +++ | +++ | +++ |
| KE63 | − | − | + | − | +++ | +++ | +++ | +++ |
| KE94 | − | − | + | − | +++ | +++ | +++ | +++ |
| Control mAb: GT184 | − | + | + | − | ++ | ++ | +++ | +++ |

| | Affinity (hFGFR3) | | | Affinity (mFGFR3) | | |
|---|---|---|---|---|---|---|
| FGFR3 antibodies | Ka ($M^{-1}s^{-1}$) | Kd ($s^{-1}$) | KD (nM) | Ka | Kd | KD (nM) |
| KC18 | 7.92E+05 | 3.47E−04 | 1.4 | 1.74E+05 | 1.10E−03 | 6.30 |
| KE35 | 4.14E+05 | 1.20E−03 | 2.89 | 5.71E+5 | 1.08E−03 | 1.89 |
| KE42 | 4.60E+05 | 5.67E−04 | 1.23 | 7.39E+5 | 6.00E−04 | 0.81 |
| KE58 | 1.15E+06 | 1.43E−03 | 1.2 | 1.67E+05 | 9.18E−04 | 5.50 |
| KE63 | 8.87E+05 | 7.45E−04 | 0.8 | 4.36E+05 | 2.91E−03 | 6.70 |
| KE94 | 9.40E+05 | 5.95E−04 | 0.6 | 7.05E+05 | 1.48E−03 | 2.10 |
| Control mAb: GT184 | 4.23E+05 | 1.20E−03 | 2.8 | 4.15E+05 | 1.52E−03 | 3.7 |

Sequence Analysis of Anti-FGFR3 Monoclonal Antibodies

Prior to sequence analyses, the isotype of each clone was determined using the IsoStrip Mouse Monoclonal Antibody Isotyping Kit (Roche Applied Science, Indianapolis, Ind.). The heavy (VH) and light (VL) chain variable regions of clones were sequenced using 5'RACE (Rapid Amplification of cDNA Ends) Kit (Clontech, Mountain View, Calif.) as per the manufacturer's instruction. Total RNA was extracted from each hybridoma clone using the RNeasy Miniprep kit according to the manufacturer's instructions (Qiagen, Germantown, Md.). Full-length first strand cDNAs containing 5'ends were generated by polymerase chain reaction (PCR) using 5'RACE kits (Clontech). The VH and VL genes were amplified by TA cloning kit (Invitrogen) with primers, 5'primer (5'RACE kit, Clontech), and 3' primer of IgG isotype specific heavy chain and 3'primer of kappa light chain.

```
                            -continued
Kappa light chain 3'Primer:
                                    (SEQ ID NO: 5)
5'-CTCATTCCTGTTGAAGCTCTTGAC-3'
```

The amplified cDNAs were cloned into pCR2.1 vectors (Invitrogen) and transformed using a TOPO-TA cloning kit (Invitrogen) as per the manufacturer's instructions. Plasmids were isolated from 2 ml of an LB culture, inoculated from a single colony and grown overnight, using QIAprep spin miniprep kit (Qiagen) and sequenced using M13 Forward and M13 Reverse primers included in the TOPO-TA cloning kit (Invitrogen). The VH and VL gene sequences were analyzed using the IMGT V-Quest web server to identify and confirm variable region sequences. VH and VL sequences of each antibody are provided below in Table 3:

TABLE 3

Antibody VH and VL amino acid sequences

| Antibody ID | Sequence |
|---|---|
| KC18 VH | QVQLQQSGAELVRPGASVTLSCKASGDTFTDFEIHWVKQTPVHGLEWIGDI DPETGGTAYNQKFRGRAMLTADRSSSTAYMELRSLTSEDSAVYYCTRTYDG YPYAMDYWGQGTSVTVSS (SEQ ID NO: 6) |
| KC18 VL | DIVMSQSPSSLAVSVGEKVTMSCKSSQSLLYSNNQKNYLAWYQQKPGQSPK LLIYWASTRESGVPDRFTGSGSGTDFTLTISSVKAEDLAVYYCQQYYSYRTF GGGTKLEIK (SEQ ID NO: 7) |
| KE35 VH | EVQLQQSGPELVKPGASVKMSCKASGYTFTDYNMHWVKQSHGKSLEWIGY INPNNGGTRYNQKFKGKATLTVNKSSSTAYMELRSLTSEDSAVYYCARERD YDGAMDYWGQGTSVTVSS (SEQ ID NO: 8) |
| KE35 VL | DIQMTQSPSSLSASLGGKVTITCKASQDINKFIAWYQHKPGKGPRLLIHYTST LQPGIPSRFSGSGSGRDYSFSISNLEPEDIATYYCLQYDNLLWTFGGGTKLEIK (SEQ ID NO: 9) |
| KE42 VH | EVQLQQSGPELVKPGASVKMSCKASGYTFTDYNMHWVKQSHGKSLQWIG YINPNNGGTNYNQNFKDKATLTVNKSSTTAYMELRSLTSEDSAVYYCARER DYDGSMDFWGQGTSVTVSS (SEQ ID NO: 10) |
| KE42 VL | DIQMTQSPSSLSASLGGKVTITCKASQDINKFIAWYQHKPGKGPRLLIHYTST LQPGIPSRFSGSGSGRDYSFSISNLEPEDIATYFCLQYDNLLWTFGGGTKLEIK (SEQ ID NO: 11) |
| KE58 VH | EVQLQQSGPDLVKPGASVKISCKASGYTVTDYYMNWVKQSHGKSLEWIGD INPNNGVTTYNQKFKDKATLTVDKSSSTAYMELRSLTSEDSAVYYCAREED FDGFDYWGQGTTLTVSS (SEQ ID NO: 12) |
| KE58 VL | DIVMTQSHKFMSTSVGDRVSITCKASQDVSTGVAWYQQKPGQSPQLLIYWA STRHTGVPDRFTGSGSGTDYILTIRSVQAEDLALYYCQQHYSTPLTFGAGTK LELK (SEQ ID NO: 13) |
| KE63 VH | QVQLQQSGAELVRPGASVTLSCKASGSTFSDFEIHWVKQTPVHGLEWIGGID PETGGTAYNQKFKGKAILTADRSSSTAYMELRSLTSEDSAVYYCTRNYDGY SQTMDYWGQGTSVTVSS (SEQ ID NO: 14) |
| KE63 VL | NIMMTQSPSSLAVSAGEKVTMSCKSSQSVLYSSNQKNYLAWYQQKPGQSP KLLIYWASTRESGVPDRFTGSGSGTDFTLTISSVQAEDLAVYYCHQYLSSYT FGGGTKLEMK (SEQ ID NO: 15) |
| KE94 VH | QVQLQQSGAELVRPGASVTLSCKASGSTFTDFEIHWVKQTPVHGLEWIGAID PETGGTAYNQKFKGKAILTAVKSSSTAYMGLRSLTSEDSAVYYCTRNYDGY SRTMDYWGQGTSVTVSS (SEQ ID NO: 16) |
| KE94 VL | NIMMTQSPSSLAVSAGEKVTMSCKSSQSVLYSSNQKNYLAWYQQKPGQSP KLLIYWASTRESGVPDRFTGSGSGTDFSLSISSVQTEDLAVYYCHQYLSSYTF GGGTRLEMK (SEQ ID NO: 17) |

The CDR regions for the VH and VL sequences recited above are provided below in Table 4:

TABLE 4

Antibody Heavy chain and Light chain CDR regions

HEAVY Chain

| VH Chain ID | HCDR1-IMGT | HCDR2-IMGT | HCDR3-IMGT |
|---|---|---|---|
| KC18_VH | GDTFTDFE (SEQ ID NO: 70) | IDPETGGT (SEQ ID NO: 71) | TRTYDGYPYAMDY (SEQ ID NO: 72) |
| KE35_VH | GYTFTDYN (SEQ ID NO: 76) | INPNNGGT (SEQ ID NO: 77) | ARERDYDGAMDY (SEQ ID NO: 78) |
| KE42_VH | GYTFTDYN (SEQ ID NO: 82) | INPNNGGT (SEQ ID NO: 83) | ARERDYDGSMDF (SEQ ID NO: 84) |
| KE58_VH | GYTVTDYY (SEQ ID NO: 88) | INPNNGVT (SEQ ID NO: 89) | AREEDFDGFDY (SEQ ID NO: 90) |
| KE63_VH | GSTFSDEE (SEQ ID NO: 94) | IDPETGGT (SEQ ID NO: 95) | TRNYDGYSQTMDY (SEQ ID NO: 96) |

TABLE 4-continued

Antibody Heavy chain and Light chain CDR regions

| KE94_VH | GSTFTDFE (SEQ ID NO: 100) | IDPETGGT (SEQ ID NO: 101) | TRNYDGYSRTMDY (SEQ ID NO: 102) |

LIGHT Chain

| VL Chain ID | LCDR1-IMGT | LCDR2-IMGT | LCDR3-IMGT |
| --- | --- | --- | --- |
| KC18_VL | QSLLYSNNQKNY (SEQ ID NO: 73) | WAS (SEQ ID NO: 74) | QQYYSYRT (SEQ ID NO: 75) |
| KE35_VL | QDINKF (SEQ ID NO: 79) | YTS (SEQ ID NO: 80) | LQYDNLLWT (SEQ ID NO: 81) |
| KE42_VL | QDINKF (SEQ ID NO: 85) | YTS (SEQ ID NO: 86) | LQYDNLLWT (SEQ ID NO: 87) |
| KE58_VL | QDVSTG (SEQ ID NO: 91) | WAS (SEQ ID NO: 92) | QQHYSTPLT (SEQ ID NO: 93) |
| KE63_VL | QSVLYSSNQKNY (SEQ ID NO: 97) | WAS (SEQ ID NO: 98) | HQYLSSYT (SEQ ID NO: 99) |
| KE94_VL | QSVLYSSNQKNY (SEQ ID NO: 103) | WAS (SEQ ID NO: 104) | HQYLSSYT (SEQ ID NO: 105) |

Inhibition of FGF1 Ligand Binding by Anti-FGFR3 Antibodies

To test if the isolated antibodies could inhibit the binding between FGF1 ligand and FGFR3, an FGF1 ligand blocking assay was conducted. For the FGFR1 ligand blocking assay, human FGFR3 cells, FGFR3-300.19 and FGFR3$^{G380R}$-300.19, were pre-incubated with various concentration of anti-FGFR3 antibodies and isotype controls, prior to addition of human FGF1 ligand (R&D Systems). Binding of hFGF1 to FGFR3 expressed on the cells was determined by FACS assay using biotinylated anti-FGF1 antibody followed by incubation with a streptavidin-fluorescent secondary antibody. The anti-FGFR3 antibodies which bound to the EC domain, including KC18, KE35, KE42, KE58, KE63, and KE94, all blocked binding of FGF1 to FGFR3 on these cells.

An ELISA-based blocking assay using human and mouse FGF1 ligand was conducted. Each well of 96-well plates was coated with either human or mouse FGFR3 proteins to capture both/either anti-hFGFR3 antibody and/or FGF1 ligand, then incubated with various concentrations of anti-FGFR3 antibody and isotype controls, prior to addition of human FGF1 ligand. Binding of FGF1 ligand was determined by addition of a substrate to induce a quantifiable chemiluminescence reaction. Inhibition of FGF1 binding to human FGFR3 and mouse FGFR3 proteins by the anti-FGFR3 antibodies was detected by ELISA, respectively.

Epitope Binning of Anti-FGFR3 Antibodies

Using a Biacore T100 (GE Healthcare, Piscataway, N.J.), anti-FGFR3 antibodies were immobilized on a Biacore CM5 chip and ECD proteins of FGFR3 were injected. Competition of second anti-FGFR3 antibodies (Ab2) bound to FGFR3 protein captured by immobilized anti-FGFR3 antibodies (Ab1) were determined. The anti-FGFR3 antibodies were immobilized on a Biacore chip for approximately 100 response units (RU). Flow cell 1 remained blank for reference subtraction on each chip. The ECD FGFR3 protein and mouse anti-FGFR3 antibodies (Ab2) prepared in HBS-EP+ running buffer were injected for 3 minutes and 5 minutes at a flow rate of 50 µl/min, respectively. The Ab1 surface was regenerated between cycles using 10 mM glycine-HCl (pH 2.0) at 50 µl/min for 1 minutes. Sensorgrams were fit to a 1:1 binding model and analyzed using double-reference subtraction by BiaEvaluation software (GE Healthcare). It was determined that anti-FGFR3 antibodies KC18, KE35, KE42, KE58, KE63, and KE94 competed for the same region on FGFR3 around the D2 domain.

Hydrogen deuterium exchange (HDX) mass spectrometry was also used to determine the epitopes on FGFR3 for these antibodies by measuring the amide hydrogen deuterium exchange on FGFR3. HDX mass spectrometry measured amide hydrogen deuterium exchange over time and quenched at 0° C. and pH 2.5 along with protease digestion. Briefly, the antibody to be tested and antigen were mixed such that about 90% of the antibody is bound to the antigen at room temperature. Deuterium exchange was performed with a 10-fold dilution into D$_2$O at neutral pH. Quenching was then performed by holding the reaction mixture for 1 minute at about 0 to 1° C. to reduce disulfide bonds. Protease digestion was performed with protease XIII and pepsin. HDX mass spectrometry is described in further detail in Pradzińska et al. (Amino Acids. 48: 2809-2820. 2016). The FGFR3 sequence used in the HDX assay is recited below, and corresponds to the D2D3 region, corresponding to D143 to E365 of FGFR3 Isoform IIIc:

(SEQ ID NO: 134)
DTGVDTGAPYWTRPERMDKKLLAVPAANTVRFRCPAAGNPTPSISWLKNG

REFRGEHRIGGIKLRHQQWSLVMESVVPSDRGNYTCVVENKFGSIRQTYT

LDVLERSPHRPILQAGLPANQTAVLGSDVEFHCKVYSDAQPHIQWLKHVE

VNGSKVGPDGTPYVTVLKTAGANTTDKELEVLSLHNVTFEDAGEYTCLAG

NSIGFSHHSAWLVVLPAEEELVE

Figure 2:
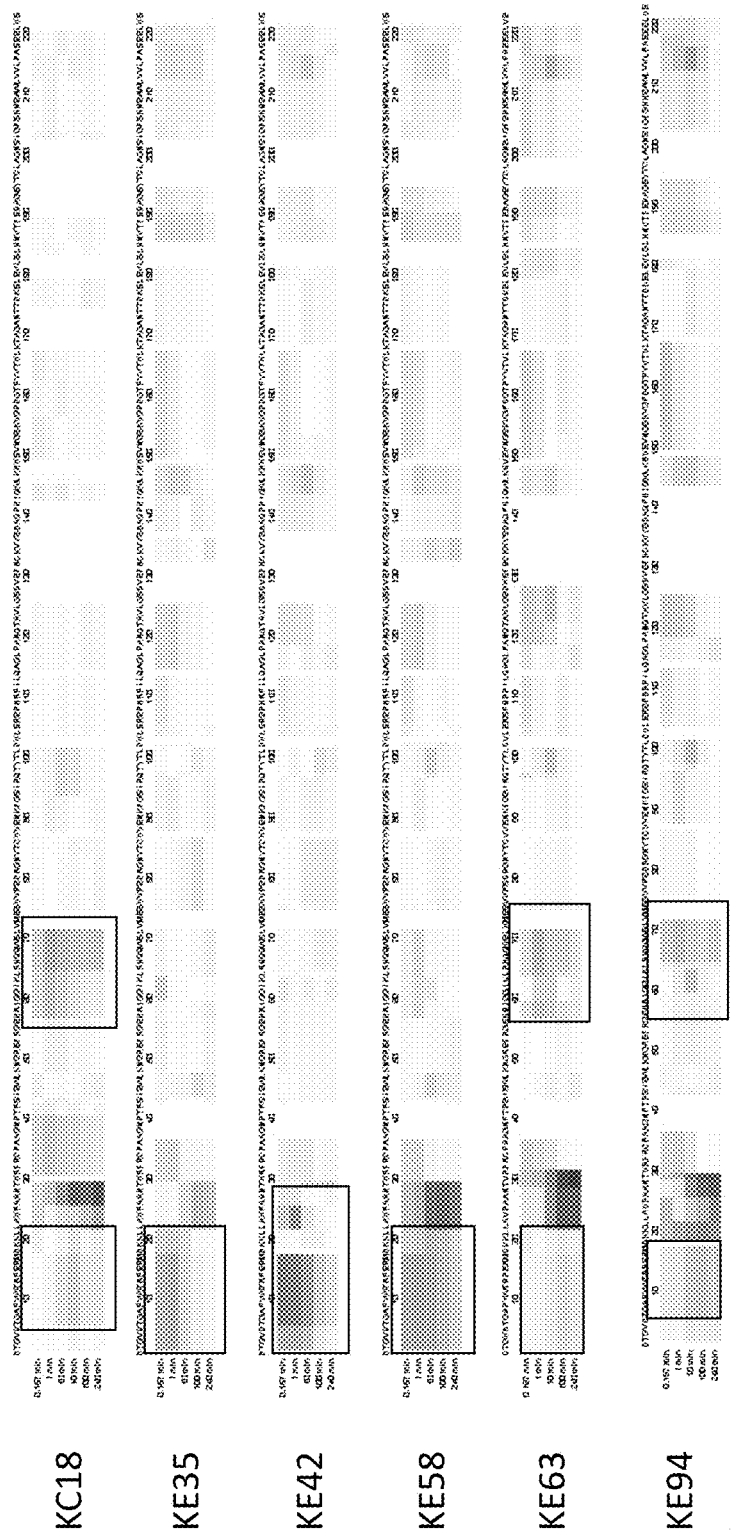
FIG. 2 depicts heat maps generated with hydrogen deuterium exchange (HDX) mass spectrometry used to determine the epitopes on FGFR3 for select antibodies by measuring the amide hydrogen deuterium exchange on FGFR3.

The results (FIG. 2) indicated that KE35 and KE58 bind to the N-terminus of the D2 region (D143 to L163); KE42 binds to N-terminus of the D2 region (D143 to N170); while KC18, KE94, and KE63 bind to N-terminus and middle of the D2 region (D143 to D160 and G197 to L213).

Internalization Assay

Figure 3:
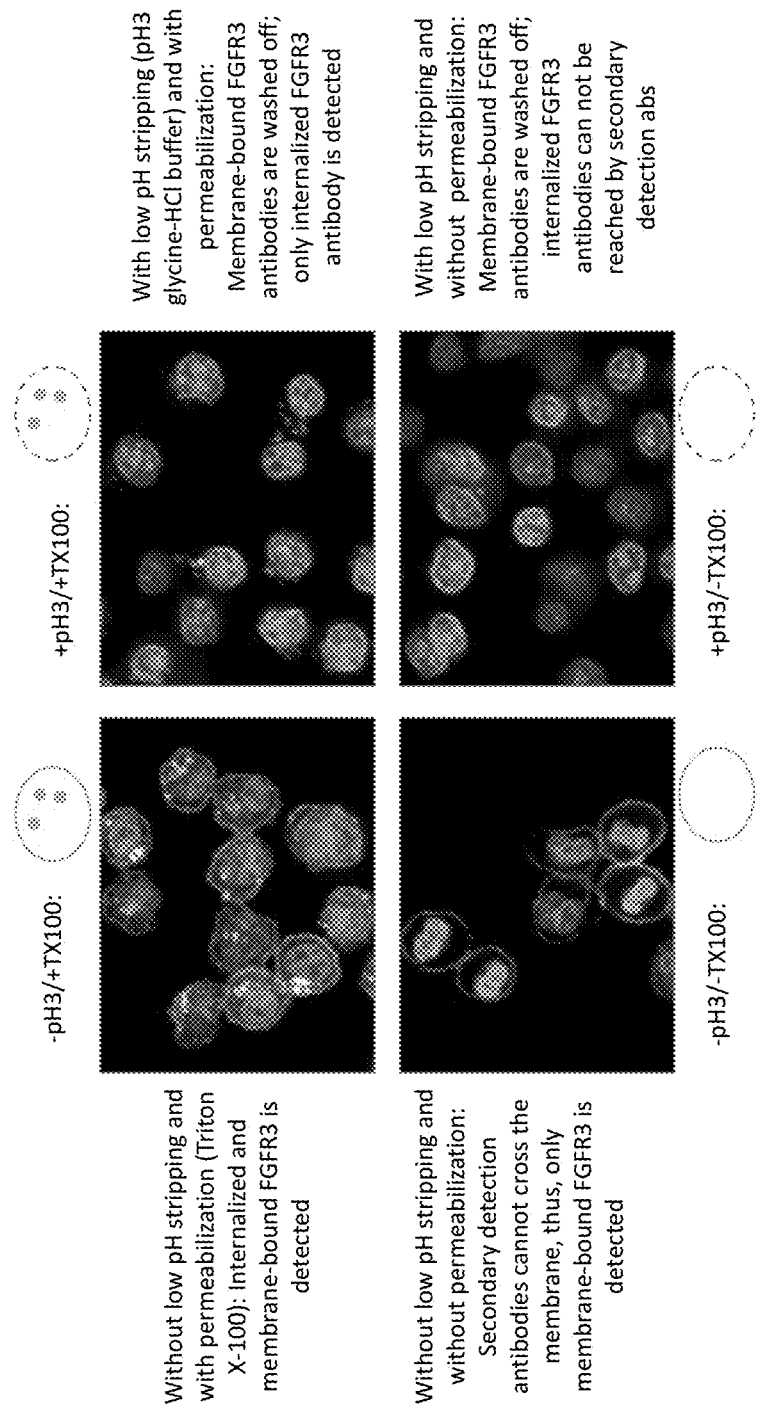
FIG. 3 depicts fluorescent images from internalization assays to detect internalization of anti-FGFR3 antibodies in KMS-11 cells.
Figure 4:
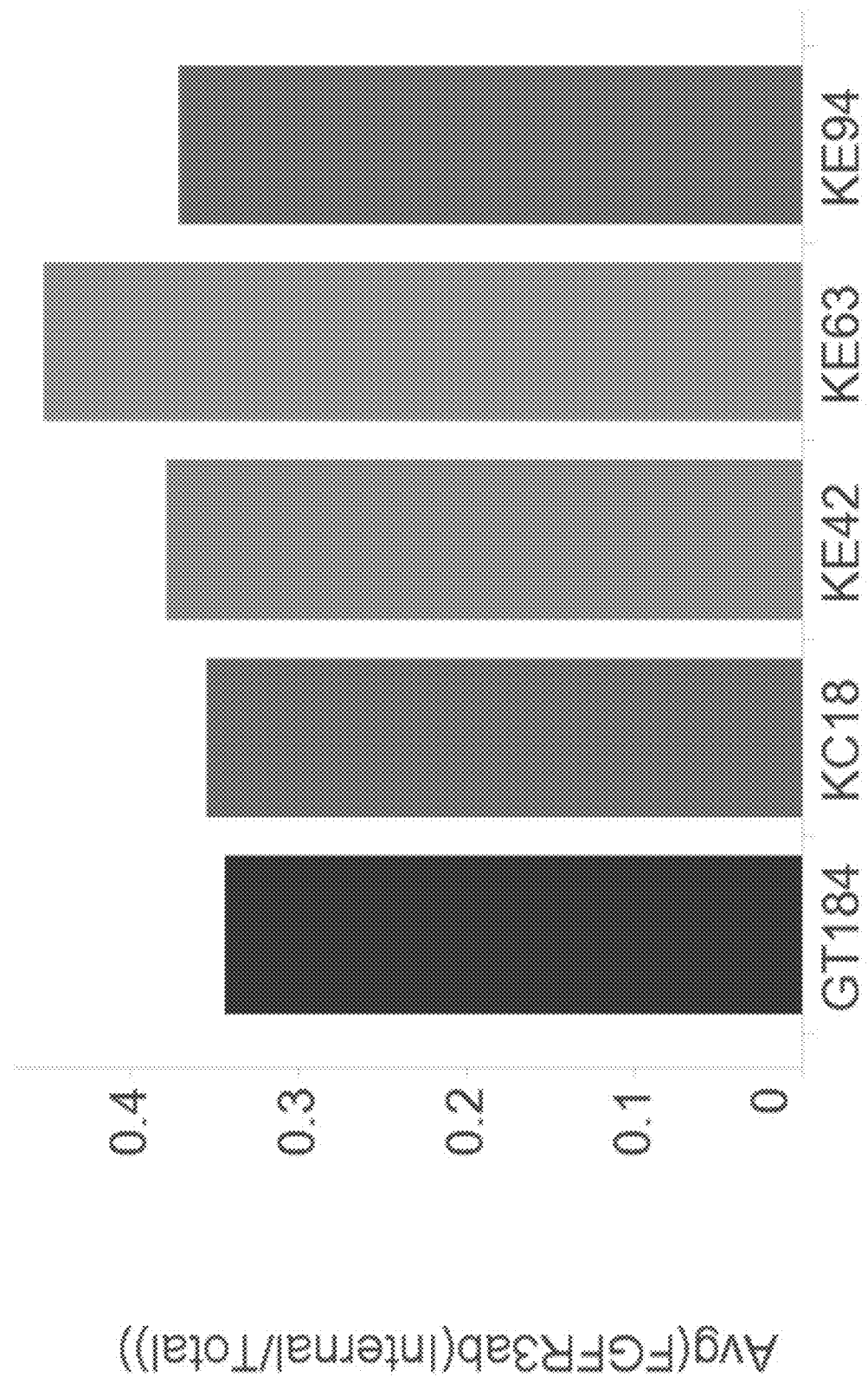
FIG. 4 graphically depicts the average amount of anti-FGFR3 antibody internalization relative to the total amount of antibody.

Internalization of anti-FGFR3 antibodies was evaluated in KMS-11 cells (JCRB cell bank, Japan). The KMS-11 cells were incubated with each antibody at a final concentration of 2 µg/ml for 30 minutes, 1, 2, 5, and 24 hours, then placed at 4° C. before washing the cells with PBS ($Ca^{2+}$ and $Mg^{2+}$). A subset of samples was washed with glycine-HCl buffer (pH 4) and fixed with 4% paraformaldehyde (Sigma). Another subset of samples was permeabilized with Triton X-100 (Sigma). The cells with immunofluorescence staining buffer, containing dye and fluorescent conjugated secondary antibody, were imaged by a PerkinElmer Opera high-throughput automated microscope and analyzed using the PerkinElmer Columbus image management system (PerkinElmer, Hopkinton, Mass.). Internalization of anti-FGFR3 antibodies was observed in KMS-11 cells treated with glycine-HCl and Triton X-100. The cell surface staining of each antibody was detected in a subset without treatment of glycine-HCl and Triton X-100 (FIG. 3). The ratio of the fluorescence signal for internalized antibody (+pH3/+TX100) to total antibody (−pH3/+TX100) then allows comparison of the degree of internalization for different antibodies (FIG. 4). The results indicate that the anti-FGFR3 antibodies were effectively internalized into the KMS-11 cells.

Dimerization of FGFR3 Assay

Figure 5A:
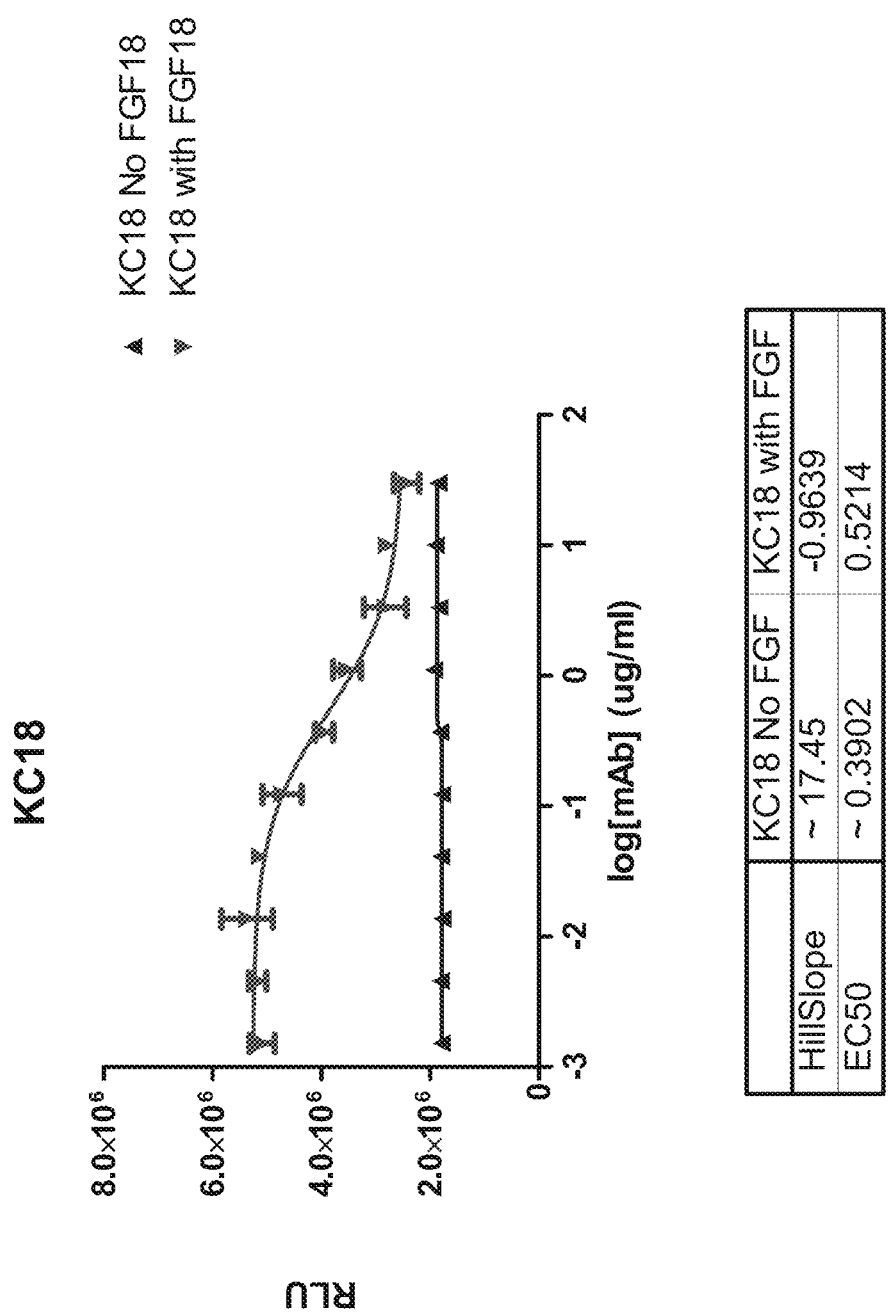
FIG. 5A-FIG. 5C graphically depict inhibition of FGFR3 dimerization by anti-FGFR3 antibody KC18 (FIG. 5A), KE58 (FIG. 5B), KE94 (FIG. 5C). Inhibition was evaluated by a chemiluminescent assay in U2OS cells co-expressing fusion protein of 0-galactosidase-prolink (PK) and FGFR3 (FGFR3-PK) and β-galactosidase-enzyme acceptor (EA) and FGFR3 (FGFR3-EA).
Figure 5B:
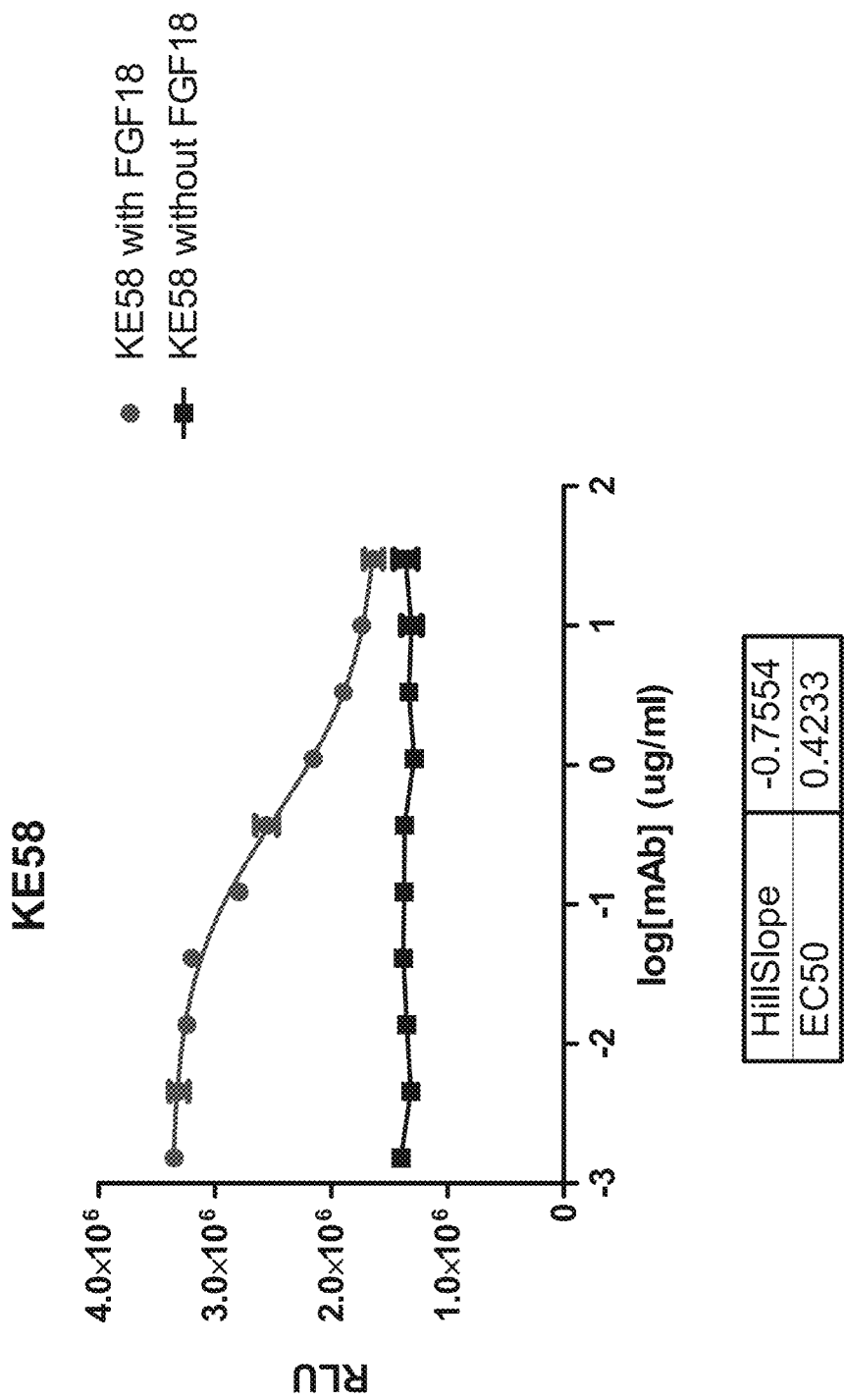
Figure 5C:
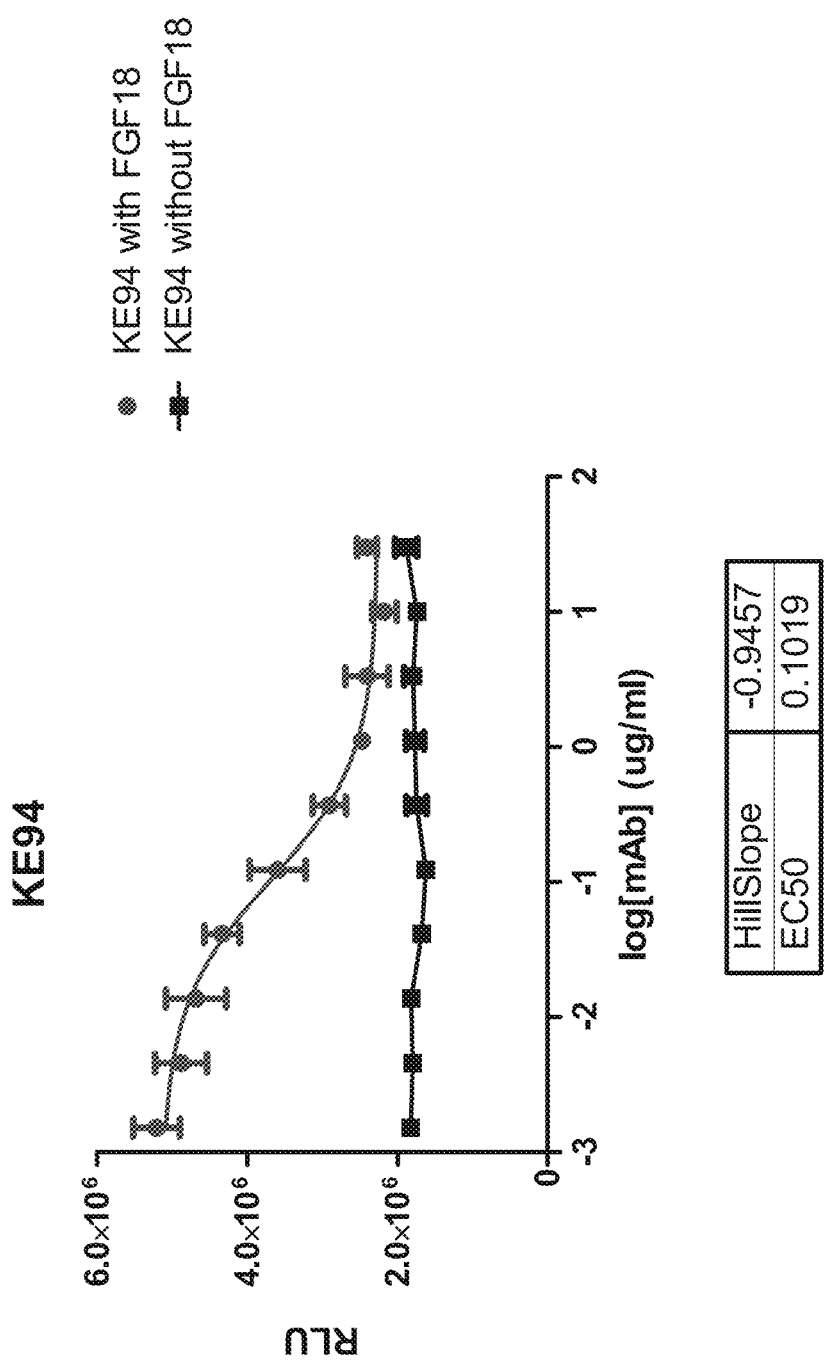

Inhibition of FGFR3 dimerization by anti-FGFR3 antibodies was evaluated by a chemiluminescent assay. U20S cells co-expressing a fusion protein of β-galactosidase-prolink (PK) and FGFR3 (FGFR3-PK) and β-galactosidase-enzyme acceptor (EA) and FGFR3 (FGFR3-EA) were developed by DiscoveRx (Fremont, Calif.). β-galactosidase is in an inactive form and when dimerization occurs the prolink and enzyme acceptor come together and are cleaved by the now activated β-galactosidase. The cells were pre-incubated with anti-FGFR3 antibodies at various concentrations before addition of FGF18 ligand to induce dimerization of FGFR3 proteins, then incubated at 37° C. overnight. The substrate was added to the cells and chemiluminescent signal was measured by EnVision (PerkinElmer). Blocking of FGFR3 dimerization by anti-FGFR3 antibodies was observed (FIG. 5A-FIG. 5C).

Humanization

Figure 6:
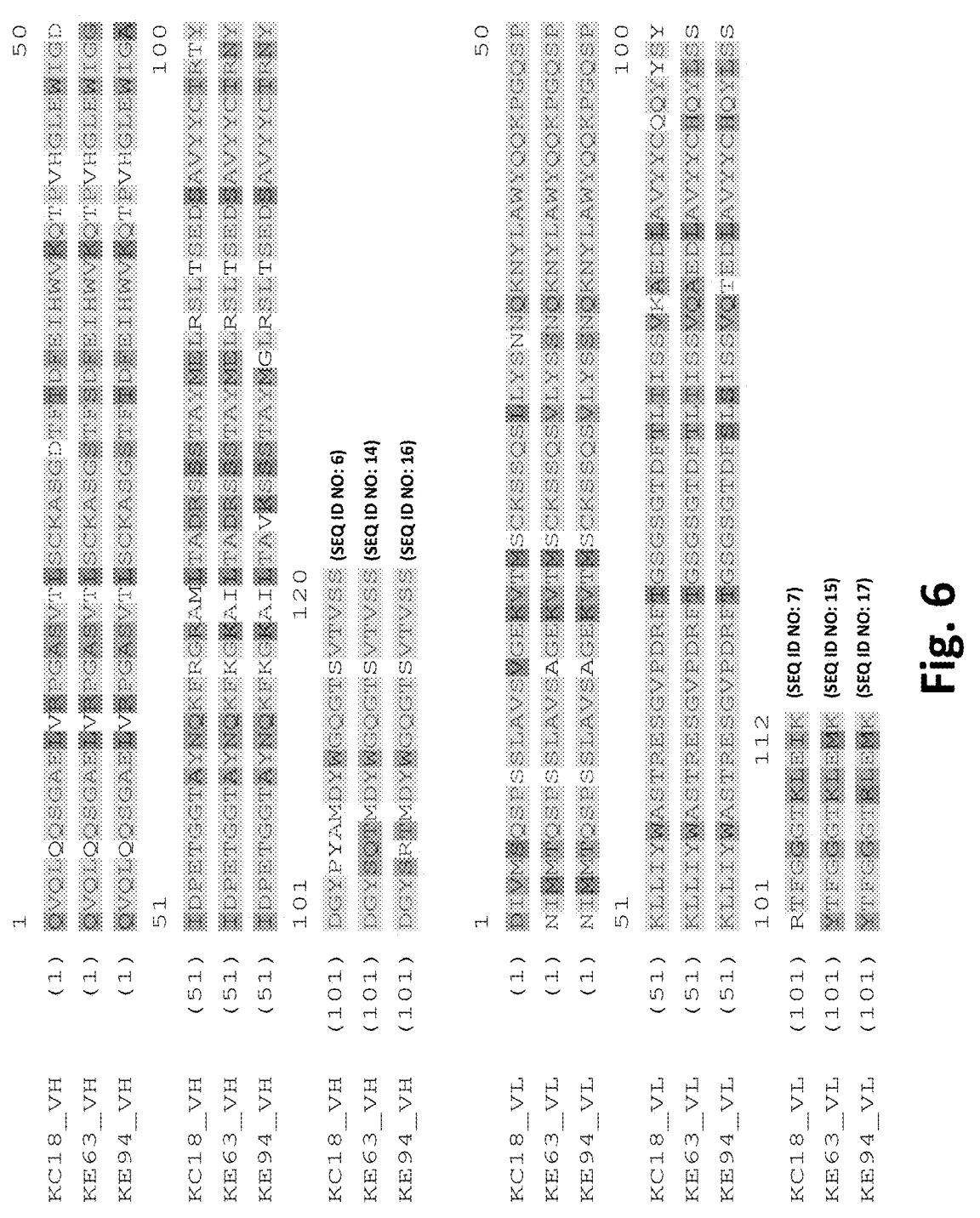

Humanized variants of KC18, KE63 and KE94 clones were generated as follows: 1) Structural models of the Fv regions of these antibodies in complex with FGFR3 were generated by the Molecular Operating Environment (MOE) from the Chemical Computing Group using KC18-FGFR3 complex structure as template given their high sequence similarity with KC18 (FIG. 6); 2) The VH and VL sequences were searched against the human germline sequence, and the most similar human germline Fv sequence and J region were identified. CDRs from KC18, KE63 and KE94 were then grafted onto the framework of the closest human germline genes; 3) Analysis was performed to identify amino acids that were likely to be important for the FGFR3 binding properties of the antibodies. Selected Vernier zone and key contact residues were mutated back to mouse residues after examination within the structural models; and 4) Potential liability sites were removed.

Heavy chain of KC18_Hrw1-3 and _HV1.69rw2-4, and light chain of KC18_Lrw1-3 were designed by the method described above. Further analysis to introduce back-mutations, stabilizing mutations and to eliminate other unwanted motifs, additional heavy and light chains of KC18 variants were identified KC18_VH1, VH1b-c, VH2-3, VH3b-c and VH4, and KC18_VL1, VL1b-d, VL2, VL3, VL3b, VL4, VL5 and VL6, respectively. Heavy chains KE63 VH1-6 and light chains KE63_VL1-4 were designed. Particularly, initial KE63 (KE63_VH1 and KE63_VL1) humanized constructs were designed, then further modifications to the heavy and light chain were designed (KE63_VH2-6 and KE63_VL2-4) to introduce back-mutations, stabilizing mutations and to eliminate other unwanted motifs. Similar methods were also used to design KE94 humanized constructs KE94VH-6. Notably, KE63 and KE94 share the same set of VL designs, namely KE63_VL1-4 here. Tables 5, 6, and 7 indicate the strategy used to pair the heavy and light chain variants for KC18, KE63 and KE94, respectively, including the human and mouse germline identity percentage.

TABLE 5

Human and mouse germline identity percentage of the designed KC18 variants

| KC18 | | | Lrw1 | Lrw2 | Lrw3 | VL1 | VL1d | VL1c |
|---|---|---|---|---|---|---|---|---|
| | Human | | 93.07% | 96.04% | 95.05% | 95.05% | 93.07% | 94.06% |
| | Mouse | | 88.12% | 87.13% | 86.14% | 88.12% | 88.12% | 89.11% |
| Hrw1 | 83.67% | 74.49% | KC18_Hu1 | KC18_Hu7 | KC18_Hu13 | | | |
| Hrw2 | 84.73% | 75.51% | KC18_Hu2 | KC18_Hu8 | KC18_Hu14 | | | |
| Hrw3 | 84.69% | 75.51% | KC18_Hu3 | KC18_Hu9 | KC18_Hu15 | | | |
| HV1.69rw2 | 83.67% | 72.45% | KC18_Hu4 | KC18_Hu10 | KC18_Hu16 | | | |
| HV1.69rw3 | 83.67% | 72.45% | KC18_Hu5 | KC18 Hu11 | KC18_Hu17 | | | |
| HV1.69rw4 | 83.67% | 72.45% | KC18_Hu6 | KC18_Hu12 | KC18_Hu18 | | | |
| VH1 | 80.61% | 75.51% | | | | KC18_Hu19 | | KC18_Hu23 |
| VH1b | 84.69% | 73.47% | | | | | | |
| VH1c | 82.65% | 73.47% | | | | | KC18_Hu38 | |
| VH2 | 77.55% | 78.57% | | | | | | |
| VH3 | 84.69% | 73.47% | | | | KC18_Hu20 | | KC18_Hu24 |
| VH3b | 85.71% | 74.49% | | | | | | |
| VH3c | 84.69% | 74.49% | | | | | KC18_Hu39 | |
| VH4 | 78.57% | 79.59% | | | | | | |

| KC18 | | | VL1b | VL2 | VL3 | VL3b | VL4 | VL5 | VL6 |
|---|---|---|---|---|---|---|---|---|---|
| | Human | | 94.06% | 90.10% | 86.14% | 85.15% | 81.19% | 81.19% | 81.19% |
| | Mouse | | 87.13% | 91.09% | 79.21% | 80.20% | 86.14% | 81.19% | 85.15% |
| Hrw1 | 83.67% | 74.49% | | | | | | | |
| Hrw2 | 84.73% | 75.51% | | | | | | | |
| Hrw3 | 84.69% | 75.51% | | | | | | | |
| HV1.69rw2 | 83.67% | 72.45% | | | | | | | |
| HV1.69rw3 | 83.67% | 72.45% | | | | | | | |

TABLE 5-continued

Human and mouse germline identity percentage of the designed KC18 variants

| | | | VL1 | VL2 | VL3 | VL4 | |
|---|---|---|---|---|---|---|---|
| HV1.69rw4 | 83.67% | 72.45% | | | | | |
| VH1 | 80.61% | 75.51% | | KC18_Hu29 | | | |
| VH1b | 84.69% | 73.47% | KC18_Hu40 | | KC18_Hu31 | KC18_Hu35 | |
| VH1c | 82.65% | 73.47% | | | | | |
| VH2 | 77.55% | 78.57% | | KC18_Hu27 | | KC18_Hu35 | KC18_Hu37 |
| VH3 | 84.69% | 73.47% | | | KC18_Hu30 | | |
| VH3b | 85.71% | 74.49% | KC18_Hu41 | | KC18_Hu32 | | |
| VH3c | 84.69% | 74.49% | | | | | |
| VH4 | 78.57% | 79.59% | | KC18_Hu28 | | KC18_Hu34 | |

TABLE 6

Human and mouse germline identity percentage of the designed KE63 variants

| KE63 | | | KE63_VL1 | KE63_VL2 | KE63_VL3 | KE63_VL4 |
|---|---|---|---|---|---|---|
| | Human | | 93.07% | 93.07% | 91.09% | 91.09% |
| | Mouse | | 90.00% | 89.00% | 87.00% | 87.00% |
| KE63_VH1 | 83.67% | 74.49% | KE63_Hu1 | KE63_Hu2 | KE63_Hu3 | KE63_Hu4 |
| KE63_VH2 | 86.73% | 73.47% | KE63_Hu5 | KE63_Hu6 | KE63_Hu7 | KE63_Hu8 |
| KE63_VH3 | 85.71% | 74.49% | KE63_Hu9 | KE63_Hu10 | KE63_Hu11 | KE63_Hu12 |
| KE63_VH4 | 86.73% | 73.47% | KE63_Hu13 | KE63_Hu14 | KE63_Hu15 | KE63_Hu16 |
| KE63_VH5 | 82.65% | 73.47% | KE63_Hu17 | KE63_Hu18 | KE63_Hu19 | KE63_Hu20 |
| KE63_VH6 | 81.63% | 72.45% | KE63_Hu21 | KE63_Hu22 | KE63_Hu23 | KE63_Hu24 |

TABLE 7

Human and mouse germline identity percentage of the designed KE94 variants

| KE94 | | | KE94_VL1 | KE94_VL2 | KE94_VL3 | KE94_VL4 |
|---|---|---|---|---|---|---|
| | Human | | 93.07% | 93.07% | 91.09% | 91.09% |
| | Mouse | | 90.00% | 89.00% | 87.00% | 87.00% |
| KE94_VH1 | 82.65% | 77.55% | KE94_Hu1 | KE94_Hu2 | KE94_Hu3 | KE94_Hu4 |
| KE94_VH2 | 85.71% | 76.53% | KE94_Hu5 | KE94_Hu6 | KE94_Hu7 | KE94_Hu8 |
| KE94_VH3 | 84.69% | 77.55% | KE94_Hu9 | KE94_Hu10 | KE94_Hu11 | KE94_Hu12 |
| KE94_VH4 | 83.67% | 78.57% | KE94_Hu13 | KE94_Hu14 | KE94_Hu15 | KE94_Hu16 |
| KE94_VH5 | 82.65% | 77.55% | KE94_Hu17 | KE94_Hu18 | KE94_Hu19 | KE94_Hu20 |
| KE94_VH6 | 81.63% | 76.53% | KE94_Hu21 | KE94_Hu22 | KE94_Hu23 | KE94_Hu24 |

Amino acid sequences for the humanized variants of KC18, KE64 and KE94, without the constant regions, are depicted below in Table 8. Nucleic acid sequences for the humanized variants of KC18, KE64 and KE94, without the constant regions, are depicted below in Table 9. The heavy and light constant regions are indicated in SEQ ID NO: 54 and SEQ ID NO: 55, respectively.

TABLE 8

Amino acid sequences of humanized variants of KC18, KE64 and KE94

| Antibody ID | Sequence |
|---|---|
| KC18 Hu18 VH | EVQLVQSGAEVKKPGATVKLSCKASGDTFTDFEIHWVQQAPGKGL EWIGDVDPETGGTAYAEKFQGRATLTADRSTDTAYMELSSLRSEDT AVYYCTRTYDGYPYAFDYWGQGTLVTVSS (SEQ ID NO: 18) |
| KC18 Hu18 VL | DIVMTQSPDSLAVSLGERATINCKSSQSVLYSNNNKNYLAWYQQKP GQSPKLLIYWASTRESGVPDRFSGSGSGTDFTLTISSVQAEDVAVYY CQQYYSYRTFGGGTKVEIK (SEQ ID NO: 19) |
| KE63 Hu01 VH | QVQLVQSGAEVKKPGASVKVSCKASGSTFSDFEIHWVRQAPGQGL EWIGGIDPETGGTAYNQKFQGRVTITADRSTSTAYMELSSLRSEDTA VYYCTRNYDGYSQTFDYWGQGTLVTVSS (SEQ ID NO: 20) |
| KE63 Hu02 VH | QVQLVQSGAEVKKPGASVKVSCKASGSTFSDFEIHWVRQAPGQGL EWIGGIDPETGGTAYNQKFQGRVTITADRSTSTAYMELSSLRSEDTA VYYCTRNYDGYSQTFDYWGQGTLVTVSS (SEQ ID NO: 21) |

TABLE 8-continued

Amino acid sequences of humanized variants of KC18, KE64 and KE94

| Antibody ID | Sequence |
| --- | --- |
| KE63 Hu03 VH | QVQLVQSGAEVKKPGASVKVSCKASGSTFSDFEIHWVRQAPGQGL<br>EWIGGIDPETGGTAYNQKFQGRVTITADRSTSTAYMELSSLRSEDTA<br>VYYCTRNYDGYSQTFDYWGQGTLVTVSS (SEQ ID NO: 22) |
| KE63 Hu04 VH | QVQLVQSGAEVKKPGASVKVSCKASGSTFSDFEIHWVRQAPGQGL<br>EWIGGIDPETGGTAYNQKFQGRVTITADRSTSTAYMELSSLRSEDTA<br>VYYCTRNYDGYSQTFDYWGQGTLVTVSS (SEQ ID NO: 23) |
| KE63 Hu01 VL | DIVMTQSPDSLAVSLGERVTINCKSSQSVLYSSNQKNYLAWYQQKP<br>GQSPKLLIYWASTRESGVPDRFSGSGSGTDFTLTISSLQAEDVAVYY<br>CHQYLSSYTFGQGTKLEIK (SEQ ID NO: 24) |
| KE63 Hu02 VL | DIVMTQSPDSLAVSLGERVTINCKSSQSVLYSSNQKNYLAWYQQKP<br>GQSPKLLIYWASTRESGVPDRFSGSGSGTDFTLTISSLQAEDVAVYY<br>CHQYLSPYTFGQGTKLEIK (SEQ ID NO: 25) |
| KE63 Hu03 VL | DIVMTQSPDSLAVSLGERVTINCKSSQSVLYSDNQKNYLAWYQQKP<br>GQSPKLLIYYASTRESGVPDRFSGSGSGTDFTLTISSLQAEDVAVYY<br>CHQYLSPYTFGQGTKLEIK (SEQ ID NO: 26) |
| KE63 Hu04 VL | DIVMTQSPDSLAVSLGERVTINCKSSQSVLYSDNQKNYLAWYQQKP<br>GQSPKLLIYFASTRESGVPDRFSGSGSGTDFTLTISSLQAEDVAVYYC<br>HQYLSPYTFGQGTKLEIK (SEQ ID NO: 27) |
| KE94 Hu01 VH | QVQLVQSGAEVKKPGASVKVSCKASGSTFTDFEIHWVRQAPGQGL<br>EWIGAIDPETGGTAYNQKFQGRVTITADKSTSTAYMELSSLRSEDTA<br>VYYCTRNYDGYSRTFDYWGQGTLVTVSS (SEQ ID NO: 28) |
| KE94 Hu02 VH | QVQLVQSGAEVKKPGASVKVSCKASGSTFTDFEIHWVRQAPGQGL<br>EWIGAIDPETGGTAYNQKFQGRVTITADKSTSTAYMELSSLRSEDTA<br>VYYCTRNYDGYSRTFDYWGQGTLVTVSS (SEQ ID NO: 29) |
| KE94 Hu03 VH | QVQLVQSGAEVKKPGASVKVSCKASGSTFTDFEIHWVRQAPGQGL<br>EWIGAIDPETGGTAYNQKFQGRVTITADKSTSTAYMELSSLRSEDTA<br>VYYCTRNYDGYSRTFDYWGQGTLVTVSS (SEQ ID NO: 30) |
| KE94 Hu04 VH | QVQLVQSGAEVKKPGASVKVSCKASGSTFTDFEIHWVRQAPGQGL<br>EWIGAIDPETGGTAYNQKFQGRVTITADKSTSTAYMELSSLRSEDTA<br>VYYCTRNYDGYSR1FDYWGQGTLVTVSS (SEQ ID NO: 31) |
| KE94 Hu01 VL | DIVMTQSPDSLAVSLGERVTINCKSSQSVLYSSNQKNYLAWYQQKP<br>GQSPKLLIYWASTRESGVPDRFSGSGSGTDFTLTISSLQAEDVAVYY<br>CHQYLSSYTFGQGTKLEIK (SEQ ID NO: 32) |
| KE94 Hu02 VL | DIVMTQSPDSLAVSLGERVTINCKSSQSVLYSSNQKNYLAWYQQKP<br>GQSPKLLIYWASTRESGVPDRFSGSGSGTDFTLTISSLQAEDVAVYY<br>CHQYLSPYTFGQGTKLEIK (SEQ ID NO: 33) |
| KE94 Hu03 VL | DIVMTQSPDSLAVSLGERVTINCKSSQSVLYSDNQKNYLAWYQQKP<br>GQSPKLLIYYASTRESGVPDRFSGSGSGTDFTLTISSLQAEDVAVYY<br>CHQYLSPYTFGQGTKLEIK (SEQ ID NO: 34) |
| KE94 Hu04 VL | DIVMTQSPDSLAVSLGERVTINCKSSQSVLYSDNQKNYLAWYQQKP<br>GQSPKLLIYFASTRESGVPDRFSGSGSGTDFTLTISSLQAEDVAVYYC<br>HQYLSPYTFGQGTKLEIK (SEQ ID NO: 35) |
| IgG1 Constant Heavy | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTP<br>EVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQ<br>KSLSLSPG (SEQ ID NO: 54) |
| IgG1 Constant Light | RTVAAPSVFIFPPSDEQLKSGTASVVCLLNNFYPREAKVQWKVDNA<br>LQSGNSQESVTEQDSKDSTYSLSSTLTLSKADYEKHKVYACEVTHQ<br>GLSSPVTKSFNRGEC (SEQ ID NO: 55) |
| KC18Hrw1 | QVQLVQSGAEVKKPGASVKVSCKASGDTFTDFEIHWVRQAPGQGL<br>EWIGDIDPETGSTSYAQKFQGRATLTADRSTSTAYMELSSLRSEDTA<br>VYYCTRTYDGYPYAMDYWGQGTLVTVSS (SEQ ID NO: 106) |

TABLE 8-continued

Amino acid sequences of humanized variants of KC18, KE64 and KE94

| Antibody ID | Sequence |
| --- | --- |
| KC18Hrw2 | QVQLVQSGAEVKKPGASVKVSCKASGDTFTDYEIHWVRQAPGQGL EWIGDIDPETGSTSYAQKFQGRATLTADRSTSTAYMELSSLRSEDTA VYYCTRTYDGYPYAMDYWGQGTLVTVSS (SEQ ID NO: 107) |
| KC18Hrw3 | QVQLVQSGAEVKKPGASVKVSCKASGDTFTDYEIHWVRQAPGQGL EWIGDIDPETGSTSYAQKFQGRATLTADRSTSTAYMELSSLRSEDTA VYYCTRTYDGYPYAMDYWGQGTSVTVSS (SEQ ID NO: 108) |
| KC18HV1-69rw2 | EVQLVQSGAEVKKPGATVKLSCKASGDTFTDFEIHWVQQAPGKGL EWIGDVDPETGGTAYAEKFQGRATLTADRSTDTAYMELSSLRSEDT AVYYCTRTYDGYPYAMDYWGQGTLVTVSS (SEQ ID NO: 109) |
| KC18HV1-69rw3 | EVQLVQSGAEVKKPGATVKLSCKASGDTFTDFEIHWVQQAPGKGL EWIGDVDPETGGTAYAEKFQGRATLTADRSTDTAYMELSSLRSEDT AVYYCTRTYEGYPYAMDYWGQGTLVTVSS (SEQ ID NO: 110) |
| KC18HV1-69rw4 | EVQLVQSGAEVKKPGATVKLSCKASGDTFTDFEIHWVQQAPGKGL EWIGDVDPETGGTAYAEKFQGRATLTADRSTDTAYMELSSLRSEDT AVYYCTRTYDGYPYAFDYWGQGTLVTVSS (SEQ ID NO: 111) |
| KC18Lrw1 | DIVMTQSPDSLAVSLGERATINCKSSQSLLYSNNQKNYLAWYQQKP GQSPKLLIYWASTRESGVPDRFSGSGSGTDFTLTISSVQAEDVAVYY CQQYYSYRTFGGGTKVEIK (SEQ ID NO: 112) |
| KC18Lrw2 | DIVMTQSPDSLAVSLGERATINCKSSQSVLYSSNNKNYLAWYQQKP GQSPKLLIYWASTRESGVPDRFSGSGSGTDFTLTISSVQAEDVAVYY CQQYYSYRTFGGGTKVEIK (SEQ ID NO: 113) |
| KC18Lrw3 | DIVMTQSPDSLAVSLGERATINCKSSQSVLYSNNNKNYLAWYQQKP GQSPKLLIYWASTRESGVPDRFSGSGSGTDFTLTISSVQAEDVAVYY CQQYYSYRTFGGGTKVEIK (SEQ ID NO: 114) |
| KC18_CL_VH1 | QVQLVQSGAEVVKPGATVKISCKASGDTFTDFEIHWVQQAPGKGL EWIGDIDPETGGTAYNEKFQGRATLTADRSTSTAYMELSSLRSEDT AVYYCARTYDGYPYAMDYWGQGTTVTVSS (SEQ ID NO: 115) |
| KC18_CL_VH1b | QVQLVQSGAEVVKPGATVKISCKASGYTFTDFEIHWVQQAPGKGL EWIGDVDPETGGTAYAEKFQGRATITADRSTSTAYMELSSLRSEDT AVYYCARTYDGYPYAMDYWGQGTTVTVSS (SEQ ID NO: 116) |
| KC18_CL_VH1c | QVQLVQSGAEVVKPGATVKISCKASGYTFTDFEIHWVQQAPGKGL EWIGDVEPETGGTAYAEKFQGRATITADRSTSTAYMELSSLRSEDA AVYYCARTYDGYPYAMDYWGQGTTVTVSS (SEQ ID NO: 117) |
| KC18_CL_VH2 | QVQLVQSGAEVVKPGATVKLSCKASGDTFTDFEIHWVKQAPGKGL EWIGDIDPETGGTAYNEKFQGRATLTADRSTSTAYMELSSLRSEDT AVYYCTRTYDGYPYAMDYWGQGTTVTVSS (SEQ ID NO: 118) |
| KC18_CL_VH3 | QVQLVQSGAEVVKPGASVKVSCKASGDTFTDFEIHWVKQAPGQGL EWIGDIDPESGGTAYNQKFQGRVTMTADRSISTAYMELSRLRSDDT AVYYCARTYDGYPYAMDYWGQGTTVTVSS (SEQ ID NO: 119) |
| KC18_CL_VH3b | QVQLVQSGAEVVKPGASVKVSCKASGYTFTDFEIHWVKQAPGQGL EWIGDIDPESGGTAYNQKFQGRVTMTADRSISTAYMELSRLRSDDT AVYYCARTYDGYPYAMDYWGQGTTVTVSS (SEQ ID NO: 120) |
| KC18_CL_VH3c | QVQLVQSGAEVVKPGASVKVSCKASGYTFTDFEIHWVKQAPGQGL EWIGDIEPESGGTAYNQKFQGRVTMTADRSISTAYMELSRLRSDDA AVYYCARTYDGYPYAMDVWGQGTTVTVSS (SEQ ID NO: 121) |
| KC18_CL_VH4 | QVQLVQSGAEVVKPGASVKLSCKASGDTFTDFEIHWVKQAPGQGL EWIGDIDPETGGTAYNQKFQGRATLTADRSSSTAYMELSRLRSDDT AVYYCTRTYDGYPYAMDYWGQGTTVTVSS (SEQ ID NO: 122) |
| KC18_CL_VL1 | DIVMTQSPDSLAVSLGERVTINCKSSQSVLYSSNQKNYLAWYQQKP GQPPKLLIYWASTRESGVPDRFSGSGSGTDFTLTISSVQAEDVAVYY CQQYYSYRTFGGGTKLEIK (SEQ ID NO: 123) |
| KC18_CL_VL1b | DIVMTQSPDSLAVSLGERVTINCKSSQSVLYSNNQKNYLAWYQQKP GQPPKLLIYWASTRESGVPDRFSGSGSGTDFTLTISSVQAEDVAVYY CQQYYSYRTFGGGTKLEIK (SEQ ID NO: 124) |
| KC18_CL_VL1c | DIVMTQSPDSLAVSLGERVTINCKSSQSVLYSSNQKNYLAWYQQKP GQSPKLLIYWASTRESGVPDRFSGSGSGTDFTLTISSVQAEDVAVYY CQQYYSYRTFGGGTKLEIK (SEQ ID NO: 125) |

TABLE 8-continued

Amino acid sequences of humanized variants of KC18, KE64 and KE94

| Antibody ID | Sequence |
| --- | --- |
| KC18_CL_VL1d | DIVMTQSPDSLAVSLGERVTINCKSSQSVLYSSNQKNYLAWYQQKP GQSPKLLIYYASTRESGVPDRFSGSGSGTDFTLTISSVQAEDVAVYY CQQYYSYRTFGGGTKLEIK (SEQ ID NO: 126) |
| KC18_CL_VL2 | DIVMTQSPSSLAVSLGERVTMNCKSSQSLLYSNNQKNYLAWYQQK PGQSPKLLIYWASTRESGVPDRFSGSGSGTDFTLTISSVQAEDVAVY YCQQYYSYRTFGGGTKLEIK (SEQ ID NO: 127) |
| KC18_CL_VL3 | DIVMTQSPLSLPVTVGEPVSISCRSSQSLLHSNNQKNYLAWYLQKPG QSPQLLIYWGSTRASGVPDRFSGSGSGTDFTLKISRVEAEDVGVYYC QQYYSYRTFGGGTKLEIK (SEQ ID NO: 128) |
| KC18_CL_VL3b | DIVMTQSPLSLPVTVGEPVSISCRSSQSLLYSNNQKNYLAWYLQKPG QSPQLLIYWGSTRASGVPDRFSGSGSGTDFTLKISRVEAEDVGVYYC QQYYSYRTFGGGTKLEIK (SEQ ID NO: 129) |
| KC18_CL_VL4 | DIVMTQSPLSLAVTVGEKVSISCRSSQSLLYSNNQKNYLAWYQQKP GQSPKLLIYWGSTRESGVPDRFSGSGSGTDFTLTISRVEAEDVGVYY CQQYYSYRTFGGGTKLEIK (SEQ ID NO: 130) |
| KC18_CL_VL5 | DIQMTQSPSSLSVSVGDRVTMTCRASQGISYSNNQKNYLAWYQQK PGKSPKLLIYWASTRQSGVPSRFSGSGSGTDFTLTISSVQAEDVAVY YCQQYYSYRTFGGGTKLEIK (SEQ ID NO: 131) |
| KC18_CL_VL6 | DIQMTQSPSSLSVSVGDRVTMTCRSSQSLLYSNNQKNYLAWYQQK PGKSPKLLIYWASTRQSGVPSRFSGSGSGTDFTLTISSVQAEDVAVY YCQQYYSYRTFGGGTKLEIK (SEQ ID NO: 132) |

TABLE 9

Nucleic acid sequences of humanized variants of KC18, KE64 and KE94 (HC: heavy chain; LC: light chain)

| Antibody ID | Sequence |
| --- | --- |
| KC18 Hu18 HC | GAGGTACAACTTGTCCAGTCAGGTGCGGAGGTTAAAAAACCGGG GGCCACAGTTAAACTGAGCTGCAAGGCTAGCGGTGATACTTTTA CCGATTTTGAGATACACTGGGTTCAGCAGGCTCCGGGGAAAGGG CTTGAATGGATTGGTGATGTTGACCCCGAAACGGGCGGAACCGC GTATGCAGAGAAGTTTCAAGGTAGGGCAACGCTCACTGCGGACA GAAGCACAGACACGGCATACATGGAGCTTAGTTCTCTCCGCTCT GAGGATACCGCTGTTTATTATTGTACTAGAACCTATGATGGATAT CCATACGCATTCGATTATTGGGGCAAGGGACTCTTGTCACAGT CAGCTCCGCTTCAACCAAGGGACCTTCTGTCTTTCCTCTGGCCCC TTCAAGCAAGAGCACTTCCGGAGGGACTGCCGCACTCGGGTGCC TTGTGAAAGATTACTTCCCAGAGCCTGTCACCGTCAGCTGGAATT CAGGCGCTCTGACTAGCGGAGTGCACACCTTCCCCGCTGTGCTTC AGTCCTCCGGACTCTACTCTCTGAGCAGCGTGGTGACCGTGCCGT CCTCTTCTCTGGGGACCCAGACTTATATCTGCAACGTCAATCATA AGCCTTCTAATACCAAGGTGGACAAGAAGGTGGAACCCAAATCA TGTGACAAGACCCACACCTGTCCGCCCTGTCCGGCACCCGAACT GCTGGGTGGCCCTTCCGTGTTCCTTTTCCCTCCAAAGCCGAAGGA CACTCTTATGATTTCTCGCACTCCCGAAGTGACTTGCTCGTGGT GGATGTGTCCCATGAGGATCCAGAGGTCAAGTTCAACTGGTACG TGGACGGTGTGGAAGTCCACAACGCCAAGACTAAGCCGAGAGA GGAACAGTACAATTCAACCTATCGGGTGGTGAGCGTCCTGACCG TGCTGCACCAGGACTGGCTTAACGGAAAGGAGTACAAGTGCAA AGTGTCAAACAAGGCACTGCCCGCTCCGATCGAAAAGACCATTA GCAAAGCTAAGGGCCAGCCCAGAGAACCCCAAGTCTATACCCTT CCACCCAGCCGGGACGAGCTGACCAAAAACCAGGTGTCACTCAC TTGTCTCGTGAAGGGTTTCTACCCCTCAGACATCGCCGTCGAATG GGAGTCCAATGGTCAGCCAGAGAACAACTACAAAACCACCCCTC CCGTGCTGGACAGCGACGGGTCTTTCTTTCTCTACTCAAAGCTGA CCGTGGATAAGTCTCGCTGGCAGCAAGGGAATGTGTTTTCCTGTT CAGTGATGCATGAGGCCCTTCATAATCATTACACCCAAAAGTCA CTGAGCCTGTCTCCCGGA (SEQ ID NO: 36) |
| KC18 Hu18 LC | GACATAGTGATGACTCAATCCCCAGATTCACTCGCCGTATCACTC GGAGAAAGAGCCACAATTAATTGTAAGAGTAGTCAGTCAGTCCT TTACTCTAATAACAACAAAAATTACCTGGCCTGGTACCAACAGA AACCAGGTCAATCTCCTAAACTGCTTATCTACTGGGCTAGTACCC |

TABLE 9-continued

Nucleic acid sequences of humanized variants of KC18, KE64 and KE94
(HC: heavy chain; LC: light chain)

| Antibody ID | Sequence |
|---|---|
| | GAGAATCAGGAGTTCCCGATAGGTTTTCTGGGTCTGGGAGCGGC<br>ACCGACTTCACACTCACAATCTCTAGCGTACAGGCTGAAGATGT<br>AGCCGGTGTATTACTGCCAACAGTATTATTCATACAGGACCTTCG<br>GTGGTGGCACCAAAGTAGAAATCAAACGCACTGTGGCAGCCCCT<br>TCTGTGTTTATCTTCCCACCCTCCGACGAGCAGCTCAAGTCCGGT<br>ACCGCCTCTGTCGTCTGCCTGCTGAACAATTTCTACCCAAGAGAG<br>GCCAAGGTGCAGTGGAAGGTGGACAACGCACTGCAAAGCGGTA<br>ATTCACAAGAGTCAGTCACCGAACAAGACTCAAAGGACAGCAC<br>CTACTCACTGTCATCCACCCTGACTCTCTCAAAGGCTGACTACGA<br>AAAGCACAAAGTGTATGCTTGTGAAGTCACTCATCAGGGCCTTT<br>CTAGCCCTGTGACCAAGAGCTTCAACAGAGGCGAATGC (SEQ ID<br>NO: 37) |
| KE63 Hu01 HC | CAGGTACAGTTGGTACAGTCAGGAGCGGAGGTTAAAAAACCAG<br>GGGCGTCTGTGAAAGTCTCATGTAAAGCGAGCGGAAGCACGTTT<br>AGCGATTTCGAGATTCACTGGGTGAGACAAGCACCCGGTCAGGG<br>CCTGGAATGGATTGGAGGGATCGACCCGGAAACAGGGGGTACA<br>GCATATAACCAAAAGTTTCAGGGACGGGTCACTATAACGGCTGA<br>CAGGAGCACGTCAACTGCGTATATGGAATTGTCCAGTTTGAGGT<br>CAGAAGATACGGCAGTCTACTACTGCACAAGAAATTATGATGGA<br>TACTCTCAAACGTTTGATTATTGGGGTCAGGGGACCCTGGTAAC<br>AGTCAGCTCAGCTTCAACCAAGGGACCTTCTGTCTTTCCTCTGGC<br>CCCTTCAAGCAAGAGCACTTCCGGAGGGACTGCCGCACTCGGGT<br>GCCTTGTGAAAGATTACTTCCCAGAGCCTGTCACCGTCAGCTGG<br>AATTCAGGCGCTCTGACTAGCGGAGTGCACACCTTCCCCGCTGT<br>GCTTCAGTCCTCCGGACTCTACTCTCTGAGCAGCGTGGTGACCGT<br>GCCGTCCTCTTCTCTGGGGACCCAGACTTATATCTGCAACGTCAA<br>TCATAAGCCTTCTAATACCAAGGTGGACAAGAAGGTGGAACCCA<br>AATCATGTGACAAGACCCACACCTGTCCGCCCTGTCCGGCACCC<br>GAACTGCTGGGTGGCCCTTCCGTGTTCCTTTTCCCTCCAAAGCCG<br>AAGGACACTCTTATGATTTCTCGCACTCCCGAAGTGACTTGCGTC<br>GTGGTGGATGTGTCCCATGAGGATCCAGAGGTCAAGTTCAACTG<br>GTACGTGGACGGTGTGGAAGTCCACAACGCCAAGACTAAGCCG<br>AGAGAGGAACAGTACAATTCAACCTATCGGGTGGTGAGCGTCCT<br>GACCGTGCTGCACCAGGACTGGCTTAACGGAAAGGAGTACAAGT<br>GCAAAGTGTCAAACAAGGCACTGCCCGCTCCGATCGAAAAGACC<br>ATTAGCAAAGCTAAGGGCCAGCCCAGAGAACCCCAAGTCTATAC<br>CCTTCCACCCAGCCGGGACGAGCTGACCAAAAACCAGGTGTCAC<br>TCACTTGTCTCGTGAAGGGTTTCTACCCCTCAGACATCGCCGTCG<br>AATGGGAGTCCAATGGTCAGCCAGAGAACAACTACAAAACCAC<br>CCCTCCCGTGCTGGACAGCGACGGGTCTTTCTTTCTCTACTCAAA<br>GCTGACCGTGGATAAGTCTCGCTGGCAGCAAGGGAATGTGTTTT<br>CCTGTTCAGTGATGCATGAGGCCCTTCATAATCATTACACCCAAA<br>AGTCACTGAGCCTGTCTCCCGGA (SEQ ID NO: 38) |
| KE63 Hu02 HC | CAGGTACAGTTGGTACAGTCAGGAGCGGAGGTTAAAAAACCAG<br>GGGCGTCTGTGAAAGTCTCATGTAAAGCGAGCGGAAGCACGTTT<br>AGCGATTTCGAGATTCACTGGGTGAGACAAGCACCCGGTCAGGG<br>CCTGGAATGGATTGGAGGGATCGACCCGGAAACAGGGGGTACA<br>GCATATAACCAAAAGTTTCAGGGACGGGTCACTATAACGGCTGA<br>CAGGAGCACGTCAACTGCGTATATGGAATTGTCCAGTTTGAGGT<br>CAGAAGATACGGCAGTCTACTACTGCACAAGAAATTATGATGGA<br>TACTCTCAAACGTTTGATTATTGGGGTCAGGGGACCCTGGTAAC<br>AGTCAGCTCAGCTTCAACCAAGGGACCTTCTGTCTTTCCTCTGGC<br>CCCTTCAAGCAAGAGCACTTCCGGAGGGACTGCCGCACTCGGGT<br>GCCTTGTGAAAGATTACTTCCCAGAGCCTGTCACCGTCAGCTGG<br>AATTCAGGCGCTCTGACTAGCGGAGTGCACACCTTCCCCGCTGT<br>GCTTCAGTCCTCCGGACTCTACTCTCTGAGCAGCGTGGTGACCGT<br>GCCGTCCTCTTCTCTGGGGACCCAGACTTATATCTGCAACGTCAA<br>TCATAAGCCTTCTAATACCAAGGTGGACAAGAAGGTGGAACCCA<br>AATCATGTGACAAGACCCACACCTGTCCGCCCTGTCCGGCACCC<br>GAACTGCTGGGTGGCCCTTCCGTGTTCCTTTTCCCTCCAAAGCCG<br>AAGGACACTCTTATGATTTCTCGCACTCCCGAAGTGACTTGCGTC<br>GTGGTGGATGTGTCCCATGAGGATCCAGAGGTCAAGTTCAACTG<br>GTACGTGGACGGTGTGGAAGTCCACAACGCCAAGACTAAGCCG<br>AGAGAGGAACAGTACAATTCAACCTATCGGGTGGTGAGCGTCCT<br>GACCGTGCTGCACCAGGACTGGCTTAACGGAAAGGAGTACAAGT<br>GCAAAGTGTCAAACAAGGCACTGCCCGCTCCGATCGAAAAGACC<br>ATTAGCAAAGCTAAGGGCCAGCCCAGAGAACCCCAAGTCTATAC<br>CCTTCCACCCAGCCGGGACGAGCTGACCAAAAACCAGGTGTCAC<br>TCACTTGTCTCGTGAAGGGTTTCTACCCCTCAGACATCGCCGTCG<br>AATGGGAGTCCAATGGTCAGCCAGAGAACAACTACAAAACCAC |

TABLE 9-continued

Nucleic acid sequences of humanized variants of KC18, KE64 and KE94
(HC: heavy chain; LC: light chain)

| Antibody ID | Sequence |
| --- | --- |
| | CCCTCCCGTGCTGGACAGCGACGGGTCTTTCTTTCTCTACTCAAA<br>GCTGACCGTGGATAAGTCTCGCTGGCAGCAAGGGAATGTGTTTT<br>CCTGTTCAGTGATGCATGAGGCCCTTCATAATCATTACACCCAAA<br>AGTCACTGAGCCTGTCTCCCGGA (SEQ ID NO: 39) |
| KE63 Hu03 HC | CAGGTACAGTTGGTACAGTCAGGAGCGGAGGTTAAAAAACCAG<br>GGGCGTCTGTGAAAGTCTCATGTAAAGCGAGCGGAAGCACGTTT<br>AGCGATTTCGAGATTCACTGGGTGAGACAAGCACCCGGTCAGGG<br>CCTGGAATGGATTGGAGGGATCGACCCCGGAAACAGGGGGTACA<br>GCATATAACCAAAAGTTTCAGGGACGGGTCACTATAACGGCTGA<br>CAGGAGCACGTCAACTGCGTATATGGAATTGTCCAGTTTGAGGT<br>CAGAAGATACGGCAGTCTACTACTGCACAAGAAATTATGATGGA<br>TACTCTCAAACGTTTGATTATTGGGGTCAGGGGACCCTGGTAAC<br>AGTCAGCTCAGCTTCAACCAAGGGACCTTCTGTCTTTCCTCTGGC<br>CCCTTCAAGCAAGAGCACTTCCGGAGGGACTGCCGCACTCGGGT<br>GCCTTGTGAAAGATTACTTCCCAGAGCCTGTCACCGTCAGCTGG<br>AATTCAGGCGCTCTGACTAGCGGAGTGCACACCTTCCCCGCTGT<br>GCTTCAGTCCTCCGGACTCTACTCTCTGAGCAGCGTGGTGACCGT<br>GCCGTCCTCTTCTCTGGGGACCCAGACTTATATCTGCAACGTCAA<br>TCATAAGCCTTCTAATACCAAGGTGGACAAGAAGGTGGAACCCA<br>AATCATGTGACAAGACCCACACCTGTCCGCCCTGTCCGGCACCC<br>GAACTGCTGGGTGGCCCTTCCGTGTTCCTTTTCCCTCCAAAGCCG<br>AAGGACACTCTTATGATTTCTCGCACTCCCGAAGTGACTTGCGTC<br>GTGGTGGATGTGTCCCATGAGGATCCAGAGGTCAAGTTCAACTG<br>GTACGTGGACGGTGTGGAAGTCCACAACGCCAAGACTAAGCCG<br>AGAGAGGAACAGTACAATTCAACCTATCGGGTGGTGAGCGTCCT<br>GACCGTGCTGCACCAGGACTGGCTTAACGGAAAGGAGTACAAGT<br>GCAAAGTGTCAAACAAGGCACTGCCCGCTCCGATCGAAAAGACC<br>ATTAGCAAAGCTAAGGGCCAGCCCAGAGAACCCCAAGTCTATAC<br>CCTTCCACCCAGCCGGGACGAGCTGACCAAAAACCAGGTGTCAC<br>TCACTTGTCTCGTGAAGGGTTTCTACCCCTCAGACATCGCCGTCG<br>AATGGGAGTCCAATGGTCAGCCAGAGAACAACTACAAAACCAC<br>CCCTCCCGTGCTGGACAGCGACGGGTCTTTCTTTCTCTACTCAAA<br>GCTGACCGTGGATAAGTCTCGCTGGCAGCAAGGGAATGTGTTTT<br>CCTGTTCAGTGATGCATGAGGCCCTTCATAATCATTACACCCAAA<br>AGTCACTGAGCCTGTCTCCCGGA (SEQ ID NO: 40) |
| KE63 Hu04 HC | CAGGTACAGTTGGTACAGTCAGGAGCGGAGGTTAAAAAACCAG<br>GGGCGTCTGTGAAAGTCTCATGTAAAGCGAGCGGAAGCACGTTT<br>AGCGATTTCGAGATTCACTGGGTGAGACAAGCACCCGGTCAGGG<br>CCTGGAATGGATTGGAGGGATCGACCCCGGAAACAGGGGGTACA<br>GCATATAACCAAAAGTTTCAGGGACGGGTCACTATAACGGCTGA<br>CAGGAGCACGTCAACTGCGTATATGGAATTGTCCAGTTTGAGGT<br>CAGAAGATACGGCAGTCTACTACTGCACAAGAAATTATGATGGA<br>TACTCTCAAACGTTTGATTATTGGGGTCAGGGGACCCTGGTAAC<br>AGTCAGCTCAGCTTCAACCAAGGGACCTTCTGTCTTTCCTCTGGC<br>CCCTTCAAGCAAGAGCACTTCCGGAGGGACTGCCGCACTCGGGT<br>GCCTTGTGAAAGATTACTTCCCAGAGCCTGTCACCGTCAGCTGG<br>AATTCAGGCGCTCTGACTAGCGGAGTGCACACCTTCCCCGCTGT<br>GCTTCAGTCCTCCGGACTCTACTCTCTGAGCAGCGTGGTGACCGT<br>GCCGTCCTCTTCTCTGGGGACCCAGACTTATATCTGCAACGTCAA<br>TCATAAGCCTTCTAATACCAAGGTGGACAAGAAGGTGGAACCCA<br>AATCATGTGACAAGACCCACACCTGTCCGCCCTGTCCGGCACCC<br>GAACTGCTGGGTGGCCCTTCCGTGTTCCTTTTCCCTCCAAAGCCG<br>AAGGACACTCTTATGATTTCTCGCACTCCCGAAGTGACTTGCGTC<br>GTGGTGGATGTGTCCCATGAGGATCCAGAGGTCAAGTTCAACTG<br>GTACGTGGACGGTGTGGAAGTCCACAACGCCAAGACTAAGCCG<br>AGAGAGGAACAGTACAATTCAACCTATCGGGTGGTGAGCGTCCT<br>GACCGTGCTGCACCAGGACTGGCTTAACGGAAAGGAGTACAAGT<br>GCAAAGTGTCAAACAAGGCACTGCCCGCTCCGATCGAAAAGACC<br>ATTAGCAAAGCTAAGGGCCAGCCCAGAGAACCCCAAGTCTATAC<br>CCTTCCACCCAGCCGGGACGAGCTGACCAAAAACCAGGTGTCAC<br>TCACTTGTCTCGTGAAGGGTTTCTACCCCTCAGACATCGCCGTCG<br>AATGGGAGTCCAATGGTCAGCCAGAGAACAACTACAAAACCAC<br>CCCTCCCGTGCTGGACAGCGACGGGTCTTTCTTTCTCTACTCAAA<br>GCTGACCGTGGATAAGTCTCGCTGGCAGCAAGGGAATGTGTTTT<br>CCTGTTCAGTGATGCATGAGGCCCTTCATAATCATTACACCCAAA<br>AGTCACTGAGCCTGTCTCCCGGA (SEQ ID NO: 41) |
| KE63 Hu01 LC | GATATAGTTATGACACAGAGCCCTGACTCTCTGGCTGTGAGTTTG<br>GGCGAGCGAGTAACCATTAATTGTAAGAGTTCTCAATCCGTCCT<br>CTACTCAAGCAACCAGAAAAATTACCTCGCGTGGTACCAGCAAA<br>AACCAGGACAGAGCCCCAAACTCTTGATCTATTGGGCGTCCACC<br>CGAGAGAGTGGCGTGCCAGATCGGTTTTCAGGTTCTGGATCTGG<br>TACCGACTTCACCCTTACAATCTCAAGCCTGCAAGCAGAGGATG |

TABLE 9-continued

Nucleic acid sequences of humanized variants of KC18, KE64 and KE94
(HC: heavy chain; LC: light chain)

| Antibody ID | Sequence |
| --- | --- |
| | TCGCAGTTTATTATTGCCATCAGTACCTGAGCAGCTACACATTCG<br>GACAAGGAACGAAACTGGAAATCAAACGCACTGTGGCAGCCCC<br>TTCTGTGTTTATCTTCCCACCCTCCGACGAGCAGCTCAAGTCCGG<br>TACCGCCTCTGTCGTCTGCCTGCTGAACAATTTCTACCCAAGAGA<br>GGCCAAGGTGCAGTGGAAGGTGGACAACGCACTGCAAAGCGGT<br>AATTCACAAGAGTCAGTCACCGAACAAGACTCAAAGGACAGCA<br>CCTACTCACTGTCATCCACCCTGACTCTCTCAAAGGCTGACTACG<br>AAAAGCACAAAGTGTATGCTTGTGAAGTCACTCATCAGGGCCTT<br>TCTAGCCCTGTGACCAAGAGCTTCAACAGAGGCGAATGC (SEQ<br>ID NO: 42) |
| KE63 Hu02 LC | GACATAGTAATGACCCAAAGTCCAGATTCTTTGGCCGTATCTTTG<br>GGTGAGCGCGTTACCATCAACTGTAAGTCTTCCCAGTCTGTGTTG<br>TACTCATCTAATCAAAAAAACTACCTCGCTTGGTACCAGCAGAA<br>GCCAGGTCAAAGCCCGAAACTGCTTATTTATTGGGCGTCTACGC<br>GAGAGTCTGGGGTCCCCGATCGGTTTTCAGGGTCAGGCTCTGGC<br>ACTGATTTTACTCTGACTATTTCATCCCTCCAAGCCGAAGACGTG<br>GCAGTGTATTACTGCCACCAGTATTTGAGCCCTTACACGTTTGGG<br>CAGGGGACTAAACTTGAAATCAAGCGCACTGTGGCAGCCCCTTC<br>TGTGTTTATCTTCCCACCCTCCGACGAGCAGCTCAAGTCCGGTAC<br>CGCCTCTGTCGTCTGCCTGCTGAACAATTTCTACCCAAGAGAGGC<br>CAAGGTGCAGTGGAAGGTGGACAACGCACTGCAAAGCGGTAAT<br>TCACAAGAGTCAGTCACCGAACAAGACTCAAAGGACAGCACCT<br>ACTCACTGTCATCCACCCTGACTCTCTCAAAGGCTGACTACGAA<br>AAGCACAAAGTGTATGCTTGTGAAGTCACTCATCAGGGCCTTTC<br>TAGCCCTGTGACCAAGAGCTTCAACAGAGGCGAATGC (SEQ ID<br>NO: 43) |
| KE63 Hu03 LC | GATATTGTGATGACTCAGTCACCTGACAGTCTGGCGGTTTCTTTG<br>GGCGAAAGAGTGACTATAAATTGCAAAAGCAGCCAGTCAGTTCT<br>CTATTCCGACAATCAAAAGAACTATCTCGCATGGTATCAGCAGA<br>AGCCAGGGCAATCCCCAAAATTGCTTATATACTATGCATCAACG<br>CGCGAAAGCGGTGTACCCGATCGGTTTTCAGGAAGTGGCAGTGG<br>GACCGACTTTACGCTGACAATCTCTTCCCTTCAAGCGGAGGATGT<br>CGCGGTTTATTATTGTCATCAGTATCTGAGTCCTTACACCTTTGG<br>TCAAGGGACGAAGTTGGAGATCAAACGCACTGTGGCAGCCCCTT<br>CTGTGTTTATCTTCCCACCCTCCGACGAGCAGCTCAAGTCCGGTA<br>CCGCCTCTGTCGTCTGCCTGCTGAACAATTTCTACCCAAGAGAGG<br>CCAAGGTGCAGTGGAAGGTGGACAACGCACTGCAAAGCGGTAA<br>TTCACAAGAGTCAGTCACCGAACAAGACTCAAAGGACAGCACCT<br>ACTCACTGTCATCCACCCTGACTCTCTCAAAGGCTGACTACGAA<br>AAGCACAAAGTGTATGCTTGTGAAGTCACTCATCAGGGCCTTTC<br>TAGCCCTGTGACCAAGAGCTTCAACAGAGGCGAATGC (SEQ ID<br>NO: 44) |
| KE63 Hu04 LC | GACATCGTAATGACCCAGTCCCCCGATAGTCTGGCTGTGTCTTTG<br>GGCGAGAGGGTAACGATAAACTGTAAATCAAGTCAGTCAGTGCT<br>TTACTCAGATAACCAGAAGAACTATCTTGCGTGGTATCAGCAAA<br>AGCCCGGACAGTCTCCAAAACTTCTTATATATTTCGCTTCTACCA<br>GAGAATCAGGTGTACCAGACCGCTTTTCTGGAAGCGGCTCTGGT<br>ACTGACTTTACCCTGACAATTAGTAGCTTGCAAGCTGAAGATGTT<br>GCGGTATATTATTGTCACCAATACTTGAGTCCCTATACTTTTGGC<br>CAAGGGACAAAACTGGAAATAAAGCGCACTGTGGCAGCCCCTTC<br>TGTGTTTATCTTCCCACCCTCCGACGAGCAGCTCAAGTCCGGTAC<br>CGCCTCTGTCGTCTGCCTGCTGAACAATTTCTACCCAAGAGAGGC<br>CAAGGTGCAGTGGAAGGTGGACAACGCACTGCAAAGCGGTAAT<br>TCACAAGAGTCAGTCACCGAACAAGACTCAAAGGACAGCACCT<br>ACTCACTGTCATCCACCCTGACTCTCTCAAAGGCTGACTACGAA<br>AAGCACAAAGTGTATGCTTGTGAAGTCACTCATCAGGGCCTTTC<br>TAGCCCTGTGACCAAGAGCTTCAACAGAGGCGAATGC (SEQ ID<br>NO: 45) |
| KE94 Hu01 HC | CAGGTTCAGCTGGTACAATCTGGCGCGGAAGTCAAAAAGCCAGG<br>CGCAAGTGTTAAAGTGTCTTGCAAGGCTTCAGGATCTACCTTTAC<br>AGATTTTGAAATCCACTGGGTAAGACAAGCACCTGGCCAGGGGC<br>TGGAATGGATTGGTGCCATAGACCCTGAGACGGGAGGAACCGC<br>ATATAACCAGAAATTCCAAGGTCGAGTGACTATTACTGCGGACA<br>AGTCAACATCAACTGCCTATATGGAGCTGTCTTCTTTGAGGTCAG<br>AGGATACAGCAGTTTACTACTGCACTAGAAATTACGATGGTTAT<br>TCACGGACCTTCGATTATTGGGGTCAAGGCACTCTGGTGACCGT<br>GAGTTCCGCTTCAACCAAGGGACCTTCTGTCTTTCCTCTGGCCCC<br>TTCAAGCAAGAGCACTTCCGGAGGGACTGCCGCACTCGGGTGCC<br>TTGTGAAAGATTACTTCCCAGAGCCTGTCACCGTCAGCTGGAATT<br>CAGGCGCTCTGACTAGCGGAGTGCACACCTTCCCCGCTGTGCTTC<br>AGTCCTCCGGACTCTACTCTCTGAGCAGCGTGGTGACCGTGCCGT |

TABLE 9-continued

Nucleic acid sequences of humanized variants of KC18, KE64 and KE94
(HC: heavy chain; LC: light chain)

| Antibody ID | Sequence |
|---|---|
| | CCTCTTCTCTGGGGACCCAGACTTATATCTGCAACGTCAATCATA<br>AGCCTTCTAATACCAAGGTGGACAAGAAGGTGGAACCCAAATCA<br>TGTGACAAGACCCACACCTGTCCGCCCTGTCCGGCACCCGAACT<br>GCTGGGTGGCCCTTCCGTGTTCCTTTTCCCTCCAAAGCCGAAGGA<br>CACTCTTATGATTTCTCGCACTCCCGAAGTGACTTGCGTCGTGGT<br>GGATGTGTCCCATGAGGATCCAGAGGTCAAGTTCAACTGGTACG<br>TGGACGGTGTGGAAGTCCACAACGCCAAGACTAAGCCGAGAGA<br>GGAACAGTACAATTCAACCTATCGGGTGGTGAGCGTCCTGACCG<br>TGCTGCACCAGGACTGGCTTAACGGAAAGGAGTACAAGTGCAA<br>AGTGTCAAACAAGGCACTGCCCGCTCCGATCGAAAAGACCATTA<br>GCAAAGCTAAGGGCCAGCCCAGAGAACCCCAAGTCTATACCCTT<br>CCACCCAGCCGGGACGAGCTGACCAAAAACCAGGTGTCACTCAC<br>TTGTCTCGTGAAGGGTTTCTACCCCTCAGACATCGCCGTCGAATG<br>GGAGTCCAATGGTCAGCCAGAGAACAACTACAAAACCACCCCTC<br>CCGTGCTGGACAGCGACGGGTCTTTCTTTCTCTACTCAAAGCTGA<br>CCGTGGATAAGTCTCGCTGGCAGCAAGGGAATGTGTTTTCCTGTT<br>CAGTGATGCATGAGGCCCTTCATAATCATTACACCCAAAAGTCA<br>CTGAGCCTGTCTCCCGGA (SEQ ID NO: 46) |
| KE94 Hu02 HC | CAGGTTCAGCTGGTACAATCTGGCGCGGAAGTCAAAAAGCCAGG<br>CGCAAGTGTTAAAGTGTCTTGCAAGGCTTCAGGATCTACCTTTAC<br>AGATTTTGAAATCCACTGGGTAAGACAAGCACCTGGCCAGGGGC<br>TGGAATGGATTGGTGCCATAGACCCTGAGACGGGAGGAACCGC<br>ATATAACCAGAAATTCCAAGGTCGAGTGACTATTACTGCGGACA<br>AGTCAACATCAACTGCCTATATGGAGCTGTCTTCTTTGAGGTCAG<br>AGGATACAGCAGTTTACTACTGCACTAGAAATTACGATGGTTAT<br>TCACGGACCTTCGATTATTGGGGTCAAGGCACTCTGGTGACCGT<br>GAGTTCCGCTTCAACCAAGGGACCTTCTGTCTTTCCTCTGGCCCC<br>TTCAAGCAAGAGCACTTCCGGAGGGACTGCCGCACTCGGGTGCC<br>TTGTGAAAGATTACTTCCCAGAGCCTGTCACCGTCAGCTGGAATT<br>CAGGCGCTCTGACTAGCGGAGTGCACACCTTCCCCGCTGTGCTTC<br>AGTCCTCCGGACTCTACTCTCTGAGCAGCGTGGTGACCGTGCCGT<br>CCTCTTCTCTGGGGACCCAGACTTATATCTGCAACGTCAATCATA<br>AGCCTTCTAATACCAAGGTGGACAAGAAGGTGGAACCCAAATCA<br>TGTGACAAGACCCACACCTGTCCGCCCTGTCCGGCACCCGAACT<br>GCTGGGTGGCCCTTCCGTGTTCCTTTTCCCTCCAAAGCCGAAGGA<br>CACTCTTATGATTTCTCGCACTCCCGAAGTGACTTGCGTCGTGGT<br>GGATGTGTCCCATGAGGATCCAGAGGTCAAGTTCAACTGGTACG<br>TGGACGGTGTGGAAGTCCACAACGCCAAGACTAAGCCGAGAGA<br>GGAACAGTACAATTCAACCTATCGGGTGGTGAGCGTCCTGACCG<br>TGCTGCACCAGGACTGGCTTAACGGAAAGGAGTACAAGTGCAA<br>AGTGTCAAACAAGGCACTGCCCGCTCCGATCGAAAAGACCATTA<br>GCAAAGCTAAGGGCCAGCCCAGAGAACCCCAAGTCTATACCCTT<br>CCACCCAGCCGGGACGAGCTGACCAAAAACCAGGTGTCACTCAC<br>TTGTCTCGTGAAGGGTTTCTACCCCTCAGACATCGCCGTCGAATG<br>GGAGTCCAATGGTCAGCCAGAGAACAACTACAAAACCACCCCTC<br>CCGTGCTGGACAGCGACGGGTCTTTCTTTCTCTACTCAAAGCTGA<br>CCGTGGATAAGTCTCGCTGGCAGCAAGGGAATGTGTTTTCCTGTT<br>CAGTGATGCATGAGGCCCTTCATAATCATTACACCCAAAAGTCA<br>CTGAGCCTGTCTCCCGGA (SEQ ID NO: 47) |
| KE94 Hu03 HC | CAGGTTCAGCTGGTACAATCTGGCGCGGAAGTCAAAAAGCCAGG<br>CGCAAGTGTTAAAGTGTCTTGCAAGGCTTCAGGATCTACCTTTAC<br>AGATTTTGAAATCCACTGGGTAAGACAAGCACCTGGCCAGGGGC<br>TGGAATGGATTGGTGCCATAGACCCTGAGACGGGAGGAACCGC<br>ATATAACCAGAAATTCCAAGGTCGAGTGACTATTACTGCGGACA<br>AGTCAACATCAACTGCCTATATGGAGCTGTCTTCTTTGAGGTCAG<br>AGGATACAGCAGTTTACTACTGCACTAGAAATTACGATGGTTAT<br>TCACGGACCTTCGATTATTGGGGTCAAGGCACTCTGGTGACCGT<br>GAGTTCCGCTTCAACCAAGGGACCTTCTGTCTTTCCTCTGGCCCC<br>TTCAAGCAAGAGCACTTCCGGAGGGACTGCCGCACTCGGGTGCC<br>TTGTGAAAGATTACTTCCCAGAGCCTGTCACCGTCAGCTGGAATT<br>CAGGCGCTCTGACTAGCGGAGTGCACACCTTCCCCGCTGTGCTTC<br>AGTCCTCCGGACTCTACTCTCTGAGCAGCGTGGTGACCGTGCCGT<br>CCTCTTCTCTGGGGACCCAGACTTATATCTGCAACGTCAATCATA<br>AGCCTTCTAATACCAAGGTGGACAAGAAGGTGGAACCCAAATCA<br>TGTGACAAGACCCACACCTGTCCGCCCTGTCCGGCACCCGAACT<br>GCTGGGTGGCCCTTCCGTGTTCCTTTTCCCTCCAAAGCCGAAGGA<br>CACTCTTATGATTTCTCGCACTCCCGAAGTGACTTGCGTCGTGGT<br>GGATGTGTCCCATGAGGATCCAGAGGTCAAGTTCAACTGGTACG<br>TGGACGGTGTGGAAGTCCACAACGCCAAGACTAAGCCGAGAGA<br>GGAACAGTACAATTCAACCTATCGGGTGGTGAGCGTCCTGACCG<br>TGCTGCACCAGGACTGGCTTAACGGAAAGGAGTACAAGTGCAA<br>AGTGTCAAACAAGGCACTGCCCGCTCCGATCGAAAAGACCATTA<br>GCAAAGCTAAGGGCCAGCCCAGAGAACCCCAAGTCTATACCCTT |

TABLE 9-continued

Nucleic acid sequences of humanized variants of KC18, KE64 and KE94
(HC: heavy chain; LC: light chain)

| Antibody ID | Sequence |
|---|---|
|  | CCACCCAGCCGGGACGAGCTGACCAAAAACCAGGTGTCACTCAC<br>TTGTCTCGTGAAGGGTTTCTACCCCTCAGACATCGCCGTCGAATG<br>GGAGTCCAATGGTCAGCCAGAGAACAACTACAAAACCACCCCTC<br>CCGTGCTGGACAGCGACGGGTCTTTCTTTCTCTACTCAAAGCTGA<br>CCGTGGATAAGTCTCGCTGGCAGCAAGGGAATGTGTTTTCCTGTT<br>CAGTGATGCATGAGGCCCTTCATAATCATTACACCCAAAAGTCA<br>CTGAGCCTGTCTCCCGGA (SEQ ID NO: 48) |
| KE94 Hu04 HC | CAGGTTCAGCTGGTACAATCTGGCGCGGAAGTCAAAAAGCCAGG<br>CGCAAGTGTTAAAGTGTCTTGCAAGGCTTCAGGATCTACCTTTAC<br>AGATTTTGAAATCCACTGGGTAAGACAAGCACCTGGCCAGGGGC<br>TGGAATGGATTGGTGCCATAGACCCTGAGACGGGAGGAACCGC<br>ATATAACCAGAAATTCCAAGGTCGAGTGACTATTACTGCGGACA<br>AGTCAACATCAACTGCCTATATGGAGCTGTCTTCTTTGAGGTCAG<br>AGGATACAGCAGTTTACTACTGCACTAGAAATTACGATGGTTAT<br>TCACGGACCTTCGATTATTGGGGTCAAGGCACTCTGGTGACCGT<br>GAGTTCCGCTTCAACCAAGGGACCTTCTGTCTTTCCTCTGGCCCC<br>TTCAAGCAAGAGCACTTCCGGAGGGACTGCCGCACTCGGGTGCC<br>TTGTGAAAGATTACTTCCCAGAGCCTGTCACCGTCAGCTGGAATT<br>CAGGCGCTCTGACTAGCGGAGTGCACACCTTCCCCGCTGTGCTTC<br>AGTCCTCCGGACTCTACTCTCTGAGCAGCGTGGTGACCGTGCCGT<br>CCTCTTCTCTGGGGACCCAGACTTATATCTGCAACGTCAATCATA<br>AGCCTTCTAATACCAAGGTGGACAAGAAGGTGGAACCCAAATCA<br>TGTGACAAGACCCACACCTGTCCGCCCTGTCCGGCACCCGAACT<br>GCTGGGTGGCCCTTCCGTGTTCCTTTTCCCTCCAAAGCCGAAGGA<br>CACTCTTATGATTTCTCGCACTCCCGAAGTGACTTGCGTCGTGGT<br>GGATGTGTCCCATGAGGATCCAGAGGTCAAGTTCAACTGGTACG<br>TGGACGGTGTGGAAGTCCACAACGCCAAGACTAAGCCGAGAGA<br>GGAACAGTACAATTCAACCTATCGGGTGGTGAGCGTCCTGACCG<br>TGCTGCACCAGGACTGGCTTAACGGAAAGGAGTACAAGTGCAA<br>AGTGTCAAACAAGGCACTGCCCGCTCCGATCGAAAAGACCATTA<br>GCAAAGCTAAGGGCCAGCCCAGAGAACCCCAAGTCTATACCCTT<br>CCACCCAGCCGGGACGAGCTGACCAAAAACCAGGTGTCACTCAC<br>TTGTCTCGTGAAGGGTTTCTACCCCTCAGACATCGCCGTCGAATG<br>GGAGTCCAATGGTCAGCCAGAGAACAACTACAAAACCACCCCTC<br>CCGTGCTGGACAGCGACGGGTCTTTCTTTCTCTACTCAAAGCTGA<br>CCGTGGATAAGTCTCGCTGGCAGCAAGGGAATGTGTTTTCCTGTT<br>CAGTGATGCATGAGGCCCTTCATAATCATTACACCCAAAAGTCA<br>CTGAGCCTGTCTCCCGGA (SEQ ID NO: 49) |
| KE94 Hu01 LC | GATATAGTTATGACACAGAGCCCTGACTCTCTGGCTGTGAGTTTG<br>GGCGAGCGAGTAACCATTAATTGTAAGAGTTCTCAATCCGTCCT<br>CTACTCAAGCAACCAGAAAAATTACCTCGCGTGGTACCAGCAAA<br>AACCAGGACAGAGCCCCAAACTCTTGATCTATTGGGCGTCCACC<br>CGAGAGAGTGGCGTGCCAGATCGGTTTTCAGGTTCTGGATCTGG<br>TACCGACTTCACCCTTACAATCTCAAGCCTGCAAGCAGAGGATG<br>TCGCAGTTTATTATTGCCATCAGTACCTGAGCAGCTACACATTCG<br>GACAAGGAACGAAACTGGAAATCAAACGCACTGTGGCAGCCCC<br>TTTCTGTGTTTATCTTCCCACCCTCCGACGAGCAGCTCAAGTCCGG<br>TACCGCCTCTGTCGTCTGCCTGCTGAACAATTTCTACCCAAGAGA<br>GGCCAAGGTGCAGTGGAAGGTGGACAACGCACTGCAAAGCGGT<br>AATTCACAAGAGTCAGTCACCGAACAAGACTCAAAGGACAGCA<br>CCTACTCACTGTCATCCACCCTGACTCTCTCAAAGGCTGACTACG<br>AAAAGCACAAAGTGTATGCTTGTGAAGTCACTCATCAGGGCCTT<br>TCTAGCCCTGTGACCAAGAGCTTCAACAGAGGCGAATGC (SEQ ID NO: 50) |
| KE94 Hu02 LC | GACATAGTAATGACCCAAAGTCCAGATTCTTTGGCCGTATCTTTG<br>GGTGAGCGCGTTACCATCAACTGTAAGTCTTCCCAGTCTGTGTTG<br>TACTCATCTAATCAAAAAAACTACCTCGCTTGGTACCAGCAGAA<br>GCCAGGTCAAAGCCCGAAACTGCTTATTTATTGGGCGTCTACGC<br>GAGAGTCTGGGGTCCCCGATCGGTTTTCAGGGTCAGGCTCTGGC<br>ACTGATTTTACTCTGACTATTTCATCCCTCCAAGCCGAAGACGTG<br>GCAGTGTATTACTGCCACCAGTATTTGAGCCCTTACACGTTTGGG<br>CAGGGGACTAAACTTGAAATCAAGCGCACTGTGGCAGCCCCTTC<br>TGTGTTTATCTTCCCACCCTCCGACGAGCAGCTCAAGTCCGGTAC<br>CGCCTCTGTCGTCTGCCTGCTGAACAATTTCTACCCAAGAGAGGC<br>CAAGGTGCAGTGGAAGGTGGACAACGCACTGCAAAGCGGTAAT<br>TCACAAGAGTCAGTCACCGAACAAGACTCAAAGGACAGCACCT<br>ACTCACTGTCATCCACCCTGACTCTCTCAAAGGCTGACTACGAA<br>AAGCACAAAGTGTATGCTTGTGAAGTCACTCATCAGGGCCTTTC<br>TAGCCCTGTGACCAAGAGCTTCAACAGAGGCGAATGC (SEQ ID NO: 51) |

TABLE 9-continued

Nucleic acid sequences of humanized variants of KC18, KE64 and KE94 (HC: heavy chain; LC: light chain)

| Antibody ID | Sequence |
|---|---|
| KE94 Hu03 LC | GATATTGTGATGACTCAGTCACCTGACAGTCTGGCGGTTTCTTTG<br>GGCGAAAGAGTGACTATAAATTGCAAAAGCAGCCAGTCAGTTCT<br>CTATTCCGACAATCAAAAGAACTATCTCGCATGGTATCAGCAGA<br>AGCCAGGGCAATCCCCAAAATTGCTTATATACTATGCATCAACG<br>CGCGAAAGCGGTGTACCCGATCGGTTTTCAGGAAGTGGCAGTGG<br>GACCGACTTTACGCTGACAATCTCTTCCCTTCAAGCGGAGGATGT<br>CGCGGTTTATTATTGTCATCAGTATCTGAGTCCTTACACCTTTGG<br>TCAAGGGACGAAGTTGGAGATCAAACGCACTGTGGCAGCCCCTT<br>CTGTGTTTATCTTCCCACCCTCCGACGAGCAGCTCAAGTCCGGTA<br>CCGCCTCTGTCGTCTGCCTGCTGAACAATTTCTACCCAAGAGAGG<br>CCAAGGTGCAGTGGAAGGTGGACAACGCACTGCAAAGCGGTAA<br>TTCACAAGAGTCAGTCACCGAACAAGACTCAAAGGACAGCACCT<br>ACTCACTGTCATCCACCCTGACTCTCTCAAAGGCTGACTACGAA<br>AAGCACAAAGTGTATGCTTGTGAAGTCACTCATCAGGGCCTTTC<br>TAGCCCTGTGACCAAGAGCTTCAACAGAGGCGAATGC (SEQ ID NO: 52) |
| KE94 Hu04 LC | GACATCGTAATGACCCAGTCCCCCGATAGTCTGGCTGTGTCTTTG<br>GGCGAGAGGGTAACGATAAACTGTAAATCAAGTCAGTCAGTGCT<br>TTACTCAGATAACCAGAAGAACTATCTTGCGTGGTATCAGCAAA<br>AGCCCGGACAGTCTCCAAAACTTCTTATATATTTCGCTTCTACCA<br>GAGAATCAGGTGTACCAGACCGCTTTTCTGGAAGCGGCTCTGGT<br>ACTGACTTTACCCTGACAATTAGTAGCTTGCAAGCTGAAGATGTT<br>GCGGTATATTATTGTCACCAATACTTGAGTCCCTATACTTTTGGC<br>CAAGGGACAAAACTGGAAATAAAGCGCACTGTGGCAGCCCCTTC<br>TGTGTTTATCTTCCCACCCTCCGACGAGCAGCTCAAGTCCGGTAC<br>CGCCTCTGTCGTCTGCCTGCTGAACAATTTCTACCCAAGAGAGGC<br>CAAGGTGCAGTGGAAGGTGGACAACGCACTGCAAAGCGGTAAT<br>TCACAAGAGTCAGTCACCGAACAAGACTCAAAGGACAGCACCT<br>ACTCACTGTCATCCACCCTGACTCTCTCAAAGGCTGACTACGAA<br>AAGCACAAAGTGTATGCTTGTGAAGTCACTCATCAGGGCCTTTC<br>TAGCCCTGTGACCAAGAGCTTCAACAGAGGCGAATGC (SEQ ID NO: 53) |

Affinities of the humanized KC18 antibodies to human and mouse FGFR3 were determined and are shown in Table 10 below. The affinities of these humanized antibodies are comparable to the parental KC18 antibody.

TABLE 10

Affinities to human and mouse FGFR3 of the humanized KC18 antibodies

| KC18 | hFGFR3 | | | mFGFR3 | | |
|---|---|---|---|---|---|---|
| Variants | ka | kd | KD | ka | kd | KD |
| Hu7  | 1.96E+05 | 1.06E−3  | 5.41E−09 | 1.98E+05 | 1.26E−3  | 6.36E−09 |
| Hu10 | 2.78E+05 | 1.32E−3  | 4.73E−09 | 2.86E+05 | 1.47E−3  | 5.15E−09 |
| Hu12 | 3.27E+05 | 5.27E−04 | 1.61E−09 | 3.37E+05 | 5.83E−04 | 1.73E−09 |
| Hu13 | 1.89E+05 | 8.57E−04 | 4.52E−09 | 1.93E+05 | 1.02E−3  | 5.28E−09 |
| Hu16 | 2.76E+05 | 1.04E−3  | 3.76E−09 | 2.78E+05 | 1.18E−3  | 4.23E−09 |
| Hu18 | 3.34E+05 | 4.17E−04 | 1.25E−09 | 3.37E+05 | 4.79E−04 | 1.42E−09 |
| Hu19 | 2.25E+05 | 6.75E−04 | 2.99E−09 | 2.35E+05 | 8.85E−04 | 3.78E−09 |
| Hu23 | 2.41E+05 | 6.48E−04 | 2.68E−09 | 2.54E+05 | 8.50E−04 | 3.35E−09 |
| Hu27 | 2.14E+05 | 8.34E−04 | 3.90E−09 | 2.20E+05 | 1.01E−3  | 4.60E−09 |
| Hu28 | 2.13E+05 | 9.49E−04 | 4.46E−09 | 2.10E+05 | 1.14E−3  | 5.41E−09 |
| Hu33 | 1.66E+05 | 1.14E−3  | 6.89E−09 | 1.68E+05 | 1.54E−3  | 9.15E−09 |
| Hu34 | 1.55E+05 | 1.06E−3  | 6.85E−09 | 1.64E+05 | 1.34E−3  | 8.14E−09 |
| KC18 | 2.13E+05 | 5.80E−04 | 2.73E−09 | 2.20E+05 | 8.32E−04 | 3.78E−09 |

Humanized antibodies KC18_Hu42 to KC18_49 were designed based on the sequence of KC_Hu18 to further remove liability sites, such as oxidation sites in FRWH3 and CDRH3, a deamidation site in CDRL1, and an oxidation site in CDRL2 (Table 11). At the end, two additional variants each for VH and VL were designed, which resulted in 8 more variants (KC18_Hu42-49) in addition to KC18_Hu18 (Table 12).

TABLE 11

Liability motifs in KC18_Hu18. The IMGT definition was used. Liability residues are underlined in the sequences.

| Liability Motif | Modification | Region | Sequence | Involved in binding | Proposed mutations |
|---|---|---|---|---|---|
| W | Oxidation | HFW2 | IHWVQQAPGKGLE<u>W</u>IGD (SEQ ID NO: 340) | No | Y |
| M | Oxidation | HFW3 | AYAEKFQGRATLTADRSTDTAY<u>M</u>ELSSLRSEDTAVYYC (SEQ ID NO: 341) | No | L |
| W | Oxidation | HFW4 | <u>W</u>GQGTLVTVSS (SEQ ID NO: 342) | No | Y |
| NNN | Deamidation | LCDR1 | QSVLYS<u>N</u>NNKNY (SEQ ID NO: 302) | Yes | DNQ |
| W | Oxidation | LCDR2 | <u>W</u>AS (SEQ ID NO: 74) | Yes | Y and F |

Figure 7:
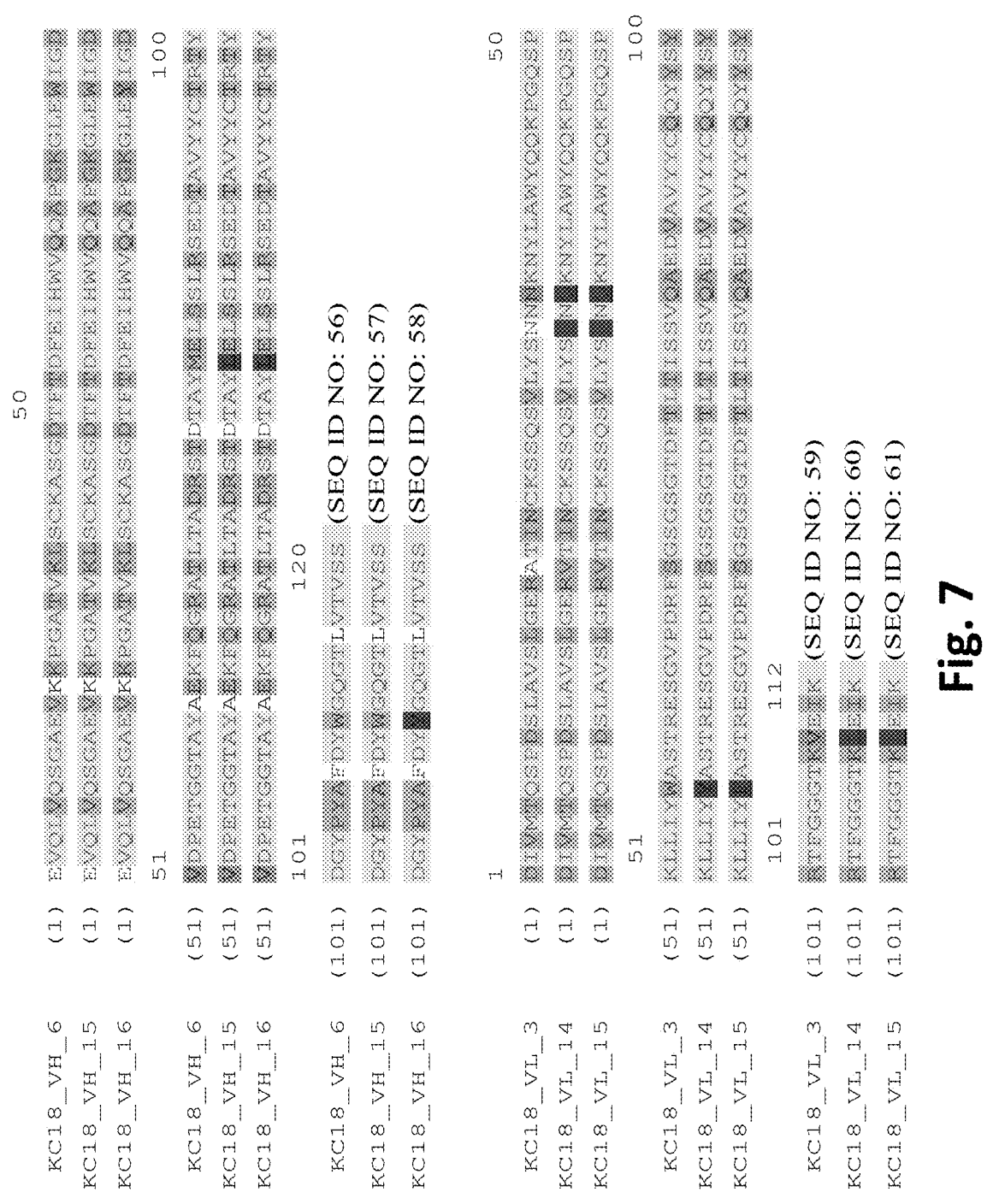

A sequence alignment of Hu18 and the newly designed variants (Hu42-49) is shown in FIG. 7. Mutations of Hu18 residues are underlined.

TABLE 12

Human and mouse germline identity percentage of the desiged KC18 variants.

| KC18 | | | KC18_VL_3 (SEQ ID NO: 59) 95.05% 86.14% | KC18_VL_14 (SEQ ID NO: 60) 92.08% 87.13% | KC18_VL_15 (SEQ ID NO: 61) 92.08% 87.13% |
|---|---|---|---|---|---|
| | Human Mouse | | | | |
| KC18_VH_6 (SEQ ID NO: 56) | 83.67% | 72.45% | KC18_Hu18 | KC18_Hu42 | KC18_Hu43 |
| KC18_VH_15 (SEQ ID NO: 57) | 82.65% | 71.43% | KC18_Hu44 | KC18_Hu45 | KC18_Hu46 |
| KC18_VH_16 (SEQ ID NO: 58) | 81.63% | 70.41% | KC18_Hu47 | KC18_Hu48 | KC18_Hu49 |

TABLE 13

Designed KC18 variant amino acid sequences.

| Antibody ID | Sequence |
|---|---|
| KC18_VH_6 | EVQLVQSGAEVKKPGATVKLSCKASGDTFTDFEIHWVQQAPGKGLEWIGDVDPETGGTAYAEKFQGRATLTADRSTDTAYMELSSLRSEDTAVYYCTRTYDGYPYAFDYWGQGTLVTVSS (SEQ ID NO: 56) |
| KC18_VH_15 | EVQLVQSGAEVKKPGATVKLSCKASGDTFTDFEIHWVQQAPGKGLEWIGDVDPETGGTAYAEKFQGRATLTADRSTDTAYLELSSLRSEDTAVYYCTRTYDGYPYAFDYWGQGTLVTVSS (SEQ ID NO: 57) |
| KC18_VH_16 | EVQLVQSGAEVKKPGATVKLSCKASGDTFTDFEIHWVQQAPGKGLEYIGDVDPETGGTAYAEKFQGRATLTADRSTDTAYLELSSLRSEDTAVYYCTRTYDGYPYAFDYYGQGTLVTVSS (SEQ ID NO: 58) |
| KC18_VL_3 | DIVMTQSPDSLAVSLGERATINCKSSQSVLYSNNNKNYLAWYQQKPGQSPKLLIYWASTRESGVPDRFSGSGSGTDFTLTISSVQAEDVAVYYCQQYYSYRTFGGGTKVEIK (SEQ ID NO: 59) |
| KC18_VL_14 | DIVMTQSPDSLAVSLGERVTINCKSSQSVLYSDNQKNYLAWYQQKPGQSPKLLIYYASTRESGVPDRFSGSGSGTDFTLTISSVQAEDVAVYYCQQYYSYRTFGGGTKLEIK (SEQ ID NO: 60) |
| KC18_VL_15 | DIVMTQSPDSLAVSLGERVTINCKSSQSVLYSDNQKNYLAWYQQKPGQSPKLLIYFASTRESGVPDRFSGSGSGTDFTLTISSVQAEDVAVYYCQQYYSYRTFGGGTKLEIK (SEQ ID NO: 61) |

TABLE 14

Designed KC18 variant sequences.

| Antibody ID | Sequence |
| --- | --- |
| KC18 Hu44<br>Heavy chain<br>nucleic acids<br>(with constant<br>region) | GAGGTTCAGTTGGTGCAAAGTGGGGCCGAGGTTAAAAAACCAGGTGC<br>AACCGTGAAACTGTCCTGCAAGGCGAGTGGTGATACATTTACAGATTT<br>TGAAATTCATTGGGTACAGCAGGCACCCGGAAAGGGATTGGAATGGAT<br>AGGAGATGTGGACCCGGAGACTGGCGGAACCGCGTACGCGGAGAAAT<br>TTCAGGGCAGAGCCACTTTGACGGCGGATAGAAGTACGGATACTGCCT<br>ACCTTGAACTGAGTTCCTTGCGGTCCGAAGATACGGCAGTTTACTATTG<br>TACTCGCACGTATGATGGCTACCCATACGCTTTCGATTATTGGGGACAA<br>GGCACTCTCGTGACCGTATCTTCAGCTTCAACCAAGGGACCTTCTGTCT<br>TTCCTCTGGCCCCTTCAAGCAAGAGCACTTCCGGAGGGACTGCCGCAC<br>TCGGGTGCCTTGTGAAAGATTACTTCCCAGAGCCTGTCACCGTCAGCTG<br>GAATTCAGGCGCTCTGACTAGCGGAGTGCACACCTTCCCCGCTGTGCTT<br>CAGTCCTCCGGACTCTACTCTCTGAGCAGCGTGGTGACCGTGCCGTCCT<br>CTTCTCTGGGGACCCAGACTTATATCTGCAACGTCAATCATAAGCCTTC<br>TAATACCAAGGTGGACAAGAAGGTGGAACCCAAATCATGTGACAAGA<br>CCCACACCTGTCCGCCCTGTCCGGCACCCGAACTGCTGGGTGGCCCTTC<br>CGTGTTCCTTTTCCCTCCAAAGCCGAAGGACACTCTTATGATTTCTCGC<br>ACTCCCGAAGTGACTTGCGTCGTGGTGGATGTGTCCCATGAGGATCCA<br>GAGGTCAAGTTCAACTGGTACGTGGACGGTGTGGAAGTCCACAACGCC<br>AAGACTAAGCCGAGAGAGGAACAGTACAATTCAACCTATCGGGTGGT<br>GAGCGTCCTGACCGTGCTGCACCAGGACTGGCTTAACGGAAAGGAGTA<br>CAAGTGCAAAGTGTCAAACAAGGCACTGCCCGCTCCGATCGAAAAGA<br>CCATTAGCAAAGCTAAGGGCCAGCCCAGAGAACCCCAAGTCTATACCC<br>TTCCACCCAGCCGGGACGAGCTGACCAAAAACCAGGTGTCACTCACTT<br>GTCTCGTGAAGGGTTTCTACCCCTCAGACATCGCCGTCGAATGGGAGT<br>CCAATGGTCAGCCAGAGAACAACTACAAAACCACCCCTCCCGTGCTGG<br>ACAGCGACGGGTCTTTCTTTCTCTACTCAAAGCTGACCGTGGATAAGTC<br>TCGCTGGCAGCAAGGGAATGTGTTTTCCTGTTCAGTGATGCATGAGGC<br>CCTTCATAATCATTACACCCAAAAGTCACTGAGCCTGTCTCCCGGA<br>(SEQ ID NO: 62) |
| KC18 Hu44<br>Heavy Chain<br>amino acids<br>(with constant<br>region) | EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPG<br>(SEQ ID NO: 63) |
| KC18 Hu46<br>Heavy Chain<br>nucleic acids<br>(with constant<br>region) | GAGGTTCAGTTGGTGCAAAGTGGGGCCGAGGTTAAAAAACCAGGTGC<br>AACCGTGAAACTGTCCTGCAAGGCGAGTGGTGATACATTTACAGATTT<br>TGAAATTCATTGGGTACAGCAGGCACCCGGAAAGGGATTGGAATGGAT<br>AGGAGATGTGGACCCGGAGACTGGCGGAACCGCGTACGCGGAGAAAT<br>TTCAGGGCAGAGCCACTTTGACGGCGGATAGAAGTACGGATACTGCCT<br>ACCTTGAACTGAGTTCCTTGCGGTCCGAAGATACGGCAGTTTACTATTG<br>TACTCGCACGTATGATGGCTACCCATACGCTTTCGATTATTGGGGACAA<br>GGCACTCTCGTGACCGTATCTTCAGCTTCAACCAAGGGACCTTCTGTCT<br>TTCCTCTGGCCCCTTCAAGCAAGAGCACTTCCGGAGGGACTGCCGCAC<br>TCGGGTGCCTTGTGAAAGATTACTTCCCAGAGCCTGTCACCGTCAGCTG<br>GAATTCAGGCGCTCTGACTAGCGGAGTGCACACCTTCCCCGCTGTGCTT<br>CAGTCCTCCGGACTCTACTCTCTGAGCAGCGTGGTGACCGTGCCGTCCT<br>CTTCTCTGGGGACCCAGACTTATATCTGCAACGTCAATCATAAGCCTTC<br>TAATACCAAGGTGGACAAGAAGGTGGAACCCAAATCATGTGACAAGA<br>CCCACACCTGTCCGCCCTGTCCGGCACCCGAACTGCTGGGTGGCCCTTC<br>CGTGTTCCTTTTCCCTCCAAAGCCGAAGGACACTCTTATGATTTCTCGC<br>ACTCCCGAAGTGACTTGCGTCGTGGTGGATGTGTCCCATGAGGATCCA<br>GAGGTCAAGTTCAACTGGTACGTGGACGGTGTGGAAGTCCACAACGCC<br>AAGACTAAGCCGAGAGAGGAACAGTACAATTCAACCTATCGGGTGGT<br>GAGCGTCCTGACCGTGCTGCACCAGGACTGGCTTAACGGAAAGGAGTA<br>CAAGTGCAAAGTGTCAAACAAGGCACTGCCCGCTCCGATCGAAAAGA<br>CCATTAGCAAAGCTAAGGGCCAGCCCAGAGAACCCCAAGTCTATACCC<br>TTCCACCCAGCCGGGACGAGCTGACCAAAAACCAGGTGTCACTCACTT<br>GTCTCGTGAAGGGTTTCTACCCCTCAGACATCGCCGTCGAATGGGAGT<br>CCAATGGTCAGCCAGAGAACAACTACAAAACCACCCCTCCCGTGCTGG<br>ACAGCGACGGGTCTTTCTTTCTCTACTCAAAGCTGACCGTGGATAAGTC<br>TCGCTGGCAGCAAGGGAATGTGTTTTCCTGTTCAGTGATGCATGAGGC<br>CCTTCATAATCATTACACCCAAAAGTCACTGAGCCTGTCTCCCGGA<br>(SEQ ID NO: 64) |
| KC18 Hu46<br>Heavy Chain<br>amino acids<br>(with constant<br>region) | EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPK |

TABLE 14-continued

Designed KC18 variant sequences.

| Antibody ID | Sequence |
|---|---|
|  | DTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPG<br>(SEQ ID NO: 65) |
| KC18 Hu44<br>Light Chain<br>nucleic acids<br>(with constant<br>region) | GACATTGTAATGACACAATCTCCCGACTCTCTTGCAGTCAGCTTGGGTG<br>AACGAGCAACTATAAATTGTAAAAGCAGCCAGTCTGTACTCTACTCTA<br>ATAACAACAAGAACTACCTCGCATGGTATCAGCAGAAACCGGGGCAA<br>AGTCCTAAACTTTTGATCTATTGGGCAAGTACCAGGGAGAGCGGAGTA<br>CCCGACAGATTCAGCGGGTCTGGATCAGGCACCGATTTTACTCTCACC<br>ATTTCTTCAGTTCAAGCTGAAGACGTCGCAGTCTACTACTGCCAGCAGT<br>ATTACAGTTACCGAACTTTTGGCGGTGGAACAAAAGTGGAAATAAAGC<br>GCACTGTGGCAGCCCCTTCTGTGTTTATCTTCCCACCCTCCGACGAGCA<br>GCTCAAGTCCGGTACCGCCTCTGTCGTCTGCCTGCTGAACAATTTCTAC<br>CCAAGAGAGGCCAAGGTGCAGTGGAAGGTGGACAACGCACTGCAAAG<br>CGGTAATTCACAAGAGTCAGTCACCGAACAAGACTCAAAGGACAGCA<br>CCTACTCACTGTCATCCACCCTGACTCTCTCAAAGGCTGACTACGAAAA<br>GCACAAAGTGTATGCTTGTGAAGTCACTCATCAGGGCCTTTCTAGCCCT<br>GTGACCAAGAGCTTCAACAGAGGCGAATGC (SEQ ID NO: 66) |
| KC18 Hu44<br>Light Chain<br>amino acids<br>(with constant<br>region) | DIVMTQSPDSLAVSLGERATINCKSSQSVLYSNNNKNYLAWYQQKPGQSP<br>KLLIYWASTRESGVPDRFSGSGSGTDFTLTISSVQAEDVAVYYCQQYYSY<br>RTFGGGTKVEIKRTVAAPSVFIFPPSDEQLKSGTASVVCLLNNFYPREAKV<br>QWKVDNALQSGNSQESVTEQDSKDSTYSLSSTLTLSKADYEKHKVYACE<br>VTHQGLSSPVTKSFNRGEC (SEQ ID NO: 67) |
| KC18 Hu46<br>Light Chain<br>nucleic acids<br>(with constant<br>region) | GACATAGTTATGACCCAGTCTCCAGACTCCCTCGCAGTTTCTCTCGGCG<br>AGAGAGTAACAATCAACTGTAAGTCATCACAGTCCGTACTCTACTCTG<br>ACAACCAAAAGAATTATTTGGCTTGGTATCAGCAAAAGCCAGGACAA<br>GCCCCAAACTTCTTATCTATTTTGCCAGCACTAGGGAGTCCGGGGTACC<br>CGACCGCTTTAGTGGCTCAGGTTCTGGGACAGACTTTACACTGACCATT<br>TCTAGCGTACAGGCTGAAGACGTTGCAGTCTACTACTGCCAGCAATAC<br>TATTCTTACAGAACGTTTGGCGGGGGCACAAAGTTGGAGATCAAACGC<br>ACTGTGGCAGCCCCTTCTGTGTTTATCTTCCCACCCTCCGACGAGCAGC<br>TCAAGTCCGGTACCGCCTCTGTCGTCTGCCTGCTGAACAATTTCTACCC<br>AAGAGAGGCCAAGGTGCAGTGGAAGGTGGACAACGCACTGCAAAGCG<br>GTAATTCACAAGAGTCAGTCACCGAACAAGACTCAAAGGACAGCACCT<br>ACTCACTGTCATCCACCCTGACTCTCTCAAAGGCTGACTACGAAAAGC<br>ACAAAGTGTATGCTTGTGAAGTCACTCATCAGGGCCTTTCTAGCCCTGT<br>GACCAAGAGCTTCAACAGAGGCGAATGC (SEQ ID NO: 68) |
| KC18 Hu46<br>Light Chain<br>amino acids<br>(with constant<br>region) | DIVMTQSPDSLAVSLGERVTINCKSSQSVLYSDNQKNYLAWYQQKPGQSP<br>KLLIYFASTRESGVPDRFSGSGSGTDFTLTISSVQAEDVAVYYCQQYYSR<br>TFGGGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGEC (SEQ ID NO: 69) |

TABLE 15

Humanized Anti-FGFR3 Fab fragment heavy chain amino
acid sequences.

| Antibody ID | Sequence |
|---|---|
| Fab Heavy chain | QVQLQQSGAELVRPGASVTLSCKASGDTFTDFEIHWVKQTPVHGLEWIGD<br>IDPETGGTAYNQKFRGRAMLTADRSSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSC (SEQ ID NO: 141)<br>EVQLQQSGPELVKPGASVKMSCKASGYTFTDYNMHWVKQSHGKSLEWI<br>GYINPNNGGTRYNQKFKGKATLTVNKSSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSC (SEQ ID NO: 143)<br>EVQLQQSGPELVKPGASVKMSCKASGYTFTDYNMHWVKQSHGKSLQWI<br>GYINPNNGGTNYNQNFKDKATLTVNKSSTTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSC (SEQ ID NO: 145)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD |

TABLE 15-continued

Humanized Anti-FGFR3 Fab fragment heavy chain amino acid sequences.

| Antibody ID | Sequence |
|---|---|
| | YFPEPVTVSWNSGALTSGVHTFPAVLQSSGLYSLSSVVTVPSSSLGTQTYIC<br>NVNHKPSNTKVDKKVEPKSC (SEQ ID NO: 147)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSC (SEQ ID NO: 149)<br>QVQLQQSGAELVRPGASVTLSCKASGSTFTDEEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSC (SEQ ID NO: 151)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSC (SEQ ID NO: 153)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSC (SEQ ID NO: 155)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSC (SEQ ID NO: 156)<br>QVQLQQSGAELVRPGASVTLSCKASGDTFTDFEIHWVKQTPVHGLEWIGD<br>IDPETGGTAYNQKFRGRAMLTADRSSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKS (SEQ ID NO: 164)<br>EVQLVQSGPELVKPGASVKMSCKASGYTFTDYNMHWVKQSHGKSLEWI<br>GYINPNNGGTRYNQKFKGKATLTVNKSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKS (SEQ ID NO: 165)<br>EVQLQQSGPELVKPGASVKMSCKASGYTFTDYNMHWVKQSHGKSLQWI<br>GYINPNNGGTNYNQNFKDKATLTVNKSSTTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKS (SEQ ID NO: 166)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKKVEPKS (SEQ ID NO: 167)<br>QVQLQQSGAELVRPGASVTLSCKASGSTFSDEEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKS (SEQ ID NO: 168)<br>QVQLQQSGAELVRPGASVTLSCKASGSTFTDNEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKS (SEQ ID NO: 169)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKS (SEQ ID NO: 170)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKS (SEQ ID NO: 171)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKS (SEQ ID NO: 172)<br>QVQLQQSGAELVRPGASVTLSCKASGDTFTDFEIHWVKQTPVHGLEWIGD<br>IDPETGGTAYNQKFRGRAMLTADRSSSTAYMELRSLTSEDSAVYYCTRTY<br>DGYPYAMDYWGQGTSVTVSSASTKGPSVFPLAPSSKSTSGGTAALGCLV |

TABLE 15-continued

Humanized Anti-FGFR3 Fab fragment heavy chain amino acid sequences.

| Antibody ID | Sequence |
|---|---|
| | KDYFPEPVTVSWNSGALTSGVHTFPAVLQSSGLYSLSSVVTVPSSSLGTQT<br>YICNVNHKPSNTKVDKKVEPK (SEQ ID NO: 173)<br>EVQLQQSGPELVKPGASVKMSCKASGYTFTDYNMHWVKQSHGKSLEWI<br>GYINPNNGGTRYNQKFKGKATLTVNKSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPK (SEQ ID NO: 174)<br>EVQLQQSGPELVKPGASVKMSCKASGYTFTDYNMHWVKQSHGKSLQWI<br>GYINPNNGGTNYNQNFKDKATLTVNKSSTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPK (SEQ ID NO: 175)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKKVEPK (SEQ ID NO: 176)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPK (SEQ ID NO: 177)<br>QVQLQQSGAELVRPGASVTLSCKASGTFTDNEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPK (SEQ ID NO: 178)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPK (SEQ ID NO: 179)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPK (SEQ ID NO: 180)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPK (SEQ ID NO: 181)<br>QVQLQQSGAELVRPGASVTLSCKASGDTFTDFEIHWVKQTPVHGLEWIGD<br>IDPETGGTAYNQKFRGRAMLTADRSSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEP (SEQ ID NO: 182)<br>EVQLQQSGPELVKPGASVKMSCKASGYTFTDYNMHWVKQSHGKSLEWI<br>GYINPNNGGTRYNQKFKGKATLTVNKSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEP (SEQ ID NO: 183)<br>EVQLQQSGPELVKPGASVKMSCKASGYTFTDYNMHWVKQSHGKSLQWI<br>GYINPNNGGTNYNQNFKDKATLTVNKSSTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEP (SEQ ID NO: 184)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKKVEP (SEQ ID NO: 185)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEP (SEQ ID NO: 186)<br>QVQLQQSGAELVRPGASVTLSCKASGTFTDNEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEP (SEQ ID NO: 187)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL |

TABLE 15-continued

Humanized Anti-FGFR3 Fab fragment heavy chain amino acid sequences.

| Antibody ID | Sequence |
|---|---|
| | VKDYFPEPVTVSWNSGALTSGVHTFPAVLQSSGLYSLSSVVTVPSSSLGTQ
TYICNVNHKPSNTKVDKKVEP (SEQ ID NO: 188)
EVQLVQSGAEVKKPGATVKLSCKASGDTFTDFEIHWVQQAPGKGLEWIG
DVDPETGGTAYAEKFQGRATLTADRSTDTAYLELSSLRSEDTAVYYCTRT
YDGYPYAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEP (SEQ ID NO: 189)
EVQLVQSGAEVKKPGATVKLSCKASGDTFTDFEIHWVQQAPGKGLEYIG
DVDPETGGTAYAEKFQGRATLTADRSTDTAYLELSSLRSEDTAVYYCTRT
YDGYPYAFDYYGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEP (SEQ ID NO: 190)
QVQLQQSGAELVRPGASVTLSCKASGDTFTDFEIHWVKQTPVHGLEWIGD
IDPETGGTAYNQKFRGRAMLTADRSSSTAYMELRSLTSEDSAVYYCTRTY
DGYPYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVE (SEQ ID NO: 191)
EVQLQQSGPELVKPGASVKMSCKASGYTFTDYNMHWVKQSHGKSLEWI
GYINPNNGGTRYNQKFKGKATLTVNKSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVE (SEQ ID NO: 192)
EVQLQQSGPELVKPGASVKMSCKASGYTFTDYNMHWVKQSHGKSLQWI
GYINPNNGGTNYNQNFKDKATLTVNKSSTTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVE (SEQ ID NO: 193)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTYIC
NVNHKPSNTKVDKKVE (SEQ ID NO: 194)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVE (SEQ ID NO: 195)
QVQLQQSGAELVRPGASVTLSCKASGTFTDFEIHWVKQTPVHGLEWIGA
IDPETGGTAYNQKFKGKAILTAVKSSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVE (SEQ ID NO: 196)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVE (SEQ ID NO: 197)
EVQLVQSGAEVKKPGATVKLSCKASGDTFTDFEIHWVQQAPGKGLEWIG
DVDPETGGTAYAEKFQGRATLTADRSTDTAYLELSSLRSEDTAVYYCTRT
YDGYPYAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVE (SEQ ID NO: 198)
EVQLVQSGAEVKKPGATVKLSCKASGDTFTDFEIHWVQQAPGKGLEYIG
DVDPETGGTAYAEKFQGRATLTADRSTDTAYLELSSLRSEDTAVYYCTRT
YDGYPYAFDYYGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVE (SEQ ID NO: 199)
QVQLQQSGAELVRPGASVTLSCKASGDTFTDFEIHWVKQTPVHGLEWIGD
IDPETGGTAYNQKFRGRAMLTADRSSSTAYMELRSLTSEDSAVYYCTRTY
DGYPYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKV (SEQ ID NO: 200)
EVQLQQSGPELVKPGASVKMSCKASGYTFTDYNMHWVKQSHGKSLEWI
GYINPNNGGTRYNQKFKGKATLTVNKSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKK (SEQ ID NO: 201)
EVQLQQSGPELVKPGASVKMSCKASGYTFTDYNMHWVKQSHGKSLQWI
GYINPNNGGTNYNQNFKDKATLTVNKSSTTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKK (SEQ ID NO: 202)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD |

TABLE 15-continued

Humanized Anti-FGFR3 Fab fragment heavy chain amino acid sequences.

| Antibody ID | Sequence |
|---|---|
| | YFPEPVTVSWNSGALTSGVHTFPAVLQSSGLYSLSSVVTVPSSSLGTQTYIC
NVNHKPSNTKVDKKV (SEQ ID NO: 203)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKV (SEQ ID NO: 204)
QVQLQQSGAELVRPGASVTLSCKASGSTFTDFEIHWVKQTPVHGLEWIGA
IDPETGGTAYNQKFKGKAILTAVKSSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKV (SEQ ID NO: 205)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKV (SEQ ID NO: 206)
EVQLVQSGAEVKKPGATVKLSCKASGDTFTDFEIHWVQQAPGKGLEWIG
DVDPETGGTAYAEKFQGRATLTADRSTDTAYLELSSLRSEDTAVYYCTRT
YDGYPYAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKV (SEQ ID NO: 207)
EVQLVQSGAEVKKPGATVKLSCKASGDTFTDFEIHWVQQAPGKGLEYIG
DVDPETGGTAYAEKFQGRATLTADRSTDTAYLELSSLRSEDTAVYYCTRT
YDGYPYAFDYYGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKV (SEQ ID NO: 208)
QVQLQQSGAELVRPGASVTLSCKASGSTFTDFEIHWVKQTPVHGLEWIGD
IDPETGGTAYNQKFRGRAMLTADRSSSTAYMELRSLTSEDSAVYYCTRTY
DGYPYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKK (SEQ ID NO: 209)
EVQLVQSGPELVKPGASVKMSCKASGYTFTDYNMHWVKQSHGKSLEWI
GYINPNNGGTRYNQKFKGKATLTVNKSSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKK (SEQ ID NO: 210)
EVQLQQSGPELVKPGASVKMSCKASGYTFTDYNMHWVKQSHGKSLQWI
GYINPNNGGTNYNQNFKDKATLTVNKSSTTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKK (SEQ ID NO: 211)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTYIC
NVNHKPSNTKVDKK (SEQ ID NO: 212)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKK (SEQ ID NO: 213)
QVQLQQSGAELVRPGASVTLSCKASGSTFTDFEIHWVKQTPVHGLEWIGA
IDPETGGTAYNQKFKGKAILTAVKSSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKK (SEQ ID NO: 214)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKK (SEQ ID NO: 215)
EVQLVQSGAEVKKPGATVKLSCKASGDTFTDFEIHWVQQAPGKGLEWIG
DVDPETGGTAYAEKFQGRATLTADRSTDTAYLELSSLRSEDTAVYYCTRT
YDGYPYAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKK (SEQ ID NO: 216)
EVQLVQSGAEVKKPGATVKLSCKASGDTFTDFEIHWVQQAPGKGLEYIG
DVDPETGGTAYAEKFQGRATLTADRSTDTAYLELSSLRSEDTAVYYCTRT
YDGYPYAFDYYGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKK (SEQ ID NO: 217)
QVQLQQSGAELVRPGASVTLSCKASGDTFTDFEIHWVKQTPVHGLEWIGD
IDPETGGTAYNQKFRGRAMLTADRSSSTAYMELRSLTSEDSAVYYCTRTY
DGYPYAMDYWGQGTSVTVSSASTKGPSVFPLAPSSKSTSGGTAALGCLV |

TABLE 15-continued

Humanized Anti-FGFR3 Fab fragment heavy chain amino acid sequences.

| Antibody ID | Sequence |
|---|---|
| | KDYFPEPVTVSWNSGALTSGVHTFPAVLQSSGLYSLSSVVTVPSSSLGTQT
YICNVNHKPSNTKVDK (SEQ ID NO: 218)
EVQLQQSGPELVKPGASVKMSCKASGYTFTDYNMHWVKQSHGKSLEWI
GYINPNNGGTRYNQKFKGKATLTVNKSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDK (SEQ ID NO: 219)
EVQLQQSGPELVKPGASVKMSCKASGYTFTDYNMHWVKQSHGKSLQWI
GYINPNNGGTNYNQNFKDKATLTVNKSSTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDK (SEQ ID NO: 220)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTYIC
NVNHKPSNTKVDK (SEQ ID NO: 221)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDK (SEQ ID NO: 222)
QVQLQQSGAELVRPGASVTLSCKASGTFTDFEIHWVKQTPVHGLEWIGA
IDPETGGTAYNQKFKGKAILTAVKSSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDK (SEQ ID NO: 223)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDK (SEQ ID NO: 224)
EVQLVQSGAEVKKPGATVKLSCKASGDTFTDFEIHWVQQAPGKGLEWIG
DVDPETGGTAYAEKFQGRATLTADRSTDTAYLELSSLRSEDTAVYYCTRT
YDGYPYAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDK (SEQ ID NO: 225)
EVQLVQSGAEVKKPGATVKLSCKASGDTFTDFEIHWVQQAPGKGLEYIG
DVDPETGGTAYAEKFQGRATLTADRSTDTAYLELSSLRSEDTAVYYCTRT
YDGYPYAFDYYGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDK (SEQ ID NO: 226)
QVQLQQSGAELVRPGASVTLSCKASGDTFTDFEIHWVKQTPVHGLEWIGD
IDPETGGTAYNQKFRGRAMLTADRSSSTAYMELRSLTSEDSAVYYCTRTY
DGYPYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDKTHTCP (SEQ ID NO: 227)
EVQLQQSGPELVKPGASVKMSCKASGYTFTDYNMHWVKQSHGKSLEWI
GYINPNNGGTRYNQKFKGKATLTVNKSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDKTHTCP (SEQ ID NO: 228)
EVQLQQSGPELVKPGASVKMSCKASGYTFTDYNMHWVKQSHGKSLQWI
GYINPNNGGTNYNQNFKDKATLTVNKSSTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDKTHTCP (SEQ ID NO: 229)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTYIC
NVNHKPSNTKVDKKVEPKSCDKTHTCP (SEQ ID NO: 230)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVEPKSCDKTHTCP (SEQ ID NO: 231)
QVQLQQSGAELVRPGASVTLSCKASGTFTDFEIHWVKQTPVHGLEWIGA
IDPETGGTAYNQKFKGKAILTAVKSSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVEPKSCDKTHTCP (SEQ ID NO: 232)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL |

TABLE 15-continued

Humanized Anti-FGFR3 Fab fragment heavy chain amino acid sequences.

| Antibody ID | Sequence |
|---|---|
| | VKDYFPEPVTVSWNSGALTSGVHTFPAVLQSSGLYSLSSVVTVPSSSLGTQ<br>TYICNVNHKPSNTKVDKKVEPKSCDKTHTCP (SEQ ID NO: 233)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTCP (SEQ ID NO: 234)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTCP (SEQ ID NO: 235)<br>QVQLQQSGAELVRPGASVTLSCKASGDTFTDFEIHWVKQTPVHGLEWIGD<br>IDPETGGTAYNQKFRGRAMLTADRSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTC (SEQ ID NO: 236)<br>EVQLQQSGPELVKPGASVKMSCKASGYTFTDYNMHWVKQSHGKSLEWI<br>GYINPNNGGTRYNQKFKGKATLTVNKSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTHTC (SEQ ID NO: 237)<br>EVQLQQSGPELVKPGASVKMSCKASGYTFTDYNMHWVKQSHGKSLQWI<br>GYINPNNGGTNYNQNFKDKATLTVNKSSTTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTHTC (SEQ ID NO: 238)<br>EVQLQQSGPDLVKPGASVKISCKASGYTFTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKKVEPKSCDKTHTC (SEQ ID NO: 239)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCDKTHTC (SEQ ID NO: 240)<br>QVQLQQSGAELVRPGASVTLSCKASGSTFTDFEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCDKTHTC (SEQ ID NO: 241)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTHTC (SEQ ID NO: 242)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTC (SEQ ID NO: 243)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTC (SEQ ID NO: 244)<br>QVQLQQSGAELVRPGASVTLSCKASGDTFTDFEIHWVKQTPVHGLEWIGD<br>IDPETGGTAYNQKFRGRAMLTADRSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHT (SEQ ID NO: 245)<br>EVQLQQSGPELVKPGASVKMSCKASGYTFTDYNMHWVKQSHGKSLEWI<br>GYINPNNGGTRYNQKFKGKATLTVNKSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTHT (SEQ ID NO: 246)<br>EVQLQQSGPELVKPGASVKMSCKASGYTFTDYNMHWVKQSHGKSLQWI<br>GYINPNNGGTNYNQNFKDKATLTVNKSSTTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTHT (SEQ ID NO: 247)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD |

TABLE 15-continued

Humanized Anti-FGFR3 Fab fragment heavy chain amino acid sequences.

| Antibody ID | Sequence |
|---|---|
| | YFPEPVTVSWNSGALTSGVHTFPAVLQSSGLYSLSSVVTVPSSSLGTQTYIC<br>NVNHKPSNTKVDKKVEPKSCDKTHT (SEQ ID NO: 248)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCDKTHT (SEQ ID NO: 249)<br>QVQLQQSGAELVRPGASVTLSCKASGSTFTDFEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCDKTHT (SEQ ID NO: 250)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTHT (SEQ ID NO: 251)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHT (SEQ ID NO: 252)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHT (SEQ ID NO: 253)<br>QVQLQQSGAELVRPGASVTLSCKASGDTFTDFEIHWVKQTPVHGLEWIGD<br>IDPETGGTAYNQKFRGRAMLTADRSSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTH (SEQ ID NO: 254)<br>EVQLQQSGPELVKPGASVKMSCKASGYTFTDYNMHWVKQSHGKSLEWI<br>GYINPNNGGTRYNQKFKGKATLTVNKSSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTH (SEQ ID NO: 255)<br>EVQLQQSGPELVKPGASVKMSCKASGYTFTDYNMHWVKQSHGKSLQWI<br>GYINPNNGGTNYNQNFKDKATLTVNKSSTTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTH (SEQ ID NO: 256)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKKVEPKSCDKTH (SEQ ID NO: 257)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCDKTH (SEQ ID NO: 258)<br>QVQLQQSGAELVRPGASVTLSCKASGSTFTDFEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCDKTH (SEQ ID NO: 259)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCDKTH (SEQ ID NO: 260)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTH (SEQ ID NO: 261)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYYGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTH (SEQ ID NO: 262)<br>QVQLQQSGAELVRPGASVTLSCKASGDTFTDFEIHWVKQTPVHGLEWIGD<br>IDPETGGTAYNQKFRGRAMLTADRSSSTAYMELRSLTSEDSAVYYCTRTY<br>DGYPYAMDYWGQGTSVTVSSASTKGPSVFPLAPSSKSTSGGTAALGCLV |

TABLE 15-continued

Humanized Anti-FGFR3 Fab fragment heavy chain amino acid sequences.

| Antibody ID | Sequence |
| --- | --- |
| | KDYFPEPVTVSWNSGALTSGVHTFPAVLQSSGLYSLSSVVTVPSSSLGTQT
YICNVNHKPSNTKVDKKVEPKSCDKT (SEQ ID NO: 263)
EVQLQQSGPELVKPGASVKMSCKASGYTFTDYNMHWVKQSHGKSLEWI
GYINPNNGGTRYNQKFKGKATLTVNKSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDKT (SEQ ID NO: 264)
EVQLQQSGPELVKPGASVKMSCKASGYTFTDYNMHWVKQSHGKSLQWI
GYINPNNGGTNYNQNFKDKATLTVNKSSTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDKT (SEQ ID NO: 265)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTYIC
NVNHKPSNTKVDKKVEPKSCDKT (SEQ ID NO: 266)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVEPKSCDKT (SEQ ID NO: 267)
QVQLQQSGAELVRPGASVTLSCKASGSTFTDFEIHWVKQTPVHGLEWIGA
IDPETGGTAYNQKFKGKAILTAVKSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVEPKSCDKT (SEQ ID NO: 268)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDKT (SEQ ID NO: 269)
EVQLVQSGAEVKKPGATVKLSCKASGDTFTDFEIHWVQQAPGKGLEWIG
DVDPETGGTAYAEKFQGRATLTADRSTDTAYLELSSLRSEDTAVYYCTRT
YDGYPYAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDKT (SEQ ID NO: 270)
EVQLVQSGAEVKKPGATVKLSCKASGDTFTDFEIHWVQQAPGKGLEYIG
DVDPETGGTAYAEKFQGRATLTADRSTDTAYLELSSLRSEDTAVYYCTRT
YDGYPYAFDYYGQGTLVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDKT (SEQ ID NO: 271)
QVQLQQSGAELVRPGASVTLSCKASGDTFTDFEIHWVKQTPVHGLEWIGD
IDPETGGTAYNQKFRGRAMLTADRSSSTAYMELRSLTSEDSAVYYCTRTY
DGYPYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDK (SEQ ID NO: 272)
EVQLQQSGPELVKPGASVKMSCKASGYTFTDYNMHWVKQSHGKSLEWI
GYINPNNGGTRYNQKFKGKATLTVNKSSTAYMELRSLTSEDSAVYYCA
RERDYDGAMDYWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDK (SEQ ID NO: 273)
EVQLQQSGPELVKPGASVKMSCKASGYTFTDYNMHWVKQSHGKSLQWI
GYINPNNGGTNYNQNFKDKATLTVNKSSTAYMELRSLTSEDSAVYYCA
RERDYDGSMDFWGQGTSVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDK (SEQ ID NO: 274)
EVQLQQSGPDLVKPGASVKISCKASGYTVTDYYMNWVKQSHGKSLEWIG
DINPNNGVTTYNQKFKDKATLTVDKSSSTAYMELRSLTSEDSAVYYCARE
EDFDGFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTYIC
NVNHKPSNTKVDKKVEPKSCDK (SEQ ID NO: 275)
QVQLQQSGAELVRPGASVTLSCKASGSTFSDFEIHWVKQTPVHGLEWIGG
IDPETGGTAYNQKFKGKAILTADRSSSTAYMELRSLTSEDSAVYYCTRNY
DGYSQTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVEPKSCDK (SEQ ID NO: 276)
QVQLQQSGAELVRPGASVTLSCKASGSTFTDFEIHWVKQTPVHGLEWIGA
IDPETGGTAYNQKFKGKAILTAVKSSTAYMGLRSLTSEDSAVYYCTRNY
DGYSRTMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTY
ICNVNHKPSNTKVDKKVEPKSCDK (SEQ ID NO: 277)
EVQLVQSGAEVKKPGATVKLSCKASGDTFTDFEIHWVQQAPGKGLEWIG
DVDPETGGTAYAEKFQGRATLTADRSTDTAYMELSSLRSEDTAVYYCTR
TYDGYPYAFDYWGQGTLVTVSSASTKGPSVFPLAPSSKSTSGGTAALGCL |

TABLE 15-continued

Humanized Anti-FGFR3 Fab fragment heavy chain amino acid sequences.

| Antibody ID | Sequence |
|---|---|
| | VKDYFPEPVTVSWNSGALTSGVHTFPAVLQSSGLYSLSSVVTVPSSSLGTQ<br>TYICNVNHKPSNTKVDKKVEPKSCDK (SEQ ID NO: 278)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDK (SEQ ID NO: 279)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDK (SEQ ID NO: 280)<br>QVQLQQSGAELVRPGASVTLSCKASGDTFTDFEIHWVKQTPVHGLEWIGD<br>IDPETGGTAYNQKFRGRAMLTADRSSTAYMELRSLTSEDSAVYYCTRTY<br>DGYPYAMDYWGQGTSVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCD (SEQ ID NO: 281)<br>EVQLQQSGPELVKPGASVKMSCKASGYTFTDYNMHWVKQSHGKSLEWI<br>GYINPNNGGTRYNQKFKGKATLTVNKSSTAYMELRSLTSEDSAVYYCA<br>RERDYDGAMDYWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCD (SEQ ID NO: 282)<br>EVQLQQSGPELVKPGASVKMSCKASGYTFTDYNMHWVKQSHGKSLQWI<br>GYINPNNGGTNYNQNFKDKATLTVNKSSTTAYMELRSLTSEDSAVYYCA<br>RERDYDGSMDFWGQGTSVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCD (SEQ ID NO: 283)<br>EVQLQQSGPDLVKPGASVKISCKASGYTVTDYYMNWVKQSHGKSLEWIG<br>DINPNNGVTTYNQKFKDKATLTVDKSSSTAYMELRSLTSEDSAVYYCARE<br>EDFDGFDYWGQGTTLTVSSASTKGPSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKKVEPKSCD (SEQ ID NO: 284)<br>QVQLQQSGAELVRPGASVTLSCKASGSTFSDFEIHWVKQTPVHGLEWIGG<br>IDPETGGTAYNQKFKGKAILTADRSSSTAYMELRSLTSEDSAVYYCTRNY<br>DGYSQTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCD (SEQ ID NO: 285)<br>QVQLQQSGAELVRPGASVTLSCKASGSTFTDNEIHWVKQTPVHGLEWIGA<br>IDPETGGTAYNQKFKGKAILTAVKSSSTAYMGLRSLTSEDSAVYYCTRNY<br>DGYSRTMDYWGQGTSVTVSSASTKGPSVFPLAPSSKSTSGGTAALGCLVK<br>DYFPEPVTVSWNSGALTSGVHTFPAVLQSSGLYSLSSVVTVPSSSLGTQTY<br>ICNVNHKPSNTKVDKKVEPKSCD (SEQ ID NO: 286)<br>EVQLVQSGAEVKKPGATVKLSCKASGDTFTDFEIHWVQQAPGKGLEWIG<br>DVDPETGGTAYAEKFQGRATLTADRSTDTAYMELSSLRSEDTAVYYCTR<br>TYDGYPYAFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQ<br>TYICNVNHKPSNTKVDKKVEPKSCD (SEQ ID NO: 287)<br>EVQLVQSGAEVKKPGATVKLSCKASGDTFTDFEIHWVQQAPGKGLEWIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCD (SEQ ID NO: 288)<br>EVQLVQSGAEVKKPGATVKLSCKASGDTFTDFEIHWVQQAPGKGLEYIG<br>DVDPETGGTAYAEKFQGRATLTADRSTDTAYLELSSLRSEDTAVYYCTRT<br>YDGYPYAFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCD (SEQ ID NO: 289) |

TABLE 16

Humanized Anti-FGFR3 Fab fragment light chain amino acid sequences.

| Antibody ID | Sequence |
|---|---|
| Fab Light chain | DIVMSQSPSSLAVSVGEKVTMSCKSSQSLLYSNNQKNYLAWYQQKPGQS<br>PKLLIYWASTRESGVPDRFTGSGSGTDFTLTISSVKAEDLAVYYCQQYYSY<br>RTFGGGTKLEIKRTVAAPSVFIFPPSDEQLKSGTASVVCLLNNFYPREAKV<br>QWKVDNALQSGNSQESVTEQDSKDSTYSLSSTLTLSKADYEKHKVYACE<br>VTHQGLSSPVTKSFNRGEC (SEQ ID NO: 142) |

TABLE 16-continued

Humanized Anti-FGFR3 Fab fragment light chain amino acid sequences.

| Antibody ID | Sequence |
|---|---|
| | DIQMTQSPSSLSASLGGKVTITCKASQDINKFIAWYQHKPGKGPRLLIHYTS<br>TLQPGIPSRFSGSGSGRDYSFSISNLEPEDIATYYCLQYDNLLWTFGGGTKL<br>EIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSP<br>VTKSFNRGEC (SEQ ID NO: 144)<br>DIQMTQSPSSLSASLGGKVTITCKASQDINKFIAWYQHKPGKGPRLLIHYTS<br>TLQPGIPSRFSGSGSGRDYSFSISNLEPEDIATYFCLQYDNLLWTFGGGTKL<br>EIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSP<br>VTKSFNRGEC (SEQ ID NO: 146)<br>DIVMTQSHKFMSTSVGDRVSITCKASQDVSTGVAWYQQKPGQSPQLLIY<br>WASTRHTGVPDRFTGSGSGTDYILTIRSVQAEDLALYYCQQHYSTPLTFG<br>AGTKLELKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQ<br>GLSSPVTKSFNRGEC (SEQ ID NO: 148)<br>NIMMTQSPSSLAVSAGEKVTMSCKSSQSVLYSSNQKNYLAWYQQKPGQS<br>PKLLIYWASTRESGVPDRFTGSGSGTDFTLTISSVQAEDLAVYYCHQYLSS<br>YTFGGGTKLEMKRTVAAPSVFIFPPSDEQLKSGTASVVCLLNNFYPREAK<br>VQWKVDNALQSGNSQESVTEQDSKDSTYSLSSTLTLSKADYEKHKVYAC<br>EVTHQGLSSPVTKSFNRGEC (SEQ ID NO: 150)<br>NIMMTQSPSSLAVSAGEKVTMSCKSSQSVLYSSNQKNYLAWYQQKPGQS<br>PKLLIYWASTRESGVPDRFTGSGSGTDFSLSISSVQTEDLAVYYCHQYLSS<br>YTFGGGTRLEMKRTVAAPSVFIFPPSDEQLKSGTASVVCLLNNFYPREAKV<br>QWKVDNALQSGNSQESVTEQDSKDSTYSLSSTLTLSKADYEKHKVYACE<br>VTHQGLSSPVTKSFNRGEC (SEQ ID NO: 152)<br>DIVMTQSPDSLAVSLGERATINCKSSQSVLYSNNNKNYLAWYQQKPGQSP<br>KLLIYWASTRESGVPDRFSGSGSGTDFTLTISSVQAEDVAVYYCQQYYSY<br>RTFGGGTKVEIKRTVAAPSVFIFPPSDEQLKSGTASVVCLLNNFYPREAKV<br>QWKVDNALQSGNSQESVTEQDSKDSTYSLSSTLTLSKADYEKHKVYACE<br>VTHQGLSSPVTKSFNRGEC (SEQ ID NO: 67)<br>DIVMTQSPDSLAVSLGERVTINCKSSQSVLYSDNQKNYLAWYQQKPGQSP<br>KLLIYFASTRESGVPDRFSGSGSGTDFTLTISSVQAEDVAVYYCQQYYSYR<br>TFGGGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGEC (SEQ ID NO: 69)<br>DIVMTQSPDSLAVSLGERVTINCKSSQSVLYSDNQKNYLAWYQQKPGQSP<br>KLLIYYASTRESGVPDRFSGSGSGTDFTLTISSVQAEDVAVYYCQQYYSYR<br>TFGGGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGEC (SEQ ID NO: 154) |

In certain embodiments, an anti-FGFR3 F(ab) fragment of the present application comprises a heavy chain of Table 15, and a light chain in Table 16.

In certain embodiments, the antibody F(ab) fragment heavy chain comprises the amino acid sequence of SEQ ID NO: 141, 164, 173, 182, 191, 200, 209, 218, 227, 236, 245, 254, 263, 272, or 281, and the antibody F(ab) fragment light chain comprises the amino acid sequence of SEQ ID NO: 142.

In certain embodiments, the antibody F(ab) fragment heavy chain comprises the amino acid sequence of SEQ ID NO: 143, 165, 174, 183, 192, 201, 210, 219, 228, 237, 246, 255, 264, 273, or 282, and the antibody F(ab) fragment light chain comprises the amino acid sequence of SEQ ID NO: 144.

In certain embodiments, the antibody F(ab) fragment heavy chain comprises the amino acid sequence of SEQ ID NO: 145, 166, 175, 184, 193, 202, 211, 220, 229, 238, 247, 256, 265, 274, or 283 and the antibody F(ab) fragment light chain comprises the amino acid sequence of SEQ ID NO: 146.

In certain embodiments, the antibody F(ab) fragment heavy chain comprises the amino acid sequence of SEQ ID NO: 147, 167, 176, 185, 194, 203, 212, 221, 230, 239, 248, 257, 266, 275, or 284, and the antibody F(ab) fragment light chain comprises the amino acid sequence of SEQ ID NO: 148.

In certain embodiments, the antibody F(ab) fragment heavy chain comprises the amino acid sequence of SEQ ID NO: 149, 168, 177, 186, 195, 204, 213, 222, 231, 240, 249, 258, 267, 276, or 285, and the antibody F(ab) fragment light chain comprises the amino acid sequence of SEQ ID NO: 150.

In certain embodiments, the antibody F(ab) fragment heavy chain comprises the amino acid sequence of SEQ ID NO: 151, 169, 178, 187, 196, 205, 214, 223, 232, 241, 250, 259, 268, 277, or 286, and the antibody F(ab) fragment light chain comprises the amino acid sequence of SEQ ID NO: 152.

In certain embodiments, the antibody F(ab) fragment heavy chain comprises the amino acid sequence of SEQ ID NO: 153, 170, 179, 188, 197, 206, 215, 224, 233, 242, 251, 260, 269, 278, or 287, and the antibody F(ab) fragment light chain comprises the amino acid sequence of SEQ ID NO: 67.

In certain embodiments, the antibody F(ab) fragment heavy chain comprises the amino acid sequence of SEQ ID NO: 153, 170, 179, 188, 197, 206, 215, 224, 233, 242, 251, 260, 269, 278, or 287, and the antibody F(ab) fragment light chain comprises the amino acid sequence of SEQ ID NO: 154.

In certain embodiments, the antibody F(ab) fragment heavy chain comprises the amino acid sequence of SEQ ID NO: 153, 170, 179, 188, 197, 206, 215, 224, 233, 242, 251, 260, 269, 278, or 287, and the antibody F(ab) fragment light chain comprises the amino acid sequence of SEQ ID NO: 69.

In certain embodiments, the antibody F(ab) fragment heavy chain comprises the amino acid sequence of SEQ ID NO: 155, 171, 180, 189, 198, 207, 216, 225, 234, 243, 252, 261, 270, 279, or 288, and the antibody F(ab) fragment light chain comprises the amino acid sequence of SEQ ID NO: 67.

In certain embodiments, the antibody F(ab) fragment heavy chain comprises the amino acid sequence of SEQ ID NO: 155, 171, 180, 189, 198, 207, 216, 225, 234, 243, 252, 261, 270, 279, or 288, and the antibody F(ab) fragment light chain comprises the amino acid sequence of SEQ ID NO: 154.

In certain embodiments, the antibody F(ab) fragment heavy chain comprises the amino acid sequence of SEQ ID NO: 155, 171, 180, 189, 198, 207, 216, 225, 234, 243, 252, 261, 270, 279, or 288, and the antibody F(ab) fragment light chain comprises the amino acid sequence of SEQ ID NO: 69.

In certain embodiments, the antibody F(ab) fragment heavy chain comprises the amino acid sequence of SEQ ID NO: 156, 172, 181, 190, 199, 208, 217, 226, 235, 244, 253, 262, 271, 280, or 289, and the antibody F(ab) fragment light chain comprises the amino acid sequence of SEQ ID NO: 67.

In certain embodiments, the antibody F(ab) fragment heavy chain comprises the amino acid sequence of SEQ ID NO: 156, 172, 181, 190, 199, 208, 217, 226, 235, 244, 253, 262, 271, 280, or 289, and the antibody F(ab) fragment light chain comprises the amino acid sequence of SEQ ID NO: 154.

In certain embodiments, the antibody F(ab) fragment heavy chain comprises the amino acid sequence of SEQ ID NO: 156, 172, 181, 190, 199, 208, 217, 226, 235, 244, 253, 262, 271, 280, or 289, and the antibody F(ab) fragment light chain comprises the amino acid sequence of SEQ ID NO: 69.

In Vitro Analysis

Figure 9A:
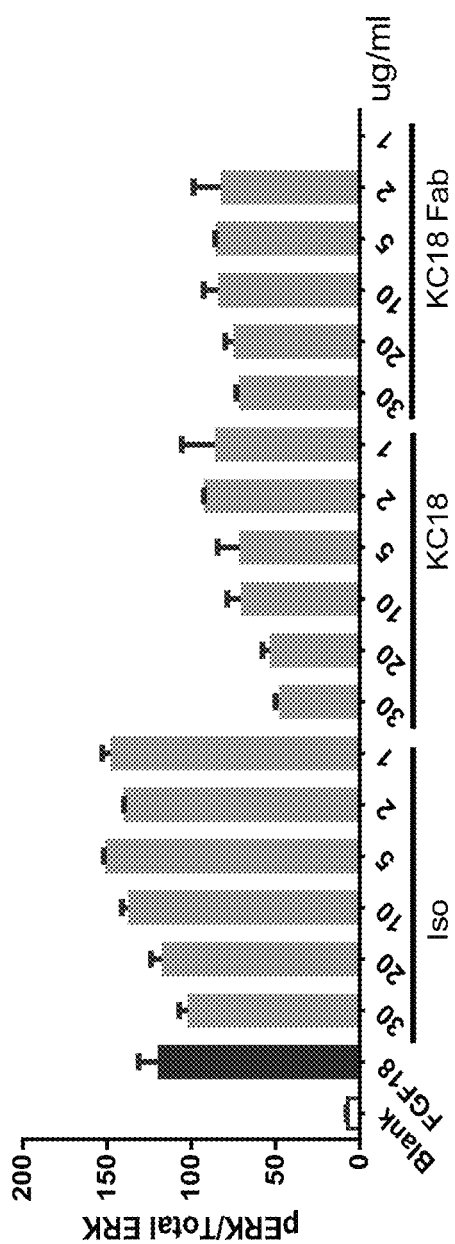
FIG. 9A-FIG. 9B graphically depict relative Erk phosphorylation inhibition by anti-FGFR3 antibodies KC18 (FIG. 9A), KE63 (FIG. 9B), and KE94 (FIG. 9B) and their corresponding Fab fragments.
Figure 9B:
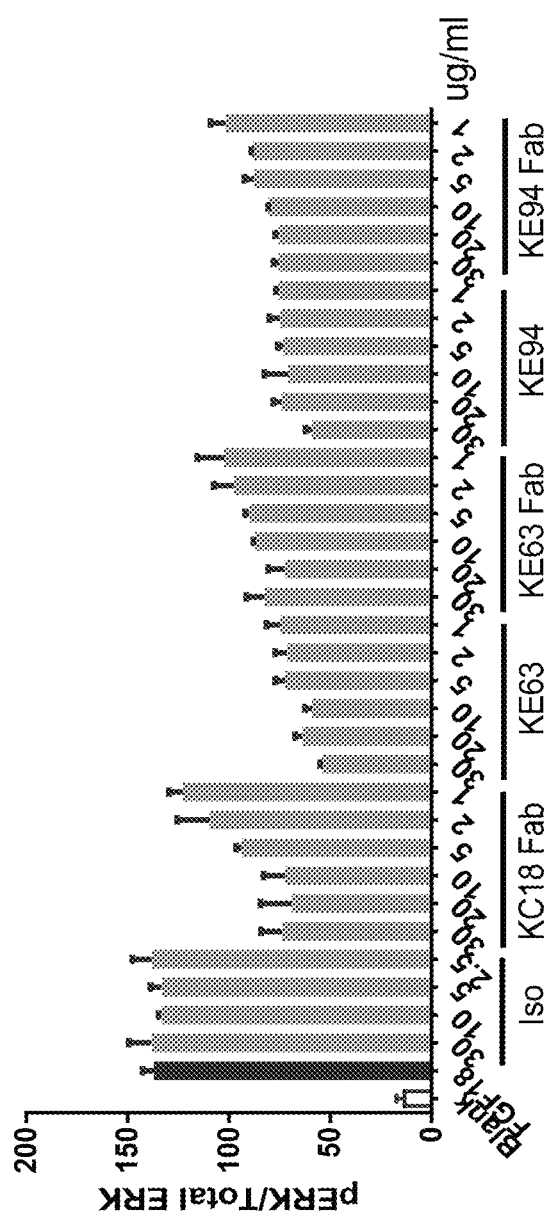

Antibodies were screened for binding and specificity to FGFR3. Activity was assessed using a Homogenous Time-Resolved Fluorescence (HTRF) assay to evaluate the level of inhibition on Erk phosphorylation using mouse primary rib chondrocytes. Briefly, primary mouse rib chondrocyte cells isolated from the achondroplasia mouse model were pretreated for 2 hours with anti-FGFR3 antibodies with a concentration ranging from 0.016 µg/ml to 100 µg/ml. Cells were then stimulated with FGF18 for 5 minutes. The reaction was then stopped, total Erk was measured using the HTRF assay, and Phospho-Erk (Thr202/Tyr204) was measured in a separate HTRF assay. The percent inhibition of Erk phosphorylation was measured by taking the ratio of Phospho-Erk over total Erk and multiplying by 100. Particularly, mouse antibodies KC18, KE63, and KE94 and their corresponding Fab fragments were tested in the HTRF assay, all of which inhibited Erk phosphorylation (FIG. 9A and FIG. 9B).

To determine the effects of different mouse antibody formats on inhibition of Erk phosphorylation, KC18 mouse antibody in various formats, including full-length antibody (IgG), Fab, a one-armed, monovalent antibody (MetMab), and pegylated (PEG) Fab fragment were tested in the HTRF assay and compared to isotype control (Iso). Also, KC18 Fab with half-life extension using a human albumin nanobody (KC18 Fab-HLE) was tested, with and without human serum albumin (HSA) or mouse serum albumin (MSA).

The full-length KC18 mouse antibody has a heavy chain of SEQ ID NO: 291 (with mIgG2a Fc sequence), and a light chain of SEQ ID NO: 292. The KC18 mouse Fab antibody has a heavy chain of SEQ ID NO: 293, and a light chain of SEQ ID NO: 294.

(SEQ ID NO: 291)
QVQLQQSGAELVRPGASVTLSCKASGDTFTDFEIHWVKQTPVHGLEWI

GDIDPETGGTAYNQKFRGRAMLTADRSSSTAYMELRSLTSEDSAVYYC

TRTYDGYPYAMDYWGQGTSVTVSSAKTTAPSVYPLAPVCGDTTGSSVT

LGCLVKGYFPEPVTLTWNSGSLSSGVHTFPAVLQSDLYTLSSSVTVTS

STWPSQSITCNVAHPASSTKVDKKIEPRGPTIKPCPPCKCPAPPVAGP

SVFIFPPKIKDVLMISLSPIVTCVVVDVSEDDPDVQISWFVNNVEVHT

AQTQTHREDYNSTLRVVSALPIQHQDWMSGKEFKCKVNNKGLPSSIER

TISKPKGSVRAPQVYVLPPPEEEMTKKQVTLTCMVTDFMPEDIYVEWT

NNGKTELNYKNTEPVLDSDGSYFMYSKLRVEKKNWVERNSYSCSVVHE

GLHNHHTTKSFSRTPGK (SEQ ID NO: 292)
DIVMSQSPSSLAVSVGEKVTMSCKSSQSLLYSNNQKNYLAWYQQKPGQ

SPKLLIYWASTRESGVPDRFTGSGSGTDFTLTISSVKAEDLAVYYCQQ

YYSYRTFGGGTKLEIKRADAAPTVSIFPPSSEQLTSGGASVVCFLNNF

YPKDINVKWKIDGSERQNGVLNSWTDQDSKDSTYSMSSTLTLTKDEYE

RHNSYTCEATHKTSTSPIVKSFNRNEC (SEQ ID NO: 293)
QVQLQQSGAELVRPGASVTLSCKASGDTFTDFEIHWVKQTPVHGLEWI

GDIDPETGGTAYNQKFRGRAMLTADRSSSTAYMELRSLTSEDSAVYYC

TRTYDGYPYAMDYWGQGTSVTVSSAKTTAPSVYPLAPVCGDTTGSSVT

LGCLVKGYFPEPVTLTWNSGSLSSGVHTFPAVLQSDLYTLSSSVTVTS

STWPSQSITCNVAHPASSTKVDKKI (SEQ ID NO: 294)
DIVMSQSPSSLAVSVGEKVTMSCKSSQSLLYSNNQKNYLAWYQQKPGQ

SPKLLIYWASTRESGVPDRFTGSGSGTDFTLTISSVKAEDLAVYYCQQ

YYSYRTFGGGTKLEIKRADAAPTVSIFPPSSEQLTSGGASVVCFLNNF

YPKDINVKWKIDGSERQNGVLNSWTDQDSKDSTYSMSSTLTLTKDEYE

RHNSYTCEATHKTSTSPIVKSFNRNEC

Figure 10A:
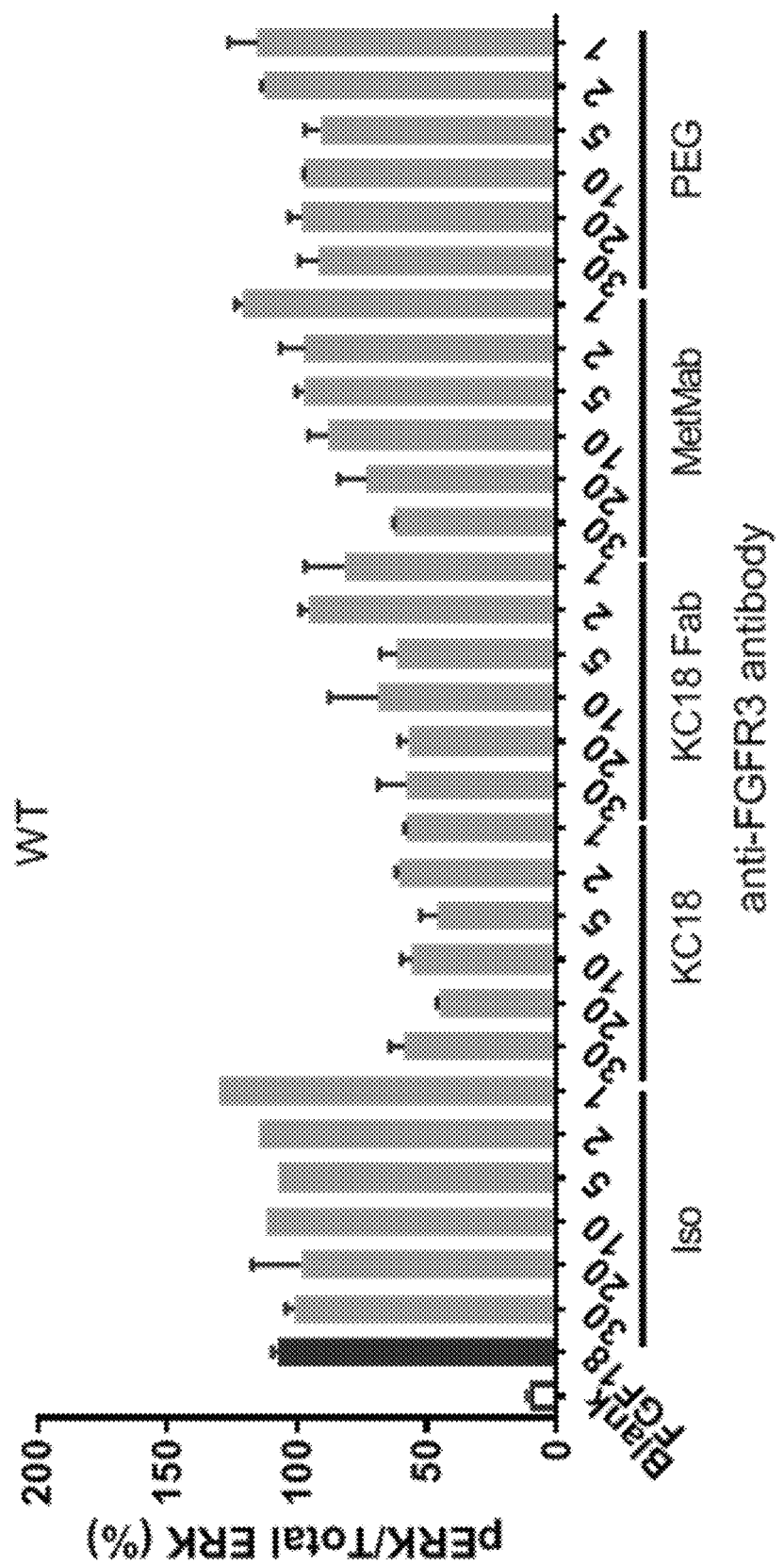
FIG. 10A-FIG. 10C graphically depict relative Erk phosphorylation inhibition by anti-FGFR3 antibody KC18 in different formats.
Figure 10B:
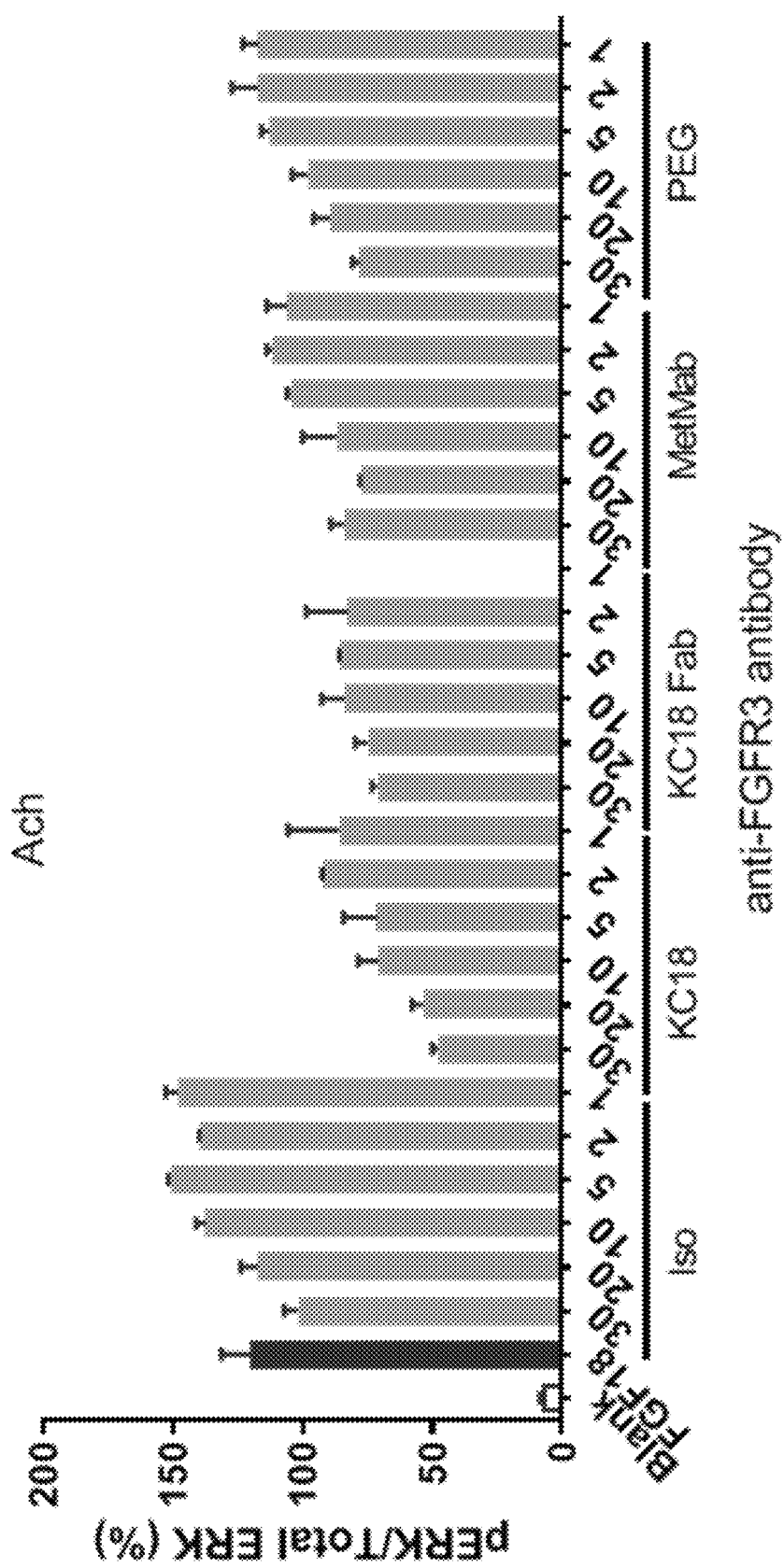
Figure 10C:
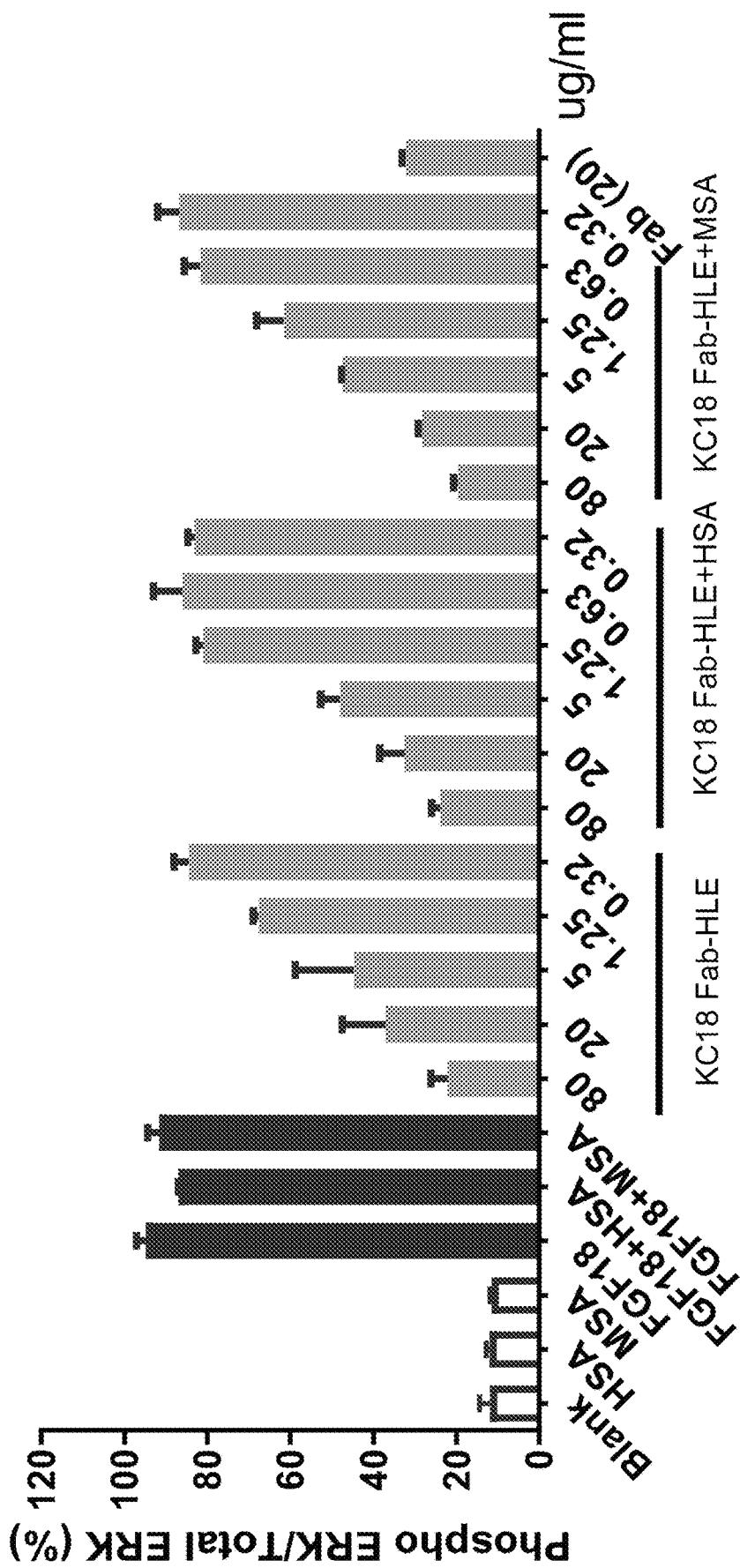

All formats inhibited Erk phosphorylation (FIG. 10A to FIG. 10C). The antibody format referred to in FIG. 10A as "MetMab" is described in further detail in Merchant et al. (PNAS. 110(32): E2987-E2996. 2013).

Figure 8A:
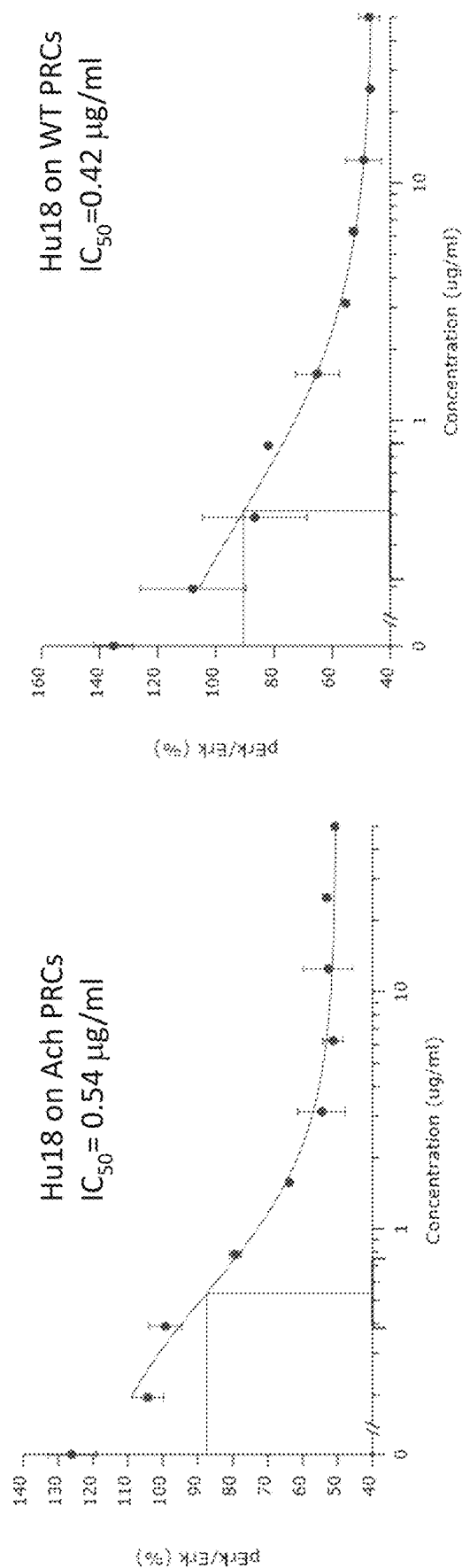
FIG. 8A-FIG. 8C depict graphs demonstrating $IC_{50}$ values for the inhibition of Erk phosphorylation by humanized anti-FGFR3 antibodies Hu18 (FIG. 8A), Hu44 (FIG. 8B), and Hu46 (FIG. 8C). Inhibition of Erk phosphorylation was determined by a homogenous time-resolved fluorescence (HTRF) assay.
Figure 8B:
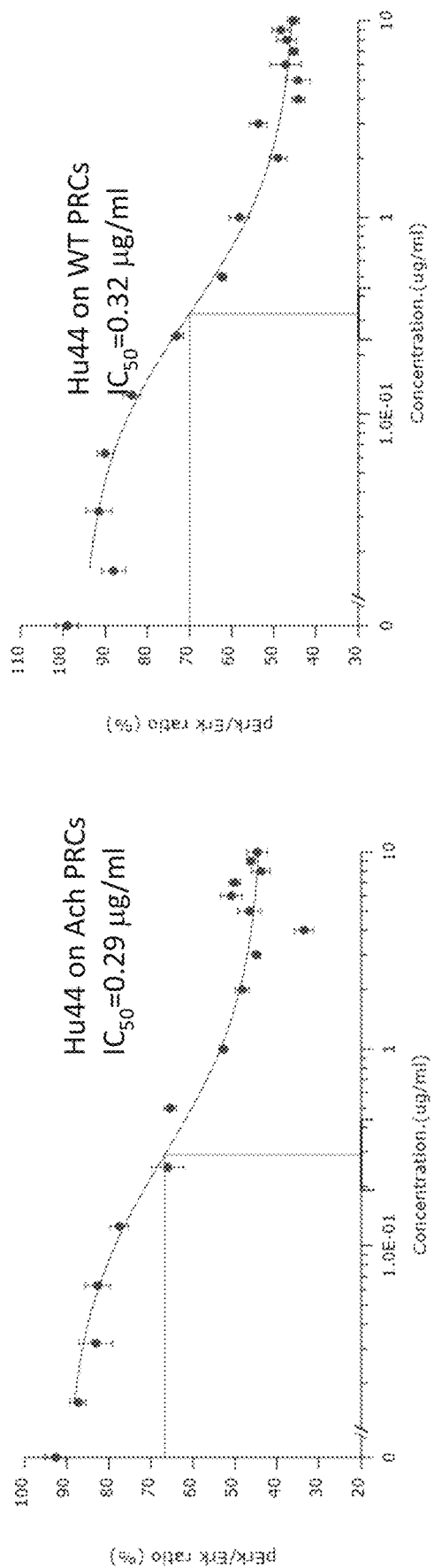
Figure 8C:
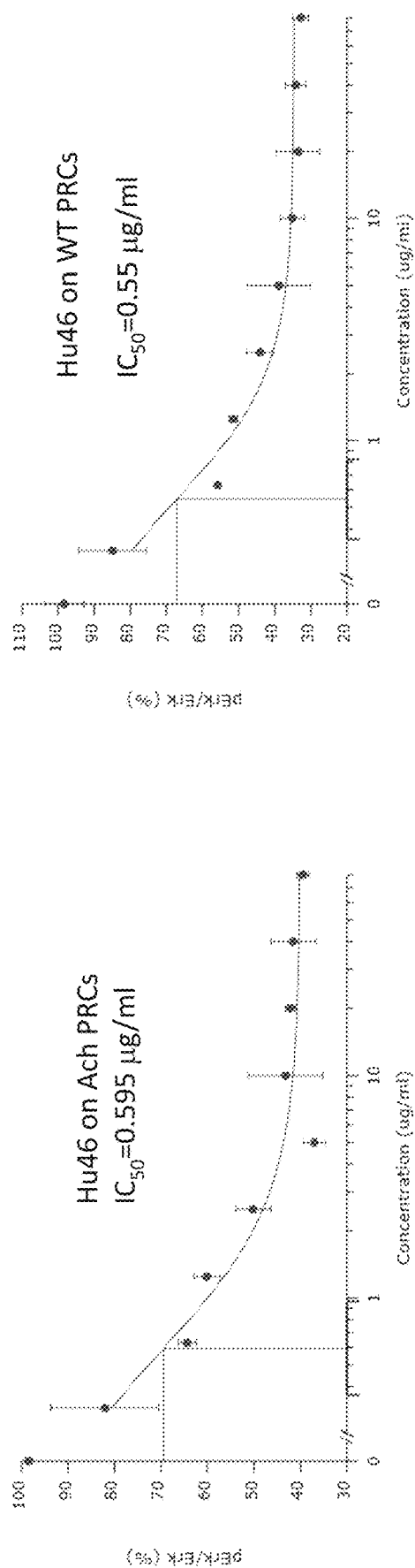
Figure 11:
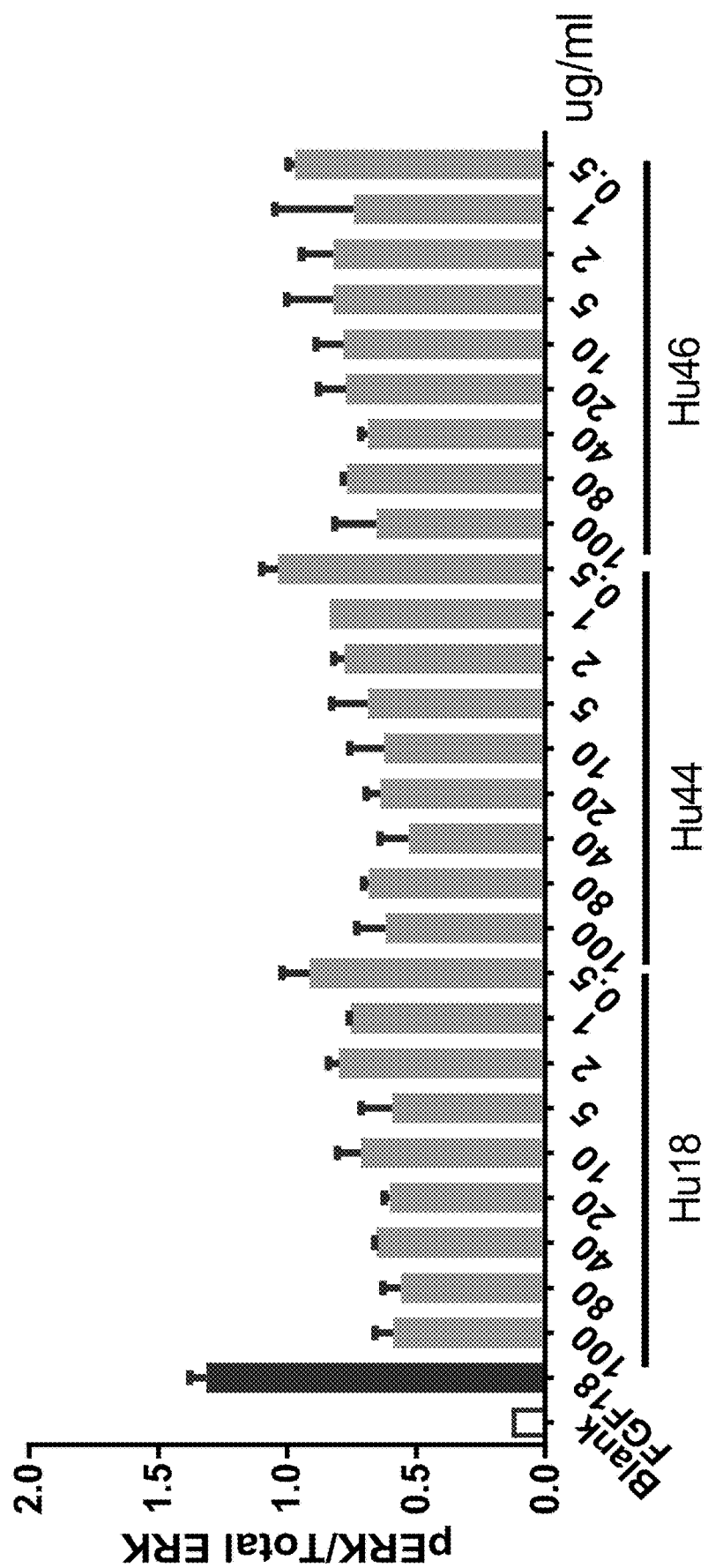
FIG. 11 graphically depicts inhibition of Erk phosphorylation by humanized anti-FGFR3 antibodies Hu18, Hu44, and Hu46. Inhibition of Erk phosphorylation was determined using an HTRF assay.

Humanized FGFR3 antibodies, including Hu18, Hu44, and Hu46, were also tested in the HTRF assay, and found to inhibit Erk phosphorylation (FIG. 11). The IC$_{50}$s of these humanized antibodies were determined, as well (FIG. 8A to FIG. 8C, respectively).

In Vivo Analysis

For in vivo evaluation of the antibodies, an achondroplasia mouse model (Ach) was used. The achondroplasia mouse is a transgenic mouse that overexpresses the mouse FGFR3 protein having the G380R mutation under control of the collagen II promoter (Shazeeb et al., (2018) Sci Rep 8, 469).

Figure 12B:
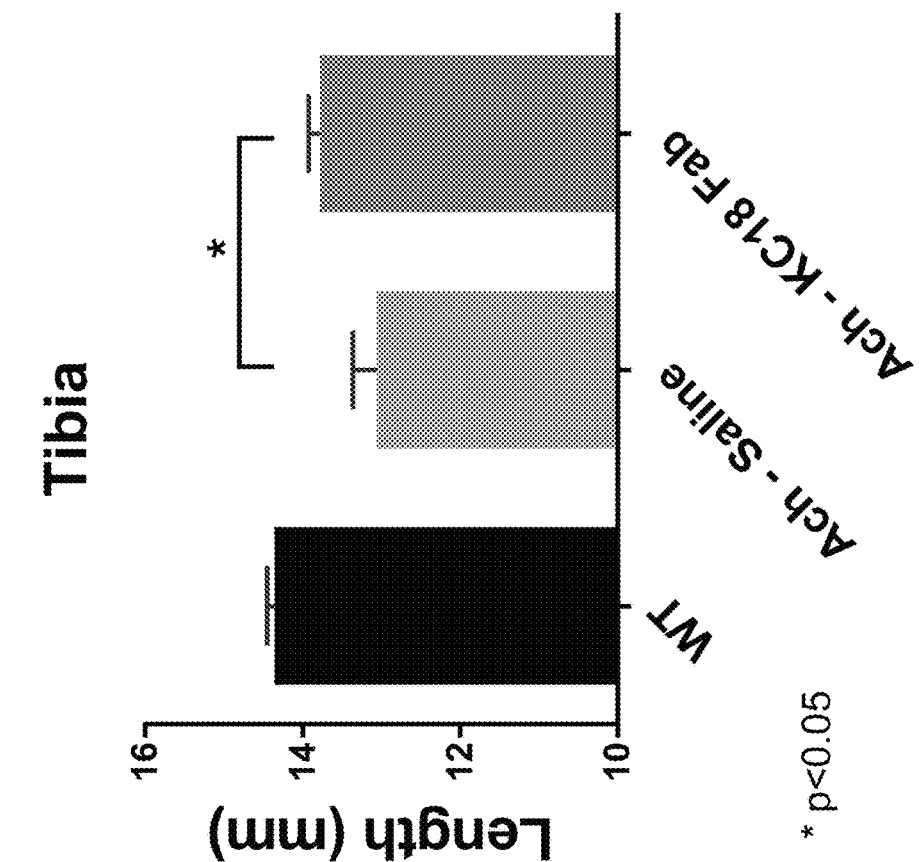
FIG. 12A-FIG. 12B graphically depict femur (FIG. 12A) and tibia (FIG. 12B) length in an achondroplasia mouse model (Ach), which is a transgenic mouse that overexpresses the mouse FGFR3 protein with the G380R mutation under the collagen II promoter. Mice were administered the KC18 fab fragment subcutaneously from 3 days of age to 20 days of age.
Figure 12A:
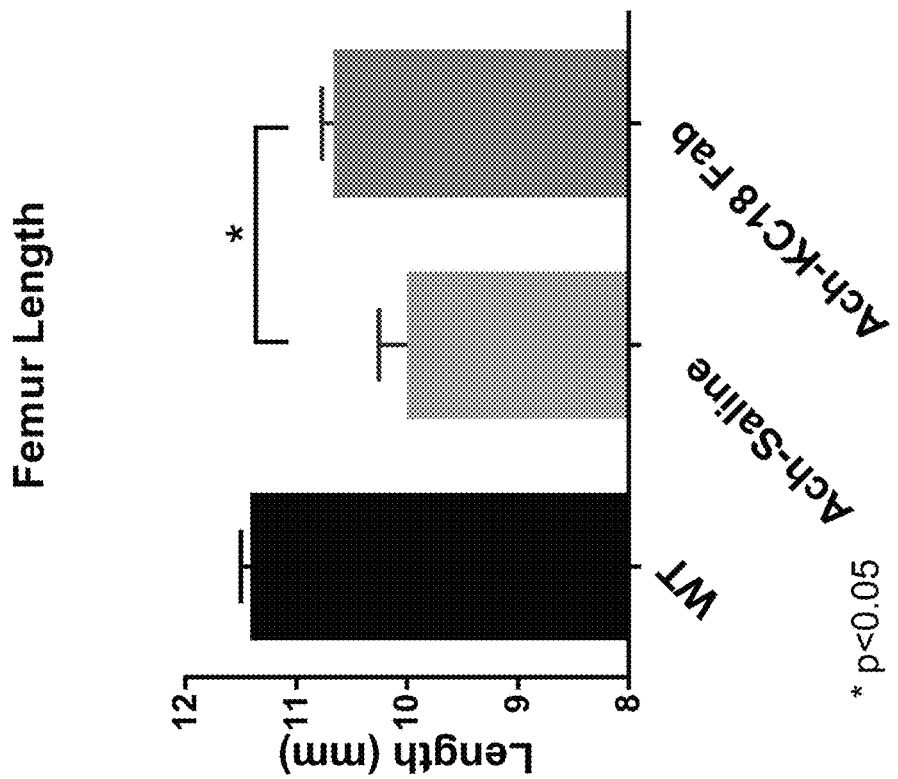
Figure 13B:
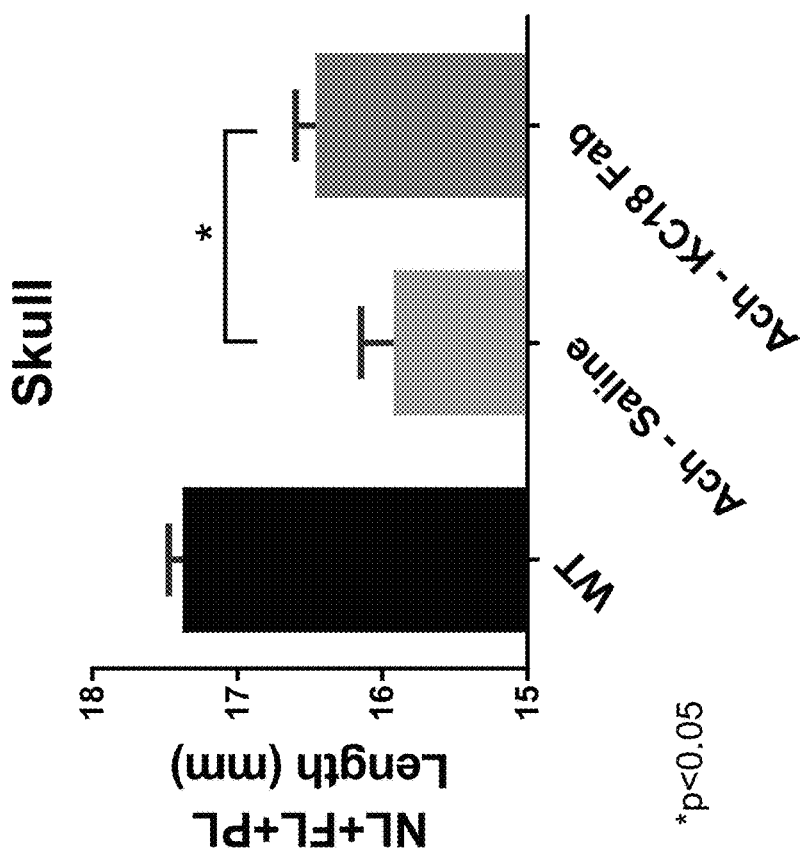
FIG. 13A-FIG. 13B graphically depict vertebrae (FIG. 13A) and skull (FIG. 13B) length in the Ach mouse model. For skull measurements, NL=nasal length; FL=frontal length; and PL=parietal length.
Figure 13A:
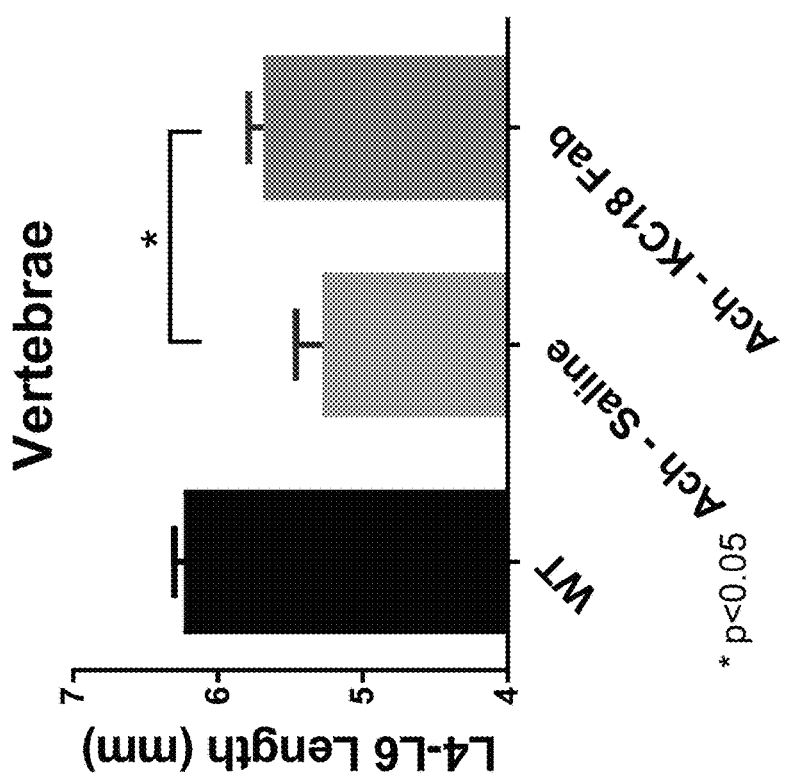
Figure 14:
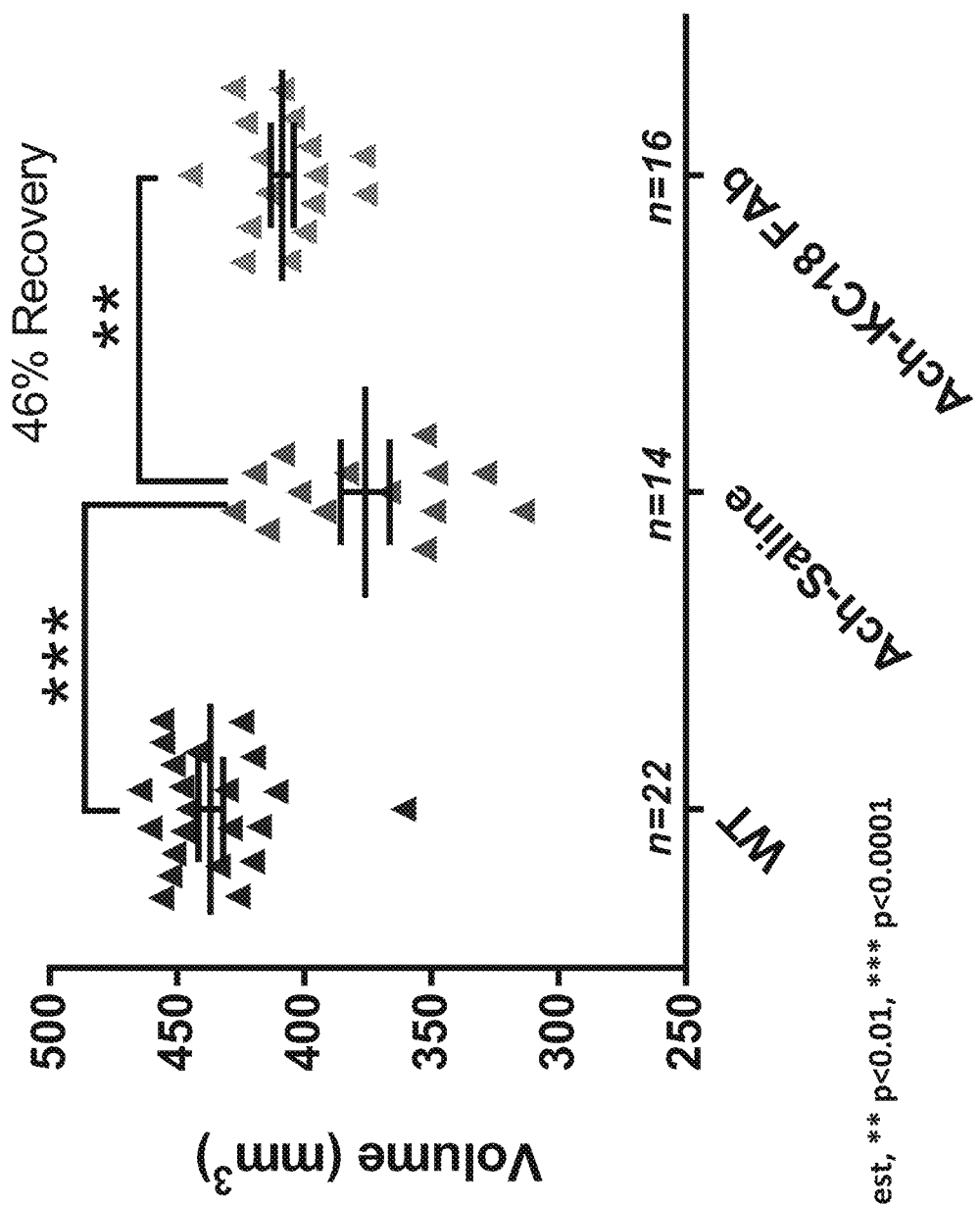
FIG. 14 graphically depicts brain volume in the WT and Ach mouse model treated by saline or KC18 fab fragment.
Figures 15A, 15B:
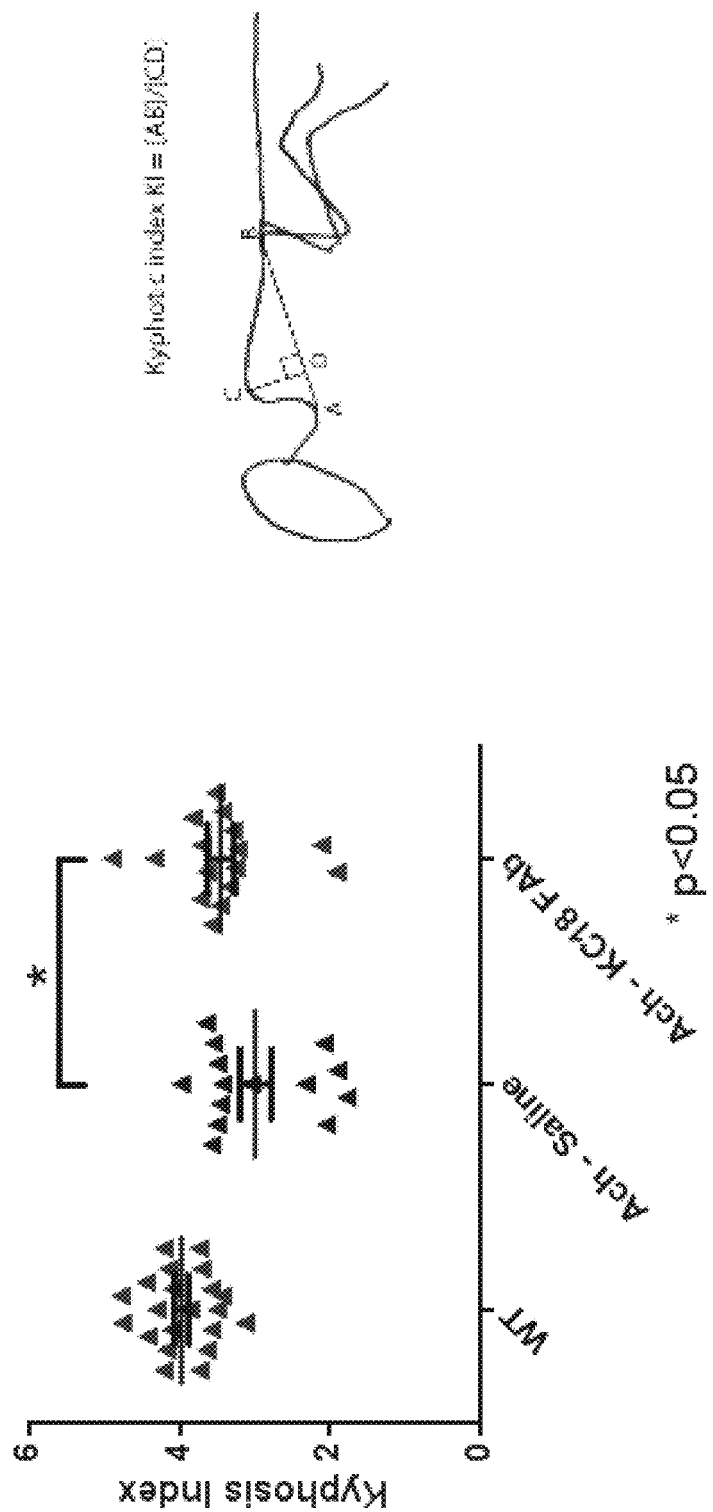
FIG. 15A graphically depicts Kyphosis Index in the WT and Ach mouse model treated by saline or KC18 fab fragment.
FIG. 15B depicts the calculation of Kyphotic Index using a mouse model.
Figure 16A:
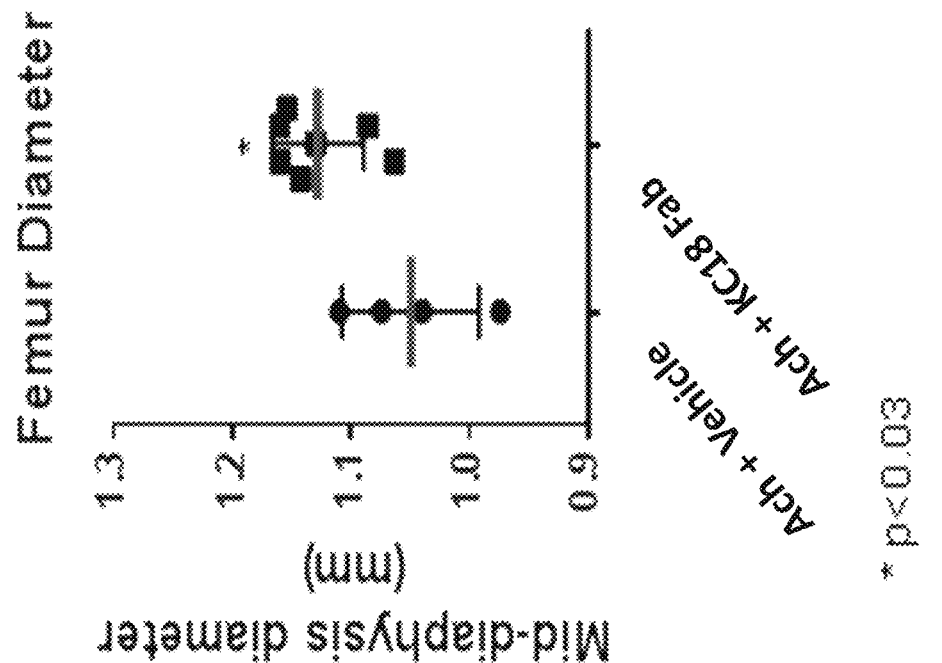
FIG. 16A graphically depicts femur growth plate (GP) volume in Ach mouse model treated by vehicle or KC18 fab fragment.
Figure 16B:
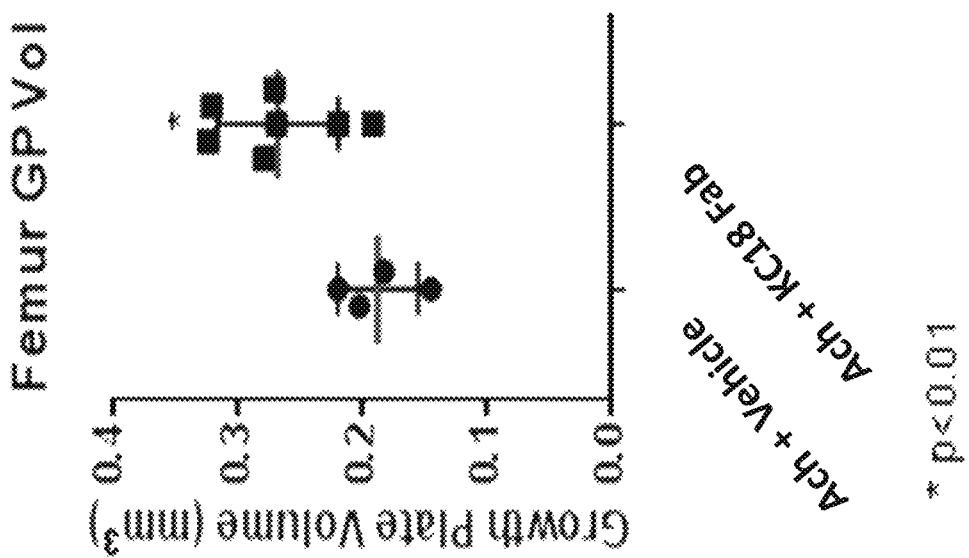
FIG. 16B depicts femur diameter in Ach mouse model treated by vehicle or KC18 fab fragment.
Figure 17:
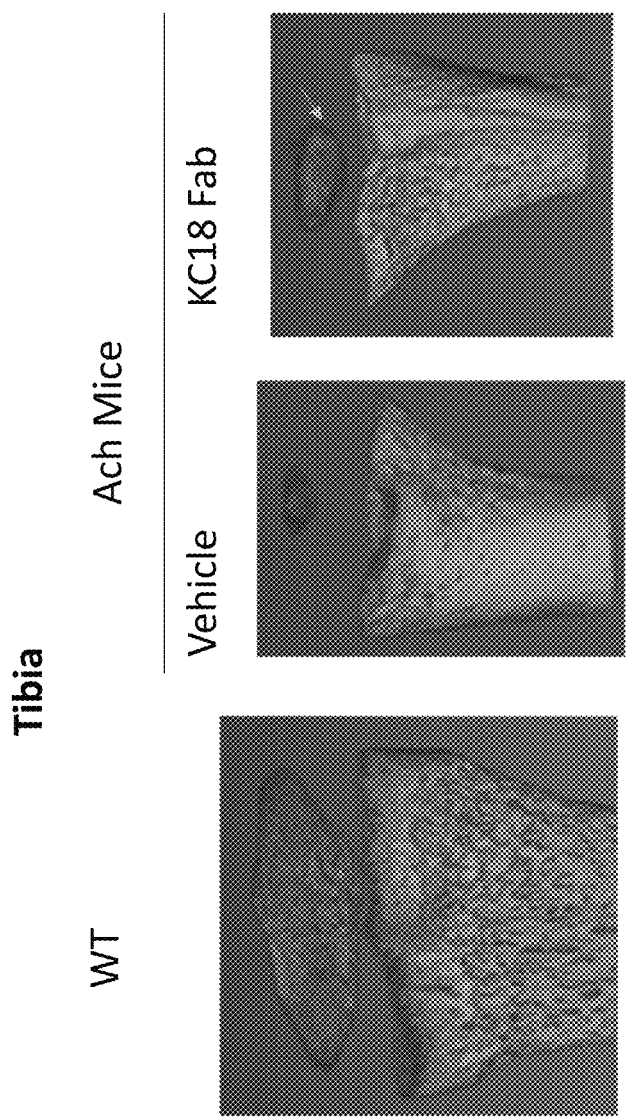
FIG. 17 graphically depicts increased secondary ossification center in tibia in Ach mouse model compared to those treated with vehicle.

The mice were genotyped at 1 day of age, and randomized to either a control (i.e., saline) group or an antibody dosed group. Achondroplasia mice (G380R) received a daily dose subcutaneously (SC) from 3 days of age to 20 days of age. The mice were then euthanized, and bones were collected at 21 days of age for microCT analysis. Tibias, femurs, vertebrae and skulls were used for the analysis, and lengths were measured using 3D microCT analysis. AMIRA (V6.0.1, FEI, Hillsboro, Oreg., USA) was used for all numerical analysis of bone lengths. The lengths of leg bones were measured using seed points along the bone, and a 3D length tool in AMIRA. The results indicated that achondroplasia (Ach) mice treated with KC18 Fab had a significantly increased tibia and femur length (FIG. 12A and FIG. 12B), a significantly increased vertebra and skull length (FIG. 13A and FIG. 13B), a significantly increased brain volume (FIG. 14), and corrected vertebral abnormalities as measured by Kyphosis Index (FIG. 15A-FIG. 15B). Ach mice treated with KC18 Fab also had several improved bone parameters, including femur growth plate volume, and femur diameter (FIG. 16A and FIG. 16B). Ach mice treated with KC18 Fab also had improved bone age as shown by more developed secondary ossification center in tibia (FIG. 17) compared to those treated with vehicle.

In summary, achondroplasia is the most common form of dwarfism due to activating mutations in the FGFR3 gene. FGFR3 protein is expressed in the growth plate and its function is to regulate proper growth. However, the activating mutations lead to excessive inhibition of chondrocyte proliferation and differentiation which is the main cause for the short stature and other skeletal deformities. The antibodies generated herein are specific to FGFR3 and inhibit FGFR3 activity. The mechanism of action of the antibody is to inhibit ligand binding and prevent activation of the receptor. The antibodies described herein can block ligand activation and subsequently inhibit downstream signaling measured by the decrease in Erk phosphorylation. This translates into inhibition of receptor activity. In vivo testing of anti-FGFR3 antibodies in the Ach mouse model demonstrated efficacy on the axial and appendicular skeleton. More specifically, a significant increase in femur and tibia length, skull length as well as lumbar length were observed.

What is claimed:

1. An antigen-binding protein or antigen-binding fragment thereof that specifically binds to fibroblast growth factor receptor 3 (FGFR3), comprising an antibody heavy chain variable (VH) domain and an antibody light chain variable (VL) domain,
wherein the VH domain comprises a CDR-H1 sequence comprising the amino acid sequence of GDTFTDFE (SEQ ID NO: 70), a CDR-H2 sequence comprising the amino acid sequence of VDPETGGT (SEQ ID NO: 297), and a CDR-H3 sequence comprising the amino acid sequence of TRTYDGYPYAFDY (SEQ ID NO: 301); and
wherein the VL domain comprises a CDR-L1 sequence comprising the amino acid sequence of QSVLYSNNNKNY (SEQ ID NO: 302), a CDR-L2 sequence comprising the amino acid sequence of WAS (SEQ ID NO: 74), and a CDR-L3 sequence comprising the amino acid sequence of QQYYSYRT (SEQ ID NO: 75).

2. The antigen binding protein or antigen-binding fragment thereof of claim 1, wherein the VH domain is at least about 90% identical to the amino acid sequence of SEQ ID NO: 57, and the VL domain is at least about 90% identical to the amino acid sequence of SEQ ID NO: 19.

3. The antigen binding protein or antigen-binding fragment thereof of claim 1, wherein the antibody heavy chain is at least 95% identical to the amino acid sequence of SEQ ID NO: 63, and the antibody light chain is at least 95% identical to the amino acid sequence of SEQ ID NO: 67.

4. The antigen binding protein or antigen-binding fragment thereof of claim 1, wherein the antibody heavy chain comprises the amino acid sequence of SEQ ID NO: 63, and the antibody light chain comprises the amino acid sequence of SEQ ID NO: 67.

5. The antigen binding protein or antigen-binding fragment thereof of claim 1, wherein the antigen binding protein or antigen-binding binding fragment thereof comprises an Fc region.

6. The antigen binding protein or antigen-binding fragment thereof of claim 5, wherein the Fc region is a human IgG1 Fc region.

7. The antigen binding protein or antigen-binding fragment thereof of claim 1, wherein the antigen binding protein or antigen-binding binding fragment thereof comprises an antibody F(ab), F(ab')2, Fab'-SH, Fv, or scFv fragment.

8. The antigen binding protein or antigen-binding fragment thereof of claim 7, wherein the antibody F(ab) fragment comprises the sequence of SEQ ID NO: 56 followed by the first about 100 to about 110 amino acids of SEQ ID NO: 54.

9. The antigen binding protein or antigen-binding fragment thereof of claim 7, wherein the antibody F(ab) fragment comprises a heavy chain comprising the sequence of SEQ ID NO: 57 followed by the first about 100 to about 110 amino acids of SEQ ID NO: 54.

10. The antigen binding protein or antigen-binding fragment thereof of claim 7, wherein the antibody F(ab) fragment comprises a heavy chain comprising the sequence of SEQ ID NO: 58 followed by the first about 100 to about 110 amino acids of SEQ ID NO: 54.

11. A pharmaceutical composition comprising the antigen binding protein or antigen-binding fragment of claim 1, and a pharmaceutically acceptable carrier.

12. The antigen binding protein or antigen-binding fragment thereof of claim 1, wherein the antigen binding protein or antigen-binding binding fragment thereof comprises an antibody F(ab) fragment.

13. An antigen-binding protein or antigen-binding fragment thereof that specifically binds to fibroblast growth factor receptor 3 (FGFR3), comprising an antibody heavy chain variable (VH) domain and an antibody light chain variable (VL) domain, wherein: the VH domain comprises the amino acid sequence of SEQ ID NO: 57, and
the VL domain comprises the amino acid sequence of SEQ ID NO: 19.

14. A pharmaceutical composition comprising the antigen binding protein or antigen-binding fragment of claim 13, and a pharmaceutically acceptable carrier.

15. An antibody F(ab) fragment, wherein the antibody F(ab) fragment comprises an antibody F(ab) fragment heavy chain comprising the amino acid sequence of SEQ ID NO: 155, 171, 180, 189, 198, 207, 216, 225, 234, 243, 252, 261, 270, 279, or 288, and an antibody F(ab) fragment light chain comprising the amino acid sequence of SEQ ID NO: 67.

16. A pharmaceutical composition comprising the antigen binding protein or antigen-binding fragment of claim 15, and a pharmaceutically acceptable carrier.

* * * * *